(12) United States Patent
Kunz et al.

(10) Patent No.: US 6,491,938 B2
(45) Date of Patent: Dec. 10, 2002

(54) THERAPEUTIC INHIBITOR OF VASCULAR SMOOTH MUSCLE CELLS

(75) Inventors: Lawrence L. Kunz, Redmond; John M. Reno, Brier, both of WA (US)

(73) Assignee: NeoRx Corporation, Seattle, WA (US)

( * ) Notice: Subject to any disclaimer, the term of this patent is extended or adjusted under 35 U.S.C. 154(b) by 0 days.

(21) Appl. No.: 09/896,208

(22) Filed: Jun. 29, 2001

(65) Prior Publication Data

US 2002/0025979 A1 Feb. 28, 2002

Related U.S. Application Data

(62) Division of application No. 08/829,991, filed on Mar. 31, 1997, and a continuation-in-part of application No. PCT/US96/02125, filed on Feb. 15, 1996, which is a continuation-in-part of application No. 08/450,793, filed on May 25, 1995, now Pat. No. 5,811,447, which is a continuation-in-part of application No. 08/389,712, filed on Feb. 15, 1995, which is a continuation of application No. 08/062,451, filed on May 13, 1993.

(51) Int. Cl.$^7$ ................................................. A61F 2/00
(52) U.S. Cl. .................... 424/423; 435/975; 604/890.1; 604/891.1
(58) Field of Search ...................... 435/975; 604/890.1, 604/891.1; 424/423

(56) References Cited

U.S. PATENT DOCUMENTS

| | | | |
|---|---|---|---|
| 2,914,563 A | 11/1959 | Allen et al. ................ 260/570 |
| 3,010,965 A | 11/1961 | Elpern ........................ 260/293 |
| 3,168,565 A | 2/1965 | Palopoli et al. .......... 260/570.7 |
| 3,288,806 A | 11/1966 | DeWald et al. ......... 260/326.5 |
| 3,445,473 A | 5/1969 | Ruschig et al. .......... 260/293.4 |
| 3,634,517 A | 1/1972 | Palopoli et al. ............ 260/590 |
| 3,940,422 A | 2/1976 | Harita et al. .............. 260/340 |
| 4,070,484 A | 1/1978 | Harita et al. .............. 424/319 |
| 4,093,709 A | 6/1978 | Sok Choi et al. ........... 424/19 |
| 4,133,814 A | 1/1979 | Jones et al. ................ 260/326 |
| 4,205,685 A | 6/1980 | Yoshida et al. ............ 128/399 |
| 4,219,656 A | 8/1980 | Press et al. .................. 549/64 |
| 4,221,785 A | 9/1980 | Sorenson .................... 424/230 |
| 4,230,862 A | 10/1980 | Suarez et al. .............. 546/237 |
| 4,235,988 A | 11/1980 | Fildes et al. ................ 528/79 |
| 4,239,778 A | 12/1980 | Venton et al. .............. 424/305 |
| 4,282,246 A | 8/1981 | Holland ...................... 424/275 |
| 4,287,190 A | 9/1981 | Boettcher et al. .......... 424/230 |
| 4,307,111 A | 12/1981 | Crawley ..................... 424/278 |
| 4,310,523 A | 1/1982 | Neumann ................... 424/240 |
| 4,315,028 A | 2/1982 | Scheinberg ................. 424/290 |
| 4,317,915 A | 3/1982 | Confalone et al. ........... 549/68 |
| 4,323,707 A | 4/1982 | Suarez et al. .............. 564/324 |
| 4,332,791 A | 6/1982 | Raaf et al. ................... 424/52 |
| 4,339,429 A | 7/1982 | Raaf et al. ................... 424/49 |
| 4,380,635 A | 4/1983 | Peters ........................ 546/324 |
| 4,382,143 A | 5/1983 | Shepherd .................... 549/68 |
| 4,389,330 A | 6/1983 | Tice et al. ............. 427/213.36 |
| 4,418,068 A | 11/1983 | Jones ........................ 424/267 |
| 4,428,963 A | 1/1984 | Confalone et al. .......... 424/275 |
| 4,440,754 A | 4/1984 | Sorenson .................... 424/140 |
| 4,442,119 A | 4/1984 | Magarian et al. ........... 424/274 |
| 4,485,096 A | 11/1984 | Bell ............................ 424/95 |
| 4,485,097 A | 11/1984 | Bell ............................ 424/95 |
| 4,487,780 A | 12/1984 | Scheinberg ................. 424/294 |
| 4,491,574 A | 1/1985 | Seifter et al. ................ 424/10 |
| 4,512,762 A | 4/1985 | Spears ......................... 604/21 |
| 4,536,516 A | 8/1985 | Harper et al. .............. 514/574 |
| 4,555,402 A | 11/1985 | Matsuda et al. ............ 424/122 |
| 4,577,636 A | 3/1986 | Spears ........................ 128/654 |
| 4,605,644 A | 8/1986 | Foker ......................... 514/45 |
| 4,629,694 A | 12/1986 | Harpel ........................ 435/7 |
| 4,657,928 A | 4/1987 | Sorenson .................... 514/499 |
| 4,664,097 A | 5/1987 | McGrath et al. ........... 128/1 R |
| 4,670,428 A | 6/1987 | Sorenson .................... 514/184 |
| 4,675,189 A | 6/1987 | Kent et al. .................. 424/490 |
| 4,696,949 A | 9/1987 | Toivola et al. .............. 514/648 |
| 4,705,647 A | 11/1987 | Yamaguchi et al. ........ 252/512 |
| 4,732,763 A | 3/1988 | Beck et al. ................. 424/433 |
| 4,744,981 A | 5/1988 | Pavanasasivam ........... 424/85 |
| 4,757,059 A | 7/1988 | Sorenson .................... 514/159 |
| 4,758,554 A | 7/1988 | Sorenson et al. ........... 514/186 |
| 4,758,555 A | 7/1988 | Sorenson .................... 514/186 |
| 4,760,051 A | 7/1988 | Pickart ........................ 514/6 |
| 4,767,758 A | 8/1988 | Breccia et al. ............ 514/231.5 |
| 4,824,436 A | 4/1989 | Wolinsky ..................... 604/53 |
| 4,824,661 A | 4/1989 | Wagner ....................... 424/52 |
| 4,826,672 A | 5/1989 | Milius et al. ................. 424/1 |
| 4,835,002 A | 5/1989 | Wolf et al. ................. 426/590 |
| RE32,944 E | 6/1989 | Harita et al. ............... 562/455 |
| 4,839,155 A | 6/1989 | Mccague ..................... 424/1 |

(List continued on next page.)

FOREIGN PATENT DOCUMENTS

| | | | |
|---|---|---|---|
| DE | 4401554 | 8/1994 | ......... A61K/31/135 |
| DE | 4320896 | 1/1995 | ........... A61K/31/40 |
| DE | 4320898 | 1/1995 | ......... A61K/31/135 |

(List continued on next page.)

OTHER PUBLICATIONS

Perez, J.R., et al., "Regulation of Adhesion and Growth of Fibrosarcoma Cells by NF–kb RelA Involves Transforming Growth Factor Beta", *Molecular and Cellular Biology*, 14, 5326–5332, (1994).

(List continued on next page.)

*Primary Examiner*—Samuel Barts
(74) *Attorney, Agent, or Firm*—Schwegman, Lundbereg, Woessner & Kluth, P.A.

(57) ABSTRACT

Methods are provided for inhibiting stenosis or restenosis following vascular trauma in a mammalian host, comprising administering to the host a therapeutically effective dosage of a cytostatic agent and/or cytoskeletal inhibitor so as to biologically stent the traumatized vessel. Also provided is a method to inhibit or reduce vascular remodeling following vascular trauma, comprising administering an effective amount of a cytoskeletal inhibitor. Further provided are pharmaceutical compositions and kits comprising the therapeutic agents of the invention.

18 Claims, 21 Drawing Sheets

U.S. PATENT DOCUMENTS

| | | | |
|---|---|---|---|
| 4,840,939 A | 6/1989 | Leveen et al. ................. 514/25 |
| 4,853,377 A | 8/1989 | Pollack ....................... 514/161 |
| 4,859,585 A | 8/1989 | Sonnenschein et al. ........ 435/29 |
| 4,867,973 A | 9/1989 | Goers et al. ................. 530/387 |
| 4,879,225 A | 11/1989 | Morgan, Jr. et al. .......... 435/68 |
| 4,879,315 A | 11/1989 | Magarian et al. ............ 514/754 |
| 4,897,255 A | 1/1990 | Fritzberg et al. .............. 424/1 |
| 4,900,561 A | 2/1990 | Abdel-Monem et al. ........ 426/2 |
| 4,906,452 A | 3/1990 | Sivam ......................... 424/10 |
| 4,929,602 A | 5/1990 | Harker et al. ................. 514/18 |
| 4,935,415 A | 6/1990 | Nakano et al. .............. 514/211 |
| 4,948,594 A | 8/1990 | Abdel-Monem et al. ........ 426/2 |
| 4,952,607 A | 8/1990 | Sorenson ..................... 514/589 |
| 4,956,188 A | 9/1990 | Anderson .................... 426/74 |
| 4,959,355 A | 9/1990 | Fischbarg et al. ............. 514/23 |
| RE33,403 E | 10/1990 | Stolle et al. ................... 424/87 |
| 4,962,091 A | 10/1990 | Eppstein et al. ............... 514/2 |
| 4,968,350 A | 11/1990 | Bindschaedler et al. .... 106/170 |
| 4,973,601 A | 11/1990 | Dowd et al. ................. 514/410 |
| 4,973,755 A | 11/1990 | Grafe et al. ................. 564/324 |
| 4,990,538 A | 2/1991 | Harris et al. ................. 514/648 |
| 4,994,033 A | 2/1991 | Shockey et al. ............. 604/101 |
| 4,994,384 A | 2/1991 | Prather et al. ........... 435/172.2 |
| 4,996,225 A | 2/1991 | Toivola et al. .............. 514/428 |
| 4,997,652 A | 3/1991 | Wong ......................... 424/428 |
| 4,999,347 A | 3/1991 | Sorenson ..................... 514/159 |
| 5,008,279 A | 4/1991 | Franckowiak et al. ....... 514/345 |
| 5,009,659 A | 4/1991 | Hamlin et al. ................ 606/191 |
| 5,015,578 A | 5/1991 | Schroeder et al. .......... 435/119 |
| 5,015,666 A | 5/1991 | Magarian et al. ............ 514/754 |
| 5,019,504 A | 5/1991 | Christen et al. ............. 435/123 |
| 5,023,237 A | 6/1991 | Pickart et al. ................. 514/18 |
| 5,026,537 A | 6/1991 | Daddona et al. ............. 424/1.1 |
| 5,030,637 A | 7/1991 | Einzig et al. ................ 514/304 |
| 5,032,679 A | 7/1991 | Brandley et al. ............. 536/21 |
| 5,037,641 A | 8/1991 | Juhos et al. ................... 424/59 |
| 5,043,335 A | 8/1991 | Kleinschroth et al. ....... 514/211 |
| 5,047,431 A | 9/1991 | Schickaneder et al. ..... 514/648 |
| 5,049,132 A | 9/1991 | Schaffer et al. ............. 604/101 |
| 5,053,033 A | 10/1991 | Clarke et al. .................. 606/3 |
| 5,059,166 A | 10/1991 | Fischell et al. ................ 600/3 |
| 5,066,789 A | 11/1991 | Srinivasan et al. .......... 530/388 |
| 5,073,633 A | 12/1991 | Schroeder et al. .......... 540/545 |
| 5,075,321 A | 12/1991 | Schreiber .................... 514/317 |
| 5,082,834 A | 1/1992 | Sorenson ..................... 514/159 |
| 5,093,330 A | 3/1992 | Caravatti et al. ............ 514/211 |
| 5,098,903 A | 3/1992 | Magarian et al. ............ 514/255 |
| 5,099,504 A | 3/1992 | Christen et al. ............. 435/123 |
| 5,100,885 A | 3/1992 | Abrams et al. .............. 514/184 |
| 5,102,402 A | 4/1992 | Dror et al. ................... 604/265 |
| 5,108,989 A | 4/1992 | Amento et al. ................ 514/12 |
| 5,112,305 A | 5/1992 | Barath et al. ................ 704/96 |
| 5,114,719 A | 5/1992 | Sabel et al. ................. 424/422 |
| 5,114,847 A | 5/1992 | Jungfer et al. ................ 435/41 |
| 5,116,864 A | 5/1992 | March et al. ................ 514/455 |
| 5,118,791 A | 6/1992 | Burnier et al. ............... 530/326 |
| 5,120,535 A | 6/1992 | Marquardt et al. ......... 424/85.5 |
| 5,126,348 A | 6/1992 | McMurray ................... 514/264 |
| 5,140,012 A | 8/1992 | McGovern et al. ............ 514/19 |
| 5,145,684 A | 9/1992 | Liversidge et al. .......... 424/489 |
| 5,145,838 A | 9/1992 | Pickart ........................ 514/18 |
| 5,166,143 A | 11/1992 | Ondetti et al. ................ 514/89 |
| 5,166,191 A | 11/1992 | Cronin et al. ................. 514/12 |
| 5,167,960 A | 12/1992 | Ito et al. ..................... 424/423 |
| 5,171,217 A | 12/1992 | March et al. ................ 604/53 |
| 5,176,617 A | 1/1993 | Fischell et al. ................ 600/3 |
| 5,180,366 A | 1/1993 | Woods ........................ 604/96 |
| 5,185,260 A | 2/1993 | Crissman et al. ........... 435/244 |
| 5,189,046 A | 2/1993 | Burch et al. ................. 514/330 |
| 5,189,212 A | 2/1993 | Ruenitz ....................... 562/468 |
| 5,192,525 A | 3/1993 | Yang et al. .................... 424/11 |
| 5,199,939 A | 4/1993 | Dake et al. ..................... 600/3 |
| 5,208,019 A | 5/1993 | Hanson et al. ................ 424/85 |
| 5,208,238 A | 5/1993 | King .......................... 514/255 |
| 5,211,940 A | 5/1993 | Ishiguro et al. ............... 424/49 |
| 5,213,576 A | 5/1993 | Abiuso et al. ................. 604/96 |
| 5,213,580 A | 5/1993 | Slepian et al. ................. 623/1 |
| 5,216,021 A | 6/1993 | Sorenson ..................... 514/499 |
| 5,216,024 A | 6/1993 | Markaverich et al. ....... 514/543 |
| 5,216,126 A | 6/1993 | Cox et al. .................... 530/350 |
| 5,219,548 A | 6/1993 | Yang et al. ..................... 424/1 |
| 5,221,620 A | 6/1993 | Purchio et al. ............... 435/69 |
| 5,226,430 A | 7/1993 | Spears et al. ................ 128/898 |
| 5,229,495 A | 7/1993 | Ichijo et al. ................. 530/350 |
| 5,232,444 A | 8/1993 | Just et al. ..................... 604/96 |
| 5,232,911 A | 8/1993 | Vidal .......................... 514/12 |
| 5,234,957 A | 8/1993 | Mantelle .................... 514/772 |
| 5,238,714 A | 8/1993 | Wallace et al. ............. 427/213 |
| 5,238,950 A | 8/1993 | Clader et al. ............... 514/360 |
| 5,242,397 A | 9/1993 | Barath et al. ................. 604/96 |
| 5,248,764 A | 9/1993 | Flanagan et al. ............ 530/324 |
| 5,254,594 A | 10/1993 | Niikura et al. .............. 514/648 |
| 5,260,224 A | 11/1993 | Stossel et al. ............... 436/503 |
| 5,262,319 A | 11/1993 | Iwata et al. ............... 435/240.4 |
| 5,268,358 A | 12/1993 | Fretto et al. .................. 514/12 |
| 5,268,455 A | 12/1993 | Cianciolo .................... 530/404 |
| 5,270,047 A | 12/1993 | Kauffman et al. ........... 424/422 |
| 5,280,016 A | 1/1994 | Conrad et al. ................. 514/56 |
| 5,280,040 A | 1/1994 | Labroo et al. ............... 514/422 |
| 5,280,109 A | 1/1994 | Miyazono et al. .......... 530/399 |
| 5,282,785 A | 2/1994 | Shapland et al. .............. 604/21 |
| 5,283,257 A | 2/1994 | Gregory et al. ............. 514/458 |
| 5,284,763 A | 2/1994 | Derynk et al. .............. 435/240 |
| 5,284,869 A | 2/1994 | Bisaccia et al. ............. 514/455 |
| 5,288,711 A | 2/1994 | Mitchell et al. ............... 514/56 |
| 5,288,735 A | 2/1994 | Trager et al. ............... 514/363 |
| 5,296,492 A | 3/1994 | Shiozawa et al. ........... 514/337 |
| 5,304,325 A | 4/1994 | Kaufman et al. ............ 252/312 |
| 5,304,541 A | 4/1994 | Purchio et al. ................ 514/12 |
| 5,308,622 A | 5/1994 | Casscells et al. ............ 424/422 |
| 5,308,862 A | 5/1994 | Ohlstein et al. ............. 514/411 |
| 5,314,679 A | 5/1994 | Lewis et al. ................... 424/9 |
| 5,316,766 A | 5/1994 | Baldus et al. ................. 424/94 |
| 5,324,736 A | 6/1994 | Magarin et al. ............. 514/317 |
| 5,324,739 A | 6/1994 | Gerwick et al. ............. 514/365 |
| 5,326,757 A | 7/1994 | Demopoulos ............... 514/167 |
| 5,328,471 A | 7/1994 | Slepian ....................... 607/101 |
| 5,332,576 A | 7/1994 | Mantelle .................... 424/443 |
| 5,332,584 A | 7/1994 | Scher et al. ................. 424/408 |
| 5,340,925 A | 8/1994 | Lioubin et al. .............. 530/395 |
| 5,342,926 A | 8/1994 | Hattner ....................... 534/10 |
| 5,344,926 A | 9/1994 | Murakata et al. ........... 540/545 |
| 5,346,702 A | 9/1994 | Na et al. ..................... 424/490 |
| 5,346,897 A | 9/1994 | King .......................... 514/290 |
| 5,346,993 A | 9/1994 | Miyazono et al. .......... 530/399 |
| 5,354,562 A | 10/1994 | Platz et al. .................. 424/489 |
| 5,354,774 A | 10/1994 | Deckelbaum et al. ....... 514/455 |
| 5,354,801 A | 10/1994 | O'Toole et al. ............. 524/461 |
| 5,356,713 A | 10/1994 | Charmot et al. ............ 428/407 |
| 5,358,844 A | 10/1994 | Stossel et al. ................. 435/2 |
| 5,362,424 A | 11/1994 | Lee et al. .................... 264/4.3 |
| 5,362,478 A | 11/1994 | Desai et al. .................. 424/9 |
| 5,364,632 A | 11/1994 | Benita et al. ............... 424/450 |
| 5,364,843 A | 11/1994 | King .......................... 514/15 |
| 5,380,716 A | 1/1995 | Conrad et al. ................ 514/56 |
| 5,384,332 A | 1/1995 | Fontana ..................... 514/648 |
| 5,385,935 A | 1/1995 | Tamai et al. ................ 514/535 |
| 5,389,670 A | 2/1995 | Fontana ..................... 514/443 |
| 5,391,557 A | 2/1995 | Cullinan et al. ............. 514/324 |
| 5,393,763 A | 2/1995 | Black et al. ................. 514/333 |
| 5,393,772 A | 2/1995 | Yue et al. .................... 514/410 |

| Patent No. | Date | Inventor | Class |
|---|---|---|---|
| 5,393,785 A | 2/1995 | Labrie et al. | 514/622 |
| 5,395,610 A | 3/1995 | King | 424/10 |
| 5,395,842 A | 3/1995 | Labrie et al. | 514/320 |
| 5,401,730 A | 3/1995 | Sauvage et al. | 514/165 |
| 5,407,609 A | 4/1995 | Tice et al. | 264/46 |
| 5,407,658 A | 4/1995 | Hattner | 424/1.65 |
| 5,411,988 A | 5/1995 | Bockow et al. | 514/560 |
| 5,418,252 A | 5/1995 | Williams | 514/443 |
| 5,420,243 A | 5/1995 | Ogawa et al. | 530/324 |
| 5,423,885 A | 6/1995 | Williams | 623/1 |
| 5,423,923 A | 6/1995 | Cullinan | 514/324 |
| 5,424,331 A | 6/1995 | Shlyankevich | 514/456 |
| 5,426,123 A | 6/1995 | Fontana | 514/651 |
| 5,429,634 A | 7/1995 | Narcisco | 604/890.1 |
| 5,434,166 A | 7/1995 | Glasebrook | 514/317 |
| 5,436,243 A | 7/1995 | Sachs et al. | 514/231 |
| 5,439,689 A | 8/1995 | Hendrickson et al. | 424/490 |
| 5,439,923 A | 8/1995 | Cullinan | 514/324 |
| 5,439,931 A | 8/1995 | Sales | 514/443 |
| 5,441,734 A | 8/1995 | Reichert et al. | 424/85.7 |
| 5,441,947 A | 8/1995 | Dodge et al. | 514/179 |
| 5,441,964 A | 8/1995 | Bryant et al. | 514/324 |
| 5,441,965 A | 8/1995 | Sall et al. | 514/324 |
| 5,441,966 A | 8/1995 | Dodge | 514/324 |
| 5,441,986 A | 8/1995 | Thompson | 514/648 |
| 5,444,164 A | 8/1995 | Purchio et al. | 536/23.5 |
| 5,445,941 A | 8/1995 | Yang | 435/6 |
| 5,446,053 A | 8/1995 | Keohane | 514/324 |
| 5,446,072 A | 8/1995 | Mantelle | 514/772.6 |
| 5,447,941 A | 9/1995 | Zuckerman | 514/324 |
| 5,451,414 A | 9/1995 | Steward | 426/74 |
| 5,451,589 A | 9/1995 | Dodge | 514/324 |
| 5,451,590 A | 9/1995 | Dodge | 514/324 |
| 5,451,603 A | 9/1995 | Piggott | 514/422 |
| 5,453,436 A | 9/1995 | Ohlstein | 514/411 |
| 5,453,442 A | 9/1995 | Bryant et al. | 514/408 |
| 5,453,492 A | 9/1995 | Butzow et al. | 530/413 |
| 5,455,275 A | 10/1995 | Fontana | 514/648 |
| 5,457,113 A | 10/1995 | Cullinan et al. | 514/319 |
| 5,457,116 A | 10/1995 | Black et al. | 514/324 |
| 5,457,117 A | 10/1995 | Black et al. | 514/337 |
| 5,458,568 A | 10/1995 | Racchini et al. | 604/19 |
| 5,460,807 A | 10/1995 | Cardin et al. | 424/78 |
| 5,461,064 A | 10/1995 | Cullinan | 514/324 |
| 5,461,065 A | 10/1995 | Black et al. | 514/324 |
| 5,462,925 A | 10/1995 | Ogawa et al. | 514/12 |
| 5,462,937 A | 10/1995 | Cullinan et al. | 514/212 |
| 5,462,949 A | 10/1995 | Jones et al. | 514/324 |
| 5,462,950 A | 10/1995 | Fontana | 514/324 |
| 5,466,810 A | 11/1995 | Godfrey | 546/202 |
| 5,468,746 A | 11/1995 | Casagrande et al. | 514/235.5 |
| 5,470,876 A | 11/1995 | Proctor | 514/492 |
| 5,470,883 A | 11/1995 | Stromberg | 514/648 |
| 5,472,985 A | 12/1995 | Grainger et al. | 514/651 |
| 5,478,847 A | 12/1995 | Draper | 514/333 |
| 5,478,860 A | 12/1995 | Wheeler et al. | 514/449 |
| 5,480,888 A | 1/1996 | Kodama et al. | 514/320 |
| 5,480,903 A | 1/1996 | Piggott et al. | 514/422 |
| 5,480,904 A | 1/1996 | Bryant et al. | 514/443 |
| 5,482,851 A | 1/1996 | Derynck et al. | 435/240.1 |
| 5,482,949 A | 1/1996 | Black et al. | 514/324 |
| 5,482,950 A | 1/1996 | Bryant et al. | 514/324 |
| 5,484,795 A | 1/1996 | Bryant et al. | 514/319 |
| 5,484,796 A | 1/1996 | Bryant et al. | 514/319 |
| 5,484,797 A | 1/1996 | Bryant et al. | 514/319 |
| 5,484,798 A | 1/1996 | Bryant et al. | 514/324 |
| 5,484,808 A | 1/1996 | Grinnell | 514/443 |
| 5,489,587 A | 2/1996 | Fontana | 514/233.5 |
| 5,491,159 A | 2/1996 | Malamas | 514/374 |
| 5,491,173 A | 2/1996 | Toivola et al. | 514/648 |
| 5,492,921 A | 2/1996 | Bryant et al. | 514/324 |
| 5,492,922 A | 2/1996 | Palkowitz | 514/324 |
| 5,492,926 A | 2/1996 | Cullinan et al. | 514/422 |
| 5,492,927 A | 2/1996 | Gitter et al. | 514/443 |
| 5,496,828 A | 3/1996 | Cullinan et al. | 514/324 |
| 5,496,851 A | 3/1996 | Grinnell et al. | 514/443 |
| 5,498,775 A | 3/1996 | Novak et al. | 514/25 |
| 5,508,292 A | 4/1996 | Sall et al. | 514/324 |
| 5,510,370 A | 4/1996 | Hock et al. | 514/443 |
| 5,512,268 A | 4/1996 | Grinstaff et al. | 454/9.322 |
| 5,516,781 A | 5/1996 | Morris et al. | 514/291 |
| 5,516,807 A | 5/1996 | Hupe et al. | 514/673 |
| 5,519,042 A | 5/1996 | Morris et al. | 514/378 |
| 5,521,171 A | 5/1996 | Sorenson | 514/188 |
| 5,521,172 A | 5/1996 | Bryant et al. | 514/212 |
| 5,521,191 A | 5/1996 | Greenwald | 514/262 |
| 5,521,198 A | 5/1996 | Zuckerman | 514/324 |
| 5,525,624 A | 6/1996 | Gitter et al. | 514/443 |
| 5,527,337 A | 6/1996 | Stack et al. | 606/198 |
| 5,534,527 A | 7/1996 | Black et al. | 54/333 |
| 5,538,892 A | 7/1996 | Donahoe et al. | 435/240.2 |
| 5,541,174 A | 7/1996 | Sorenson | 514/186 |
| 5,545,409 A | 8/1996 | Laurencin et al. | 424/426 |
| 5,545,569 A | 8/1996 | Grainger et al. | 436/518 |
| 5,552,415 A | 9/1996 | May | 514/324 |
| 5,552,433 A | 9/1996 | Bryant et al. | 514/443 |
| 5,556,768 A | 9/1996 | Bryant et al. | 514/443 |
| 5,563,054 A | 10/1996 | Briggs et al. | 435/127 |
| 5,563,146 A | 10/1996 | Morris et al. | 514/291 |
| 5,567,713 A | 10/1996 | Cullinan et al. | 514/324 |
| 5,571,714 A | 11/1996 | Dasch et al. | 435/240.27 |
| 5,571,808 A | 11/1996 | Leeds | 514/212 |
| 5,574,047 A | 11/1996 | Bumol et al. | 514/324 |
| 5,576,345 A | 11/1996 | Mansson et al. | 514/449 |
| 5,578,703 A | 11/1996 | Ichijo et al. | 530/350 |
| 5,580,898 A | 12/1996 | Trojanowski et al. | 514/449 |
| 5,583,153 A | 12/1996 | Brahn | 514/449 |
| 5,595,722 A | 1/1997 | Grainger et al. | 424/9.2 |
| 5,597,578 A | 1/1997 | Brown et al. | 424/422 |
| 5,599,844 A | 2/1997 | Grainger et al. | 514/651 |
| 5,605,700 A | 2/1997 | DeGregorio et al. | 424/448 |
| 5,610,166 A | 3/1997 | Singh | 514/324 |
| 5,610,168 A | 3/1997 | Draper | 514/333 |
| 5,616,608 A | 4/1997 | Kinsella et al. | 514/449 |
| 5,622,975 A | 4/1997 | Singh et al. | 514/324 |
| 5,635,489 A | 6/1997 | Haley | 514/21 |
| 5,639,274 A | 6/1997 | Fischell et al. | 604/96 |
| 5,641,790 A | 6/1997 | Draper | 514/333 |
| 5,646,160 A | 7/1997 | Morris et al. | 514/291 |
| 5,652,259 A | 7/1997 | May | 514/422 |
| 5,656,450 A | 8/1997 | Boyan et al. | 435/68.1 |
| 5,656,587 A | 8/1997 | Sporn et al. | 514/2 |
| 5,658,883 A | 8/1997 | Ogawa et al. | 514/12 |
| 5,658,927 A | 8/1997 | Magarian et al. | 514/315 |
| 5,658,951 A | 8/1997 | Magarian et al. | 514/596 |
| 5,660,873 A | 8/1997 | Nikolaychik et al. | 427/2.24 |
| 5,665,728 A | 9/1997 | Morris et al. | 514/291 |
| 5,681,835 A | 10/1997 | Willson | 514/237.5 |
| 5,686,467 A | 11/1997 | Bumol et al. | 514/324 |
| 5,686,476 A | 11/1997 | May | 514/324 |
| 5,688,813 A | 11/1997 | Sall et al. | 514/324 |
| 5,693,607 A | 12/1997 | Segarini et al. | 514/2 |
| 5,705,477 A | 1/1998 | Sporn et al. | 514/2 |
| 5,705,609 A | 1/1998 | Ruoslahti et al. | 530/329 |
| 5,716,981 A | 2/1998 | Hunter et al. | 514/449 |
| 5,726,186 A | 3/1998 | Grese | 514/321 |
| 5,731,144 A | 3/1998 | Toothman et al. | 435/6 |
| 5,731,200 A | 3/1998 | Ichijo et al. | 435/365 |
| 5,731,424 A | 3/1998 | Toothman et al. | 536/23.1 |
| 5,733,925 A | 3/1998 | Kunz et al. | 514/499 |
| 5,747,510 A | 5/1998 | Draper | 514/333 |
| 5,767,079 A | 6/1998 | Glaser et al. | 514/12 |

| | | | | |
|---|---|---|---|---|
| 5,770,609 A | 6/1998 | Grainger et al. ............ 514/319 |
| 5,773,479 A | 6/1998 | Grainger et al. ............ 514/651 |
| 5,776,184 A | 7/1998 | Tuch ............................ 623/1 |
| 5,811,447 A | 9/1998 | Kunz et al. ................. 514/411 |
| 5,821,234 A | 10/1998 | Dzau ............................ 514/44 |
| 5,824,048 A | 10/1998 | Tuch ............................ 623/1 |
| 5,824,647 A | 10/1998 | Postlethwaite et al. ....... 514/13 |
| 5,847,007 A | 12/1998 | Grainger et al. ............ 514/651 |
| 5,945,456 A | 8/1999 | Grainger et al. ............ 514/651 |
| 5,981,568 A | 11/1999 | Kunz et al. ................. 514/411 |
| 6,074,659 A | 6/2000 | Kunz et al. ................. 424/423 |

FOREIGN PATENT DOCUMENTS

| | | | |
|---|---|---|---|
| EP | 0002341 | 6/1979 | .......... C07C/65/10 |
| EP | 0024096 | 2/1981 | ............ C07F/1/08 |
| EP | 0054168 | 6/1982 | .......... C07C/93/06 |
| EP | 0095875 | 12/1983 | .......... C07C/33/26 |
| EP | 0260066 | 3/1988 | ........ C07C/217/54 |
| EP | 0290012 | 11/1988 | |
| EP | 0297946 | 1/1989 | .......... A61K/31/40 |
| EP | 0302034 | 2/1989 | .......... C08B/37/10 |
| EP | 0365863 | 5/1990 | .......... C07D/413/04 |
| EP | 0374044 | 6/1990 | .......... C12N/15/16 |
| EP | 0377526 B1 | 7/1990 | ............ C07F/1/08 |
| EP | 0411893 | 2/1991 | .......... C12N/15/13 |
| EP | 0451202 | 10/1991 | ............ A61K/9/70 |
| EP | 0524093 | 1/1993 | ........ C07D/305/14 |
| EP | 0577215 | 1/1993 | ............ A61K/9/14 |
| EP | 0526102 | 2/1993 | .......... A61M/29/02 |
| EP | 0542679 | 5/1993 | .......... C12N/15/12 |
| EP | 0588518 | 2/1994 | .......... A61K/31/165 |
| EP | 0584952 | 3/1994 | .......... A61K/31/445 |
| EP | 0606613 | 7/1994 | ........ G01N/33/531 |
| EP | 0622076 | 11/1994 | .......... A61K/31/165 |
| EP | 0629697 | 12/1994 | .......... C12N/15/63 |
| EP | 0635270 | 1/1995 | .......... A61K/38/29 |
| EP | 0639577 | 2/1995 | ............ C07F/9/65 |
| EP | 0659413 A2 | 6/1995 | ........ A61K/31/445 |
| EP | 0659415 A2 | 6/1995 | ........ A61K/31/445 |
| EP | 0659418 | 6/1995 | ........ A61K/31/445 |
| EP | 0659419 A1 | 6/1995 | ........ A61K/31/445 |
| EP | 0659429 A1 | 6/1995 | ........ A61K/31/445 |
| EP | 0664121 | 7/1995 | ........ A61K/31/445 |
| EP | 0664122 | 7/1995 | ........ A61K/31/445 |
| EP | 0664123 | 7/1995 | ........ A61K/31/445 |
| EP | 0664124 A1 | 7/1995 | ........ A61K/31/445 |
| EP | 0664125 | 7/1995 | |
| EP | 0664198 | 7/1995 | .......... B29C/45/14 |
| EP | 0665015 | 8/1995 | .......... A61K/31/57 |
| EP | 0668075 | 8/1995 | .......... A61K/31/00 |
| EP | 0670162 | 9/1995 | ........ A61K/31/445 |
| EP | 0673936 | 9/1995 | .......... C07D/401/06 |
| EP | 0674903 | 10/1995 | ........ A61K/31/445 |
| EP | 0675121 | 10/1995 | .......... C07D/333/56 |
| EP | 0684259 A1 | 11/1995 | ............ C07K/5/09 |
| EP | 0691130 | 1/1996 | .......... A61K/31/71 |
| EP | 0699673 | 3/1996 | .......... C07D/333/56 |
| FR | 2255063 | 7/1975 | .......... A61K/31/38 |
| GB | 1015787 | 1/1966 | |
| GB | 1587084 | 3/1981 | |
| GB | 1587084 | 5/1981 | ........ C07D/333/38 |
| GB | 2273873 | 6/1994 | .......... A61K/31/48 |
| IT | 1247527 | 4/1991 | |
| JP | 59-042375 | 3/1984 | ........ C07D/333/32 |
| JP | 6025288 | 2/1994 | |
| JP | 59042375 | 3/1994 | |
| JP | 09-255570 | 3/1996 | .......... A61K/31/35 |
| WO | 85/00107 | 1/1985 | .......... A61K/31/13 |
| WO | 88/10259 | 12/1988 | .......... C07D/313/00 |
| WO | 89/12068 | 12/1989 | ............ C07K/7/26 |
| WO | 90/01969 | 3/1990 | ........ A61M/29/00 |
| WO | 90/07328 | 7/1990 | ............ A61K/9/70 |
| WO | 90/11676 | 10/1990 | |
| WO | 90/12597 | 11/1990 | .......... A61K/47/48 |
| WO | 90/13293 | 11/1990 | .......... A61K/31/40 |
| WO | 91/08291 | 6/1991 | .......... C12N/15/16 |
| WO | 91/15219 | 10/1991 | .......... A61K/37/00 |
| WO | 91/15222 | 10/1991 | .......... A61K/37/02 |
| WO | 91/17731 | 11/1991 | ............ A61F/7/12 |
| WO | 92/00330 | 1/1992 | .......... C07K/15/28 |
| WO | 92/06068 | 4/1992 | ........ C07C/217/18 |
| WO | 92/08480 | 5/1992 | .......... A61K/37/36 |
| WO | 92/11872 | 7/1992 | .......... A16K/47/48 |
| WO | 92/11890 | 7/1992 | .......... A61K/25/00 |
| WO | 92/11895 | 7/1992 | .......... A61K/31/00 |
| WO | 92/13867 | 8/1992 | .......... C07H/15/12 |
| WO | 92/18546 | 10/1992 | .......... C08B/37/10 |
| WO | 92/19273 | 11/1992 | .......... A61K/49/02 |
| WO | 92/19612 | 11/1992 | .......... C07D/333/38 |
| WO | 92/21363 | 12/1992 | .......... A61K/37/02 |
| WO | 93/02065 | 2/1993 | ........ C07D/305/14 |
| WO | 93/04191 | 3/1993 | ............ C12Q/1/00 |
| WO | 93/07748 | 4/1993 | .......... A01N/43/16 |
| WO | 93/09228 | 5/1993 | .......... C12N/15/12 |
| WO | 93/09790 | 5/1993 | |
| WO | 93/09800 | 5/1993 | .......... A61K/37/02 |
| WO | 93/09802 | 5/1993 | .......... A61K/37/02 |
| WO | 93/10808 | 6/1993 | .......... A61K/37/02 |
| WO | 93/11120 | 6/1993 | ........ C07D/263/62 |
| WO | 93/11757 | 6/1993 | .......... A61K/31/135 |
| WO | 93/16724 | 9/1993 | .......... A61K/39/00 |
| WO | 93/17121 | 9/1993 | .......... C12P/17/02 |
| WO | 93/19746 | 10/1993 | .......... A61K/31/135 |
| WO | 93/19769 | 10/1993 | .......... A61K/37/02 |
| WO | 93/24476 | 12/1993 | ........ C07D/305/14 |
| WO | 94/03644 | 2/1994 | ............ C12Q/1/68 |
| WO | 94/04164 | 3/1994 | .......... A61K/31/795 |
| WO | 94/04178 | 3/1994 | .......... A61K/37/02 |
| WO | 94/07529 | 4/1994 | .......... A61K/39/00 |
| WO | 94/08604 | 4/1994 | .......... A61K/37/00 |
| WO | 94/08605 | 4/1994 | .......... A61K/37/00 |
| WO | 94/09764 | 5/1994 | .......... A61K/31/00 |
| WO | 94/09812 | 5/1994 | .......... A61K/37/36 |
| WO | 94/10187 | 5/1994 | .......... C07H/21/02 |
| WO | 94/15589 | 7/1994 | ............ A61K/9/50 |
| WO | 94/15590 | 7/1994 | ............ A61K/9/51 |
| WO | 94/15646 | 7/1994 | .......... A61K/48/00 |
| WO | 94/16706 | 8/1994 | .......... A61K/31/535 |
| WO | 94/17786 | 8/1994 | ............ A61K/9/16 |
| WO | 94/18345 | 8/1994 | ............ C12Q/1/68 |
| WO | 94/18954 | 9/1994 | .......... A61K/9/48 |
| WO | 94/18967 | 9/1994 | .......... A61K/31/415 |
| WO | 94/18968 | 9/1994 | .......... A61K/31/415 |
| WO | 94/19001 | 9/1994 | .......... A61K/37/02 |
| WO | 94/19003 | 9/1994 | .......... A61K/37/02 |
| WO | 94/20096 | 9/1994 | .......... A61K/31/40 |
| WO | 94/20097 | 9/1994 | .......... A61K/31/40 |
| WO | 94/20098 | 9/1994 | .......... A61K/31/40 |
| WO | 94/20099 | 9/1994 | .......... A61K/31/40 |
| WO | 94/20116 | 9/1994 | .......... A61K/31/735 |
| WO | 94/20117 | 9/1994 | .......... A61K/31/74 |
| WO | 94/20126 | 9/1994 | .......... A61K/37/02 |
| WO | 94/20127 | 9/1994 | .......... A61K/37/02 |
| WO | 94/21679 | 9/1994 | .......... C07K/13/00 |
| WO | 94/190001 | 9/1994 | .......... A61K/37/02 |
| WO | 94/23068 | 10/1994 | ............ C12Q/1/68 |
| WO | 94/23699 | 10/1994 | ............ A61K/9/14 |
| WO | 94/25020 | 11/1994 | .......... A61K/31/335 |
| WO | 94/25053 | 11/1994 | .......... A61K/37/02 |
| WO | 94/25588 | 11/1994 | .......... C12N/15/11 |
| WO | 94/26291 | 11/1994 | .......... A61K/37/02 |
| WO | 94/26303 | 11/1994 | .......... A61K/39/00 |

| | | | | |
|---|---|---|---|---|
| WO | 94/27612 | 12/1994 | | |
| WO | 94/28721 | 12/1994 | .......... | A01N/43/42 |
| WO | 95/03036 | 2/1995 | ............ | A61K/9/16 |
| WO | 95/03795 | 2/1995 | ......... | A61K/31/335 |
| WO | 95/04544 | 2/1995 | .......... | A61K/38/22 |
| WO | 95/05191 | 2/1995 | .......... | A61K/38/00 |
| WO | 95/10611 | 4/1995 | ........... | C12N/15/12 |
| WO | 95/17095 | 6/1995 | .......... | A01N/43/38 |
| WO | 95/19987 | 7/1995 | ........... | C07H/21/00 |
| WO | 95/20582 | 8/1995 | ......... | C07D/305/14 |
| WO | 94/26888 | 10/1995 | ........... | C12N/15/11 |
| WO | 95/30900 | 11/1995 | .......... | G01N/33/50 |
| WO | 95/33736 | 12/1995 | ......... | C07D/305/14 |
| WO | 96/01102 | 1/1996 | ............ | A61K/9/06 |
| WO | 96/07402 | 3/1996 | ......... | A61K/31/075 |
| WO | 96/15224 | 5/1996 | ............ | C12N/5/00 |
| WO | 96/20698 | 7/1996 | ............ | A61K/9/51 |
| WO | 96/21442 | 7/1996 | .......... | A61K/31/40 |
| WO | 96/21443 | 7/1996 | .......... | A61K/31/40 |
| WO | 96/24356 | 8/1996 | .......... | A61K/31/55 |
| WO | 96/25176 | 8/1996 | .......... | A61K/47/48 |
| WO | 96/36349 | 11/1996 | .......... | A61K/38/17 |
| WO | 96/40098 | 12/1996 | ......... | A61K/31/135 |
| WO | 97/10334 | 3/1997 | ........... | C12N/15/11 |
| WO | 97/15319 | 5/1997 | | |
| WO | 97/21455 | 6/1997 | ........ | A61M/005/00 |
| WO | 97/22697 | 6/1997 | | |
| WO | 97/33552 | 9/1997 | ......... | A61K/005/00 |
| WO | 97/45105 | 12/1997 | | |

OTHER PUBLICATIONS

Pinto, H.C., et al., "Tamoxifen–associated Steatohepatitis C Report of Three Cases", *Journal of Hepatology*, 23, 95–97, (1995).

Podzimek, et al., "O/W Microemulsions", *J. Dispersion Science and Technology*, I, 341–359, (1980).

Popma, J.J., et al., "Factors Influencing Restenosis after Coronary Angioplasty", *The American Journal of Medicine*, 88, 1–16N—1–24N, (Jan., 1990).

Post, M.J., et al., "Restenosis is Partly Due to Intimal Hyperplasia and Partly to Remodeling of the Injured Arterial Wall", *European Heart Journal*, Abstract No. P1164, p. 201, (1993).

Post, M.J., et al., "The Relative Importance of Arterial Remodeling Compared with Intimal Hyperplasia in Lumen Renarrowing After Balloon Angioplasty", *Circulation*, 89, 2816–2821, (Jun., 1994).

Post, M.J., et al., "Which Part of the Angiographic Diameter Reduction After Balloon Dilation is Due to Intimal Hyperplasia?", *JACC*, 21, Abstract No. 851–95, I–36A, (Feb., 1993).

Potter, et al., "A Mechanism Hypothesis for DNA Adduct Formation Following Hepatic Oxidative Metabolism.", *Carcinogensis*, 15, 439–442, (1994).

Pouton, C.W., "Self–Emulsifying Drug Delivery Systems: Assessment of the Efficiency of Emulsification", *International Journal of Pharmaceutics*, 27, 335–348, (1985).

Pupita, G., et al., "Myocardial Ischemia Caused by Distal Coronary–Artery Constriction in Stable Angina Pectoris", *The New England Journal of Medicine*, 323, 514–520, (1990).

Rainsford, K.D., et al., "Concerning the Merits of Copper Aspirin as a Potential Anti–Inflammatory Drug", *J. Pharm. Pharmac.*, 28, 83–86, (1976).

Rainsford, K.D., et al., "Gastric Mucus Effusion Elicited by Oral Copper Compounds: Potential Anti–Ulcer Activity", *Experientia*, 32, 1172–1173, (1976).

Raisz, L.G., "Estrogen and Bone: New Pieces to the Puzzle", *Nature Medicine*, 2, 1077–1078, (1996).

Raloff, "Tamoxifen Puts Cancer of Starvation Diet", *Science News*, 146, 292, (Nov. 5, 1994).

Rauterberg, J., et al., "Collagens in Atherosclerotic Vessel Wall Lesions", *Current Topics in Pathology*, 87, 163–192, (1993).

Ray, P., et al., "Repression of interleukin–6 gene expression by 17beta–estradiol: Inhibition of the DNA–binding activity of the transcription factors NF–IL6 and NF–6B by the estrogen receptor", *FEBS Letters*, 409, 79–85, (1997).

Razavi, M., "Unusual Forms of Coronary Artery Disease", *Cleveland Clinic Consultations*, 7, 25–46, (1975).

Recchia, F., et al., "Interferon–beta, Retinoids, and Tamoxifen in the Treatment of Metastatic Breast Cancer: A Phase II Study", *Journal of Interferon and Cytokine Research*, 15, 605–610, (1995).

Reckless, J., et al., "Tamoxifen Decreases Cholesterol Sevenfold and Abolishes Lipid Lesion–Development in Apolipoprotein E Knockout Mice", *Circulation*, 95, 1542–1548, (1997).

Reid, V.C., et al., "Fragmentation of DNA in P388D, Macrophages Exposed to Oxided Low–Density Lipoprotein", *FEBS Letters*, 332, 218–220, (1993).

Reilly, C.F., "Rat Vascular Smooth Muscle Cells Immortalized with SV40 Large T Antigen Possess Defined Smooth Muscle Cell Characteristics Including Growth Inhibition by Heparin", *Journal of Cellular Physiology*, 142, 342–351, (1990).

Reiner, Z., et al., "Antiestogen Tamoxifen Reduces Lipoprotein(a)", Abstracts, The Second International Conference on Lipoprotein (a), New Orleans, LA, 124, (Nov. 12–14, 1992).

Reis, G.J., et al., "Randomized Trial of Fish Oil for Prevention of Restenosis After Coronary Angioplasty", *The Lancet*, 177–181, (1989).

Ribeiro, G., et al., "Adjuvant Tamoxifen for Male Breast Cancer (MBC)", *Br. J. Cancer*, 65, 252–254, (1992).

Rieckmann, P., et al., "Tumor Necrosis Factor–a Messenger RNA Expression in Patients with Relapsing–Remitting Multiple Sclerosis is Associated with Disease Activity", *Ann. Neurol*, 37, 82–88, (1996).

Riessen, et al., "Regional Difference in the Distribution of the Proteglycans Biglycan and Decorin in the Extracellular Matrix of Atheroslcerotic and Restenotic Human Coronary Arteries", *Amer. J. Path*, 144, 962–974, (May 1994).

Riessen, R., et al., "Prospects for Site–Specific Delivery of Pharmacologic and Molecular Therapies", *Journal of the American College of Cardiology*, 23, 1234–1244. (Apr., 1994).

Ross, R., "The Pathogenesis of Atherosclerosis: A Perspective for the 1990s", *Nature*, 362, 801–809, (Apr. 29, 1993).

Ross, R., et al., "Chronic Inflammation , PGF, TGFbeta, and Smooth Muscle Proliferation", *J. Cell. Biochem.*, S15C, Abstract No. H006, 142, (1991).

Ross, R., et al., "Chronic Inflammation, PDGF, TFTB, and Smooth Muscle Proliferation", *Molecular Mechanism of Vascular Diseases*, Abstract No. G006, 96, (1991).

Rutqvist, L.E., et al., "Cardiac and Thromboembolic Morbidity Among Postmenopausal Woment with Early–Stage Breast Cancer in a Randomized Trial of Adjuvant Tamoxifen", *Journal of the National Cancer Institute*, 85, 1398–1406, (1993).

Rutsch, W., et al., "Benestent–II Pilot Study: 6 Months Follow Up of Phase 1", *Abstract, Society of Cardiology*, (1995).

Saarto, T., et al., "Antiatherogenic Effects of Adjuvant Antiestrogens: A Randomized Trial Comparing the Effects of Tamoxifen and Toremifene on Plasma Lipid Levels in Postmenopausal Women with Node–Positive Breast Cancer", *Journal of Clinical Oncology*, 14, 429–433, (Feb., 1996).

Sagitani, et al., "Microemulsions Systems with a Nonionic Cosurfant", *J. Dispersion Science and Technology*, 1 (2), 151–164, (1980).

Saito, H., et al., "Influence of Maternal Drug Metabolism on the Fetal Toxicity Induced by Acetylsalicylic Acid", *The Journal of Toxicological Sciences*, 7, 177–184, (1982).

Sanders, et al., "Controlled Release of a Lutenizing Hormone–Releasing Hormone Analogue from Poly(d,l–lactide–co–glycolide) Microspheres.", *J. Pharmaceutical Science*, 73, 1294–1297, (1984).

Sanderson, J.A., et al., "Antibody–Coated Microspheres for Drug Delivery to Prevent Restenosis", *Circulation*, 90, Abstract No. 2734, p. I-508, (Oct., 1994).

Sargent, L.M., et al., "Induction of Hepatic Aneuploidy in Vivo by Tamoxifen, Toremifene and Idoxifene in Female Sprague–Dawley Rats", *Carcinogenesis*, 17, 1051–1056, (1996).

Schatz, R.A., et al., "A View of Vascular Stents", *Circulation*, 79, 445–457, (1989).

Schlaak, J.F., et al., "Different Cytokine Profiles in the Synovial Fluid of Patients with Osteoarthritis, Rheumatoid Arthritis and Seronegative Spondylarthropathies", *Clinical and Experimental Rheumatology*, 14, 155–162, (1996).

Schlingemann, et al., "Expression of the High Molecular Weight Molenoma–Associated Antigen by Pericytes During Angiogensis in Tumors and in Healing Wounds.", *Amer. J. Pathology*, 136, 1393–1405, (1990).

Schmidt, E.B., et al., "Long–Term Supplementation with n–3 Fatty Acids, II: Effect on Neutrophil and Monocyte Chemotaxis", *Scand. J. Clin. Lab. Invest.*, 52, 229–236, (1992).

Schneiderman, et al., "Increased Type 1 Plasminogen Activator Inhibitor Gene Expression in Atherosclerotic Human Arteries.", *PNAS (USA)*, 89, 6998–7002, (1992).

Schoenemanne, et al., "The Differential Diagnoses of Spontaneous Pneumothorax and Pulmonary Lymphangioleimyomatosis Clinical Picture Diagnoses and Theory.", *Chirag*, 61, 301–303, (1990); reported in Biosis, 90, 432367 (1990)., English abstract only.

Schulze, et al., "English language translation of WO 85/00107".

Schwartz, C.J., et al., "The Pathogenesis of Atherosclerosis: An Overview", *Clin. Cardiol.*, 14, I–1—I–16, (1991).

Schwartz, G.G., et al., "Pathophysiology of Chronic Stable Angina", *In: Atherosclerosis and Coronary Artery Disease*, V. Fuster, et al., (eds.), Lippencott–Raven Publishers, Philadelphia, pp. 1389–1400, (1996).

Schwartz, R.S., et al., "Restenosis After Balloon Angioplasty—A Practical Proliferative Model in Porcine Coronary Arteries", *Circulation*, 82, 2190–2200, (1990).

Schwartz, R.S., et al., "The Restenosis Paradigm Revisited: An Alternative Proposal for Cellular Mechanisms", *JACC*, 20, 1284–1293, (Nov. 1, 1992).

Schwartz, S.M., et al., "Maintenance of Integrity in Aortic Endothelium", *Federation Proceedings*, 29, 2618–2625, (Jul., 1980).

Sedlacek, S., "Estrogenic Properties of Tamoxifen on Serum Lipids in Postmenopausal Women with Breast Cancer (BCA)", *Breast Cancer Research and Treatment*, 14, Abstract No. 82, 153, (1989).

Serruys, P.W., et al., "A Comparison of Balloon–Expandable–Stent Implantation with Balloon Angioplasty in Patients with Coronary Artery Disease", *The New England Journal of Medicine*, 333, 489–495, (Aug., 1994).

Serruys, P.W., et al., "Heparin–Coated Palmaz–Schatz Stents in Human Coronary Arteries—Early Outcome of the Benestent–II Pilot Study", *Circulation*, 93, 412–422, (Feb. 1996).

Shanahan, C.M., et al., "High Expression of Genes for Calcification–regulating Proteins in Human Atherosclerotic Plaques", *Journal of Clinical Investigation*, 93, 2393–2402, (Jun., 1994).

Shanahan, C.M., et al., "Isolation of Gene Markers of Differentiated and Proliferating Vascular Smooth Muscle Cells", *Circulation Research*, 73, 193–204, (1993).

Shapiro, L.M., "Echocardiographic Features of Impaired Ventricular Function in Diabetes Mellitus", *British Heart Journal*, 47, 439–444, (1982).

Shewmon, et al., "Tamoxifen and Estrogen Lower Circulating Lipoprotein(a) Concentrations in Healthy Postmenopausal Women", *Arteriosclerosis and Thrombosis*, 14, 1589–1593, (1994).

Shewmon, et al., "Tamoxifen Decreases Lipoprotein (a) in Patients with Breast Cancer.", *Metabolism*, 43, 531–532, (May 1994).

Shewmon, et al., "Tamoxifen Lowers Lp(a) in Males with Heart Disease", *Supplement I Circulation*, 86, 1345, (1992).

Shimaoka, I., et al., "Purification of a Copper Binding Peptide from the Mushroom Grifola frondosa and Its Effects on Copper Absorption", *J. Nutr. Biochem.*, 4, 33–38, (1993).

Shoji, et al., "Enhancement of Anti–Inflammatory Effects of Biphenylylactic Acid by its Incorporation into Lipid Microspheres.", *J. Pharm. Pharmacol*, 38, 118–121, (1986).

Siebenlist, U., et al., "Structure, Regulation and Function of NF–kB", *Annu. Rev. Cell. Biol.*, 10, 405–455, (1994).

Simpson, J.B., et al., "Precutaneous Coronary Atherectomy", *Circulation*, 78, 61st Scientific Session, Abstract No. 0326, p. II–82, (Oct., 1988).

Singh, et al., "Phylogenetic Analysis of Platelet–derived Growth Factor by Radio–Receptor Assay.", *J. Cell Biol.*, 95, 667–671, (1982).

Sismondi, et al., "Metabolic Effects of Tamoxifen in Postmenopause.", *Anticancer Res.*, 14, 2237–2244, (1994).

Snow, A.D., et al., "Heparin Modulates the Composition of the Extracellular Matrix Domain Surrounding Arterial Smooth Muscle Cells", *American Journal of Pathology*, 137, 313–330, (Aug., 1990).

Soderberg, L.S., et al., "Copper(II) (3,5–Diisopropylsalicylate)sub2 Accelerates Recovery of B and T Cell Reactivity Following Irradiation", *Scand. J. Immunol.*, 26, 495–502, (1987).

Soderberg, L.S., et al., "Copper(II)sub2(3,5–diisopropylsalicylate)sub4 Stimulates Hemopoiesis in Normal and Irradiated Mice", *Exp. Hematol.*, 16, 577–580, (1988).

Soderberg, L.S., et al., "Postirradiation Treatment with Copper(II)sub2(3,5–diisopropysalicylate)sub4 Enhances Radiation Recovery and Hemopoietic Regeneration", *Exp. Hematol.*, 18, 801–805, (1990).

Soderberg, L.S., et al., "Radiation Recovery Agents", *DN & P*, 3, 600–605, (1990).

Sollott, S.J., et al., "Taxol Inhibits Neointimal Smooth Muscle Cell Accumulation after Angioplasty in the Rat", *The Journal of Clinical Investigation*, 95, 1869–1876, (Apr., 1995).

Song, C., "Dexamethasine–nanoparticles for intra–arterial localization in restenosis in rats", *Proceec. Intern. Symp. Control. Rel. Mater*, 22, 444–445, (1995).

Song, J., et al., "Tamoxifen (Estrogen Antagonist) Inhibits Voltage–Gated Calcium Current an Contractility in Vascular Smooth Muscle from Rats", *The Journal of pharmacology and Experimental Therapeutics*, 227, 1444–1453, (1996).

Sorenson, J.R., "Copper Complexes Offer a Physiological Approach to Treatment of Chronic Disease", *Progress in Medicinal Chemistry*, 26, 437–568, (1989).

Sorenson, J.R., "Essential Metalloelement Metabolism and Radiation Protection and Recovery", *Radiation Research*, 132, 19–29, (1992).

Sorenson, J.R., "Pharmacological Activities of Copper Compounds", *In: Handbook of Metal–Ligand Interactions in Biological Fluids—Bioinorganic Medicine*, vol. 2, Berton, G., (ed.), Marcel Dekker, Inc., New York, 1128–1139, (1995).

Sorenson, J.R., "The Ulcerogenic Potential of Copper Aspirinate Seems to be More Imaginary than Real", *Journal of Pharmaceutical Sciences*, 73, Open Forum, 1875–1878, (1984).

Sorenson, J.R., et al., "Antieoplastic Activities of Some Copper Salicylates", *In: Trace Substances in Environmental Health*, vol. XVI, Hemphill, D.D., (ed.), University of Missouri, Columbia, 362–369, (1982).

Sorenson, J.R., et al., "Bis(3,5–diisopropylsalicylato)copper(II), a Potent Radioprotectant with Superoxide Dismutase Mimetic Activity", *J. Med. Chem.*, 27, 1747–1749, (1984).

Sorenson, J.R., et al., "Copper Complexes as 'Radiation Recovery' Agents", *Chemistry in Britain*, 25, 169–171, (1989).

Sorenson, J.R., et al., "Copper–, Iron–, Manganese–and Zinc–3,5–diisopropylsalicylate Complexes Increase Survival of Gamma–Irradiated Mice", *Eur. J. Med. Chem.*, 28, 221–229, (1993).

Sorenson, J.R., et al., "Radiation Protection and Radiation Recovery with Essential Metalloelement Chelates", *P.S.E.B.M.*, 210, 191–204, (1995).

Speir, et al., "Potential Role of Human Cytomegalovirus and p53 Interaction in Coronary Restenosis", *Science*, 265, 391–394, (Jul., 1994).

Srivastava, K.C., "Effects of Dietary Fatty Acids, Prostaglandins and Related Compounds on the Role of Platelets in Thrombosis", *Biochem. Exp. Biol.*, 16, 317–338, (1980).

Standley, P.R., et al., "Tamoxifen (an Antiestrogen) Reduces K Positive–and Agonist–Induced Vascular Contractility in Rat Resistance Vessels", Abstract No. 159 (Source and Date Unavailable).

Steele, P.M., et al., "Balloon Angioplasty—Nature History of the Pathophysiological Response to Injury in a Pig Model", *Circulation Research*, 57, 105–112, (1985).

Sterpetti, A.V., et al., "Formation of Myointimal Hyperplasia and Cytokine Production in Experimental Vein Grafts", *Surgery*, 123(4), 461–469, (1998).

Stevenson, F., et al., "Idiotypic DNA Vaccines agains B–cell Lymphoma", *Immunological Reviews*, 145, 211–228, (1995).

Stork, G., et al., "Total Synthesis of Cytochalasin B", *Journal of the American Chemical Society*, 100, 7775–7777, (1978).

Stouffer, et al., "TGF beta Has a Biphasic, Concentration Dependent Effect on EFG and PDGR–BB Induced Smooth Muscle Cell Proliferation, Inflammation, Growth Regulatory Molecules and Atherosclerosis.", *J. Cellular Biochem*, Supplement 18A, Abstract No. A321, 288, (1994).

Streuli, C.H., et al., "Extracellular Matrix Regulates Expression of the TGF–Beta 1 Gene", *J. Cell Biol.*, 120, 253–260, (1993).

Suckling, K.E., "Atherosclerosis Patents: Clues to the Next Drug Generation", *Bio/Technology*, 12, 1379–1380, (Dec., 1994).

Suckling, K.E., "Emerging Strategies for the Treatment of Atherosclerosis as Seen from the Patent Literature", *Biochemical Society Transactions*, 21, 660–662, (Mar. 30, 1993).

Sudo, K., et al., "Antiestrogen–Binding Sites Distinct from the Estrogen Receptor: Subcellular Localization, Ligand Specificity, and Distribution in Tissues of the Rat", *Endocrinology*, 112, 425–434, (1983).

Szekanecz, Z., et al., "Increased Synovial Expression of Transforming Growth Factor (TGF)–B Receptor Endoglin and TGF–B1 in Rheumatoid Arthritis: Possible Interactions in the Pathogenesis of the Disease", *Clinical Immunology and Immunopathology*, 76, 187–194, (Aug. 1995).

Tabas, I., et al., "The Actin Cytoskeleton is Important for the Stimulation of Cholesterol Esterification by Atherogenic Lipoprotein in Machrophages", *The Journal of Biological Chemistry*, 269, 22547–22556, (Sep. 9, 1994).

Takashima, K., et al., "The Hypocholesterolemic Action of TA–7552 and its Effects on Cholesterol Metabolism in the Rat", *Atherosclerosis*, 107, 247–257, (1994).

Tamm, C., "The Antibiotic Complex of the Verrucarins and Boridins", *Fortschr. Chem. Org. Naturst.*, 31, 61–117, (1973).

Tanaka, et al., "Prominent Inhibitory Effects pf Tranilast on Migration and Proliferation of and Collagen Synthesis by Vascular Smooth Muscle Cells.", *Atherosclerosis*, 107, 179–185, (1994).

Tanenbaum, S.W., "Microbiological, Preparative and Analytical Aspects of Cytochalasin Production", *In: Cytochalasins—Biochemical and Cell Biological Aspects*, Tanenbaum, S.W., (ed.), Elsevier/North–Holland Biomedical Press, 2–14, (1978).

Testart, J., et al., "The Action of Anti–Inflammatory Drugs to the Fertility of Female Rats with Intrauterine Contraceptive Devices", *J. Reprod. Fert.*, 63, 257–261, (1981).

Thompson, J.T., et al., "Comparison of Recombinant Transforming Growth Factor–beta −2 and Placebo as an Adjunctive Agent for Macular Hole Surgery", *Ophthalmology*, 15(4), 700–706, (1998).

Thompson, N.L., et al., "Expression of Transforming Growth Factor–B1 in Specific Cells and Tissues of Adult and Neonatal Mice", *Journal of Cell Biology*, 108, 661–669, (1989).

Tice, et al., "Biodegradable controlled–release parental systems", *Pharmaceutical Technology*, 26–35, (1984).

Topol, E.J., et al., "The Restenosis "Antitheory"", *Mayo Clin. Proc.*, 68, 88–90, (1993).

Treasure, C.B., et al., "Hypertension and Left Ventricular Hypertrophy Are Associated With Impaired Endothelium-Mediated Relaxation in Human Coronary Resistance Vessels", *Circulation*, 87, 86–93, (1993).

Treiber, A., et al., "Chemical and Biological Oxidation of Thiohene: Preparation and Complete Characterization of Thiophene S–Oxide Dimers and Evidence for Thiophene S–Oxide as an Intermediate in Thiophene Metabolism in Vivo and in Vitro", *J. Am. Chem. Soc.*, 119, 1565–1571, (1997).

Van Sickle, W.A., et al., "An Alternative Mechanism for the Inhibition of Cholesterol Biosynthesis in HepG2 Cells by N–[(1,5,9)–Trimethyldecyl]–4alpha, 10–dimethyl–8–aza–trans–decal–3beta–ol (MDL 28, 815)", *The Journal of Pharmacology and Experimental Therapeutics*, 267, 1243–1249, (1993).

Vanhoutte, "Hypercholesteolaemia, Atherosclerosis and Release of Endothelium–Derived Relaxing Factor by Aggregating Platelets", *Eur. Heart J.*, 12, Suppl. E, 25–32, (1991).

Vargas, et al., "Oestradiol Inhibits Smooth Muscle Cell Proliferation of Pig Coronary Artery.", *Br. J. Pharmacol.*, 109, 612–617, (1993).

Vawter, M.P., et al., "TGF B1 and TGF B2 Concentrations are Elevated in Parkinson's Disease in Ventricular Cerebrospinal Fluid", *Experimental Neurology*, 142, 313–322, (1996).

Vidensek, N., et al., "Taxol Content in Bark, Wood, Root, Leaf, Twig, and Seedling from Several Taxus Species", *Journal of Natural Products*, 53, 1609–1610, (Nov./Dec., 1990).

Vijayagopal, P., et al., "Human Monocyte–Derived Machrophages Bind Low–Density–Lipoprotein–Proteoglycan Complexes by a Receptor Different from the Low–Density–Lipoprotein Receptor", *Biochemical Journal*, 289, 837–844, (1993).

Vijayagopal, P., et al., "Lipoprotein–Proteoglycan Complexes Induce Continued Cholesteryl Ester Accumulation in Foam Cells from Rabbit Atherosclerotic Lesions", *J. Clin. Invest.*, 91, 1011–1018, (1993).

Voisard, R., et al., "The in–vitro Effect of Antineoplastic Agents on Proliferative Activity and Cytoskeletal Components of Plaque–derived Smooth–muscle Cells from Human Coronary Arteries", *Coronary Artery Disease*, 4, 935–942, (1993).

von Schacky, C., et al., "Long–Term Effects of Dietary Marine omega–3 Fatty Acids upon Plasma and Cellular Lipids, Platelet Function, and Eicosanoid Formation in Humans", *J. Clin. Invest.*, 76, 1626–1631, (1985).

Vrudhula, V.M., et al., "Selective Synthetic Transformations with Roridin A", *Abstracts, 199th American Chemical Society National Meeting*, Abstract No. 50, Boston, MA, (Apr. 22–27, 1990).

Wakefield, et al., "Latent Transforming Growth Factor–B from Human Platelets: A High Molecular Weight Complex Containing Precursor Sequences.", *J. Biol. Chem.*, 263, 7646–7654, (1988).

Wakefield, et al., "Recombinant Latent Transforming Growth Factor–B, has a Longer Plasma Half–Line in Rats thatn Active Transforming Growth Factor–B, and a Different Tissue Distribution.", *J. Clin. Invest.*, 86, 1976–1984, (1990).

Waksman, R., et al., "Intracoronary Radiation Before Stent Implantation Inhibits Neointima Formation in Stented Porcine Coronary Arteries", *Circulation*, 92, 1383–1386, (1995).

Wallace, J.M., et al., "Dietary Fish Oil Supplementation Alter Leukocyte Function and Cytokine Production in Healthy Women", *Arteriosclerosis, Thrombosis and Vascular Biology*, 15, 185–189, (1995).

Waller, B.F., "Atherosclerotic and Nonatherosclerotic Coronary Artery Factors in Acute Myocardial Infarction", *In: Acute Myocardial Infarction*, Pepine, C.J., (ed.), F.A. Davis Company, Philadelphia, 29–104, (1989).

Wang, X.L., et al., "Circulating Transforming Growth Factor Beta1 and Coronary Artery Disease", *Cardiovascular Research*, 34, 404–410, (1997).

Watson, et al., "TGF–B1 and 25–Hydroxcholesterol Stimulate Osteoblast–Like Vascular Cells to Calcify", *J. Clin. Invest.*, 93, 2106–2113, (May 1994).

Wei, C.M., et al., "Binding of Trichodermin to Mammalian Ribosomes and Its Inhibition by Other 12,13–Epoxytrichotheces", *Molecular & Cellular Biochemistry*, 3, 215–219, (May 30, 1974).

Weissberg, P.L., et al., "Approaches to the Development of Selective Inhibitors of Vascular Smooth Muscle Cell Proliferation", *Cardiovascular Research*, 27, 1191–1198, (1993).

Weissberg, P.L., et al., "Effects of TGF–Beta on Vascular Smooth Muscle Cell Growth", *In: Growth Factors and the Cardiovascular System*, Cummins, P., (ed.), Kluwer Academic Publishers, 189–205, (1993).

Weissberg, P.L., et al., "Is Vascular Smooth Muscle Cell Proliferation Beneficial?", *Lancet*, 347, 305–307, (Feb. 3, 1996).

Weissberg, P.L., et al., "The Endothelin Peptides ET–1, ET–2, ET–3 and Sarafotoxin S6b are Co–mitogenic with Platelet–Derived Growth Factor for Vascular Smooth Muscle Cells", *Atherosclerosis*, 85, 257–262, (1990).

West, G.B., "Comments on 'The Ulcerogenic Potential of Copper Aspirinate Seems to be More Imaginary than Real'", *Journal of Pharmaceutical Sciences*, 74, Open Forum, 700, (1985).

West, G.B., "Testing for Drugs Inhibiting the Formation of Gastric Ulcers", *Journal of Pharmacological Methods*, 8, 33–37, (1982).

Wickremesinhe, E.R., et al., "Taxus Callus Cultures: Initiation, Growth, Optimization, Characterization and Taxol Production", *Plant Cell, Tissue and Organ Culture*, 35, 181–193, (1993).

Wickremesinhe, E.R., et al., "Taxus Cell Suspension Cultures: Optimizing Growth and Production of Taxol", *J. Plant Physiol.*, 144, 183–188, (1994).

Wight, "Proteoglycans Structure and Function", *Cell Biol. of Extracellular Matrix, Second Editition*, E.D. Hay, Ed., Plenum Press, New York, 45–78, (1991).

Wight, et al., "Cell Biology of Arterial Proteoglycans.", *Arteriosclerosis*, 9, 1–20, (1989).

Wight, et al., "The Role of Proteoglycans in Cell Adhesion, Migration and Proliferation.", *Current Opinion in Cell Biol.*, 4, 793–801, (1992).

Wight, T.N., "The Extracellular Matrix and Atherosclerosis", *Current Opinion in Lipidology*, 6, 326–334, (1995).

Wilensky, R.L., et al., "A Prospective, Randomized, Double-Blind, Dose–Escalation Study Evaluating the Safety and Tolerability of Cytochalasin B to Reduce Vascular Remodeling Following Percutaneous Transluminal Coronary Angioplasty", Abstract, 46th Annual Scientific Session of the American College of Cardiology, 1 p., (1997).

Wilensky, R.L., et al., "Direct Intraarterial Wall Injection of Microparticles via a Catheter: A Potential Drug Delivery Strategy Following Angioplasty", *American Heart Journal*, 122, 1136–1140, (1991).

Wilensky, R.L., et al., "Regional and Arterial Localization of Radioactive Microparticles after Local Delivery by Unsupported or Supported Porous Balloon Catheters", *American Heart Journal*, 129, 852–859, (1995).

Williams, J.K., et al., "The Estrogen Receptor Agonist/Antagonist Taxomifen Inhibits Progression of Coronary Artery Atherosclerosis in Monkeys", *Circulation*, 92, Nov. 1995 AHA Meeting, (Oct. 15, 1995).

Willson, T.M., et al., "Dissection of the Molecular Mechanism of Action of GW5638, a Novel Estrogen Receptor Ligand, Provides Insights into the Role of Estrogen Receptor in Bone", *Endocrinology*, 138(9), (Sep. 1997).

Winslow, R., "Going for the Flow", *The Wall Street Journal*, (Oct. 23, 1995).

Winternitz, C.I., et al., "Development of a Polymeric Surgical Paste Formulation for Taxol", *Pharmaceutical Research*, 13, 368–375, (1996).

Wiseman, H., "Tamoxifen as an Antioxidant and Cardioprotectant", *Biochem–Soc. Symp.*, 61, 209–219, (1995).

Wiseman, L.R., et al., "Toremifene—A Review of its Pharmacological Properties and Clinical Efficacy in the Management of Advanced Breast Cancer", *Drugs*, 54, 141–160, (Jul., 1997).

Witherup, K.M., et al., "Taxus Spp. Needles Contain Amounts of Taxol Comparable to the Bark of *Taxus brevifolia*: Analysis and Isolation", *Journal of Natural Products*, 53, 1249–1255, (Sep./Oct., 1990).

Wolf, Y.G., et al., "Antibodies Against Transforming Growth Factor Betal Suppress Intimal Hyperplasia in a Rat Model", *J. Clin. Invest.*, 93, 1172–1178, (Mar. 1994).

Wolinsky, H., et al., "Use of a Perforated Balloon Catheter to Deliver Concentrated Heparin Into the Wall of the Normal Canine Artery.", *JACC*, 15, 475–481, (1990).

Wrana, et al., "Mechanism of Activation of the TGF–B Receptor", *Nature*, 370, 341–347, (Aug. 4, 1994).

Wright, G., et al., "Cytoclasin Inhibition of Slow Tension Increase in Rat Aortic Rings", *Am. J. Physiol.*, 267, H1437–H1446, (1994).

Yang, N., et al., "Developing Particle–mediated Gene–transfer Technology for Research Into Gene Therapy of Cancer", *Molecular Medicine Today*, 476–481, (1996).

Yang, N.H., et al., "Estrogen Receptor: One Transcription Factor, Two Genomic Pathways", *Calcified Tissue Intl.*, 54, 342, (1994).

Yang, N.N., et al., "Identification of an Estrogen Response Element Activated by Metabolites of 17Beta–Estradiol and Raloxifene", *Science*, 273, 1222–1225, (Oct. 30, 1996).

Young, H., et al., "Pharmacokinetics and Biodistribution of Radiolabelled Idoxifene: Prospects for the Use of PET in the Evaluation of a Novel Antioestrogen for Cancer Therapy", *Nucl. Med. Biol.*, 22, 405–411, (May 1995).

Zhang, L., et al., "MCF–7 breast carcinoma cells overexpressing FGF–1 form vascularized, metastatic tumors in ovariectomized and tamoxifen–treated nude mice", *Oncogen*, 15, 2093–2108, (1997).

Ziegler, J., "Raloxifene, Retinoids, and Lavender: A Me Too@ Tamoxifen Alternatives Under Study", *Journal of the National Cancer Institute*, 88, 1100–1102, (1996).

Zuckerman, et al., "Cytokine Regulation of Macrophage apo E. Secretion: Opposing Effects of GM–CSF and TGF–B.", *Atherosclerosis*, 96, 203–214, (1992).

Zuckerman, et al., "Exogenous Glucocorticoids Increase Macrophage Section of apo E by Cholesterol Independent Pathways.", *Atherosclerosis*, 103, 43–54, (1993).

Johnson, et al., "Coronary Atherectomy: Light Microscopic and Immunochemical Study of Excised Tissues", *Supp. II Circulation*, 78, Abstract No. 0327, p. 11–82, (1988).

Johnston, S.R., et al., "Changes in Estrogen Receptor, Progesterone Receptor, and pS2 Expression in Tamoxifen-resistant Human Breast Cancer", *Cancer Research*, 55, 3331–3338, (Aug. 1995).

Jones, R.H., et al., "Increased Susceptibility to Metal Catalysed Oxidation of Diabetic Lens beta subL Crystallin: Possible Protection by Dietary Supplementation with Acetylsalicyclic Acid", *Exp. Eye Res.*, 57, 783–790, (1993).

Jordan, A., et al., "Tubulin as a Target for Anticancer Drugs: Agents which Interact with the Mitotic Spindle", *Medicinal Research Reviews*, 18, 259–296, (1998).

Jordan, V.C., et al., "A Mutant Receptor as a Mechanism of Drug Resistance to Tamoxifen Treatment", *Annals New York Academy of Sciences*, 761, 138–147, (1995).

Jordan, V.C., et al., "Long–Term Tamoxifen Therapy to Control or to Prevent Breast Cancer: Laboratory Concept to Clinical Trials", *Hormones, Cell Biology, and Cancer: Perspectives and Potentials*, Alan R. Liss, Inc., 105–123, (1988).

Jordan, V.C., et al., "Structural Requirements for the Pharmacological Activity of Nonsteroidal Antiestrogens in Vitro", *Molecular Pharmacology*, 26, 272–278, (1984).

Jordan, V.C., et al., "Tamoxifen: Toxicities and Drug Resistance During the Treatment and Prevention of Breast Cancer", *Annu. Rev. Pharmacol. Toxicol.*, 35, 195–211, (1995).

Joswig, B.C., et al., "Transmural Myocardial Infarction in the Absence of Coronary Arterial Luminal Narrowing in a Young Man with Single Coronary Arterial Anomaly", *Catheterization and Cardiovascular Diagnosis*, 4, 297–304, (1978).

Jung, S.M., et al., "Platelet Cytoskeletal Protein Distributions in Two Triton–Insoluble Fractions and How They are Affected by Stimulants and Reagents that Modify Cytoskeletal Protein Interactions", *Thrombosis Research*, 50, 775–787, (1988).

Kakuta, T., et al., "Differences in Compensatory Vessel Enlargement, Not Intimal Formation, Account for Restenosis After Angioplasty in the Hypercholesterolemic Rabbit Model", *Circulation*, 89, 2809–2815, (1994).

Kakuta, T., et al., "The Impact of Arterial Remodeling on the Chronic Lumen Size After Angioplasty in the Atherosclerotic Rabbit", *JACC*, Abstract No. 875–95, p. 138A, (Feb., 1994).

Kambic, H., et al., "Biomaterials in Artificial Organs", *Chemical & Engineering News*, 30, 31–48, (Apr. 14, 1986).

Kaski, J.C., et al., "Local Coronary Supersensitivity to Diverse Vasoconstrictive Stimuli in Patients with Variant Angina", *Circulation*, 74, 1255–1265, (1986).

Ke, H.Z., et al., "Comparative Effects of Droloxifene, Tamoxifen, and Estrogen on Bone, Serum Cholesterol, and Uterine Histology in the Ovariectomized Rat Model", *Bone*, 20, 31–39, (1997).

Keen, C.L., et al., "Hypertension Induced Alterations in Copper and Zinc Metabolism: A Link to Vascular Disease?", *In: Biology of Copper and Complexes*, Sorenson, J.R.J., (ed.), Humana Press, Clifton, New Jersey, 141–153, (1987).

Kellen, J.A., "Tamoxifen Beyond the Antiestrogen", *BirkhΣuser*, 392 pages, (1996).

Kellen, J.A., et al., "The Effect of Toremifene on the Expression of Genes in a Rat Mammary Adenocarcinoma", *In Vivo*, 10, 511–514, (1996).

Kemp, P.R., et al., "Cloning and Analysis of the Promoter Region of the Rat SM22–Alpha Gene", *Biochem. J.*, 310, 1037–1043, (1995).

Kemp, P.R., et al., "ID—A Dominant Negative Regulator of Skeletal Muscle Differentiation—is Not Involved in Maturation or Differentiation of Vascular Smooth Muscle Cells", *FEBS Letters*, 368, 81–86, (1995).

Kemp, P.R., et al., "Inhibition of PDGF BB Stimulated DNA Synthesis in Rat Aortic Vascular Smooth Muscle Cells by the Expression of a Truncated PDGF Receptor", *FEBS Letters*, 336, 119–123, (Dec., 1993).

Kemp, P.R., et al., "The Id Gene is Activated by Serum but is Not Required for De–differentiation in Rat Vascular Smooth Muscle Cells", *Biochemical Journal*, 277, 285–288, (1991).

Kim, et al., "Suppression of Vascular Transforming Growth Factor–B1 and Extracellular Matrix Gene Expressions by Cilazapril and Nifedipine in Hypertensive Rats", *Clin. Exp. Pharmacol. Physiol. Suppl.*, 1, S355, (1995).

Kim, J., et al., "Production of Taxol and Related Taxanes in *Taxus brevifolia* Cell Cultures: Effect of Sugar", *Biotechnology Letters*, 17, 101–106, (Jan., 1995).

Kingston, D.G., et al., "Synthesis and Structure–Activity Relationships of Taxol Derivatives As Anticancer Agents", *In: New Trends in Natural Products Chemistry*, Atta–urRahman, et al., (eds.), Studies in Organic Chemistry, vol. 26, Elsevier Science Publishers B.V., Amsterdam, 219–235, (1986).

Kirschenlohr, H.L., et al., "Adult Human Aortic Smooth Muscle Cells in Culture Produce Active TGF–Beta", *Amer. J. Physiol*, 265, C571–C576, (1993).

Kirschenlohr, H.L., et al., "Cultures of Proliferating Vascular Smooth Muscle Cells from Adult Human Aorta", *In: Human Cell Culture*, Jones, G.E., (ed.), Humana Press, Inc., 24 p., (1996).

Kirschenlohr, H.L., et al., "Proliferation of Human Aortic Vascular Smooth Muscle Cells in Culture is Modulated by Active TGF–Beta", *Cardiovascular Research*, 29, 848–855, (1995).

Kleiman, N.S., et al., "Prinzmetal's Angina during 5–Fluorouracil Chemotherapy", *The American Journal of Medicine*, 82, 566–568, (1987).

Knabbe, C., et al., "Evidence That Transforming Growth Factor beta is a Hormonally Regulated Negative Growth Factor in Human Breast Cancer Cells", *Cell*, 48, 417–428, (1987).

Knabbe, C., et al., "Induction of Transforming Growth Factor–B by the Antiestrogens Droloxifene, Tamoxifen, and Toremifene in MCF–7 Cells", *Am. J. Clin. Oncol.* 14, S15–S20, (1991).

Koff, et al., "Negative Regulation of GI in Mammalian Cells: Inhibition of Cyclin E–Dependent Kinase by TGF–B.", *Science*, 260, 536–538, (1993).

Kopp, A., et al., "Transforming Growth Factor Beta2 (TGF-Beta2) Levels in Plasma of Patients with Metastatic Breast Cancer Treated with Tamoxifen", *Cancer Research*, 55, 4512–4515, (Oct. 15, 1995).

Kotoulas, I.G., et al., "Tamoxifen Treatment in Male Infertility. I. Effect on Spermatozoa", *Fertiltity and Sterility*, 61, 911–914, (May 1994).

Kovach, J.A., et al., "Serial Intravascular Ultrasound Studies Indicate that Chronic Recoil is an Important Mechanism of Restenosis Following Transcatheter Therapy", *JACC*, 21, Abstract No. 835–3, p. 484A, (1993).

Koyama, N., et al., "Regulation of Smooth Muscle Cells Migration by a New Autocrine Migration Factor and TGF––beta", *Circulation*, 84, Abstract No. 1829, II–459, (1991).

Kremer, J.M., et al., "Fish–Oil Fatty Acid Supplementation in Active Rheumatoid Arthritis", *Annals of Internal Medicine*, 106, 497–502, (1987).

Kreuzer, J., et al., "Lipoprotein(a) Displays Increased Accumulation Compared with Low–Density Lipoprotein in the Murine Arterial Wall", *Chemistry and Physics of Lipids*, 67/68, 175–190, (1990).

Kunert, W., et al., "Paclitaxel Inhibits Development of Restenosis Following Experimental Ballon Angioplasty in the Rabbit Carotid Artery", *European Heart Journal*, 17, 368, (1996).

Kuntz, R.E., et al., "Defining Coronary Restenosis—Newer Clinical and Angiographic Paradigms", *Circulation*, 88, 1310–1323, (Sep. 1993).

Kunz, L.L., et al., "Efficacy of Cytochalasin B in Inhibiting Coronary Restenosis Caused by Chronic Remodeling After Balloon Trauma in Swine", *Journal of the American College of Cardiology*, Supplement A, Abstract No. 984–23, p. 302, (Mar. 1995).

Kunz, L.L., et al., "Inhibition of Microfilament Reorganization Following Balloon Angioplasty Decreases Extent of Geometric Remodeling in Restenosis", *JACC*, 44th Annual Scientific Session, Abstract No. 122292, 1 p., (Mar. 19–22, 1995).

Kunz, L.L., et al., "Sustained Dilation and Inhibition of Restenosis in a Pig Femoral Artery Injury Model", *Circulation*, 90, 67th Scientific Sessions, Abstract No. 1598, p. I–297, (Oct., 1994).

Kuramochi, H., "Conformational Studies and Electronic Structures of Tamoxifen and Toremifene and Their Allylic Carbocations Proposed as Reactive Intermediates Leading to DNA Adduct Formation", *J. Med. Chem.*, 39, 2877–2886, (1996).

Kuzuna, S., et al., "Effects of Some Anti–Rheumatic Agents on Copper–Catalyzed Thermal Aggregation of Gamma Globulin", *Agents and Actions*, 9, 375–380, (1979).

Labhsetwar, V., "Nanoparticles for site specific delivery of U–86983 in restenosis on pig coronary arteries", *Proc. Intern. Symp. Control. Rel. Bioact. Mater.*, 22, 182–183, (1995).

Lafont, A.M., et al., "Post–Angioplasty Restenosis in the Atherosclerotic Rabbit: Proliferative Response or Chronic Constriction?", *Circulation*, 88, 66th Scientific Sessions, Abstract No. 2806, p. I–521, (1993).

Laird, J., et al., "Inhibition of Neointimal Proliferation with Low–dose Irradiation from a Beta–particle–emitting Stent", *Circulation*, 93, 529–536, (1996).

Lambert, C.R., et al., "Local Drug Delivery Catheters: Functional Comparison of Porous and Microporous Designs", *Coronary Artery Disease*, 4, 469–475, (1993).

Langbein, W., "Too Many Drugs, Too Little Value in CV Conditions", *In Vivo*, 14–20, (Jun., 1995).

Lange, R.A., et al., "Cocaine–Induced Coronary–Artery Vasoconstriction", *The New England Journal of Medicine*, 321, 1557–1562, (1989).

Lange, R.L., et al., "Nonatheromatous Ischemic Heart Disease following Withdrawal from Chronic Industrial Nitroglycerin Exposure", *Circulation*, 46, 666–678, (1972).

Lawn, R.M., et al., "Feedback Mechanism of Focal Vascular Lesion Formation in Transgenic Apolipoprotein(a) Mice", *The Journal of Biological Chemistry*, 271, 31367–31371, (1996).

Lazier, C.B., et al., "Comparison of the Effects of Tamoxifen and of a Tamoxifen Analogue that Dogs Not Bind the Estrogen Receptor on Serum Lipid Profiles in the Cockerel", *Biochem. Cell Biol.*, 68, 210–217, (1990).

Lefer, "Role of Transforming Growth Factor Beta is Cardioprotection of the Ischemic–Reperfused Myocardium", *Growth Factors and the Cardiovascular System*, P. Cummins, ed., Kluwer Academic Publishers, 249–260, (1993).

Lefer, et al., "Mechanisms of the Cardioprotective Effect of Transforming Growth Factor B1 in Feline Myocardial Ischemia and Reperfusion", *PNAS (USA)*, 90, 1018–1022, (1993).

Lefer, A.M., et al., "Mediation of Cardioprotection by Transforming Growth Factor Beta", *Science*, 249, 61–64, (1990).

Lehmann, K., et al., "Effect of cilazapril on the proliferative response after vascular damage", *J. of Cardiovascular Pharmacology*, 22, (Suppl. 4), S19–24, (1993).

Lehmann–Bruinsma, et al., "Transforming Growth Factor B2(TGF–B) Suppression of Smooth Muscle Cell (SMC) Proliferation After Balloon Angioplasty of Rat Carotid Arteries", *Clin. Res.* 42, Abstract No. 4A, (Feb. 9–12, 1994).

Leroux, et al., "New Approach for the Preparation of Nanoparticles by an Emulsification–Diffusion Method", *Eur. J. Pharm. Biopharm.* 41, 14–18, (1995).

Leroux, J.C., et al., "Internalization of poly(D L–lactic acid) nanoparticles by isolated human leukocytes and analysis of plasma proteins adsorbed onto the particles", *J. Biomed. Mater. Res.*, 28, 471–481, (1994).

Levy, M.Y., "Drug Release from Submicronized O/W Emulsion: A New In Vitro Kinetic Evaluation Model", *Intl. J. Pharmaceut*, 66, 29–37, (1990).

Levy, R.J., et al., "Strategies for Treating Arterial Restenosis using Polymeric Controlled Release Implants", *Chemical Abstracts*, 121, Abstract No. 263625g, p. 580, (1994).

Levy, R.J., et al., "Strategies for Treating Arterial Restonosis Using Polymeric Controlled Release Implants", *In: Biotechnology and Bioactive Polymers*, Proceedings of an American Chemical Society Symposium, Gebelein, C.G., (ed.), Plenum Press, New York, 259–268, (1994).

Li, et al., "Structure and Dynamics of Microemulsions which Mimic the Lipid Phase of Low–Density Lipoproteins", *Biochimica et Biophysica Acta*, 1042, 42–50, (1990).

Liaw, et al., "Osteopontin Promotes Vascular Cell Adhesion and Spreading and is Chemotactic for Smooth Muscle Cells in Vitro", *Cir. Res.*, 74, 214–224, (1992).

Lin, et al., "Expression Cloning of the TGF–B Type II Receptor, a Functional Tranmembrane Serine/Threonine Kinase.", *Cell*, 68, 775–785, (1992).

Lincoff, A.M., et al., "Local Drug Delivery for the Prevention of Restenosis", *Circulation*, 90, 2070–2084, (Oct., 1994).

Lindkaer–Jensen, S., et al., "Inhibition of Salicylate and Lithium Absorption in the Human Intestine by Copper Sulfate", *Arch. Toxicol.*, 35, 175–179, (1976).

Linn, et al., "Microemulsion for Intradermal Delivery of Cetyl Alcohol and Octyl Dimethyl Paba", *Drug Development and Industrial Pharmacy*, 16, 899–920, (1990).

Lipski, K.M., et al., "Cytochalasin B: Preparation, Analysis in Tissue Extracts, and Pharmacokinetics after Intraperitoneal Bolus Administration in Mice", *Analytical Biochemistry*, 161, 332–340, (1987).

Liu, M.D., et al., "Restenosis After Coronary Angioplasty— Potential Biologic Determinants and Role of Intimal Hyperplasia", *Circulation*, 79, 1374–87, (1989).

Lopez–Anaya, A., et al., "Pharmacokinetics and Pharmacodynamics in Copper Deficiency I", *Biological Trace Element Research*, 40, 161–176, (1994).

Lopez–Casillas, et al., "Beta–glycan Presents Ligand to the TGFBeta Signaling Receptor", *Cell*, 73, 1435–1444, (Jul. 2, 1993).

Loser, R., et al., "In Vivo and in Vitro Antiestrogenic Action of 3–Hydroxytamoxifen, Tamoxifen and 4–Hydroxytamoxifen", *Eur. J. Cancer Clin. Oncol.*, 21, 985–990, (1985).

Love, et al., "Effects of Tamoxifen on Cardiovascular Risk Factors in Postmenopausal Women.", *Annals of Internal Medicine*, 115, 860–864, (1991).

Love, et al., "Effects of Tamoxifen Therapy on Lipid and Lipoprotein Levels in Postmenopausal Patients with Node–Negative Breast Cancer", *J. Natl. Cancer Ins.*, 82, 1327–1332, (1990).

Lucas, C., et al., "The Autocrine Production of Transforming Growth Factor–B1 During Lymphocyte Activation", *The Journal of Immunology*, 145(5), 1415–1422, (1990).

Luo, H., et al., "Chronic Vessel Constriction is an Important Mechanism of Restenosis After Balloon Angioplasty: An Intravascular Ultrasound Analysis", *Circulation*, 90, 67 Scientific Sessions, Abstract No. 0318, p. I–61, (1994).

Luostarinen, R., et al., "Effect of Dietary Fish Oil Supplemented with Different Doses of Vitamin E On Neutrophil Chemotaxis in Healthy Volunteers", *Nutrition Research*, 12, 1419–1430, (1992).

Macander, et al., "Balloon Angioplasty for Treatment of In–Stent Restenosis: Feasiblity, Safety, and Efficacy", *Catheterization and Cardiovascular Diagnosis*, 37, 125–131, (1990).

Magarian, "The Medicinal Chemistry of Nonsteroidal Antiestrogens: A Review", *Current Medicinal Chemistry*, 1, 61–104, (1994).

Majack, R.A., et al., "Role of PDGF–A Expresion in the Control of Vascular Smooth Muscle Cell Growth by Transforming Growth Factor–B", *The Journal of Cell Biology*, 111, 239–247, (1990).

Majesky, M.W., et al., "Production of Transforming Growth Factor beta1 During Repair of Arterial Injury", *J. Clin. Invest.*, 88, 904–910, (1991).

Malcolmson, et al., "A Comparison Betweein Nonionic Micelles and Microemulsions as a Means of Incorporating the Poorly Water Soluble Drug Diazepam", *J. Pharm. Pharmcol*, 42, 6P, (1990).

Mambetisaeva, E.T., et al., "Effect of New Synthetic Cholesterol Derivatives on Cholesterol Metabolism in Cultured Rabbit Hepatycytes", *Biokhimiya (Russia)*, 58, Translation, Plenum Publishing Corporation, 1126–1132, (1993).

Manasek, F.J., et al., "The Sensitivity of Developing Cardiac Myofibrils to Cytochalasin–B", *Proc. Natl. Acad. Sci. USA*, 69, 308–213, (Feb., 1972).

Mang, T.D., "Distribution to Normal and Tumor Tissues of Cytochalasin B after Intravenous Administration in Mice", Bachelor of Science Thesis, Syracuse University, New York, (1994).

Manucci, P.M., et al., "Effect of Tamoxifen on Measurements of Hemostasis in Healthy Women", *Arch. Intern. Med.*, 156, 1806–1810, (1996).

Marx, "CMV–p.53 Interaction May Help Explain Clogged Arteries", *Science*, 265, 320, (Jul. 1994).

Marzocchi, A., et al., "Restenosis After Coronary Angioplasty: Its Pathogenesis and Prevention", *Cardiologia*, 36, Translation, 11 p., 309–320, (1991).

Massague, "The transforming growth factor–B family", *Ann. Rev. Cell Biol.*, 6, 597–641, (1990).

McAuslan, B.R., et al., "Cellular and Molecular Mechnisms in Angiogenesis", *Trans. Ophthal. Soc. U.K.*, 100, 354–358, (1980).

McCaffrey, T.A., et al., "Fucoidan is a Non–Anticoagulant Inhibitor of Intimal Hyperplasia", *Biochemical and Biophysical Research Communications*, 184, 773–781, (1992).

McCaffrey, T.A., et al., "Transforming Growth Factor–beta Activity is Potentiated by Heparin via Dissociation of the Transforming Growth Factor–beta/alpha2–Macroglobulin Inactive Complex", *The Journal of Cell Biology*, 109, 441–448, (Jul., 1989).

McCague, R., et al., "An Efficient, Large Scale Synthesis of Idoxifene (E)–1(4–(2–(N–pyrrolidino)ethoxy)–1–(4–iodophenyl)–2–phenyl–1–butene)", *Organic Preparations and Proc. Int.*, 26, 343–346, (1994).

McCague, R., et al., "Synthesis of 4–Stannylated Tamoxifen Analogues: Useful Precursors to Radiolabelled Idoxifene and Axiridinyl 4–Iodotamoxifen.", *J. Labelled Compounds and Pharmaceuticals*, 34, 297–302, (1994).

McCaroll, et al., "Preliminary Studies on the Regulation of Secretion of Latent Transforming Growth Factor–B (TGF–B) by Endothelial Cells in Culture.", *Clin. Chem.*, 36, Abstract No. 0934, 1152, (1990).

McClean, et al., "cDNA sequence of human apolipoprotein (a) is homologous to plasminogen", *Nature*, 330, 132–137 (1987).

McCormick, et al., "Retinoid–Tamoxifen Interaction in Mammary Cancer Chemoprevention", *Carcinogenesis*, 7, 193–196, (1986).

McDonald, et al., "Fatal Myocardial Infarction in the Scottish Adjuvant Tamoxifen Trial.", *B. Med. J.*, 303, 435–437, (1991).

McDonald, C.C., et al., "Cardiac and vascular morbidity in women receiving adjuvant tamoxifen for breast cancer in a randomised trial", *BMJ*, 311, 977–980, (Oct. 14, 1995).

McDonnell, D.P., et al., "Analysis of Estrogen Receptor Function in Vitro Reveals Three Distinct Classes of Antiestrogens", *Molecular Endocrinology*, 9, 659–669, (Jun. 1995).

McLaughlin, C.S., et al., "Inhibition of Protein Synthesis by Trichothecenes", *In: Mycotoxins in Human and Animal Health*, Pathotox Publishers, Inc., 263–273, (1977).

McQuiggan, J.D., "Tissue Distribution of Cytochalasin B After Intraperitoneal Bolus and Microencapsulated Injection in Mice and its Effect on beta–N–Acetylglucosaminidase Activity in Cultured B16–BL6 Melanoma Cells", Masters' Thesis, Syracuse University, New York, 41 p., (Dec. 1988).

Merrilees, et al., "Synthesis of TGF–B1 by Vascular Endothelial Cells is Correlated with Cell Spreading.", *J. Vasc. Res.*, 29, 376–384, (1992).

Metcalfe, J.C., et al., "Protein Markers of Lesion Development in the Vessels of Transgenic Apo(a) Mice", *Journal of Cellular Biochemistry*, Supplement 18A, Abstract No. E212, p. 280, (1994).

Metcalfe, J.C., et al., "Transforming Growth Factor–beta and the Protection From Cardiovascular Injury Hypothesis", *Biochemical Society Transactions*, 23, 403–406, (1995).

Meyer, S.C., "Functionalized Cytochalasins for Potential Biotechnology Transfer", Ph. D. Thesis (Selected Pages), Syracuse University, New York, 13 p., (May, 1994).

Middlebrook, J.L., et al., "Binding of T–2 Toxin to Eukaryotic Cell Ribosomes", *Biochemical Pharmacology*, 38, 3103–3110, (1989).

Middlebrook, J.L., et al., "Specific Association of T–2 Toxin with Mammalian Cells", *Biochemical Pharmacology*, 38, 3093–3102, (1989).

Milner, M.R., et al., "Usefulness of Fish Oil Supplements in Preventing Clinical Evidence of Restenosis After Percutaneous Transluminal Coronary Angioplasty", *Am. J. Cardiol.*, 64, 294–299, (1989).

Mints, G.S., et al., "Chronic Compensatory Arterial Dilation Following Coronary Angioplasty: An Intravascular Ultrasound Study", *JACC*, Abstract No. 875–97, p. 138A, (Feb., 1994).

Mints, G.S., et al., "Geometric Remodeling is the Predominant Mechanism of Clinical Restenosis After Coronary Angioplasty", *JACC*, Abstract No. 875–42, p. 138A, (Feb., 1994).

Mintz, G.S., et al., "Mechanisms of Late Arrival Response to Transcatheter Therapy: A Serial Quantitative Angiographic and Intravascular Ultrasound Study", *Circulation*, 90, Abstract No. 117, p. I–24, (Oct., 1994).

Mirjalili, N., et al., "Gas Phase Composition Effects on Suspension Cultures of *Taxus cuspidata*", *Biotechnology and Bioengineering*, 48, 123–132, (1995).

Mirjalili, N., et al., "Methyl Jasmonate Induced Production of Taxol in Suspension Cultures of *Taxus Cuspidata*: Ethylene Interaction and Induction Models", *Biotechnol. Prog.*, 12, 110–118, (1996).

Mitchell, L.L., et al., "Copper Deficiency Depresses Rat Aortae Superoxide Dismutase Activity and Prostacyclin Synthesis", *Prostaglandins*, 35, 977–986, (1988).

Molling, K., "Naked DNA for Vaccine or Therapy", *J. Mol. Med.*, 75, 242–246, (1997).

Moorthy, B., et al., "Tamoxifen Metabolic Activation: Comparison of DNA Adducts Formed by Microsomal and Chemical Activation of Tamoxifen and 4–Hydroxytamoxifen with DNA Adducts Formed in Vivo", *Cancer Research*, 56, 53–57, (Jan. 1, 1996).

More, R.S., et al., "A Targeted Antithrobotic Conjugate with Antiplatelet and Fibrinolytic Properties which Reduces in vivo Thrombus Formation", *Cardiovascular Research*, 27, 2200–2204, (1993).

More, R.S., et al., "A targeted antithrombotic conjugate with antiplatelet and fibrinolytic properties which reduces in vivo thrombus formation", *Chemical Abstracts*, vol. 120, No. 22, (May 30, 1994).

Morisaki, et al., "Effects of transforming growth factor–B, on growth of aortic smooth muscle cells", *Atherosclerosis*, 88, 227–234, (1991).

Mosedale, D.E., et al., "Transforming Growth Factor–beta is Correlated with Smooth Muscle Cell Differentiation in Vivo", *Circulation*, 90, 67th Scientific Session, Abstract No. 1590, p. I–296, (Oct., 1994).

Mueller, B.M., et al., "Antibody Conjugates with Morpholinodoxorubicin and Acid–Cleavable Linkers", *Bioconjugate Chem. 1*, 325–330, (1990).

Murphy, C.S., et al., "Structural Components Necessary For The Antiestrogenic Activity of Tamoxifen", *J. Steroid Biochem*, 34, 1–6, (1989).

Murphy, C.S., et al., "Structure–Activity Relationships of Nonisomerizable Derivatives of Tamoxifen: Importance of Hydroxyl Group and Side Chain Positioning for Biological Activity", *Molecular Pharmacology*, 39, 421–428, (1991).

Murphy, L.C., et al., "Differential Effects of Tamoxifen and Analogs with Nonbasic Side Chains on Cell Proliferation in Vitro", *Endocrinology*, 116, 1071–1078, (1985).

Myer, R.O., et al., "Performance and Carcass Characteristics of Swine When Fed Diets Containing Canola Oil and Added Copper to Alter the Unsaturated:Saturated Ration of Pork Fat", *J. Anim. Sci.*, 70, 1417–1423, (1992).

Nabel, "Recombinant Gene Expression in Vivo Within Endocthelial Cells of the Arterial Wall", *Science*, 244, 1342–1344, (1989).

Nabel, E.G., et al., "Direct Transfer of Transforming Growth Factor Beta 1 Group Into Arteries Stimulates Fibrocellular Hyperplasia", *Proc. Natl. Acad. Sci. USA*, 90, 10759–10763, (1993).

Nagakawa, Y., et al., "Effect of Eicosapentaenoic Acid on the Platelet Aggregation and Composition of Fatty Acid in Man", *Atherosclerosis*, 47, 71–75, (1983).

Naito, M., et al., "Vascular Endothelial Cell Migration In Vitro: Roles of Cyclic Nucleotides, Calcium Ion and Cytoskeletal System", *Artery*, 17, 21–31, (1989).

Nakagawa, et al., "A Case of Acute Myocardinal Infarction Intracoronary Arteries Due To Hormone Therapy.", *Angiology*, 45, 333–338, (May 1994).

Nakao, J., et al., "Calcium Dependency of Aortic Smooth Muscle Cell Migration Induced by 12–L–Hydroxy–5,8,10, 14–eicosatetraenoic Acid", *Atherosclerosis*, 46, 309–319, (1983).

Navarro, S.E., et al., "Notes from Transcatheter Cardiovascular Therapeutics 1995 Conference", *USB Securities, Equity Research—Medical Technology*, 10 p., (Mar. 3, 1995).

Nayfield, S.G., et al., "Tamoxifen–Associated Eye Disease: A Review", *Journal of Clinical Oncology*, 14(3), 1018–1026, (1996).

Nikol, S., et al., "Expression of Transforming Growth Factor Beta 1 is Increased in Human Vascular Restenosis Lesions", *J. Clin. Invest.*, 90, 1582–1592, (1992).

Nunes, G.L., et al., "Vitamins C and E Improve the Response to Coronary Balloon Injury in the Pig: Effect of Vascular Remodeling", *Circulation*, 88, Abstract No. 1994, p. I–372, (Oct., 1993).

O'Brien, et al., "Osteopontin mRNA and Protein are Overexposed in Human Coronary Atherectormy Specimens: Clues to Lesion Calcification.", *Circulation*, 88, Abstract No. 3330, I–609, (1993).

O'Connor–McCourt, et al., "Latent Transforming Growth Factor–B in Serum: A Specific Complex with a2–macroglobin", *J. Biol. Chem.* 262, 14090–14099, (1987).

O'Leary, V.J., et al., "The Resistance of Low Density Lipoprotein to Oxidation Promoted by Copper and Its Use as an Index of Antioxidant Therapy", *Atherosclerosis*, 119, 169–179, (1996).

Ohmi, K., et al., "Effect of K252a, A protein kinase inhibitor, on the proliferation of vascular smooth muscle cells", *Biochemical and Biophysical Research Communications*, 173(3), 976–981, (1990).

Ohno, et al., "Gene Therapy for Vascular Smooth Muscle Proliferation After Afterial Injury", *Science*, 265, 781–784, (Aug. 5, 1994).

Okuyama, S., et al., "Copper Complexes of Non–Steroidal Antiinflammatory Agents: Analgesic Activity and Possible Opoid Receptor Activation", *Agents and Actions*, 21, 130–144, (1987).

Oliveira, M.M., et al., "Isolation and Characterization of Smooth Muscle Cell Membranes", *Biochemica et Biophysica Acta*, 332, 221–232, (1974).

Opherk, D., et al., "Four–Year Follow–up Study in Patients With *Angina Pectoris* and Normal Coronary Arteriograms ("Syndrome X")", *Circulation*, 80, 1610–1616, (1989).

Orlov, S.N., et al., "Altered beta–Adrenergic Regulation of Na–K–Cl Cotransport in Cultured Smooth Muscle Cells From the Aorta of Spontaneously Hypertensive Rats", *American Journal of Hypertension*, 8, 739–747, (1995).

Osborne, et al., "Microemulsions as Topical Drug Delivery Vehicles: In Vitro Trandermal Studies of a Model Hydrophilic Drug", *J. Pharm. Pharmcol.*, 43, 451–454, (1991).

Osborne, M.R., et al., "Identification of the Major Tamoxifen–Deoxyguanosine Adduct Formed in the Liver DNA of Rats Treated with Tamoxifen", *Cancer Research*, 56, 66–71, (1996).

Osipow, "Transparent Emulsion", *J. Soc. Cosmetic Chemists*, 277–285, (1963).

Owens, G.K., et al., "Transforming Growth Factor–B–induced Growth Inhibition and Cellular Hypertrophy in Cultured Vascular Smooth Muscle Cells", *The Journal of Cell Biology*, 107, 771–780, (1988).

Ozer, et al., "New Roles of low density lipoproteins and vitamin E in the pathogenesis of atherosclerosis", *Biochem Mol. Biol. Intern*, 35, 117–124, (1995).

Palmaz, J.C., et al., "Intravascular Stents", *In: Advances in Vascular Surgery*, vol. 1, Mosby–Year Book Inc.,, 107–135, (1993).

Pandey, B.L., et al., "A Study of the Effects of Tamrabhasma, an Indigenous Preparation of Copper on Experimental Gastric Ulcers and Secretion", *Indian Journal of Experimental Biology*, 21, 258–264, (1983).

Pardee, A.B., et al., "Control of Cell Proliferation", *Cancer*, 39, 2747–2754, (1977).

Pardoll, D., et al., "Exposing the Immunology of Naked DNA Vaccines", *Immunity*, 3, 165–169, (1995).

Parthasatathy, S., et al., "A Role for Endothelial Cell Lipoxygenase in the Oxidative Modification of Low Density Lipoprotein", *Proc. Nat'l Acad. Sci.*, USA, 86, 1046–1050, (1989).

Pathak, et al., "Enhanced Stability of Physostigmine Salicylate in Submicron o/w Emulsion", *International Journal of Pharmaceutics*, 65, 169–175, (1990).

Pedron, N., et al., "The Effect of Acetylsalicyclic Acid on Menstral Blood Loss in Women with IUDs", *Contraception*, 36, 295–303, (1987).

Pennisi, E., "Drug's Link to Genes Reveals Estrogen's Many Sides", *Science*, 273, 1171, (Aug. 30, 1996).

Peress, N.S., et al., "Differential Expression of TGF–B1, 2 and 3 Isotypes in Alzheimer's Disease: A Comparative Immunohistochemical Study with Cerebral Infarction, Aged Human and Mouse Control Brains", *Journal of Neuropathology and Experimental Neurology*, 54, 802–811, (Nov. 1995).

Peress, N.S., et al., "Glial Transforming Growth Factor (TGF) –B Isotypes in Multiple Sclerosis: Differential Glial Expression of TGF–B1, 2, and 3 Isotypes in Multiple Sclerosis", *Journal of Neuroimmunology*, 71, 115–123, (1996).

Edelman, E.R., et al., "Effect of Controlled Adventitial Heparin Delivery on Smooth Muscle Cell Proliferation Following Endothelial Injury", *Proc. Natl. Acad. Sci. USA*, 87, 3773–3777, (May, 1990).

Eldridge, J.H., et al., "Biodegradable and Biocompatible Poly(DL–Lactide–Co–Glycolide) Microspheres as an Adjuvant for Staphylococcal Enterotoxin B Toxoid Which Enhances the Level of Toxin–Neutralizing Antibodies", *Infection and Immunity*, 59, 2978–2986, (Sep. 1991).

Ellis, S.G., et al., "In–Hospital Cost of Percutaneous Coronary Revascularization: Critical Determinants and Implications", *Circulation*, 92, 741–747, (1995).

Endres, S., et al., "The Effect of Dietary Supplementation with n–3 Polyunsaturated Fatty Acids on the Synthesis of Interleukin–1 and Tumor Necrosis Factor by Mononuclear Cells", *N. Engl. J. Med.*, 320, 265–271, (1989).

Epstein, S.E., et al., "Cytotoxic Effects of a Recombinant Chimeric Toxin on Rapidly Proliferating Vascular Smooth Muscle Cells", *Circulation*, 84, 778–787, (1991).

Esnouf, M.P., et al., "The Inhibition of the Vitamin K–Dependent Carboxylation of Glutamyl Residues in Prothombin by Some Copper Complexes", *FEBS Letters*, 107, 146–150, (1979).

Espinosa, E., et al., "17■–Estradiol and Smooth Muscle Cell Proliferation in Aortic Cells of Male and Female Rats", *Biochemical and Biophysical Research Communication*, 221, 8–14, (1996).

Evans, G.L., et al., "Tissue–Selective Actions of Estrogen Analogs", *Bone*, 17, 181S–190S, (Oct. 1995).

Fanelli, C., et al., "Restenosis Following Coronary Angioplasty", *American Heart Journal*, 119, 357–368, (Feb., 1990).

Farhat, et al., "In Vitro Effect of Oestradiol on Thymidine Uptake in Pulmonary Vascular Smooth Muscle Cell: Role of the Endothelium.", *Br. J. Pharmacol.*, 107, 679–683, (1992).

Faxon, D.P., et al., "Restenosis Following Transluminal Angioplasty in Experimental Atherosclerosis", *Arteriosclerosis*, 4, 189–195, (May–Jun., 1984).

Fay, M.J., et al., "Effects of Cytochalasin B on the Uptake of Ascorbic Acid and Glucose by 3T3 Fibroblasts: Mechanism of Impaired Ascorbate Transport in Diabetes", *Life Sciences*, 46, 619–624, (1990).

Feelisch, M., et al., "Biotransformation of Organic Nitrates to Nitric Oxide by Vascular Smooth Muscle and Endothelial Cells", *Biochemical and Biophysical Research Communications*, 180, 286–293, (Oct. 15, 1991).

Ferrari, R.P., et al., "Changes of Serum Iron Transferrin and Copper Ceruloplasmin in Rats Given Cu(II)sub2(Acetylsalicyate)sub4 During Acute Inflammation", *Anticancer Res.*, 9, 771–774, (1989).

Fett–Neto, A.G., et al., "Effect of White Light on Taxol and Baccatin III Accumulation in Cell Cultures of *Taxus Cuspidata* Sieb and Zucc.", *J. Plant Physiol.*, 146, 584–590, (1995).

Fischell, T.A., et al., "Low–Dose, beta–Particle Emission From 'Stent' Wire Results in Complete, Localized Inhibition of Smooth Muscle Cell Proliferation", *Circulation*, 90, 2956–2963, (Dec., 1994).

Fischer, et al., "A Possible Mechanism in Arterial Wall for Mediation of Sex Difference in Atherosclerosis Experimental and Molecular Pathology", *Exp. Mol. Pathol.*, 43, 288–296, (1985).

Fischman, D.L., et al., "A Randomized Comparison of Coronary–Stent Placement and Balloon Angioplasty in the Treatment of Coronary Artery Disease", *The New England Journal of Medicine*, 331, 496–501, (Aug., 1994).

Fisher, M., et al., "Dietary n–3 Fatty Acid Supplementation Reduces Superoxide Production and Chemiluminescence in a Monocyte–Enriched Preparation of Leukocytes", *Am. J. Clin. Nutr.*, 51, 804–808, (1990).

Flanders, K.C., et al., "Altered Expression of Transforming Growth Factor–B in Alzheimer's Disease", *Neurology*, 45, 1561–1569, (Aug. 1995).

Flanders, K.C., et al., "Transforming Growth Factor–B1: Histochemical Localization With Antibodies to Different Epitopes", *Journal of Cell Biology*, 108, 653–660, (Feb. 1989).

Foekens, J.A., et al., "Urokinase–Type Plasminogen Activator and Its Inhibitor PAI–1: Predictors of Poor Response to Tamoxifen Therapy in Recurrent Breast Cancer", *Journal of the National Cancer Institute*, 87(10), 751–756, (May 1995).

Forrester, J.S., et al., "A Paradigm for Restenosis Based on Cell Biology: Clues for the Development of New Preventive Therapies", *JACC*, 17, 758–769, (Mar. 1, 1991).

Frautschy, S.A., et al., "Rodent Models of Alzheimer's Disease: Rat A Infusion Approaches to Amyloid Deposits", *Neurobiology of Aging*, 17, 311–321, (1996).

Frazier–Jessen, et al., "Estrogen Modulation of JE/Monocyte Chemoattractant Protein–1 mRNA Expression in Murine Macrophages", *J. Immunol.*, 1828–1845, (1994).

Friberg, et al., "Microemulsions and Solubilization by Nonionic Surfactants", *Prog. Colloid and Polymer Sci.*, 56, 16–20, (1975).

Frye, L.L., et al., "Oxolanosterol Oximes: Dual–Action Inhibitors of Cholesterol Biosynthesis", *Journal of Lipid Research*, 35, 1333–1344, (1994).

Fukaura, H., et al., "Induction of Circulating Myelin Basic Protein and Proteolipid Protein–Specific Transforming Growth Factor–B1–Secreting Th3 T Cells by Oral Administration of Myelin in Multiple Sclerosis Patients", *J. Clin. Invest.*, 98, 70–77, (1996).

Fukuda, et al., "Distinct Expression of Transforming Growth Factor–B Receptor Subtypes on Vascular Smooth Muscle Cells from Spontaneously Hypertensive Rats and Wistar–Kyoto Rats", *Clin. Exp. Pharmacol. Physiol. Suppl.*, 1, S120, (1995).

Fulop, T., et al., "Age–Dependent Variations of Intralysosomal Enzyme Release from Human PMN Leukocytes under Various Stimuli", *Immunobiol.*, 171, 302–310, (1986).

Furr, B.J., et al., "The Pharmacology and Clinical Uses of Tamoxifen", *Pharmac. Ther.*, 25, 127–205, (1984).

Garg, U.C., et al., "Nitric Oxide–Generating Vasodilators and 8–Bromo–Cyclic Guanosine Monophosphate Inhibit Mitogenesis and Proliferation of Cultured Rat Vascular Smooth Muscle Cells", *Journal of Clinical Investigation*, 83, 1774–1777, (May, 1989).

Garrigues, et al., "The Melanoma Proteoglycan: Restricted Expression on Microspikes, a Specific Microdomain of the Cell Surface.", *J. Cell. Biol.*, 103, 1699–1710, (Nov. 1986).

Gasco, et al., "In Vitro Permeation of Azelaic Acid from Viscosized Microemulsions", *International Journal of Pharmaceutics*, 69, 193–196, (1991).

Gasco, M.R., et al., "Long–acting Delivery Systems for Peptides: Reduced Plasma Testosterone Levels in Male Rats after a Single Injection", *Intl. J. of Pharmaceut*, 62, 119–123, (1990).

Gebhardt, R., et al., "Differential Inhibitory Effects of Garlic–Derived Organosulfur Compounds on Cholesterol Biosynthesis in Primary Rat Hepatocyte Cultures", *Lipids*, 31, 1269–1276, (1996).

Gebhardt, R., et al., "Inhibition of Cholesterol Biosynthesis by Allicin and Ajoene in Rat Hepatocytes and HepG2 Cells", *Biochimica et Biophysica Acta*, 1213, 57–62, (1994).

Gertz, S.D., et al., "Geometric Remodeling Is Not the Principal Pathogenic Process in Restenosis After Balloon Angioplasty", *Circulation*, 90, 3001–3009, (Dec., 1994).

Giachelli, et al., "Osteopontin is Elevated During Neointima Formation in Rat Arteries and is a Novel Component of Human Atherosclerosis Plaques", *J. Clin. Invest.*, 92, 1686–1696, (Oct. 1993).

Gibbons, G.H., et al., "The Emerging Concept of Vascular Remodeling", *New England Journal of Medicine*, 330, 1431–1438, (1994).

Gibson, D.M., et al., "Initiation and Growth of Cell Lines of *Taxus Brevifolia* (Pacific Yew)", *Plant Cell Reports*, 12, 479–482, (1993).

Glagov, S., "Intimal Hyperplasia, Vascular Modeling, and the Restenosis Problem", *Circulation*, 89, 2888–2891, (1994).

Glagov, S., et al., "Compensatory Enlargement of Human Atherosclerotic Coronary Arteries", *New England Journal of Medicine*, 316, 1371–1375, (May 28, 1987).

Goldman, et al., "Influence of Pressure on Permeability of Normal and Diseased Muscular Arteries to Horseradish Peroxidase.", *Atherosclerosis*, 65, 215–225, (1987).

Goodnight, S.H., et al., "The Effects of n–3 Fatty Acids on Atherosclerosis and the Vascular Response to Injury", *Arch. Pathol. Lab. Med.*, 117, 102–106, (Jan., 1993).

Gradishar, W.J., et al., "Clinical Potential of New Antiestrogens", *Journal of Clinical Oncology*, 15, 840–852, (1997).

Grainger, D.J., "Taking Tamoxifen To Heart", *Nature Medicine*, 1, Reply to Letter by H. Wiseman, p. 1226, (Dec., 1995).

Grainger, D.J., et al., "A Large Accumulation of NonMuscle Myosin Occurs at First Entry into M Phase in Rat Vascular Smooth–Muscle Cells.", *Biochemical Journal*, 277, 145–151, (1991).

Grainger, D.J., et al., "A Pivotal Role for TGF–beta in Atherogenesis?", *Biol. Rev.*, 70, 571–596, (1995).

Grainger, D.J., et al., "Activation of Transforming Growth Factor–beta is Inhibitied by Apolipoprotein (a) in vivo", *Circulation*, 90, 67th Scientific Session, Abstract No. 3353, p. I–623, (Oct., 1994).

Grainger, D.J., et al., "Activation of Transforming Growth Factor–beta is Inhibited in Transgenic Apolipoprotein(a) Mice", *Nature*, 370, 460–462, (Aug. 11, 1994).

Grainger, D.J., et al., "Active and Acid–Activatable TGF-beta in Human Sera, Platelets and Plasma", *Clinica Chemica Acta.*, 235, 11–31, (Feb., 1995).

Grainger, D.J., et al., "Active TGF–beta is Depressed Five-Fold in Triple Vessel Disease Patients Compared with Syndrome X Patients", *Journal of Cellular Biochemistry*, 18A, Abstract No. E111, p. 267, (1994).

Grainger, D.J., et al., "Active Transforming Growth Factor–beta is Depressed in Patients with Three Vessel Coronary Artery Disease", *Circulation*, 90, 67th Scientific Sessions, Abstract No. 2754, p. I–512, (Oct., 1994).

Grainger, D.J., et al., "Effect of Tamoxifen in the Rat Carotid Injury Model In Vivo", Manuscript in Preparation, (1996).

Grainger, D.J., et al., "Heparin Decreases the Rate of Proliferation of Rat Vascular Smooth Muscle Cells by Releasing Transforming Growth Factor beta–like Activity from Serum", *Cardiovascular Research*, 27, 2238–2247, (1993).

Grainger, D.J., et al., "Hexamethylenebisacetamide Selectively Inhibits the Proliferation of Human and Rat Vascular Smooth–Muscle Cells", *Biochemical Journal*, 283, 403–408, (1992).

Grainger, D.J., et al., "Mitogens for Adult Rat Aortic Vascular Smooth Muscle Cells in Serum–Free Primary Culture", *Cardiovascular Research*, 28, 1238–1242, (1994).

Grainger, D.J., et al., "Proliferation of Human Smooth Muscle Cells Promoted by Lipoprotein(a)", *Science*, 260, 1655–1658, (Jun. 11, 1993).

Grainger, D.J., et al., "Release and Activation of Platelet Latent TFG–Beta in Blood Clots During Dissolution with Plasmin", *Nature Medicine*, 1, 932–937, (1995).

Grainger, D.J., et al., "Tamoxifen Decreases the Rate of Proliferation of Rat Vascular Smooth–Muscle Cells in Culture by Inducing Production of Transforming Growth Factor Beta", *Biochem J.* 294, 109–112, (1993).

Grainger, D.J., et al., "Tamoxifen Elevates Transforming Growth Factor–beta and Suppresses Diet–Induced Formation of Lipid Lesions in Mouse Aorta", *Nature Medicine*, 1, 1067–1073, (Oct., 1995).

Grainger, D.J., et al., "Tamoxifen: Teaching an Old Drug New Tricks?", *Nature Medicine*, 2, 381–385, (Apr., 1996).

Grainger, D.J., et al., "The Serum Concentration of Active Transforming Growth Factor–beta) is Severly Depressed in Advanced Atherosclerosis", *Nature Medicine*, 1, 74–80, (Jan., 1995).

Grainger, D.J., et al., "Transforming Growth Factor beta Decreases the Rate of Proliferation of Rat Vascular Smooth Muscle Cells by Extending the G2 Phase of the Cell Cycle and Delays the Rise in Cyclic AMP Before Entry into M Phase", *Biochemical Journal*, 299, 227–235, (1994).

Grainger, D.J., et al., "Transforming Growth Factor beta is Sequestered into an Inactive Pool by Lipoproteins", *Journal of Lipid Research*, 38, 117–125, (1997).

Grainger, D.J., et al., "Transforming Growth Factor–beta and Cardiovascular Protection", *In: The Endothelium in Clinical Practice*, Rubanyi, G.M., et al., (eds), Marcel Dekker, Inc., New York, 203–243, (1997).

Grainger, D.J., et al., "Transforming Growth Factor–beta: The Key to Understanding Lipoprotein(a)?", *Current Opinion In Lipidology*, 6, 81–85, (1995).

Gref, et al., "Biodegradable Long–Circulating Polymeric Nanoshoeres.", *Science*, 263, 1600–1603, (Mar. 18, 1994).

Grese, T.A., et al., "Structure–Activity Relationships of Selective Estrogen Receptor Modulators: Modification to the 2–Arylbenzothiophene Core of Raloxifen", *J. Med. Chem.*, 40, 146–167, (1997).

Grey, A.B., et al., "The Effect of the Anti–Estrogen Tamoxifen on Cardiovascular Risk Factors in Normal Postmenopausal Women", *J. Clinical Endocrinology and Metabolism*, 80, 3191–3195, (1995).

Grigg, L.E., et al., "Determinants of Restenosis and Lack of Effect of Dietary Supplementation with Eicosapentaenoic Acid on the Incidence of Coronary Artery Restenosis After Angioplasty", *JACC*, 13, 665–672, (1989).

Guetta, V., et al., "Effect of the Antiestrogen Tamoxifen on Low–Density Lipoprotein Concentrations and Oxidation in Postmenopausal Women", *The American Journal of Cardiology*, 76, 1072–1073, (Nov. 15, 1995).

Gulino, A., et al., "Heterogeneity of Binding Sites for Tamoxifen and Tamoxifen Derivatives in Estrogen Target and Nontarget Fetal Organs and Guinea Pig", *Cancer Research*, 42, 1913–1921, (May 1982).

Gylling, H., et al., "Tamoxifen and Toremifene Lower Serum Cholesterol by Inhibition of Delta8–Cholesterol Conversion to Lathosterol in Women with Breast Cancer", *Journal of Clinical Oncology*, 13, 2900–2905, (1995).

Gylling, H., et al., "Tamoxifen Decreases Serum Cholesterol by Inhibiting Cholesterol Synthesis", *Atherosclerosis*, 96, 245–247, (1992).

Hahn, L., et al., "The Influence of Acetylsalicylic Acid and Paracetamol on Menstrual Blood Loss in Women With and Without an Intrauterine Contraceptive Device", *Am. J. Obstet. Gynecol.*, 135, 393–396, (1979).

Hall, I.H., et al., "Hypolipidemic Activity of Tetrakis–mu–(trimethylamine–boranecarboxylato)–bis(trimethylamine–carboxyboran e)–dicopper(II) in Rodents and Its Effect on Lipid Metabolism", *J. Pharmaceut. Sci.*, 73, 973–977, (1984).

Hanke, H., et al., "Inhibition of Cellular Proliferation After Experimental Balloon Angioplasty by Low–Molecular–Weight Heparin", *Circulation*, 85, 1548–1556, (Apr. 1992).

Hardcastle, I.R., et al., "Homologs of Idoxifene: Variation of Estrogen Receptor Binding and Calmodulin Antagonism with Chain Length", *J. Med. Chem.*, 39, 999–1004, (1996).

Harpel, et al., "Plasmin Catalysis Binding of Lipoprotein (A) to Immobilized Fibrinogen and Fibrin.", *Proc. Natl. Acad. Sci. USA*, 86, 3847–3851, (1989).

Harrison, D.C., "Nonatherosclerotic Coronary Artery Disease", *In: Atherosclerosis and Coronary Artery Disease*, V. Fuster, et al., (eds.), Lippencott–Raven Publishers, pp. 757–772, (1996).

Hayden, L.J., "Inhibitors of Gastric Lesion in the Rat", *J. Pharm. Pharmac.*, 30, 244–246, (1978).

Hayes, D.F., et al., "Randomized Comparison of Tamoxifen and Two Separate Doses of Toremifene in Postmenopausal Patients with Metastatic Breast Cancer", *Journal of Clinical Oncology*, 13, 2556–2566, (Oct. 1995).

Hehrlein, C., et al., "Low–Dose Radiactive Endovascular Stents Prevent Smooth Muscle Cell Proliferation and Neointimal Hyperplasia in Rabbits", *Circulation*, 92, 1570–1575, (1995).

Hehrlein, C., et al., "Pure Beta–particle–emitting Stents Inhibit Neointima Formation in Rabbits", *Circulation*, 93, 641–645, (1996).

Heldin, et al., "Demonstration of an Antibody Against Platelet–Derived Growth Factor.", *Exp. Cell. Res.*, 136, 255–261, (Dec. 1981).

Heller, et al., "Preparation of Polyacetals by the Reaction of Divinyl Ethers and Polyols.", *J. Polymer Science*, Polymer Letters Edition, 18, 293–297, (Apr. 1980).

Henriksson, et al., "Hormonal Regulation of Serum Lp (a) Levels.", *J. Clin. Invest.*, 89, 1166–1171, (Apr. 1992).

Hoff, H.F., et al., "Modification of Low Density Lipoprotein with 4–Hydroxynonenal Induces Uptake by Macrophages", *Arteriosclerosis*, 9, 538–549, (Jul./Aug., 1989).

Hofmann, J., et al., "Enhancement of the Antiproliferative Effect of cis–Diamminedichloroplatinum(II) and Nitrogen Mustard by Inhibitors of Protein Kinase C", *Int. J. Cancer*, 42, 382–388, (1988).

Holland, J.A., et al., "Atherogenic Levels of Low–Density Lipoprotein Increase Endocytotic Activity in Cultured Human Endothelial Cells", *American Journal of Pathology*, 140, 551–558, (1992).

Holmes, Jr., D.R., "Remodeling Versus Smooth Muscle Cell Hyperpasia.", *Restenosis Summit VI*, The Cleveland Clinic Foundation, 222–223, (1994).

Howell, A., et al., "New Endocrine Therapies for Breast Cancer", *European Journal of Cancer*, 32A, 576–588, (1996).

Huang, S.S., et al., "Transforming Growth Factor Beta Peptide Antagonists and Their Conversion to Partial Agonists", *The Journal of Biological Chemistry*, 272(43), 27155–27159, (1997).

Huehns, T.Y., et al., "Adventitia as a Target for Intravascular Local Drug Delivery", *Heart*, 75, 537–538, (1996).

Hughes, D.E., et al., "Estrogen Promotes Apoptosis of Murine Osteoclasts Mediated by TGF–beta", *Nature Medicine*, 2, 1132–1136, (1996).

Hwang, et al., "Effects of Platelet–Contained Growth Factors (PDGF, EGF, IGF–1, and TGF–B) on DNA Synthesis in Porcine Aortic Smooth Muscle Cells in Culture.", *Exp. Cell Res.*, 200, 358–360, (1992).

Isner, J.M., "Vascular Remodeling: Honey, I Think I Shrunk the Artery", *Circulation*, 89, 2937–2841, (Jun., 1994).

Jande, S.S., et al., "Effects of Cytochalasin B and Dihydrocytochalasin B on Calcium Transport by Intestinal Absorptive Cells", *Calcified Tissue International*, 33, 143–151, (1981).

Jarvis, B.B., et al., "Allelopathic Agents from *Parthenium hysterophorus* and *Baccharis megapotamica*", *In: Chemistry of Alleopathy: Biochemical Interactions Among Plants*, ACS Symposium Series No. 268, Thompson, A.C., (ed.),, 149–159, (1985).

Jarvis, B.B., et al., "Macrocyclic and Other Novel Trichothecenes: Their Structure, Synthesis, and Biological Significance", *Acc. Chem. Res.*, 15, 388–395, (1982).

Jenkins, G.M., et al., "Local Delivery of Taxol Inhibits Neointimal Regrowth Following Balloon Injury of the Rat Carotid Artery", *Circulation*, 90, 67th Scientific Sessions, Abstract No. 1596, p. I-297, (Oct., 1994).

"Breast Cancer Prevention Trial Should Resume, ODAC Says", *The Breast Cancer Letter*, 20, 4–5, (Jun. 17, 1994).

"Churchill's Medical Dictionary", *definition of "cytostatic"*, 473, (1989).

"Coronary Artery Disease: Restenosis and Reocclusion After Surgical and Nonsurgical Inverventions, Part I", *Drug & Market Development*, 5, 121–129, (Sep. 26, 1994).

"Cytochalasins", *In: The Merck Index, Eleventh Edition*, Merck & Co., Rahway, NJ, 438–439, (1989).

"Glaxo Wellcome Preclinical Data: Preclinical studies conducted with GW 5638, a selective estrogen receptor modulator developed by Glaxo Wellcome, indicate that the compound acts both as an agonist and antagonist at estrogen receptor within specific . . . ", *R & D Focus Drug News*, (Sep. 8, 1997).

"Growth Factor Via Gene Therapy Abates Sore Rheumatoid Joints", *BioWorld Today: The Daily Biotechnology Newspaper*, 9(115), Leff, David N., Editor, 1, (Jun. 17, 1998).

"Health Report—The Good News", *Time*, 23, (Apr. 1, 1996).

"Heparin", *In: Modern Pharmacology*, Craig, C.R., et al., (eds.), Little, Brown and Company, Boston, MA, p. 399, (1982).

"ICI United States, Inc., Tamoxifen citrate, Summary For Basis of Approval", (Dec. 30, 1977).

"Micellar and Lyotropic Liquid Crystalline Phases Containing Nonionic Active Substances", *In: Lyotropic Liquid Crystals and the Structure of Biomembranes*, S. Fribert, (ed.), Advances in Chemistry Series, No. 152, American Chemical Society, 28–42, (1976).

"Muscle–Binding Gene Sees Two–Track Payoff: Human Therapies, Animal Meat", *BioWorld Today: The Daily Biotechnology Newspaper*, 8(85), Leff, David N., Editor, 1–3, (May 2, 1997).

"Nolvadex Tamoxifene Citrate", *ICI Pharma*, 64033–02, Rev. L/07/92.

"Prevention of Coronary Heart Disease", *In: Avery's Drug Treatment—Principles and Practice of Clinical Pharmacology and Therapeutics*, Speight, T. M., (ed.), Williams and Wilkins, Baltimore, 594–595, (1987).

"Quantikine—Human TGFbeta1 Immunoassay", Product Brochure, Catalog No. DB100, R&D Systems, Inc.,, p. 1–19.

"Schering/Orion Fareston Anti–Estrogen for Treatment of Metastatic Breast Cancer 'Similar' to Tamoxifen, FDA Oncologic Committee Says in Approval Vote", *F–D–C Reports*, 15–16, (Oct. 23, 1995).

"Shiga Medical Center for Adult Diseases, The Impact of Tranilast on Restenosis Following Coronary Angioplasty: The Tranilast Restenosis Following Angioplasty Trial (TREAT)", *Circulation*, 90, I–82, Abstract No. 0, (Oct. 1988).

"Tamoxifen therapy found safe for survivors of breast cancer", *Fred Hutchinson Cancer Research Center Newsletter*, 1(21), (Oct. 1995).

"Toprol XLTM Tablets", *In: Physician's Desk Reference.*, 658–660, (Probably 1992).

Agarwal, A.K., et al., "Estrogen Receptor–Binding Affinity of Tamoxifen Analogs with Various Side Chains and their Biologic Profile in Immature Rat Uterus", *Steroids*, 56, 486–489, (1991).

AinMelk, Y., et al., "Tamoxifen Citrate Therapy in Male Fertility", *Fertility and Sterility*, 48, 113–117, (Jul. 1987).

Alberts, B., et al., "Actin Filaments are Continually Formed and Broken Down in Cells", *In: Molecular Biology of the Cell*, Garland Publishing, London, 571, (1983).

Alderidge, D.C., et al., "The Structures of Cytochalasins A and B", *J. Chem. Soc.*, 17, 1667–1676, (1967).

Alich, A.A., et al., "Comparison of Aspirin and Copper Aspirinate with Respect to Gastric Mucosal Damage in the Rat", *Journal of Pharmaceutical Sciences*, 72, 1457–1461, (Dec. 1983).

Alich, A.A., et al., "Gastric Mucosal Damage Due to Aspirin and Copper Aspirinate Assessed by Gastric Mucosal Potential Difference Changes", *Journal of Pharmacological and Toxicological Methods*, 27, 245–250, (Jul. 1992).

Alich, A.A., et al., "Response to: 'The Ulcerogenic Potential of Copper Aspirinate Seems to be More Imaginary than Real'", *Journal of Pharmaceutical Sciences*, 73, Open Forum, 1876–1877, (Dec. 1984).

Allemann, et al., "Distribution, Kinetics, and Elimination of Radioactivity after Intravenous and Intramuscular Injection of 14C–Savoxepoine Loaded Poly (D,L–lactic acid) Nanospheres to Rats", *J. Controlled Release*, 29, 97–104, (1994).

Allemann, E., et al., "Drug Loaded Poly(lactic acid) Nanoparticles Produced by a Versible Salting–out Process: Purification of an Injectable Dosage Form", *Eur. J. Pharm. Biopharm*, 39, 13–18, (1993).

Allen, K.E., et al., "Evidence For The Metabolic Activation of Non–Steroidal Antioestrogens: A Study of Structure–Activity Relationships ", *Br. J. Pharmac.*, 71, 83–91, (1980).

Anderson, et al., "Effects of Acetate Dialysate on Transforming Growth Factor B1–interleukin and B2–micorglobulin Plasma Levels", *Kidney International*, 40, 1110–1117, (1991).

Anker, et al., "Plasma Levels of the Atherogenic Amino Acid Homocysteine in Post–Menopausal Women with Breast Cancer Treated with Tamoxifen", *Int. J. Cancer*, 60, 365–368, (1995).

Arao, Y., et al., "A synthetic oestrogen antagonist, tamoxifen, inhibits oestrogen–induced transcriptional, but not post–transcriptional, regulation of gene expression", *Biochem. J.*, 313, 269–274, (1996).

Aschermann, M., "Restenosis after percutaneous transluminal coronary angioplasty Pathophysiology, new trends in prevention and treatment", *Cor Vasa*, 36, 211–218, (1994).

Assoian, et al., "Type Beta Transforming Growth Factor in Human Platelets: Release During Platelet Degranulation and Action on Vascular Smooth Muscle Cells", *J. Cell Biol.*, 102, 1217–1223, (Apr. 1986).

Assoian, R.K., et al., "Cellular Transformation by Coordinated Action of Three Peptide Growth Factors from Human Platelets", *Nature*, 309, 804–806. (Jun. 28, 1984).

Attwood, et al., "A Light Scattering Study on Oil–in–Water Microemulsions", *Int'l J. Pharm*, 52, 165–171 (1989).

Bagdade, J.D., et al., "Effects of Tamoxifene Treatment of Plasma Lipids and Lipoprotein Lipid Composition", *J. Clinical Endocrinology and Metabolism*, 70, 1132–1135, (1990).

Baim, D.S., et al., "Nonatherosclerotic Coronary Heart Disease", In: The Heart: Arteries and Veins, Sixth Edition, Logue, R.B., et al., (eds.), McGraw–Hill Book Company, New York, 1016–1025, (1986).

Bamburg, J.R., et al., "Biological and Biochemical Actions of Trichothecene Mycotoxins", In: Progress in Molecular and Subcellular Biology, vol. 8, Hahn, F.E., et al., (eds.), Springer–Verlag, New York, p. 41–110, (1983).

Bang, H.O., et al., "The Composition of the Eskimo Food in North Western Greenland", Am. J. Clin. Nutr., 33, 2657–2661, (1980).

Baquial, J.G., et al., "Down–Regulation of NADPH–Diaphorase (Nitric Oxide Synthase) May Account for the Pharmocological Activities of Cu(II)sub2(3,5–Diisopropylsalicylate)sub4", J. Inorganic Biochem., 60, 133–148, (1995).

Baral, E., et al., "Modulation of Lymphokine–Activated Killer Cell–Mediated Cytotoxicity By Estradiol and Tamoxifen", Int. J. Cancer, 66, 214–218, (1996).

Barath, et al., "Low Dose of Antitumor Agents Prevents Smooth Muscle Cell Proliferation After Endothelial Injury", JACC, 13, 252A, (Feb. 1989).

Barbacid, M., et al., "Binding of [acetyl–14C]Trichodermin to the Peptidyl Transferase Center of Eukaryotic Ribosomes", Euro. J. Biochem., 44, 437–444, (1974).

Barinaga, "Gene Therapy for Clogged Arteries Passes to Test in Pigs", Science, 265, 738, (Aug. 5, 1994).

Beck, et al., "Poly(DL–lactide–co–glycolide)/norethisterone microacapsules: an injectable biodegradable contraceptive", Biol. Reprod., 28, 186–195, (1983).

Beck, L., et al., "Vascular Development: Cellular and Molecular Regulation", The FASEB Journal, 11, 365–373, (1997).

Benita, et al., "Submicron Emulsions as Colloidal Drug Carriers for Intravenous Administration: Comprehensive Physicochemical Characterization", J. of Pharmaceutical Sciences, 82, 1069–1079, (Nov. 1993).

Bertelli, et al., "Adjuvant Tamoxifen in Primary Breast Cancer: Influence on Plasma Lipids and Antitrhombin III Levels", Breast Cancer Res. and Treatment, 12, 307–310, (1988).

Bier, J.D., et al., "Arterial Remodeling: Importance in Primary Versus Restenotic Lesions", JACC, Abstract No. 875–96, p. 139A, (Feb., 1994).

Bittiner, S.B., et al., "A Double–Blind, Randomised, Placebo–Controlled Trial of Fish Oil in Psoriasis", The Lancet, 1, 378–380, (Feb. 20, 1988).

Bluming, "Hormone Replacement Therapy: Benefits and Risks for the General Postmenopausal Female Population and for Women with a History of Prevously Treated Breast Cancer", Seminars in Oncology, 20, 662–674, (Dec. 1993).

Bogyo, D., et al., "Cytochalasin–B–induced Immunosuppression of Murine Allogenic Anti–Tumor Response and the Effect of Recombinant Human Interleukin–2", Cancer Immunol. Immunother., 32, 400–405, (1991).

Border, W.A., et al., "Targeting TGF–Beta for Treatment of Disease", Nature Medicine, 1(10), 1000–1001, (Oct. 1995).

Bousquet, P.F., et al., "Effects of Cytochalasin B in Culture In Vivo on Murine Madison 109 Lung Carcinoma and on B16 Melanoma", Cancer Research, 50, 1431–1439, (Mar. 1, 1990).

Brand, C., et al., "Transforming Growth Factor Beta1 Decreases Cholesterol Supply to Mitochondria via Repression of Steroidogenic Acute Regulatory Protein Expression", The Journal of Biochemistry, 273(11), 6410–6416, (1998).

Brody, J.E., "Study Finds New Estrogen Offers Benefit Without Risk", The New York Times, A32, (Dec. 4, 1997).

Brott, B.C., et al., "Vessel Remodeling After Angioplasty: Comparative Anatomic Studies", JACC, Abstract No. 875–43, p. 138A, (Feb., 1994).

Bruengger, et al., "Smooth Muscle Cell of the Canine Prostate in Spontaneous Benign Hyperplasia, Steroid Induced Hyperplasia and Estrogen or Tamoxifen Treated Dogs", J. Urology, 130, 1208–1210, (Dec. 1983).

Bruning, et al., "Tamoxifen, Serum Lipoproteins and Cardiovascular Risk", Br. J. Cancer, 58, 497–499, (1988).

Bumol, et al., "Unique Glycoprotein–proteoglycan Complex Defined by Monoclonal Antibody on Human Melanoma Cells", PNAS USA 79, 1245–1249, (Feb. 1982).

Burr, M.L., et al., "Effects of Changes in Fat, Fish and ibre Intakes on Death and Myocardial Reinfarction: Diat and Reinfarction Trial (DART)", The Lancet, 757–761, (Sep. 30, 1989).

Burton, T.M., "Lilly Osteoporosis Treatment Shows Promise", The Wall Street Journal, p. A3, A6, (Jun. 6, 1997).

Butta, A., et al., "Induction of Transforming Growth Factor Beta1 in Human Breast Cancer in Vivo Following Tamoxifen Treatment", Cancer Research, 52, 4261–4164, (1992).

Camenzind, E., et al., "Use of Locally Delivered Conventional Drug Therapies", Semin. Intervent. Cardiol., 1, 67–76, (Mar. 1996).

Cannon, M., et al., "Competition Between Trichodermin and Several Other Sesquiterpene Antibiotics for Binding to their Receptor Site(s) on Eukaryotic Ribosomes", Biochem. J., 160, 137–145, (1976).

Casscells, W., et al., "Elimination of Smooth Muscle Cells in Experimental Restenosis: Targeting of Fibroblast Growth Factor Receptors", Proc. Natl. Acad. Sci. USA, 89, 7159–7163, (1992).

Chaldakov, G.N., et al., "Cyclic AMP–and Cytochalasin B–induced Arborization in Cultured Aortic Smooth Muscle Cells: Its Cytopharmacological Characterization", Cell and Tissue Research, 255, 434–442, (1989).

Chander, et al., "Pyrrolidino–4–iodotamoxifen and 4–iodotamoxifen, New Analogues of the Antiestrogen Tamoxifen for the Treatment of Breast Cancer", Cancer Res., 51, 5851–5858, (Nov. 1, 1991).

Chandrasekar, B., et al., "Dietary Omega–3 Lipids Delay the Onset and Progression of Autoimmune Lupus Nephritis by Inhibiting Transforming Growth Factor Beta mRNA and Protein Expression", Journal of Autoimmunity, 8, 381–393, (1995).

Chandy, T., et al., "Chitosan Matrix for Oral Sustained Delivery of Ampicillin", Biomaterials, 14, 939–944, (1993).

Chang, M.P., et al., "Comparison of the Intoxication Pathways of Tumor Necrosis Factor and Diphtheria Toxin", Infection and Immunity, 58, 2644–2650, (Aug., 1990).

Chao, et al., "Altered Cytokine Release in Peripheral Blood Mononuclear Cell Cultures from Patients with the Chronic Fatigue Syndrome", Cytokine, 3, 292–298, (Jul. 1991).

Chapman, G.D., et al., "A Bioabsorbable Stent: Initial Experimental Results", Supplement III Circulation, 82, Abstract No. 0283, III–72, (Oct. 1990).

Charlier, et al., "Tamoxifen in the Treatment of Breast Cancer", *J. Gynecol. Obstet Biol. Reprod.*, 23, 751–756, (1994).

Charlier, C., et al., "Tamoxifen and Its Active Metabolite Inhibit Growth of Estrogen Receptor–Negative MDA–MB–435 Cells", *Biochemical Pharmacology*, 49(3), 351–358, (Jan. 1995).

Chauhan, A., et al., "Activation of Transforming Growth Factor–beta is Inversely Correlated with Three Major Risk Factors for Coronary Artery Disease: Lipoprotein(a), LDL–Cholesterol and Plasminogen Activator Inhibitor–1", *Circulation*, 90, 67th Scientific Sessions, Abstract No. 3354, p. I–623, (Oct., 1994).

Cheitlin, M.D., et al., "Myocardial Infarction without Atherosclerosis", *JAMA*, 231, 951–959, (1975).

Clark, D.A., et al., "Coronary Artery Spasm: Medical Management, Surgical Denervation, and Autotransplantation", *The Journal of Thoracic and Cardiovascular Surgery*, 73, 332–339, (1977).

Clark, S.C., et al., "Tolerance and Responses To Tamoxifen and Toremifene in Male Patients with Coronary Artery Disease.", Abstract for ACC Meeting, Mar. 1999.

Clinton, S.K., "Induction in vivo of Interleukin–1 (IL–1) Gene Expression in Rabbit Aortic Tissue", *Abstracts of the 61st Scientific Sessions*, II–65.

Clowes, A.W., et al., "Kinetics of Cellular Proliferation after Arterial Injury—I. Smooth Muscle Growth in the Absence of Endothelium", *Laboratory Investigation*, 49, 327–333, (1983).

Clowes, A.W., et al., "Kinetics of Cellular Proliferation after Arterial Injury—III. Endothelium and Smooth Muscle Growth in Chronically Denuded Vessels", *Laboratory Investigation*, 54, 295–303, (1986).

Clowes, A.W., et al., "Mechanisms of Stenosis after Arterial Injury", *Laboratory Investigation*, 49, 208–215, (1983).

Clowes, A.W., et al., "Significance of Quiescent Smooth Muscle Migration in the Injured Rat Carotid Artery", *Circulation Research*, 56, 139–145, (Jan., 1985).

Cohen, et al., "Controlled Delivery Systems for Proteins Based on Poly(lactic/glycolic acid) Microspheres", *Pharmaceutical Research*, 8, 713–720, (1991).

Cole, R.J., et al., "The Cytochalasins", *In: Handbook of Toxic Fungal Metabolics*, Academic Press, New York, p. 264–265, 281–282, (1981).

Colletta, A.A., et al., "Anti–oestrogens induce the secretion of active transforming growth factor beta from human fetal fibroblasts", *Br. J. Cancer*, 62, 405–409, (1990).

Comezoglu, F.T., et al., "Serum Stability and Cytotoxicity of the Macrocyclic Trichothecenes Roridin A, Verrucarin A and Their Monoclonal Antibody Conjugates", *Proceedings of the American Association for Cancer Research*, 31, Abstract No. 1723, p. 291, (Mar., 1990).

Coombes, R.C., et al., "Idoxifene: Report of a Phase I Study in Patients with Metastatic Breast Cancer", *Cancer Research*, 55, 1070–1074, (Mar. 1, 1995).

Cotton, P., "Restenosis Trials Suggest Role for Remodeling", *JAMA*, 271, 1302–1305, (May 4, 1994).

Cowsar, et al., "Poly(actide–co–glycolide) Microcapsules for Controlled Release of Steroids", *Methods Enzymology*, 112, 101–116, (1985).

Craig, et al., "Anticoagulant Drugs", In Modern Pharmacology, Little, Brown and Co., Boston, 399, (1982).

Crissman, H.A., et al., "Transformed Mammalian Cells are Dificient in Kinase–Mediated Control of Progression Through the G1 Phase of the Cell Cycle", *Proc. Natl. Acad. Sci. USA*, 88, 7580–7584, (Sep., 1991).

Csernok, E., et al., "Transforming Growth Factor–beta (TGF–beta) Expression and Interaction with Proteinase 3 (PR3) in Anti–Neutrophil Cytoplasmic Antibody (ANCA)–associated Vasculitis", *Clin. Exp. Immunol.*, 105, 104–111, (1996).

Cunningham, A., et al., "A Study of the Structural Basis of the Carcinogenicity of Tamoxifen, and Toremifene and their Metabolites", *Mutation Research*, 349, 85–94, (1996).

Currier, J.W., et al., "Restenosis After Percutaneous Transluminal Coronary Angioplasty: Have We Been Aiming at the Wrong Target?", *JACC*, 25, 516–520, (Feb., 1995).

Dangas, G., et al., "Management of Restenosis after Coronary Intervention", *American Heart Journal*, 132, 428–436, (1996).

Danielpour, "Improved Sandwich Enzyme–linked Immunosorbent Assays Transforming Growth Factor B1", *J. Immunol. Methods*, 158, 17–25, (1993).

Danielpour, D., et al., "Evidence for Differential Regulation of TGF–Beta1 and TGF–Beta2 Expression in Vivo by Sandwich Enzyme–linked Immunosorbent Assays", *Annals N.Y. Acad. Sci.*, 593, 300–302, (1990).

Danielpour, D., et al., "Immunodetection and Quantitation of the Two Forms of Transforming Growth Factor–Beta (TGF–Beta1 and TGF–Beta2) Secreted by Cells in Culture", *J. Cell. Physiol.*, 138, 79–86, (1989).

Dasch, J.R., et al., "Capture Immunoassays Specific for TGF–Beta1 and TGF–Beta2: Use in Pharmacokinetic Studies", *Annals N.Y. Acad. Sci.*, 593, 303–305, (1990).

Davies, A.M., et al., "Peroxidase Activation of Tamoxifen and Toremifene Resulting in DNA Damage and Covalently Bound Protein Adducts", *Carcinogenesis*, 16, 539–545, (1995).

de Alvare, L.R., et al., "Mechanism of Superoxide Anion Scagenging Reaction by Bis–(Salicylanto)–Copper(II) Complex", *Biochem. Biophys. Res. Comm.*, 69, 687–694, (1976).

deAlvare, L.R., et al., "Mechanism of Superoxide Anion Scavenging Reaction by Bis–(Salicylato)–Copper(II) Complex", *Biochemical and Biophysical Research Communications*, 69, 687–694, (1976).

Dehmer, G.J., et al., "Reduction in the Rate of Early Restenosis After Coronary Angioplasty by a Diet Supplemented with n–3 Fatty Acids", *N. Engl. J. Med.*, 319, 733–740, (1988).

Delmas, P.D., "Effects of Raloxifene on Bone Mineral Density, Serum Cholesterol Concentrations, and Uterine Endometrium in Postmenopausal Women", *The New England Journal of Medicine*, 337(23), (1997).

Detre, K., et al., "Percutaneous Transluminal Coronary Angioplasty in 1985–1986 and 1977–1981", *The New England Journal of Medicine*, 318, 265–270, (Feb. 4, 1988).

Di Mario, C., et al., "Is the Mechanism of Restenosis Device–Independent? Serial Assessment with Intracoronary Ultrasound", *Circulation*, 90, Abstract No. 115, p. I–24, (1994).

DiGiacomo, R.A., et al., "Fish–Oil Dietary Supplementation in Patients with Raynaud's Phenomenon: A Double–Blind, Controlled, Prospective Study", *Am. J. Med.*, 86, 158–164, (Feb. 1989).

DiLuccio, R.C., et al., "Sustained–Release Oral Delivery of Theophylline by Use of Polyvinyl Alcohol and Polyvinyl Alcohol–Methyl Acrylate Polymers", *Journal of Pharmaceutical Sciences*, 83, 104–106, (Jan. 1994).

Dimond, P.F., "TGF–Beta Shows Potential as Therapeutic Agent for Macular Holes", *Genetic Engineering News*, p. 7, 19, (Feb. 1, 1993).

Donnelly, J., et al., "Protective Efficacy of Intramuscular Immunization with Naked DNA; DNA Vaccines: A New Era in Vaccinology, Margaret A. Liu et al., eds.", *Annals of the New York Academy of Sciences*, 772, 40–44, (1995).

Dove, C.R., et al., "Effect of Vitamin E and Copper on the Vitamin E Status and Performance of Growing Pigs", *J. Anim. Sci.*, 69, 2516–2523, (1991).

Dowsett, M., "New Developments in the Hormonal Treatment of Breast Cancer", In: The Treatment of Cancer: Beyond Chemotherapy, Conference Documentation, The Glouster Hotel, London, 7 p., (Mar. 13–14, 1995).

Dragan, Y.P., et al., "Comparison of the Effects of Tamoxifen and Toremifene on Liver and Kidney Tumor Promotion in Female Rats", *Carcinogenesis*, 16, 2733–2741, (1995).

Draper, M.W., et al., "Antiestrogenic Properties of Raloxifene", *Pharmacology*, 50, 209–217, (Apr. 1995).

Dyerberg, J., "Platelet—Vessel Wall Interaction: Influence of Diet", *Phil. Trans. R. Soc. Lond.*, B 294, 372–381, (1981).

Dyerberg, J., et al., "The Effect of Arachidonic–and Eicosapentaenoic Acid on the Synthesis of Prostacyclin–like Material in Human Umbilical Vasculature", *Artery*, 8, 12–17, (1980).

Ebner, et al., "Cloning of a Type I TGF–B Receptor and Its Effect on TGF–B Binding to the Type II Receptor", *Science*, 260, 1344–1348, (May 28, 1993).

FIG. 8C

5 MIN. RA–48HR. RECOVERY ON HT29

□ FREE RORIDINE A
◆ NRAN01–2'RA
■ NRAN01–13'RA x-axis: ug/ml OF RORIDIN A
y-axis: % CONTROL

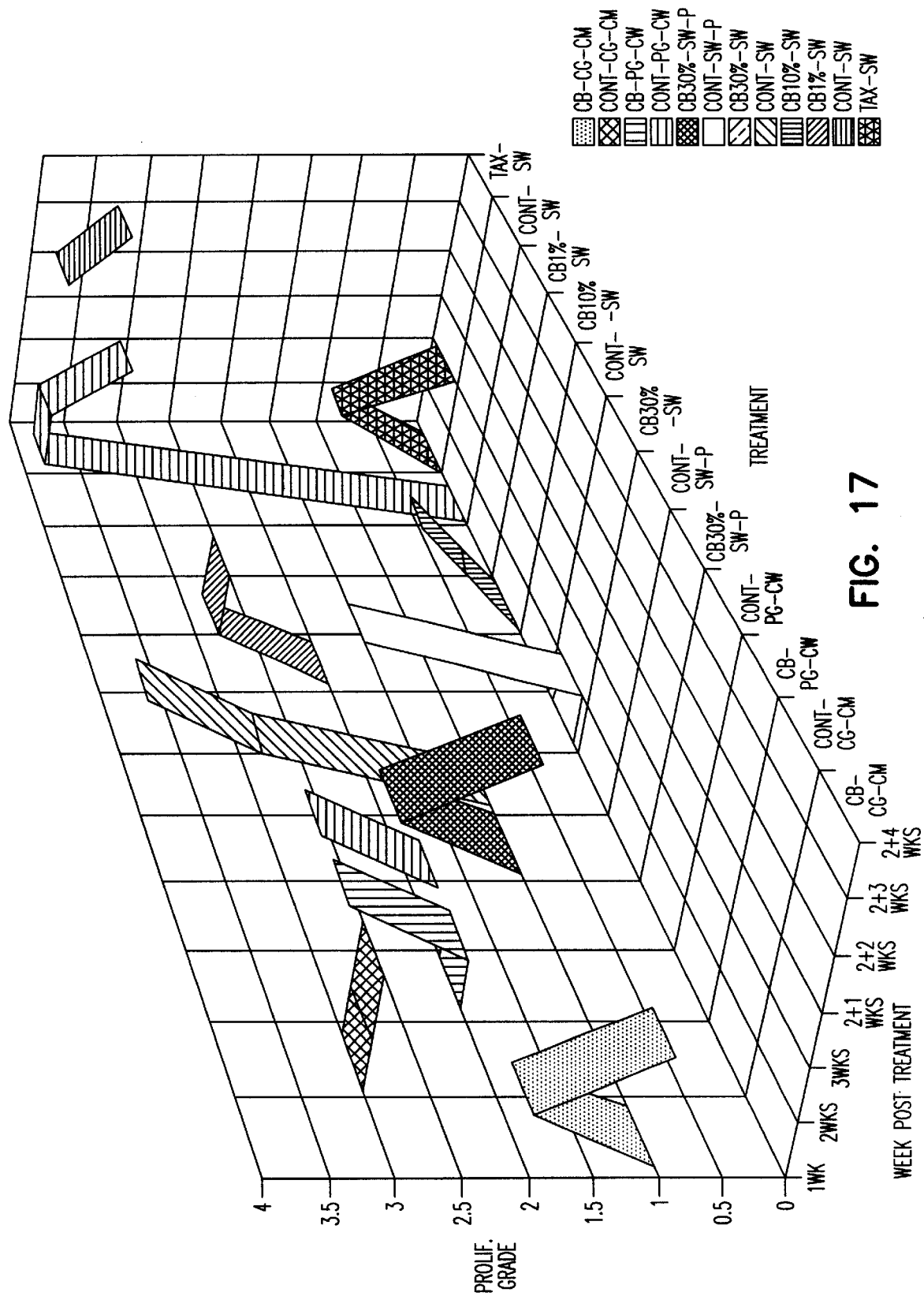

… (continued)

THERAPEUTIC INHIBITOR OF VASCULAR SMOOTH MUSCLE CELLS

RELATED APPLICATIONS

This application is a divisional application of U.S. application Ser. No. 08/829,991 filed Mar. 31, 1997, which is a continuation-in-part U.S. application Ser. No. 08/450,793, filed May 25, 1995 now U.S. Pat. No. 5,811,447, currently pending, which is a continuation of U.S. application Ser. No. 08/062,451, filed May 13, 1993; and a continuation-in-part application of international application PCT/US96/02125, filed Feb. 15, 1996, which is a continuation-in-part application of U.S. application Ser. No. 08/389,712, filed Feb. 15, 1995, currently pending, the disclosures of which are incorporated by reference herein.

BACKGROUND OF THE INVENTION

Percutaneous transluminal coronary angioplasty (PTCA) is widely used as the primary treatment modality in many patients with coronary artery disease. PTCA can relieve myocardial ischemia in patients with coronary artery disease by reducing lumen obstruction and improving coronary flow. The use of this surgical procedure has grown rapidly, with 39,000 procedures performed in 1983, nearly 150,000 in 1987, 200,000 in 1988, 250,000 in 1989, and over 500,000 PTCAs per year are estimated by 1994 (Popma et al., Amer. J. Med., 88: 16N–24N (1990); Fanelli et al, Amer. Heart Jour., 119: 357–368 (1990); Johnson et al., Circulation, 78 (Suppl. II): II-82 (1988)). Stenosis following PTCA remains a significant problem, with from 25% to 35% of the patients developing restenosis within 1 to 3 months. Restenosis results in significant morbidity and mortality and frequently necessitates further interventions such as repeat angioplasty or coronary bypass surgery. As of 1993, no surgical intervention or post-surgical treatment has proven effective in preventing restenosis.

The processes responsible for stenosis after PTCA are not completely understood but may result from a complex interplay among several different biologic agents and pathways. Viewed in histological sections, restenotic lesions may have an overgrowth of smooth muscle cells in the intimal layers of the vessel (Johnson et al., Circulation, 78 (Suppl. II): II-82 (1988)). Several possible mechanisms for smooth muscle cell proliferation after PTCA have been suggested (Popma et al., Amer. J. Med., 88: 16N–24N (1990); Fanelli et al, Amer. Heart Jour., 119: 357–368 (1990); Liu et al., Circulation, 79: 1374–1387 (1989); Clowes et al., Circ. Res., 56: 139–145 (1985)).

Compounds that reportedly suppress smooth muscle proliferation in vitro (Liu et al., Circulation, 79: 1374–1387 (1989); Goldman et al., Atherosclerosis, 65: 215–225 (1987); Wolinsky et al.,JACC, 15 (2): 475–481 (1990)) may have undesirable pharmacological side effects when used in vivo. Heparin is an example of one such compound, which reportedly inhibits smooth muscle cell proliferation in vitro but when used in vivo has the potential adverse side effect of inhibiting coagulation. Heparin peptides, while having reduced anti-coagulant activity, have the undesirable pharmacological property of having a short pharmacological half-life. Attempts have been made to solve such problems by using a double balloon catheter, i.e., for regional delivery of the therapeutic agent at the angioplasty site (e.g., Nabel et al., Science, 244: 1342–1344 (1989); U.S. Pat. No. 4,824,436), and by using biodegradable materials impregnated with a drug, i.e., to compensate for problems of short half-life (e.g., Middlebrook et al., Biochem. Pharm. , 38 (18): 3101–3110 (1989); U.S. Pat. No. 4,929,602).

At least five considerations would, on their face, appear to preclude use of inhibitory drugs to prevent stenosis resulting from overgrowth of smooth muscle cells. First, inhibitory agents may have systemic toxicity that could create an unacceptable level of risk for patients with cardiovascular disease. Second, inhibitory agents might interfere with vascular wound healing following surgery and that could either delay healing or weaken the structure or elasticity of the newly healed vessel wall. Third, inhibitory agents which kill smooth muscle cells could damage surrounding endothelium and/or other medial smooth muscle cells. Dead and dying cells also release mitogenic agents that might stimulate additional smooth muscle cell proliferation and exacerbate stenosis. Fourth, delivery of therapeutically effective levels of an inhibitory agent may be problematic from several standpoints: namely, a) delivery of a large number of molecules into the intercellular spaces between smooth muscle cells may be necessary, i.e., to establish favorable conditions for allowing a therapeutically effective dose of molecules to cross the cell membrane; b) directing an inhibitory drug into the proper intracellular compartment, i.e., where its action is exerted, may be difficult to control; and, c) optimizing the association of the inhibitory drug with its intracellular target, e.g., a ribosome, while minimizing intercellular redistribution of the drug, e.g. to neighboring cells, may be difficult. Fifth, because smooth muscle cell proliferation takes place over several weeks it would appear a priori that the inhibitory drugs should also be administered over several weeks, perhaps continuously, to produce a beneficial effect.

As is apparent from the foregoing, many problems remain to be solved in the use of inhibitory drugs to effectively treat smooth muscle cell proliferation. Thus, there is a need for a method to inhibit or reduce stenosis due to proliferation of vascular smooth muscle cells following traumatic injury to vessels such as occurs during vascular surgery. There is also a need to deliver compounds to vascular smooth muscle cells which exert inhibitory effects over extended periods of time.

SUMMARY OF THE INVENTION

The present invention provides a therapeutic method comprising the administration of at least one therapeutic agent to a procedurally traumatized, e.g., by an angioplasty procedure, mammalian vessel. Preferably, the therapeutic agent is a cytoskeletal inhibitor. Preferred cytoskeletal inhibitors in the practice of the present invention, include, for example, taxol and analogs or derivatives thereof such as taxotere, or a cytochalasin, such as cytochalasin B, cytochalasin C, cytochalasin A, cytochalasin D, or analogs or derivatives thereof. The administration of a therapeutic agent of the invention is effective to biologically stent the vessel, inhibit or reduce vascular remodeling of the vessel, inhibit or reduce vascular smooth muscle cell proliferation, or any combination thereof. The administration of the therapeutic agent preferably is carried out during the procedure which traumatizes the vessel, e.g., during the angioplasty or other vascular surgical procedure. The invention also provides therapeutic compositions and dosage forms adapted for use in the present method, as well as kits containing them.

Thus, one embodiment of the invention provides a method for biologically stenting a traumatized mammalian blood vessel. The method comprises administering to the blood vessel an amount of a cytoskeletal inhibitor in a liquid vehicle effective to biologically stent the vessel. As used herein, "biological stenting" means the fixation of the vascular lumen in a dilated state near its maximal systolic diameter, e.g., the diameter achieved following balloon dilation and maintained by systolic pressure. The method comprises the administration of an effective amount of a cytoskeletal inhibitor to the blood vessel. Preferably, the cytoskeletal inhibitor is dispersed in a pharmaceutically acceptable liquid carrier, e.g., about 0.1 to about 10 µg for cytochalasin B/ml of aqueous vehicle, and preferably administered locally via a catheter. Another preferred embodiment of the invention is a cytochalasin or analog thereof dispersed in a pharmaceutically acceptable liquid carrier at about 0.001 to about 25 µg per ml of aqueous vehicle. Preferably, a portion of the amount administered penetrates to at least about 6 to 9 cell layers of the inner tunica media of the vessel and so is effective to biologically stent the vessel.

Preferred catheter administration conditions include employing a catheter to deliver about 4 to about 25 ml of a composition comprising the cytoskeletal inhibitor dispersed or dissolved in a pharmaceutically acceptable liquid vehicle. The cytoskeletal inhibitor is delivered at a hub pressure of about 3 to about 8 atm, more preferably about 4 to about 5 atm, for about 0.5 to about 5 minutes, more preferably for about 0.7 to about 3 minutes. Preferred hydrostatic head pressures for catheter administration include about 0.3 to about 1.0 atm, more preferably about 0.5 to about 0.75 atm. The amount of therapeutic agent is controlled so as to allow vascular smooth muscle cells to continue to synthesize protein, which is required to repair minor cell trauma, and to secrete interstitial matrix, thereby facilitating the fixation of the vascular lumen preferably in a dilated state near its maximal systolic diameter, i.e., to provide a biological stent of the vessel. Preferably, the therapeutic agent is administered directly or substantially directly to the traumatized area of the vascular smooth muscle tissue.

The invention further provides a method for inhibiting or reducing vascular remodeling of a traumatized mammalian blood vessel, by administering an effective amount of a cytoskeletal inhibitor to the traumatized blood vessel.

As described hereinbelow, a dose response study showed that cytochalasin B had a two logarithmic therapeutic index (TI). A large therapeutic index allows the diffusion of therapeutic levels of the agent from the delivery system, e.g., an implantable device, without toxicity to cells immediately adjacent to the exit port of the system. Moreover, even at the maximum concentration of cytochalasin B in a liquid vehicle, there was little or no toxicity observed in cells adjacent to the delivery system. It was also found that cytochalasin B and taxol both inhibit intimal proliferation in vessels subjected to a procedural vascular trauma. This inhibition results in a more rapid and complete endothelialization of the vessel wall following the trauma.

The invention also provides a therapeutic method comprising inhibiting diminution of vessel lumen diameter by administering to a traumatized vessel of a mammal an effective amount of a cytoskeletal inhibitor. The cytoskeletal inhibitor is administered via an implantable device, wherein the implantable device is not a catheter which has a first and a second expansile member, i.e., balloons, which are disposed on opposite sides of the vessel area to be treated in order to isolate the portion of the vessel to be treated prior to cytoskeletal inhibitor administration. Preferably, the isolated portion of the vessel is not washed to remove blood prior to cytoskeletal inhibitor administration ("bloodless angioplasty"). "Isolated," as used above, does not mean occlusive contact of the actual treatment area by the catheter balloon, which is preferred in the practice of the present invention. Moreover, bloodless angioplasty, such as that described in Slepian, U.S. Pat. No. 5,328,471, i.e., in which the region to be treated is washed, may introduce trauma or further trauma to the vessel, may increase the potential for complications and is not necessary to achieve a beneficial effect.

Thus, the invention further provides a method for inhibiting or reducing diminution in vessel lumen volume in a traumatized mammalian blood vessel. The method comprises administering to the blood vessel of a mammal an effective amount of cytoskeletal inhibitor, wherein the cytoskeletal inhibitor is in substantially crystalline form and wherein the crystals are of a size which results in sustained release of the cytoskeletal inhibitor. Preferably, the crystals are of a size of about 0.1 micron to about 10 mm, preferably about 1 micron to about 25 micron, in size. Methods to determine the size of crystals useful for sustained release are well known to the art. Preferably, the cytoskeletal inhibitor is administered in situ, by means of an implantable device, wherein the cytoskeletal inhibitor is releasably embedded in, coated on, or embedded in and coated on, the implantable device. Preferably, the crystalline cytoskeletal inhibitor is releasably embedded in, or dispersed in, a adventitial wrap, e.g., a silicone membrane. For example, a preferred therapeutic implantable device of the invention comprises about 5 to about 70, preferably about 7 to about 50, and more preferably about 10 to about 30, weight percent of a cytochalasin, e.g., cytochalasin B or an analog thereof, per weight percent of the adventitial wrap. Another preferred therapeutic implantable device of the invention comprises about 1 to about 70, preferably about 2 to about 50, and more preferably about 3 to about 10, weight percent of taxol or an analog thereof per weight percent of the adventitial wrap. Alternatively, a preferred therapeutic implantable device of the invention comprises about 35 to about 70, preferably about 35 to about 60, and more preferably about 35 to about 50, weight percent of taxol or an analog thereof per weight percent of the adventitial wrap.

Alternatively, the crystalline cytoskeletal inhibitor may be suspended in a vehicle which yields a solution comprising the crystals, i.e., it is a saturated solution.

The invention further provides a therapeutic method. The method comprises administering to a traumatized mammalian blood vessel a sustained release dosage form comprising microparticles or nanoparticles comprising a cytoskeletal inhibitor, e.g., cytochalasin, taxol, or analogs thereof. The sustained release dosage form comprising a cytochalasin or analog thereof is preferably administered via an implantable device which is not a catheter used to perform bloodless angioplasty. The amount administered is effective inhibit or reduce diminution in vessel lumen area of the mammalian blood vessel. The sustained release dosage form preferably comprises microparticles of 4 to about 50 microns in diameter. The sustained release dosage form can also preferably comprise about 2 to about 50, and more preferably greater than 3 and less than 10, microns in diameter. For nanoparticles, preferred sizes include about 10 to about 5000, more preferably about 20 to about 500, and more preferably about 50 to about 200, nanometers.

Also provided is a method comprising administering to a mammalian blood vessel a dosage form of a cytochalasin or an analog thereof in a non-liquid vehicle or matrix effective inhibit or reduce diminution in vessel lumen area of the mammalian blood vessel. Preferably the dosage form is a substantially solid dosage form. As used herein, "solid form" does not include microparticles, nanoparticles, and the like. The non-liquid vehicle or matrix preferably includes, but is not limited to, a gel, paste, or a membrane which comprises the cytochalasin or analog thereof.

Also provided is a kit comprising, preferably separately packaged, at least one implantable device adapted for the in situ delivery, preferably local delivery, of at least one cytoskeletal inhibitor to a site in the lumen of a traumatized mammalian vessel and at least one unit dosage form of the cytoskeletal inhibitor in a liquid vehicle adapted for delivery by said device. The administration of at least a portion of the unit dosage form to the traumatized vessel is effective to biologically stent the vessel, inhibit or reduce the vascular remodeling of the vessel, inhibit or reduce vascular smooth muscle cell proliferation, or any combination thereof.

Further provided is a kit comprising, preferably separately packaged, an implantable device adapted for the delivery of at least one therapeutic agent to a site in the lumen of a traumatized mammalian vessel and a unit dosage form comprising at least one cytoskeletal inhibitor, wherein the administration of at least a portion of the unit dosage form is effective to inhibit or reduce diminution in vessel lumen diameter of the vessel. The device is not a catheter which has a first and a second expansile member which are disposed on opposite sides of the region to be treated so as to isolate a portion of the vessel to be treated prior to administration or wherein the isolated portion of the vessel is not washed to remove blood prior to administration.

The invention also provides a kit comprising, separately packaged, an implantable device adapted for the delivery of at least one therapeutic agent to a site in the lumen of a traumatized mammalian vessel and a unit dosage form comprising an amount of microparticles or nanoparticles comprising taxol or an analog thereof. Preferably, the kit also comprises a second unit dosage form comprising a pharmaceutically acceptable liquid carrier vehicle for dispersing said microparticles or said nanoparticles prior to delivery. The delivery of the dispersed microparticles or nanoparticles to the traumatized mammalian vessel is effective to inhibit or reduce diminution in vessel lumen diameter in the vessel.

Yet another embodiment of the invention is a pharmaceutical composition suitable for administration by means of an implantable device. The composition comprises an amount of a cytochalasin or analog thereof effective to inhibit or reduce stenosis or restenosis of a mammalian vessel traumatized by a surgical procedure and a pharmaceutically acceptable non-liquid release matrix for said cytochalasin. Preferably, the release matrix comprises a gel, paste or membrane.

Also provided is a unit dosage form. The unit dosage form comprises a vial comprising about 10 to about 30 ml of about 0.001 $\mu$g to about 25 $\mu$g of a cytoskeletal inhibitor, preferably a cytochalasin, per ml of liquid vehicle, wherein the unit dosage form is adapted for delivery via an implantable device, and wherein the vial is labeled for use in treating or inhibiting stenosis or restenosis. Preferably, the unit dosage form comprises a vial comprising about 10 to about 30 ml of about 0.01 $\mu$g to about 10 $\mu$g of cytochalasin B per ml of liquid vehicle. Thus, the volume present in a vial may be greater than, or about the same as, the volume present in the implantable device. Likewise, the volume present in the implantable device may be greater than, or about the same as, the volume administered. Similarly, the volume administered may be greater than, or about the same as, the volume which has a beneficial effect.

Further provided is a unit dosage comprising a vial comprising a cytostatic amount of a cytoskeletal inhibitor in a pharmaceutically acceptable liquid vehicle. Preferably, the cytoskeletal inhibitor comprises a cytochalasin, taxol, or an analog thereof.

The invention also provides therapeutic devices. One embodiment of the invention comprises a therapeutic shunt comprising an amount of a cytoskeletal inhibitor effective to inhibit stenosis or reduce restenosis following placement of the therapeutic shunt. Another embodiment of the invention comprises therapeutic artificial graft comprising an amount of a cytochalasin or analog thereof to inhibit stenosis or reduce restenosis following placement of the graft. Yet another embodiment of the invention comprises a therapeutic adventitial wrap comprising an amount of a cytoskeletal inhibitor effective to inhibit stenosis or reduce restenosis following placement of the wrap.

BRIEF DESCRIPTION OF THE DRAWINGS

FIG. 8C graphically depicts results similar to those presented in FIG. 8A and FIG. 8B, above, but using a marker-negative control cell type, namely HT29. The results show that the "pulse" treatment with the RA-NR-AN-01 therapeutic conjugate did not exert long-lasting inhibitory effects on the cellular activity of marker-negative control cells, as measured by metabolic activity in HT29 cells that were allowed a 48 hour recovery period prior to testing.

FIG. 17 is a graph depicting the inhibition of smooth muscle cell proliferation in traumatized vessels over time by CB or TAX in silicone, CB in a collagen gel supported by a bovine collagen mesh (CG-CM) or CB in a pluronic gel supported by a bovine collagen mesh (PG-CW).

DETAILED DESCRIPTION OF THE INVENTION

Definitions

Figure 1A:
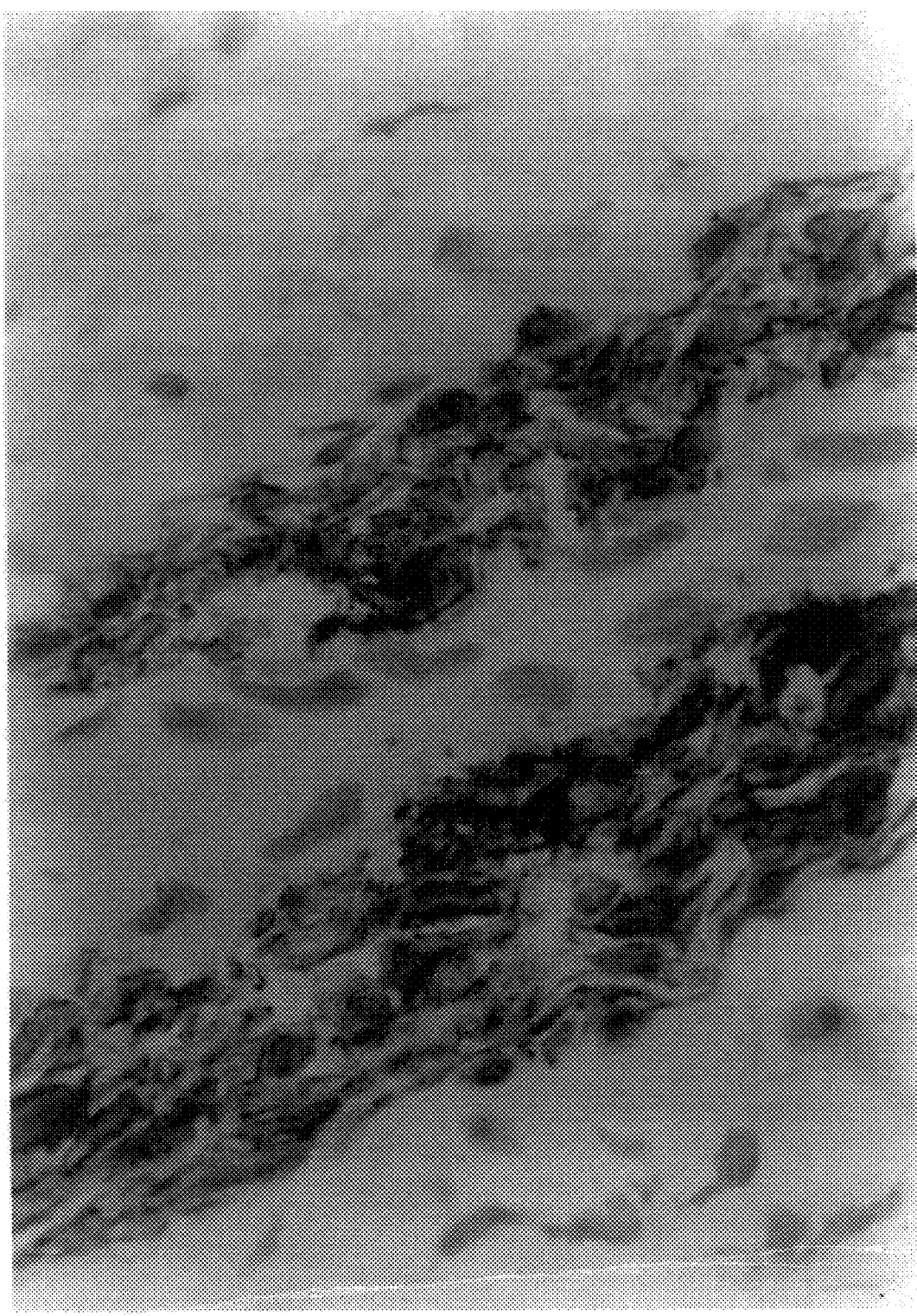
FIG. 1A is a photomicrograph of vascular smooth muscle cells of a 24-year-old male patient.

"Therapeutic conjugate" means a vascular smooth muscle or an interstitial matrix binding protein coupled (e.g., optionally through a linker moiety) to a therapeutic agent. Therapeutic conjugates of the invention are obtained by coupling a vascular smooth muscle binding protein to a therapeutic agent. In the therapeutic conjugate, the vascular smooth muscle binding protein performs the function of targeting the therapeutic conjugate to vascular smooth muscle cells or pericytes, and the therapeutic agent performs the function of inhibiting the cellular activity or proliferation of the smooth muscle cell or pericyte.

"Therapeutic agent" includes any moiety capable of exerting a therapeutic or prophylactic effect in the present method.

"Target" and "marker" are used interchangeably in describing the present conjugates to mean a molecule recognized in a specific manner by the matrix or vascular smooth muscle binding protein, e.g., an antigen, polypeptide antigen or cell surface carbohydrate (e.g., a glycolipid, glycoprotein, or proteoglycan) that is expressed on the cell surface membranes of a vascular smooth muscle cell or a matrix structure.

"Epitope" is used to refer to a specific site within the "target" molecule that is bound by the matrix or smooth muscle binding protein, e.g., a sequence of three or more amino acids or saccharides.

"Coupled" is used to mean covalent or non-covalent chemical association (i.e., hydrophobic association as through van der Waals forces or charge-charge interactions) of the matrix or vascular smooth muscle binding protein with the therapeutic agent, including by chelation. Preferably, the binding proteins are associated with the therapeutic agents by means of covalent bonding.

"Linker" means a moiety that couples the matrix or smooth muscle binding protein to a therapeutic agent, e.g., as derived from an organic chemical coupling agent.

As used herein, "substantially" pure means at least about 90%, preferably at least about 98%, and more preferably at least about 99%, free of contaminants when assayed by methods conventionally employed by the art.

As used herein, "substantially" solid or crystalline means at least about 90%, preferably at least about 98%, and more preferably at least about 99%, free of non-solid or non-crystalline forms or phases when assayed by methods conventionally employed by the art.

"Migration" of smooth muscle cells means movement of these cells in vivo from the medial layers of a vessel into the intima, which may also be studied in vitro by following the motion of a cell from one location to another (e.g., using time-lapse cinematography or a video recorder and manual counting of smooth muscle cell migration out of a defined area in the tissue culture over time).

"Proliferation" means an increase in cell number, i.e., by mitosis of the cells. As used herein "smooth muscle cells" does not refer to neoplastic vascular smooth muscle cells, i.e., cancer cells.

"Implantable device" means any material that is capable of retaining and releasing a therapeutic agent so as to deliver it in situ in a controlled fashion to a mammalian vessel. An implantable device includes devices which are placed in the lumen of the vessel, e.g., an indwelling catheter or stent, or on the exterior of a vessel, e.g., an adventitial wrap, mesh or covering, or which become a part of the vessel itself, for example to replace a portion of a diseased or traumatized vessel, e.g., a synthetic graft. The implantable device may comprise the therapeutic agent in a form which is releasably embedded in and/or coated on the device. The therapeutic agent may also be releasably embedded in and/or coated on a pharmaceutically acceptable release carrier matrix, which may be applied to and/or embedded in the device or administered directly to a vessel. The matrix is non-liquid, preferably solid. For example, a matrix useful in the practice of the invention includes, but is not limited to, a gel, a paste, or a permeable membrane. An implantable device may be implanted for a limited amount of time, e.g., catheter or infusion needle delivery of a therapeutic agent, or for a prolonged period of time, e.g., a stent or graft. Vessels, into which the implantable device of the invention may be inserted, include, but are not limited to, coronary, femoral, carotid and peripheral vessels.

"Abnormal or pathological or inappropriate" with respect to an activity or proliferation means division, growth or migration of cells, but not cancer cells, that occurs more rapidly or to a significantly greater extent than typically occurs in a normally functioning cell of the same type or in lesions not found in healthy tissue.

"Expressed" means mRNA transcription and translation with resultant synthesis, glycosylation, and/or secretion of a polypeptide by a cell, e.g., CSPG synthesized by a vascular smooth muscle cell or pericyte.

"Vascular remodeling" means a diminution in vessel lumen volume, diameter or area that is not the result of neointimal thickening or smooth muscle cell proliferation, and which generally occurs after a procedural vascular trauma. Thus, a reduction in the area ("constriction") circumscribed by the internal elastic lamina or membrane (IEL) without significant amounts of neointimal formation is termed "vascular remodeling." See Isner, *Circ.*, 89, 2937 (1994). The luminal cross-sectional area of a vessel can be measured by direct planimetering, e.g., by intravascular ultrasound (IVUS) or at necropsy. As used herein, "vascular remodeling" does not include compensatory enlargement of a vessel which accompanies neointimal proliferation so as to accommodate the intimal increase. This compensatory enlargement has also been referred to as "positive" vascular remodeling.

"Sustained release" means a dosage form designed to release a therapeutic agent therefrom for a time period from about 0.0005 to about 180, preferably from about 1–3 to about 150, and more preferably from about 30 to about 120, and even more preferably about 3 to about 21, days. Release over a longer time period is also contemplated as "sustained release" in the context of the present invention. Moreover, it is contemplated that the invention can be practiced with a locally or systemically administered sustained release dosage form.

"Dosage form" includes a formulation comprising a free (non-targeted or non-binding partner associated) therapeutic agent, as well as a sustained release formulation comprising a therapeutic agent. For example, sustained release formulations can comprise microparticles or nanoparticles, biodegradable or non-biodegradable polymeric materials, or any combination thereof, comprising a therapeutic agent dispersed therein, as well as crystalline forms of the therapeutic agent. A targeted or binding partner associated dosage form of the invention includes a sustained release therapeutic formulation comprising microparticles or nanoparticles, and/or biodegradable or non-biodegradable polymeric materials. The sustained release dosage form is linked to one or more binding proteins or peptides, so as to deliver a therapeutic agent dispersed therein to a target cell population which binds to the binding protein or peptide.

"Cytochalasin" includes a fungal metabolite exhibiting an inhibitory effect on target cellular metabolism, including prevention of contraction or migration of vascular smooth muscle cells. Preferably, cytochalasins inhibit the polymerization of monomeric actin (G-actin) to polymeric form (F-actin), thereby inhibiting cell functions requiring cytoplasmic microfilaments. Cytochalasins typically are derived from phenylalanine (cytochalasins), tryptophan (chaetoglobosins), or leucine (aspochalasins), resulting in a benzyl, indol-3-yl methyl or isobutyl group, respectively, at position C-3 of a substituted perhydroisoindole-1-one moiety (Formula I or II).

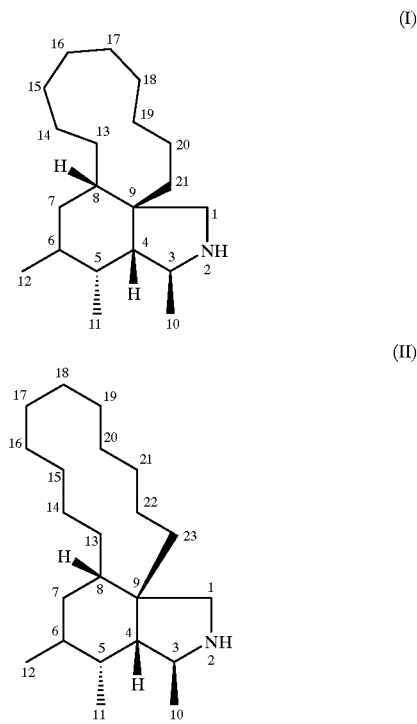

The perhydroisoindole moiety in turn contains an 11-, 13- or 14-atom carbocyclic- or oxygen-containing ring linked to positions C-8 and C-9. All naturally occurring cytochalasins contain a methyl group at C-5; a methyl or methylene group at C-12; and a methyl group at C-14 or C-16. Exemplary cytochalasins include cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D and the like, as well as functional equivalents and derivatives thereof. Certain cytochalasin derivatives are set forth in Japanese Patent Nos. 72 01,925; 72 14,219; 72 08,533; 72 23,394; 72 01924; and 72 04,164. Preferred cytochalasins include cytochalasin A, cytochalasin B and cytochalasin D. Cytochalasin B is used in this description as a typical cytochalasin.

As referred to herein, "taxol" includes taxol as well as functional analogs, equivalents or derivatives thereof. For example, derivatives and analogs of taxol include, but are not limited to, taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine and analogs or derivatives disclosed in Kingston et al. (*New Trends in Nat. Prod. Chem.*, 26, 219 (1986)), Bringli et al. (WO 93/17121), Golik et al. (EPA 639577), Kelly et al. (WO 95/20582), and Cassady and Dourous (eds., In: *Anticancer Agents Based on Natural Product Models*, Academic Press, NY (1980)), the disclosures of which are incorporated by reference herein. Methods for preparing taxol and numerous analogs and derivatives thereof are well known to the art.

"Macrocyclic trichothecene" is intended to mean any one of the group of structurally related sesquiterpenoid macrocyclic mycotoxins produced by several species of fungi and characterized by the 12,13-epoxytrichothec-9-ene basic structure, e.g., verrucarins and roridins that are the products of secondary metabolism in the soil fungi *Myrothecium verrucaria* and *Myrothecium roridium.*

There are two broad classes of trichothecenes: those that have only a central sesquiterpenoid structure and those that have an additional macrocyclic ring (simple and macrocyclic trichothecenes, respectively). The simple trichothecenes may be subdivided into three groups (i.e., Group A, B, and C) as described in U.S. Pat. Nos. 4,744,981 and 4,906,452 (incorporated herein by reference). Representative examples of Group A simple trichothecenes include: scirpene, roridin C, dihydrotrichothecene, scirpen-4,8-diol, verrucarol, scirpentriol, T-2 tetraol, pentahydroxyscirpene, 4-deacetylneosolaniol, trichodermin, deacetylcalonectrin, calonectrin, diacetylverrucarol, 4-monoacetoxyscirpenol, 4,15-diacetoxyscirpenol, 7-hydroxydiacetoxyscirpenol, 8-hydroxydiacetoxy-scirpenol (neosolaniol), 7,8-dihydroxydiacetoxyscirpenol, 7-hydroxy-8-acetyldiacetoxyscirpenol, 8-acetylneosolaniol, NT-1, NT-2, HT-2, T-2, and acetyl T-2 toxin. Representative examples of Group B simple trichothecenes include: trichothecolone, trichothecin, deoxynivalenol, 3-acetyldeoxynivalenol, 5-acetyldeoxynivalenol, 3,15-diacetyldeoxynivalenol, nivalenol, 4-acetyhnivalenol (fusarenon-X), 4,15-idacetylnivalenol, 4,7,15-triacetylnivalenol, and tetra-acetylnivalenol. Representative examples of Group C simple trichothecenes include: crotocol and crotocin. Representative macrocyclic trichothecenes include verrucarin A, verrucarin B, verrucarin J (Satratoxin C), roridin A, roridin D, roridin E (satratoxin D), roridin H, satratoxin F, satratoxin G, satratoxin H, vertisporin, mytoxin A, mytoxin C, mytoxin B, myrotoxin A, myrotoxin B, myrotoxin C, myrotoxin D, roritoxin A, roritoxin B, and roritoxin D. In addition, the general "trichothecene" sesquiterpenoid ring structure is also present in compounds termed "baccharins" isolated from the higher plant *Baccharis megapotamica*, and these are described in the literature, for instance as disclosed by Jarvis et al. (Chemistry of Alleopathy, ACS Symposium Series No. 268: ed. A.C. Thompson, 1984, pp. 149–159) and Jarvis & Mazzola (*Acc. Chem. Res.* 15:338–395, 1982)). Trichothecenes are also produced by soil fungi of the class *Fungi imperfecti* (Bamburg, J. R. *Proc. Molec. Subcell. Biol.* 8:41–110, 1983)).

"Staurosporin" includes staurosporin, a protein kinase C inhibitor of the following formula (III), (III)

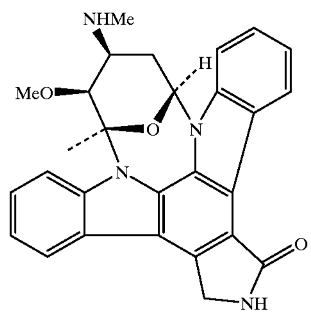

as well as diindoloalkaloids having one of the following general structures:

(IV)

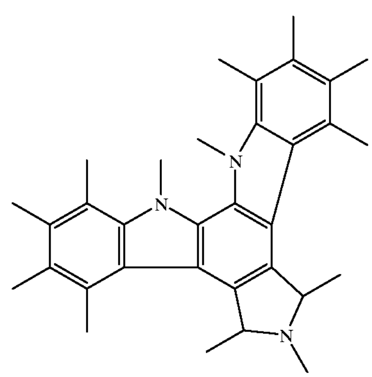

(VI)

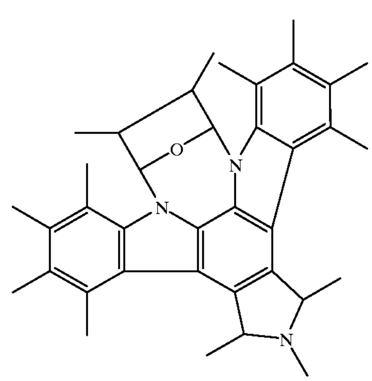

-continued

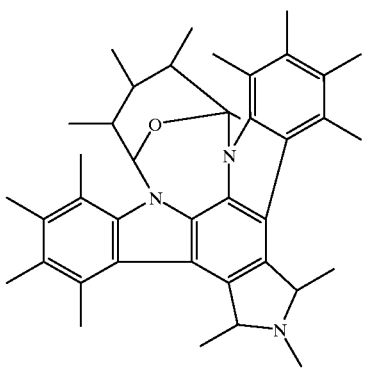

(V)

More specifically, the term "staurosporin" includes K-252 (see, for example, Japanese Patent Application No. 62,164, 626), BMY-41950 (U.S. Pat. No. 5,015,578), UCN-01 (U.S. Pat. No. 4,935,415), TAN-999 (Japanese Patent Application No. 01,149,791), TAN-1030A (Japanese Patent Application No. 01,246,288), RK-286C (Japanese Patent Application No. 02,258,724) and functional equivalents and derivatives thereof. Derivatives of staurosporin include those discussed in Japanese Patent Application Nos. 03,72,485; 01,143,877; 02,09,819 and 03,220,194, as well as in PCT International Application Nos. WO 89 07,105 and WO 91 09,034 and European Patent Application Nos. EP 410,389 and EP 296,110. Derivatives of K-252, a natural product, are known. See, for example, Japanese Patent Application Nos. 63,295,988; 62,240,689; 61,268,687; 62,155,284; 62,155, 285; 62,120,388 and 63,295,589, as well as PCT International Application No. WO 88 07,045 and European Patent Application No. EP 323,171.

As referred to herein, smooth muscle cells and pericytes include those cells derived from the medial layers of vessels and adventitial vessels which proliferate in intimal hyperplastic vascular sites following injury, such as that caused during PTCA. Characteristics of smooth muscle cells include a histological morphology (under light microscopic examination) of a spindle shape with an oblong nucleus located centrally in the cell with nucleoli present and myofibrils in the sarcoplasm. Under electron microscopic examination, smooth muscle cells have long slender mitochondria in the juxtanuclear sarcoplasm, a few tubular elements of granular endoplasmic reticulum, and numerous clusters of free ribosomes. A small Golgi complex may also be located near one pole of the nucleus. The majority of the sarcoplasm is occupied by thin, parallel myofilaments that may be, for the most part, oriented to the long axis of the muscle cell. These actin containing myofibrils may be arranged in bundles with mitochondria interspersed among them. Scattered through the contractile substance of the cell may also be oval dense areas, with similar dense areas distributed at intervals along the inner aspects of the plasmalemma.

Characteristics of pericytes include a histological morphology (under light microscopic examination) characterized by an irregular cell shape. Pericytes are found within the basement membrane that surrounds vascular endothelial cells and their identity may be confirmed by positive immuno-staining with antibodies specific for alpha smooth muscle actin (e.g., anti-alpha-sm1, Biomakor, Rehovot, Israel), HMW-MAA, and pericyte ganglioside antigens e.g., MAb 3G5 (Schlingemann et al., Am. J. Pathol. , 136: 1393–1405 (1990)); and, negative immuno-staining with antibodies to cytokeratins (i.e., epithelial and fibroblast markers) and von Willdebrand factor (i.e., an endothelial marker). Both vascular smooth muscle cells and pericytes are positive by immunostaining with the NR-AN-01 monoclonal antibody.

As used herein, the term "procedural vascular trauma" includes the effects of surgical/mechanical interventions into mammalian vasculature, but does not include vascular trauma due to the organic vascular pathologies, i.e., diseases and infections.

Thus, procedural vascular traumas within the scope of the present treatment method include (1) organ transplantation, such as heart, kidney, liver and the like, e.g., involving vessel anastomosis; (2) vascular surgery, e.g., coronary bypass surgery, biopsy, heart valve replacement, atheroectomy, thrombectomy, and the like; (3) transcatheter vascular therapies (TVT) including angioplasty, e.g., laser angioplasty and PTCA procedures, employing balloon catheters, and indwelling catheters; (4) vascular grafting using natural or synthetic materials, such as in saphenous vein coronary bypass grafts, dacron and venous grafts used for peripheral arterial reconstruction, etc.; (5) placement of a mechanical shunt, e.g., a PTFE hemodialysis shunt used for arteriovenous communications; and (6) placement of an intravascular stent, which may be metallic, plastic or a biodegradable polymer. See U.S. patent application Ser. No. 08/389,712, filed Feb. 15, 1995, which is incorporated by reference herein. For a general discussion of implantable devices and biomaterials from which they can be formed, see H. Kambic et al., "Biomaterials in Artificial Organs", Chem. Eng. News, 30 (Apr. 14, 1986), the disclosure of which is incorporated by reference herein.

Therapeutic Agents Falling Within the Scope of the Invention

Therapeutic agents useful in the practice of the invention include agents which biologically stent a vessel and/or reduce or inhibit vascular remodeling and/or inhibit or reduce vascular smooth muscle cell proliferation following a procedural vascular trauma. The therapeutic agents of the invention are selected to inhibit a cellular activity of a vascular smooth muscle cell, e.g., proliferation, migration, increase in cell volume, increase in extracellular matrix synthesis (e.g., collagens, proteoglycans, and the like), or secretion of extracellular matrix materials by the cell.

Preferably, the therapeutic agent is: a) a "cytostatic agent" which acts to prevent or delay cell division in proliferating cells by inhibiting replication of DNA or by inhibiting spindle fiber formation and the like; b) an inhibitor of migration of vascular smooth muscle cells from the medial wall into the intima, e.g., an "anti-migratory agent" e.g., a cytochalasin; c) as an inhibitor of the intracellular increase in cell volume (i.e., the tissue volume occupied by a cell; a "cytoskeletal inhibitor" or a "metabolic inhibitor"); d) an inhibitor that blocks cellular protein synthesis and/or secretion or organization of extracellular matrix (i.e., an "anti-matrix agent"); or any combination thereof.

Representative examples of "cytostatic agents" include, e.g., modified toxins, methotrexate, adriamycin, radionuclides (e.g., see Fritzberg et al., U.S. Pat. No. 4,897,255), protein kinase inhibitors (e.g., staurosporin), taxol or analogs thereof (e, taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyltransferase, reverse transcriptase, antisense oligonucleotides that suppress smooth muscle cell proliferation and the like, which when delivered into a cellular compartment at an appropriate dosage will act to impair proliferation of a smooth muscle cell or pericyte without killing the cell.

Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors, (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents for smooth muscle proliferation include: subfragments of heparin, triazolopyrimidine (Trapidil; a PDGF antagonist), lovastatin, and prostaglandins E1 or I2.

Representative examples of "anti-migratory agents" include inhibitors (i.e., agonists and antagonists, and competitive or non-competitive inhibitors) of chemotactic factors and their receptors (e.g., complement chemotaxins such as C5a, C5a desarg or C4a; extracellular matrix factors, e.g., collagen degradation fragments), or of intracellular cytoskeletal proteins involved in locomotion (e.g., actin, cytoskeletal elements, and phosphatases and kinases involved in locomotion). Representative examples of useful therapeutic agents in this category of anti-migratory agents include caffeic acid derivatives and nilvadipine (a calcium antagonist), and steroid hormones. Preferred anti-migratory therapeutic agents are the cytochalasins.

Representative examples of "cytoskeletal inhibitors", a subset of cytostatic agents, include colchicine, vinblastin, cytochalasins, taxol, or analogs or derivatives thereof that act on microtubule and microfilament networks within a cell. Preferred cytoskeletal inhibitors include cytochalasin B, cytochalasin A, cytochalasin D and taxol.

Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation into a pathologically proliferating form.

Representative examples of "metabolic inhibitors" include staurosporin, trichothecenes, and modified diphtheria and ricin toxins, *Pseudomonas exotoxin* and the like. In a preferred embodiment, the therapeutic conjugate is constructed with a therapeutic agent that is a simple trichothecene or a macrocyclic trichothecene, e.g., a verrucarin or roridin. Trichothecenes are drugs produced by soil fungi of the class *Fungi imperfecti* or isolated from *Baccharus megapotamica* (Baamburg, J. R. *Proc. Molec. Subcell. Biol.* 8:41–110, 1983; Jarvis & Mazzola, *Acc. Chem. Res.* 15:338–395, 1982). They appear to be the most toxic molecules that contain only carbon, hydrogen and oxygen (Tamm, C. *Fortschr. Chem. Org. Naturst.* 31:61–117, 1974). They are all reported to act at the level of the ribosome as inhibitors of protein synthesis at the initiation, elongation, or termination phases.

Identification of Therapeutic Agents Useful in the Practice of the Invention

The identification of therapeutic agents useful in the practice of the invention may be determined by methods well known to the art. For example, a therapeutic agent falling within the scope of the invention exhibits one or more of the following characteristics. The agent:

(i) results in retention of an expanded luminal cross-sectional area, diameter or volume of a vessel following angioplasty (e.g., PTCA, percutaneous transluminal angioplasty (PTA) or the like) or other trauma, including atheroectomy (e.g., rotoblater, laser and the like), coronary artery bypass procedures and the like; or resulting from vascular disease, e.g, atherosclerosis, eye diseases secondary to vascular stenosis or atrphy, cerebral vascular stenotic diseases or the like;

(ii) facilitates an initial increase in luminal cross-sectional area, diameter or volume that does not result in or accentuate chronic stenosis of the lumen;

(iii) inhibits target cell contraction or migration; and (iv) is cytostatic.

Methods to measure luminal cross-sectional area, volume or diameter include, but are not limited to, angiography, ultrasonic evaluation, fluoroscopic imaging, fiber optic endoscopic examination or biopsy and histology.

Preferably, a therapeutic agent employed herein will have all four properties; however, the first and third are generally more important than the second and fourth for practice of the present invention. It was found that cytochalasin B administration can result in a biological stenting effect. The biological stenting effect can be achieved using a single infusion of the therapeutic agent into the traumatized region of the vessel wall at a dose concentration ranging from about 0.1 micrograms/ml to about 1.0 micrograms/ml, and preferably about 0.01 micrograms/ml to about 10.0 micrograms/ml (Example 16).

In the case of therapeutic agents or dosage forms containing anti-migratory or anti-matrix therapeutic agents, cell migration and cell adherence in in vitro assays, respectively, may be used for determining the concentration at which a therapeutically effective dosage will be reached in the fluid space in the vessel wall created by an infusion catheter.

An agent useful in the sustained release embodiments of the present invention exhibits one or more of the following characteristics. The agent (i) causes the retention of an expanded luminal diameter or cross-sectional area following angioplasty (e.g., PTCA, percutaneous transluminal angioplasty (PTA) or the like) or other trauma, including atheroectomy (e.g., rotoblater, laser and the like), coronary artery bypass procedures or the like; or resulting from vascular disease, e.g, atherosclerosis, eye diseases secondary to vascular stenosis or atrphy, cerebral vascular stenotic diseases or the like;

(ii) inhibits target cell proliferation (e.g., following 5 minute and 24 hour exposure to the agent, in vitro vascular smooth muscle tissue cultures demonstrate a level of inhibition of $^3$H-thymidine uptake and, preferably, display relatively less inhibition of $^3$H-leucine uptake);

(iii) at a dose sufficient to inhibit DNA synthesis, produces only mild to moderate (e.g., grade 2 or 3 in the assays described below) morphological cytotoxic effects;

(iv) inhibits target cell contraction; and (v) is cytostatic.

Upon identification of a therapeutic agent exhibiting one or more of the preceding properties, the agent is subjected to a second testing protocol that involves longer exposure of vascular smooth muscle cells (VSMC) to the therapeutic agent. For example, an agent useful in the sustained release embodiments of the present invention also exhibits the following characteristics:

(i) upon long term (e.g., 5 days) exposure, the agent produces the same or similar in vitro effect on vascular smooth muscle tissue culture DNA synthesis and protein synthesis, as described above for the 5 minute and 24 hour exposures; and (ii) at an effective dose in the long term in vitro assay for DNA synthesis inhibition, the agent exhibits mild to moderate morphological cytotoxic effects over a longer term (e.g., 10 days).

Further evaluation of potentially useful anti-proliferative agents is conducted in an in vivo balloon traumatized pig femoral artery model. Preferably, these agents demonstrate a 50% or greater inhibition of cell proliferation in the tunica media vascular smooth muscle cells, as indicated by a 1 hour "BRDU flash labeling" prior to tissue collection and histological evaluation (Example 13). If an agent is effective in this assay to inhibit intimal smooth muscle proliferation by 50% or more with a single exposure, it does not require administration in a sustained release dosage form.

Agents are evaluated for sustained release if the systemic toxicity and potential therapeutic index appear to permit intravenous administration to achieve the 50% inhibition threshold, or if the agent is amenable to local delivery to the vascular smooth muscle cells via sustained release at an effective anti-proliferative dose. Agents are evaluated in a sustained release dosage form for dose optimization and efficacy studies. Preferably, anti-proliferative agents useful in the practice of the present invention decrease vascular stenosis by 50% in balloon traumatized pig femoral arteries and, more preferably, decrease vascular stenosis to a similar extent in pig coronary arteries.

Inhibition of cellular proliferation (i.e., DNA synthesis) is the primary characteristic of agents useful in sustained release dosage forms. For example, a preferred therapeutic agent exhibits a differential between $^3$H-leucine and $^3$H-thymidine uptake so that it can be administered at cytostatic doses. Moreover, cytotoxicity studies should indicate that prolonged exposure to the therapeutic agent would not adversely impact the target cells. In addition, BRDU pulsing should indicate that the therapeutic agent is effective to inhibit target cell proliferation. Any convenient method for evaluating the capability of an agent to inhibit cell proliferation may alternatively be employed, however.

Sustained Released Dosage Forms

Sustained release dosage forms of the invention may comprise microparticles and/or nanoparticles having a therapeutic agent dispersed therein or may comprise the therapeutic agent in pure, preferably crystalline, solid form. For sustained release administration, microparticle dosage forms comprising pure, preferably crystalline, therapeutic agents are preferred. The therapeutic dosage forms of this aspect of the present invention may be of any configuration suitable for sustained release. Preferred sustained release therapeutic dosage forms exhibit one or more of the following characteristics:

microparticles (e.g., from about 0.5 micrometers to about 100 micrometers in diameter, with about 0.5 to about 2 micrometers more preferred; or from about 0.01 micrometers to about 200 micrometers in diameter, preferably from about 0.5 to about 50 micrometers, and more preferably from about 2 to about 15 micrometers) or nanoparticles (e.g., from about 1.0 nanometer to about 1000 nanometers in diameter, with about 50 to about 250 nanometers being more preferred; or from about 0.01 nanometer to about 1000 nanometers in diameter, preferably from about 50 to about 200 nanometers), free flowing powder structure;

biodegradable structure designed to biodegrade over a period of time preferably between from about 0.5 to about 180 days, preferably from about 1–3 to about 150 days, or from about 3 to about 180 days, with from about 10 to about 21 days more preferred; or non-biodegradable structure to allow therapeutic agent diffusion to occur over a time period of between from about 0.5 to about 180 days, more preferably from about 30 to about 120 days; or from about 3 to about 180 days, with from about 10 to about 21 days preferred;

biocompatible with target tissue and the local physiological environment into which the dosage form to be administered, including yielding biocompatible biodegradation products;

facilitate a stable and reproducible dispersion of therapeutic agent therein, preferably to form a therapeutic agent-polymer matrix, with active therapeutic agent release occurring by one or both of the following routes: (1) diffusion of the therapeutic agent through the dosage form (when the therapeutic agent is soluble in the shaped polymer or polymer mixture defining the dimensions of the dosage form); or (2) release of the therapeutic agent as the dosage form biodegrades; and/or for targeted dosage forms, capability to have, preferably, from about 1 to about 10,000 binding protein/peptide to dosage form bonds and more preferably, a maximum of about 1 binding peptide to dosage form bond per 150 square angstroms of particle surface area. The total number of binding protein/peptide to dosage form bonds depends upon the particle size used. The binding proteins or peptides are capable of coupling to the particles of the therapeutic dosage form through covalent ligand sandwich or non-covalent modalities as set forth herein.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Preferred larger microparticle therapeutic dosage forms of the present invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the present invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver anti-proliferative therapeutic agents.

Preferred sustained release dosage forms of the present invention comprise biodegradable microparticles or nanoparticles. More preferably, biodegradable microparticles or nanoparticles are formed of a polymer containing matrix that biodegrades by random, nonenzymatic, hydrolytic scissioning to release therapeutic agent, thereby forming pores within the particulate structure.

Polymers derived from the condensation of alpha hydroxycarboxylic acids and related lactones are preferred for use in the present invention. A particularly preferred moiety is formed of a mixture of thermoplastic polyesters (e.g., polylactide or polyglycolide) or a copolymer of lactide and glycolide components, such as poly(lactide-co-glycolide). An exemplary structure, a random poly(DL-lactide-co-glycolide), is shown below, with the values of x and y being manipulable by a practitioner in the art to achieve desirable microparticle or nanoparticle properties.

$$H\left[O-CH(CH_3)-\overset{O}{\underset{\|}{C}}-O-CH(CH_3)-\overset{O}{\underset{\|}{C}}\right]_x \left[O-CH_2-\overset{O}{\underset{\|}{C}}-O-CH_2-\overset{O}{\underset{\|}{C}}\right]_y OH$$

Other agents suitable for forming particulate dosage forms of the present invention include polyorthoesters and polyacetals (*Polymer Letters*, 18:293 (1980) and polyorthocarbonates (U.S. Pat. No. 4,093,709) and the like.

Preferred lactic acid/glycolic acid polymer containing matrix particles of the present invention are prepared by emulsion-based processes, that constitute modified solvent extraction processes, see, for example, processes described by Cowsar et al., "Poly(Lactide-Co-Glycolide) Microcapsules for Controlled Release of Steroids," *Methods Enzymology*, 112:101–116, 1985 (steroid entrapment in microparticles); Eldridge et al., "Biodegradable and Biocompatible Poly(DL-Lactide-Co-Glycolide) Microspheres as an Adjuvant for Staphylococcal Enterotoxin B Toxoid Which Enhances the Level of Toxin-Neutralizing Antibodies," *Infection and Immunity*, 59:2978–2986, 1991 (toxoid entrapment); Cohen et al., "Controlled Delivery Systems for Proteins Based on Poly(Lactic/Glycolic Acid) Microspheres," *Pharmaceutical Research*, 6:713–720, 1991 (enzyme entrapment); and Sanders et al., "Controlled Release of a Luteinizing Hormone-Releasing Hormone Analogue from Poly(D,L-Lactide-Co-Glycolide) Microspheres," *J. Pharmaceutical Science*, 73(9):1294–1297, 1984 (peptide entrapment).

In general, the procedure for forming particle dosage forms of the present invention involves dissolving the polymer in a halogenated hydrocarbon solvent, dispersing a therapeutic agent solution (preferably aqueous) therein, and adding an additional agent that acts as a solvent for the halogenated hydrocarbon solvent but not for the polymer. The polymer precipitates out from the polymer-halogenated hydrocarbon solution onto droplets of the therapeutic agent containing solution and entraps the therapeutic agent. Preferably the therapeutic agent is substantially uniformly dispersed within the sustained release dosage form of the present invention. Following particle formation, they are washed and hardened with an organic solvent. Water washing and aqueous nonionic surfactant washing steps follow, prior to drying at room temperature under vacuum.

For biocompatibility purposes, particulate dosage forms, characterized by a therapeutic agent dispersed in the matrix of the particles, are sterilized prior to packaging, storage or administration. Sterilization may be conducted in any convenient manner therefor. For example, the particles can be irradiated with gamma radiation, provided that exposure to such radiation does not adversely impact the structure or function of the therapeutic agent dispersed in the therapeutic agent-polymer matrix or the binding protein/peptide attached thereto. If the therapeutic agent or binding protein/peptide is so adversely impacted, the particle dosage forms can be produced under sterile conditions.

Release of the therapeutic agent from the particle dosage forms of the present invention can occur as a result of both diffusion and particle matrix erosion. The biodegradation rate directly effects the kinetics of therapeutic agent release. The biodegradation rate is regulable by alteration of the composition or structure of the sustained release dosage form. For example, alteration of the lactide/glycolide ratio in preferred dosage forms of the present invention can be conducted, as described by Tice et al., "Biodegradable Controlled-Release Parenteral Systems," *Pharmaceutical Technology*, pp. 26–35, 1984; by inclusion of agents that alter the rate of polymer hydrolysis, such as citric acid and sodium carbonate, as described by Kent et al., "Microencapsulation of Water Soluble Active Polypeptides," U.S. Pat. No. 4,675,189; by altering the loading of therapeutic agent in the lactide/glycolide polymer, the degradation rate being inversely proportional to the amount of therapeutic agent contained therein, by judicious selection of an appropriate analog of a common family of therapeutic agents that exhibit different potencies so as to alter said core loadings; and by variation of particle size, as described by Beck et al., "Poly(DL-Lactide-Co-Glycolide)/Norethisterone Microcapsules: An Injectable Biodegradable Contraceptive," *Biol. Reprod.*, 28:186–195, 1983, or the like. All of the aforementioned methods of regulating biodegradation rate influence the intrinsic viscosity of the polymer containing matrix, thereby altering the hydration rate thereof.

The preferred lactide/glycolide structure is biocompatible with the mammalian physiological environment. Also, these preferred sustained release dosage forms have the advantage that biodegradation thereof forms lactic acid and glycolic acid, both normal metabolic products of mammals.

Functional groups required for binding of the protein/peptide to the particle dosage form are optionally included in or on the particle matrix and are attached to the non-degradable or biodegradable polymeric units. Functional groups that are useful for this purpose include those that are reactive with peptides, e.g., carboxyl groups, amine groups, sulfhydryl groups and the like. Preferred binding enhancement moieties include the terminal carboxyl groups of the preferred (lactide-glycolide) polymer containing matrix or the like.

Therapeutic agents useful in the sustained release dosage forms of the present invention preferably are those that inhibit vascular smooth muscle cell activity without killing the cells (i.e., cytostatic therapeutic agents). A cytostatic agent can also be defined as a moiety capable of inhibiting one or more pathological activities of the target cells for a time sufficient to achieve a therapeutic benefit. Preferred therapeutic agents thus exhibit one or more of the following capabilities: inhibition of DNA synthesis prior to protein synthesis inhibition, or inhibition of migration of vascular smooth muscle cells into the intima. These therapeutic agents do not significantly inhibit protein synthesis (i.e., do not kill the target cells) and, therefore, facilitate cellular repair and matrix production, which in turn acts to stabilize the vascular wall lesion caused by angioplasty, by reducing smooth muscle cell proliferation.

Preferred therapeutic agents are protein kinase inhibitors, such as staurosporin (staurosporine is available from Sigma Chemical Co., St. Louis, Mo.), and cytoskeletal inhibitors such as the cytochalasins, e.g., cytochalasin B (Sigma Chemical Co.), nitroglycerin (DuPont Pharmaceuticals, Inc., Mauti, Puerto Rico) and taxol, or analogs or functional equivalents thereof. These compounds are cytostatic and have been shown to exert minimal protein synthesis inhibition and cytotoxicity at concentrations at which significant DNA synthesis inhibition occurs (see Example 8 and FIGS. 10A–10D). A useful protocol for identifying therapeutic agents useful in sustained release dosage form embodiments of the present invention is set forth in Example 8, for example.

To prepare one embodiment of the invention, a cytoskeletal inhibitor, e.g., cytochalasin B, is incorporated into biodegradable poly (DL-lactide-co-glycolide) microparticles or into nanoparticles. The microparticles are about 1 to about 50μ, preferably 4μ to about 15μ, and more preferably about 2 to about 15μ, in diameter. The nanoparticles are about 5 to about 500 nanometers, preferably about 10 to about 250 nanometers, and more preferably about 50 to about 200 nanometers, in diameter. The microparticles or nanoparticles comprising the therapeutic agent can be further embedded in or on an implantable device, e.g., in a stent coating, or delivered in a suitable liquid vehicle by an implantable device, e.g., via an infusion catheter. Preferably, the sustained release dosage form is biodegradable and, preferably, biodegrades over about 30–120 days. The sustained release dosage form is preferably administered during the procedural vascular trauma.

A preferred sustained release dosage form of the invention comprises biodegradable microparticles, preferably about 2 to about 15μ in diameter, which are tissue compatible and physically compatible with an implantable device, e.g., a needle infusion catheter or a microinfusion catheter. Another preferred sustained release dosage form of the invention comprises biodegradable nanoparticles, preferably about 50 to about 200 nanometers in diameter, which are tissue compatible and physically compatible with an implantable device, e.g., a needle infusion catheter or a microinfusion catheter. To deliver the sustained release dosage forms by balloon catheter, the balloon pore or hole sizes are preferably about 0.1 to about 8 micron, more preferably about 0.2 to about 0.8 micron, in diameter.

The cellular concentration of the cytoskeletal inhibitor that is attained in the tunica media and/or intima of the treated vessel is effective to inhibit vascular smooth muscle cell proliferation and migration, e.g., a cellular concentration at least about 0.1 μg/ml cytochalasin B is attained. The inhibition of the smooth muscle cells results in a more rapid and complete re-endothelialization after a procedural vascular trauma, e.g., intraventional placement of the stent. The increased rate of re-endothelialization reduces loss in luminal cross-sectional area or diameter and reduces decreases in blood flow.

Another preferred sustained release dosage form of the invention comprises a pure, solid crystalline form of a therapeutic agent, preferably, of a cytoskeletal inhibitor. This embodiment of the sustained release dosage form of the present invention preferably further comprises a tissue-compatible pharmaceutically acceptable matrix carrier that provides a supporting structure for the crystals, e.g., a shaped body of silicone, collagen gel retained in a collagen mesh, pluronic gel retained in a collagen mesh, or mannitol retained in a shaped body of silicone. Thus, for example, sustained release dosage forms comprising cytochalasin B and a pharmaceutical matrix carrier preferably comprise about 5 to about 70%, more preferably about 7 to about 40%, and even more preferably about 5 to about 30%, weight percent of cytochalasin B/weight percent of the total matrix carrier-therapeutic agent sustained release dosage form. Sustained release dosage forms comprising taxol and a pharmaceutical matrix carrier preferably comprise about 1 to about 70%, more preferably about 2 to about 50%, and even more preferably about 3 to about 8%, weight percent of taxol/weight percent of the total matrix carrier-therapeutic agent sustained release dosage form.

Identification and Preparation of Targeted Dosage Forms Useful in the Practice of the Invention Vascular smooth muscle cell binding proteins useful in the invention bind to targets on the surface of vascular smooth muscle cells. A useful vascular smooth muscle binding protein is a polypeptide, peptidic, or mimetic compound (as described below) that is capable of binding to a target or marker on a surface component of an intact or disrupted vascular smooth muscle cell. Such binding allows for either release of therapeutic agent extracellularly in the immediate interstitial matrix with subsequent diffusion of therapeutic agent into the remaining intact smooth muscle cells and/or internalization by the cell into an intracellular compartment of the entire targeted biodegradable moiety, thus permitting delivery of the therapeutic agent thereto. It will be recognized that specific targets, e.g., polypeptides or carbohydrates, proteoglycans and the like, that are associated with the cell membranes of vascular smooth muscle cells are useful for selecting (e.g., by cloning) or constructing (e.g., by genetic engineering or chemical synthesis) appropriately specific vascular smooth muscle binding proteins. Particularly useful "targets" are internalized by smooth muscle cells, e.g., as membrane constituent antigen turnover occurs in renewal. Internalization by cells may also occur by mechanisms involving phagolysosomes, clathrin-coated pits, receptor-mediated redistribution or endocytosis and the like.

Representative examples of useful vascular smooth muscle binding proteins include antibodies (e.g., monoclonal and polyclonal antibodies), F(ab')$_2$, Fab', Fab, and Fv fragments and/or complementarity determining regions (CDR) of those antibodies or functional equivalents thereof, (e.g., binding peptides and the like)); growth factors, cytokines, and polypeptide hormones and the like; and macromolecules recognizing extracellular matrix receptors (e.g., integrin and fibronectin receptors and the like).

In a preferred embodiment, e.g., a "target" is exemplified by chondroitin sulfate proteoglycans (CSPGs) synthesized by vascular smooth muscle cells and pericytes, and a discrete portion (termed an epitope herein) of the CSPG molecule having an apparent molecular weight of about 250 kD is especially preferred as a target. The 250 kD target is an N-linked glycoprotein that is a component of a larger 400 kD proteoglycan complex (Bumol et al., *PNAS USA*, 79: 1245–1249 (1982)). In one presently preferred embodiment of the invention, a vascular smooth muscle binding protein is provided by the NR-AN-01 monoclonal antibody (a subculture of NR-ML-05) that binds to an epitope in a vascular smooth muscle CSPG target molecule. The monoclonal antibody designated NR-ML-05 reportedly binds a 250 kD CSPG synthesized by melanoma cells (Morgan et al., U.S. Pat. No. 4,897,255).

Smooth muscle cells and pericytes also reportedly synthesize a 250 kD CSPG as well as other CSPGs (Schlingeman et al., supra). NR-ML-05 binding to smooth muscle cells has been disclosed (Fritzberg et al., U.S. Pat. No. 4,879,225). The hybridoma, NR-ML-05, which secretes a monoclonal antibody which binds to the 400 kD CSPG, has been deposited with the American Type Culture Collection, Rockville, Md. and granted Accession No. 9350. NR-ML-05 is the parent of, and structurally and functionally equivalent to, subclone NR-AN-01, disclosed herein.

It will be recognized that NR-AN-01 is just one example of a vascular smooth muscle binding protein that specifically associates with the 400 kD CSPG target, and that other binding proteins associating with this target and other epitopes on this target (Bumol et al., *PNAS USA*, 79: 1245–1249 (1982)) are also useful in the therapeutic conjugates and methods of the invention.

Six other murine monoclonal antibodies and two human chimeric monoclonal antibodies have also been selected, as described herein, that specifically target to the 250 kD CSPG of vascular smooth muscle cells. The antibodies also appear to be internalized by the smooth muscle cells following binding to the cell membrane. Immunoreactivity studies have also shown the binding of the murine MAbs to the 250 kD antigen in 45 human normal tissues and 30 different neoplasms and some of these results have been disclosed previously (U.S. Pat. No. 4,879,225). In this disclosure and other human clinical studies, MAbs directed to the CSPG 250 kD antigen localized to vascular smooth muscle cells in vivo. Further, it will be recognized that the amino acid residues involved in the multi-point kinetic association of the NR-AN-01 monoclonal antibody with a CSPG marker antigenic epitope (i.e., the amino acids constituting the complementarity determining regions) are determined by computer-assisted molecular modeling and by the use of mutants having altered antibody binding affinity. The binding-site amino acids and three dimensional model of the NR-AN-01 antigen binding site serve as a molecular model for constructing functional equivalents, e.g., short polypeptides ("minimal polypeptides"), that have binding affinity for a CSPG synthesized by vascular smooth muscle cells and pericytes.

For treating stenosis following vascular surgical procedures, e.g., PTCA, preferred binding proteins, e.g., antibodies or fragments, for use in the practice of the invention have a binding affinity of $>10^4$ liter/mole for the vascular smooth muscle 250 kD CSPG, and also the ability to be bound to and internalized by smooth muscle cells or pericytes.

Further, it will be recognized that the amino acid residues involved in the multi-point kinetic association of the NR-AN-01 monoclonal antibody with a CSPG marker antigenic epitope (i.e., the amino acids constituting the complementarity determining regions) can be determined by computer-assisted molecular modeling and by the use of mutants having altered antibody binding affinity. The binding-site amino acids and three dimensional model of the NR-AN-01 antigen binding site can serve as a molecular model for constructing functional equivalents, e.g., short polypeptides ("minimal polypeptides"), that have binding affinity for a CSPG synthesized by vascular smooth muscle cells and pericytes.

Three-dimensional modeling is also useful to construct other functional equivalents that mimic the binding of NR-AN-01 to its antigenic epitope, e.g., "mimetic" chemical compounds that mimic the three-dimensional aspects of NR-AN-01 binding to its epitope in a CSPG target antigen. As used herein, "minimal polypeptide" refers to an amino acid sequence of at least six amino acids in length. As used herein, the term "mimetic" refers to an organic chemical oligomer or polymer constructed to achieve the proper spacing for binding to the amino acids of, for example, an NR-AN-01 CSPG target synthesized by vascular smooth muscle cells or pericytes.

It is also envisioned that human monoclonal antibodies or "humanized" murine antibodies which bind to a vascular smooth muscle binding protein are useful in the therapeutic conjugates of their invention. For example, murine monoclonal antibody may be "chimerized" by genetically recombining the nucleotide sequence encoding the murine Fv region (i.e., containing the antigen binding sites) with the nucleotide sequence encoding a human constant domain region and an Fc region, e.g., in a manner similar to that disclosed in European Patent Application No. 411,893. Some murine residues may also be retained within the human variable region framework domains to ensure proper target site binding characteristics. Humanized vascular smooth muscle binding partners will be recognized to have the advantage of decreasing the immunoreactivity of the antibody or polypeptide in the host recipient, and may be useful for increasing the in vivo half-life and reducing the possibility of adverse immune reactions to the conjugate.

Also contemplated as useful binding peptides for sustained release dosage forms adapted for restenosis treatment are those that localize to intercellular stroma and matrix located between and among vascular smooth muscle cells. Such binding peptides can deliver the therapeutic agent to the interstitial space between the target cells. The therapeutic agent is released into the interstitial spaces for subsequent uptake by the vascular smooth muscle cells. Preferred binding peptides of this type are associated with epitopes on collagen, extracellular glycoproteins, e.g., tenascin, reticulum and elastic fibers, cytokeratin and other intercellular matrix components. Minimal peptides, mimetic organic chemical compounds, human or humanized monoclonal antibodies and the like that localize to intracellular stroma and matrix are also useful as binding peptides in this embodiment of the present invention. These binding peptides may be identified and constructed or isolated in accordance with known techniques. In preferred embodiments of the present invention, the interstitial matrix binding protein binds to a target epitope with an association constant of at least about $10^{-4}$ M.

Representative "coupling" methods for linking the therapeutic agent through covalent or non-covalent bonds to the vascular smooth muscle binding protein include chemical cross-linkers and heterobifunctional cross-linking compounds (i.e., "linkers") that react to form a bond between reactive groups (such as hydroxyl, amino, amido, or sulfhydryl groups) in a therapeutic agent and other reactive groups (of a similar nature) in the vascular smooth muscle binding protein. This bond may be, for example, a peptide bond, disulfide bond, thioester bond, amide bond, thioether bond, and the like.

In one illustrative example, conjugates of monoclonal antibodies with drugs have been summarized by Morgan and Foon (Monoclonal Antibody Therapy to Cancer: Preclinical Models and Investigations, *Basic and Clinical Tumor Immunology*, Vol. 2, Kluwer Academic Publishers, Hingham, Mass.) and by Uhr *J. of Immunol.* 133: i–vii, 1984). In another illustrative example where the conjugate contains a radionuclide cytostatic agent, U.S. Pat. No. 4,897,255, Fritzberg et al., incorporated herein by reference, is instructive of coupling methods that can be used to make the present conjugates.

The choice of coupling method will be influenced by the choice of vascular smooth muscle binding protein or peptide, interstitial matrix binding protein or peptide and therapeutic agent, and also by such physical properties as, e.g., shelf life stability, and/or by biological properties, e.g., half-life in cells and blood, intracellular compartmentalization route, and the like.

The physical and chemical character of the sustained release dosage forms of the present invention permit several alternative modes of attachment of the dosage forms to binding proteins or peptides. Dosage forms (sustained release-type) of the present invention are capable of binding to binding proteins/peptides through, for example, covalent linkages, intermediate ligand sandwich attachment, or non-covalent adsorption or partial entrapment. When the preferred poly-lactic/glycolic acid particles are formed with the therapeutic agent dispersed therein, the uncharged polymer backbone is oriented both inward (with the quasi lipophilic therapeutic agent contained therein) and outward, along with a majority of the terminal carboxy groups. These surface carboxy groups may serve as covalent attachment sites when activated by, for example, a carbodiimide) for nucleophilic groups of the binding protein/peptide. Such nucleophilic groups include lysine epsilon-amino groups (amide linkage), serine hydroxyl groups (ester linkage) or cysteine mercaptan groups (thioester linkage). Reactions with particular groups depend upon pH and the reduction state of the reaction conditions.

For example, poly-lactic/glycolic acid particles having terminal carboxylic acid groups can be reacted with N-hydroxybenztriazole in the presence of a water soluble carbodiimide of the formula R—N=C=N—R' (wherein R is a 3-dimethylaminopropyl group or the like and R' is an ethyl group or the like). The benztriazole-derivatized particles (i.e., activated imidate-bearing moieties) are then reacted with a protein/peptide nucleophilic moiety such as an available epsilon-amino moiety. Alternatively, p-nitrophenol, tetrafluorophenol, N-hydroxysuccinimide or like molecules are useful to form an active ester with the terminal carboxy groups of poly-lactic/glycolic acid particles in the presence of carbodiimide. Other binding protein/peptide nucleophilic moieties include hydroxyl groups of serine, endogenous free thiols of cysteine, thiol groups resulting from reduction of binding protein/peptide disulfide bridges using reducing agents commonly employed for that purpose (e.g., cysteine, dithiothreitol, mercaptoethanol and the like) and the like. Additionally, the terminal carboxy groups of the poly-lactic/glycolic acid particles are activatable by reaction with thionyl chloride to form an acyl chloride derivatized moiety. The derivatized particles are then reacted with binding peptide/protein nucleophilic groups to form targeted dosage forms of the present invention.

Direct conjugation of sustained release dosage form to binding protein or peptide may disrupt binding protein/peptide recognition of the target cell. Ligand sandwich attachment techniques are useful alternatives to achieve sustained release dosage form attachment to binding protein/peptide. These techniques involve the formation of a primary peptide or protein shell using a protein that does not bind to the target cell population. Binding protein/peptide is then bound to the primary peptide or protein shell to provide the resultant particle with functional binding protein/peptide. An exemplary ligand sandwich approach involves covalent attachment of avidin or streptavidin to the particles through functional groups as described above with respect to the "direct" binding approach. The binding protein or peptide is derivatized, preferably minimally, via functionalized biotin (e.g., through active ester, hydrazide, iodoacetal, maleimidyl or like functional groups). Ligand (i.e., binding peptide or protein/functionalized biotin) attachment to the available biotin binding sites of the avidin/streptavidin primary protein shell occurs through the use of a saturating amount of biotinylated protein/peptide.

For example, poly-lactic/glycolic acid particles having terminal carboxylic acid groups are activated with carbodiimide and subsequently reacted with avidin or streptavidin. The binding protein or peptide is reacted with biotinamidocaproate N-hydroxysuccinimide ester at a 1–3 molar offering of biotin-containing compound to the binding protein/peptide to form a biotinylated binding protein/peptide. A molar excess of the biotinylated binding protein/peptide is incubated with the avidin-derivatized particles to form a targeted dosage form of the present invention.

Alternatively, the particle carboxy groups are biotinylated (e.g., through carbodiimide activation of the carboxy group and subsequent reaction with amino alkyl biotinamide). The biotinylated particles are then incubated with a saturating concentration (i.e., a molar excess) of avidin or streptavidin to form protein coated particles having free biotin binding sites. These coated particles are then capable of reaction with a molar excess of biotinylated binding protein formed as described above. Another option involves avidin or streptavidin bound binding peptide or protein attachment to biotinylated particles.

In addition, binding protein/peptide-particle attachment can be achieved by adsorption of the binding peptide to the particle, resulting from the nonionic character of the partially exposed polymer backbone of the particle. Under high ionic strength conditions (e.g., 1.0 molar NaCl), hydrogen and hydrophobic particle-binding protein/peptide binding are favored.

Moreover, binding protein/peptide may be partially entrapped in the particle polymeric matrix upon formation thereof Under these circumstances, such entrapped binding protein/peptide provides residual selective binding character to the particle. Mild particle formation conditions, e.g., those employed by Cohen et al., *Pharmaceutical Research*, 8: 713–720 (1991), are preferred so as to entrap the protein or peptide in the matrix. Entrapped binding proteins are also useful in target cell reattachment of a partially degraded particle that has undergone exocytosis. Binding proteins or peptides can be bound to other polymeric particle dosage forms (e.g., non-biodegradable dosage forms) having different exposed functional groups in accordance with the principles discussed above.

Exemplary non-biodegradable polymers useful in the practice of the present invention are polystyrenes, polypropylenes, styrene acrylic acid and acrylate copolymers and the like. Such non-biodegradable polymers incorporate or can be derivatized to incorporate functional groups for attachment of binding protein/peptide, including carboxylic acid groups, aliphatic primary amino groups, aromatic amino groups and hydroxyl groups.

Carboxylic acid functional groups are coupled to binding protein or peptide using, for example, the reaction mechanisms set forth above for poly-lactic/glycolic acid biodegradable polymeric particle dosage forms. Primary amino functional groups are coupled by, for example, reaction thereof with succinic anhydride to form a terminal carboxy moiety that can be bound to binding peptide/protein as described above. Additionally, primary amino groups can be activated with cyanogen bromide and form guanidine linkages with binding protein/peptide primary amino groups. Aromatic amino functional groups are, for example, diazotized with nitrous acid to form diazonium moieties which react with binding protein/peptide tyrosines, thereby producing a diazo bond between the non-biodegradable particle and the binding protein/peptide. Hydroxyl functional groups are coupled to binding protein/peptide primary amino groups by, for example, converting the hydroxyl moiety to a moiety comprising a terminal carboxylic acid functional group. This conversion can be accomplished through reaction with chloroacetic acid followed by reaction with carbodiimide. Sandwich, adsorption and entrapment techniques, discussed above with respect to biodegradable particles, are analogously applicable to non-biodegradable particle-binding protein/peptide affixation.

In a preferred embodiment, targeting is specific for potentially proliferating cells that result in increased smooth muscle in the intimal region of a traumatized vascular site, e.g., following angioplasty, e.g., pericytes and vascular smooth muscle cells. Aspects of the invention relate to therapeutic modalities in which the therapeutic conjugate of the invention is used to delay, reduce, or eliminate smooth muscle proliferation after angioplasty, e.g., PTCA, atheroectomy and percutaneous transluminal coronary rotational atheroblation.

In another embodiment, targeting is specific for a local administration accessible pathologically proliferating or hyperactive normal cell population implicated in, e.g., degenerative eye disease, corneal pannus, hyperactive endocrine glands or the like. Aspects of this embodiment of the present invention involve therapeutic modalities wherein the therapeutic agent reduces or eliminates proliferation or hyperactivity of the target cell population.

Dosages, Formulation and Routes of Administration of the Therapeutic Agents

The amount of therapeutic agent administered is adjusted to treat vascular traumas of differing severity. For example, smaller doses are sufficient to treat lesser vascular trauma, e.g., to prevent vascular rejection following graft or transplant, while larger doses are sufficient to treat more extensive vascular trauma, e.g., to treat restenosis following angioplasty. Thus, to biologically stent a traumatized vessel, a cytoskeletal inhibitor such as cytochalasin B is administered at a systemic total dose of about 1 to about 24 ml, preferably about 1 to about 4 ml, at about 0.0011 to about 25 $\mu$g cytochalasin /ml of vehicle, e.g., 0.01 to about 10 $\mu$g cytochalasin B/ml of vehicle, preferably about 0.1 to about 10 $\mu$g cytochalasin B/ml of vehicle, and more preferably about 0.1 to about 8.0 $\mu$g cytochalasin B/ml of vehicle, although other dosages may prove beneficial. In particular, lower or higher concentrations of a cytochalasin may exert a therapeutic effect when a non-aqueous solvent is employed as the vehicle.

The administration of a sytemic dose of cytochalasin B results in about 5 to about 40, preferably about 8 to about 30, lambda of the cytochalasin B-containing solution entering the interstitial space surrounding the cells of the tunica media, and about 0.01 to about 4, preferably about 0.05 to about 3, ml of the solution being exposed to the wall of the vessel by the transport of the solution to the adventitia. Moreover, these dosages may also exhibit anti-proliferative effects.

Administration of a therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses, e.g., either before, during, or after procedural vascular trauma, before and during, before and after, during and after, or before, during and after the procedural vascular trauma. Moreover, the administration of the therapeutic agent is selected so as to not further damage the traumatized vessel.

One or more suitable unit dosage forms comprising the therapeutic agent of the invention, which may be formulated for sustained release, can be administered by a variety of routes including oral, or parenteral, including by rectal, transdermal, subcutaneous, intravenous, intramuscular, intrapulmonary and intranasal routes. When the therapeutic agents of the invention are prepared for oral administration, they are preferably combined with a pharmaceutically acceptable carrier, diluent or excipient to form a pharmaceutical formulation, preferably in unit dosage form. The total active ingredients in these formulations can comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof.

Pharmaceutical formulations containing the therapeutic agent of the invention can be prepared by procedures known in the art using well known and readily available ingredients. For example, a cytochalasin can be formulated with common excipients, diluents, or carriers, and formed into tablets, capsules, suspensions, powders, and the like. Examples of excipients, diluents, and carriers that are suitable for such formulations include the following fillers and extenders, e.g., starch, sugars, mannitol, and silicic derivatives; binding agents, for example, carboxymethyl cellulose, HPMC, and other cellulose derivatives, alginates, gelatin, and polyvinylpyrrolidone; moisturizing agents such as glycerol; disintegrating agents, e.g., calcium carbonate and sodium bicarbonate; agents for retarding dissolution, for example, paraffin; resorption accelerators such as quaternary ammonium compounds; surface active agents, e.g., cetyl alcohol, glycerol monostearate; adsorptive carriers such as kaolin and bentonite; and lubricants, for example, talc, calcium and magnesium stearate, and solid polyethyl glycols. See Fondy et al. (WO 88/10259), the disclosure of which is incorporated by reference herein.

For example, tablets or caplets containing a therapeutic agent of the invention can include buffering agents, e.g., calcium carbonate, magnesium oxide and magnesium carbonate. Caplets and tablets can also include inactive ingredients such as cellulose, pregelatinized starch, silicon dioxide, hydroxypropyl methylcellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing a therapeutic agent of the invention can contain inactive ingredients, for example, gelatin, microcrystalline cellulose, sodium lauryl sulfate, starch, talc, and titanium dioxide, and the like, as well as liquid vehicles such as polyethylene glycols (PEGs) and vegetable oil.

The therapeutic agents of the invention can also be formulated as elixirs or solutions for convenient oral administration or as solutions appropriate for parenteral administration, for instance by intramuscular, subcutaneous or intravenous routes. In the practice of certain embodiments of the present invention, the therapeutic agent is dispersed in a pharmaceutically acceptable carrier that is in liquid phase, and delivered via an implantable device, e.g., a catheter. Useful pharmaceutically acceptable carriers for these purposes include generally employed carriers, such as phosphate buffered saline solution, water, emulsions (e.g., oil/water and water/oil emulsions) and wetting agents of various types.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents, e.g., acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides, for example products marketed under the name "Miglyol", isopropyl myristate, animal, mineral and vegetable oils and polysiloxanes.

The compositions according to the invention can also contain thickening agents such as cellulose and/or cellulose derivatives. They can also contain gums, e.g., xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersions or microemulsions, lotions thickened to a greater or lesser extent, impregnated pads, ointments or sticks, or alternatively the form of aerosol formulations in spray or foam form or alternatively in the form of a cake of soap.

Additionally, the therapeutic agents are well suited to formulation as sustained release dosage forms and the like. The formulations can be so constituted that they release the active ingredient only or preferably in a particular part of the intestinal tract, e.g., over a period of time. The coatings, envelopes, and protective matrices may be made, for example, from polymeric substances or waxes.

The local delivery of the therapeutic agents of the invention can be by a variety of techniques which administer the agent at or near the traumatized vascular site. Examples of site-specific or targeted local delivery techniques are not intended to be limiting but to be illustrative of the techniques available. Examples include local delivery catheters, such as an infusion catheter, an indwelling catheter, or a needle catheter, stets, synthetic grafts, adventitial wraps, shunts and stents or other implantable devices, site specific carriers, direct injection, or direct applications.

Local delivery by an implant describes the surgical placement of a matrix that contains the therapeutic agent into the lesion or traumatized area. The implanted matrix releases the therapeutic agent by diffusion, chemical reaction, or solvent activators. See, for example, Lange, *Science*, 249, 1527 (1990).

An example of targeted local delivery by an implant is the use of a stent. Stents are designed to mechanically prevent the collapse and reocclusion of the coronary arteries or other vessels. Incorporation of a therapeutic agent into the stent can deliver the therapeutic agent directly to the lesion. Local delivery of agents by this technique is described in Koh, *Pharmaceutical Technology* (October, 1990).

For example, a metallic, plastic or biodegradable intravascular stent is employed which comprises the therapeutic agent. The stent preferably comprises a biodegradable coating, a porous or a permeable non-biodegradable coating, or a biodegradable or non-biodegradable membrane or synthetic graft sheath-like coating, e.g., PTFE, comprising the therapeutic agent. A more preferred embodiment of the invention is a coated stent wherein the coating comprises a sustained-release dosage form of the therapeutic agent. In an alternative embodiment, a biodegradable stent may also have the therapeutic agent impregnated therein, i.e., in the stent matrix.

A biodegradable stent with the therapeutic agent impregnated therein can be further coated with a biodegradable coating or with a porous non-biodegradable coating having the sustained release-dosage form of the therapeutic agent dispersed therein. This stent can provide a differential release rate of the therapeutic agent, i.e., there can be an initial faster release rate of the therapeutic agent from the coating, followed by delayed release of the therapeutic agent impregnated in the stent matrix, upon degradation of the stent matrix. The intravascular stent also provides a mechanical means of providing an increase in luminal area of a vessel.

Furthermore, the placement of intravascular stents comprising a therapeutic agent which is an inhibitor of smooth muscle cell proliferation can also reduce or prevent intimal proliferation. This inhibition of intimal smooth muscle cells and stroma produced by the smooth muscle and pericytes can lead to a more rapid and complete re-endothelization following the intraventional placement of the vascular stent. The increased rate of re-endothelization and stabilization of the vessel wall following stent placement can reduce the loss of luminal area and decreased blood flow due to vascular smooth muscle cell proliferation which is one of the primary causes of vascular stent failures.

Another example of targeted local delivery by an implant is the use of an adventitial wrap. The wrap comprises a pharmaceutically acceptable carrier matrix, e.g., a Pluronic gel which is free, or contained by a collagen mesh, which gel has dispersed therein a therapeutic agent. One embodiment of the invention is a pluronic gel (F-127, BASF) which is soluble at 4° C. but solidifies at 37° C., e.g., on contact with fluid or tissue in a human. To prepare a pluronic gel containing wrap, 4 ml of phosphate buffer, pH 7.0 (*Circ. Res.*, vol. 76, April 1995), was added to 1 g of pluronic gel F-127, which was mixed overnight at 4° C. The therapeutic agent was added to the mixture prior to local administration. The mixture may be applied directly to a surgically exposed artery wall, or may be applied to the surface of a bovine collagen mat (BioCore, Inc., Topeka, Kans.), which is then wrapped around the artery and the edges joined by sutures.

Another embodiment of the invention is the incorporation of the therapeutic agent into the expanded nodal spaces of a PTFE (Impra, Inc., Tempe, Ariz.) vascular graft-like membrane which can surround, or be placed on the interior or on the exterior surface of, an interlumenal vascular stent, which comprises metal or a biodegradable or nonbiodegradable polymer. The therapeutic agent, or a sustained release dosage form of the therapeutic agent, fills the nodal spaces of the PTFE membrane wall and/or coats the inner and/or outer surfaces of the membrane.

Yet another embodiment of the invention is a mixture of a crystalline form of a therapeutic agent in a bovine collagen gel (BioCore, Inc., Topeka, Kans.). Crystals varied in size from about 0.1 micron to about 1 mm. Generally, the crystals were pulverized to generate smaller sized crystals. This mixture is applied directly to the surface of the artery, and the surrounding subcutaneous tissues sutured around the vessel and the skin closed. Bovine collagen (BioCore, Inc., Topeka, Kans.) is dissolved in sterile saline (1:1) and the crystalline therapeutic agent added. Alternatively, the collagen gel is applied to a bovine collagen mesh which is then wrapped around the vessel and the edges sutured to hold the mesh in place. The bovine collagen mesh (BioCore, Inc.) is cut to size, e.g., 1 cm×1 cm, and the therapeutic agent-collagen gel mixture is applied to the surface of the mesh.

A further embodiment of the invention comprises the entrapment of crystalline therapeutic agent in about a 0.1 to about 3, preferably about 0.5 to about 0.7, mm thick silicone membrane, e.g., silicone polymer Q-7 4840 (Dow Corning, Midland, Mich.). The polymer (part A and B, 1:1) is mixed with a spatula. An inert filler, e.g., mannitol, is powdered and sieved to a fraction 53–75 mesh size. Mannitol and therapeutic agent are mixed in predetermined proportions and then levigated with the polymer to form a composite. The composite is filled in a slab mold and compressed to 5000 psi. The composite is then cured at 80° C. for 2 hours. The composite membrane is then cut to size, e.g., 1 cm×1 cm, wrapped around the artery and held in place by suturing the membrane edges together.

A therapeutic agent may also be coated onto the exterior of the wrap. The wrap and/or the coating is preferably biodegradable. It is preferred that the therapeutic agent is in sustained release dosage form.

Another example is a delivery system in which a polymer that contains the therapeutic agent is injected into the area of the lesion in liquid form. The polymer then solidifies or cures to form the implant which is retained in situ. This technique is described in PCT WO 90/03768 (Donn, Apr. 19, 1990).

Another example is the delivery of a therapeutic agent by polymeric endoluminal sealing. This technique uses a catheter to apply a polymeric implant to the interior surface of the lumen. The therapeutic agent incorporated into the biodegradable polymer implant and is thereby released at the surgical site. This technique is described in PCT WO 90/01969 (Schindler, Aug. 23, 1989), the disclosure of which is incorporated by reference herein.

Yet another example of local delivery is by direct injection of vesicles or microparticles into the lesion or artery wall adjacent to the lesion. These microparticles may be composed of substances such as proteins, lipids, carbohydrates or synthetic polymers. These microparticles have the therapeutic agent incorporated throughout the microparticle or onto the microparticle as a coating. Delivery systems incorporating microparticles are described in Lange, *Science*, 249,1527 (1990) and Mathiowitz et al., *J. App. Poly. Sci.*, 26, 809 (1981).

For topical administration, the therapeutic agents may be formulated as is known in the art for direct application to a target area. Conventional forms for this purpose include wound dressings, coated bandages or other polymer coverings, ointments, lotions, pastes, jellies, sprays, and aerosols. The percent by weight of a therapeutic agent of the invention present in a topical formulation will depend on various factors, but generally will be from 0.005% to 95% of the total weight of the formulation, and typically 1–25% by weight.

Conditions Amenable to Treatment by the Method of the Invention

The therapeutic agents and dosage forms of the invention are useful to treat or inhibit a diminution in vessel lumen volume, area and/or diameter associated with a procedural vascular trauma. A vascular trauma includes but is not limited to trauma associated with an interventional procedure, such as angioplasty, placement of a stent, shunt, stet, synthetic or natural graft, adventitial wrap, indwelling catheter or other implantable devices. Grafts include synthetic therapeutic agent-treated grafts, e.g., impregnated or coated grafts. As used herein, "vessels" includes mammalian vessels, e.g., coronary vessels as well as peripheral, femoral and carotid vessels. It will be recognized that the therapeutic agents and dosage forms (both free and sustained release) of the invention are not restricted in use for therapy following angioplasty; rather, the usefulness of the therapeutic agents and dosage forms will be proscribed by their ability to inhibit cellular activities of smooth muscle cells and pericytes in the vascular wall. It will be recognized that the conjugates and dosage forms of the invention are not restricted in use for therapy following angioplasty; rather, the usefulness of the therapeutic conjugates and dosage forms will be proscribed by their ability to inhibit cellular activities of smooth muscle cells and pericytes in the vascular wall. Thus, other aspects of the invention include therapeutic conjugates and dosage forms and protocols useful in early therapeutic intervention for reducing, delaying, or eliminating (and even reversing) atherosclerotic plaques and areas of vascular wall hypertrophy and/or hyperplasia. Therapeutic conjugates and dosage forms of the invention also find utility for early intervention in pre-atherosclerotic conditions, e.g., they are useful in patients at a high risk of developing atherosclerosis or with signs of hypertension resulting from atherosclerotic changes in vessels or vessel stenosis due to hypertrophy of the vessel wall.

The therapeutic agents and dosage forms of the invention are also useful in therapeutic modalities for enhancing the regrowth of endothelial cells in injured vascular tissues and in other wound sites including epithelial wounds. In these therapeutic modalities, the therapeutic agents, conjugates and dosage forms of the invention find utility in inhibiting the migration and/or proliferation of smooth muscle cells or pericytes. Smooth muscle cells and pericytes have been implicated in the production of factors in vitro that inhibit endothelial cell proliferation, and their proliferation can also result in a physical barrier to establishing a continuous endothelium. Thus, the therapeutic agents, conjugates and dosage forms of the invention find utility in promoting neo-angiogenesis and increased re-endothelialization, e.g., during wound healing, vessel grafts and following vascular surgery. The dosage forms may also release therapeutic modalities that stimulate or accelerate up re-endothelialization of the damaged vessel wall. An exemplary therapeutic agent for this purpose is vascular permeability factor.

Still other aspects of the invention relate to therapeutic modalities for enhancing wound healing in a vascular site and improving the structural and elastic properties of healed vascular tissues. In these therapeutic modalities using the therapeutic conjugate or dosage form of the invention, i.e., to inhibit the migration and proliferation of smooth muscle cells or pericytes in a vessel wall, the strength and quality of healing of the vessel wall are improved. Smooth muscle cells in the vascular wound site contribute to the normal process of contraction of the wound site which promotes wound healing. It is presently believed that migration and proliferation of smooth muscle cells and matrix secretion by transformed smooth muscle cells may detract from this normal process and impair the long-term structural and elastic qualities of the healed vessel. Thus, other aspects of the invention provide for therapeutic conjugates and dosage forms that inhibit smooth muscle and pericyte proliferation and migration as well as morphological transformation, and improve the quality of the healed vasculature.

One embodiment of the present invention involves administration of a therapeutic agent capable of inhibiting the ability of vascular smooth muscle cells to contract and/or proliferate and/or migrate. Exemplary agents useful in the practice of this aspect of the present invention are those capable of causing a traumatized artery to lose vascular tone, such that normal vascular hydrostatic pressure (i.e., blood pressure) expands the flaccid vessel to or near to its maximal physiological diameter. Loss of vascular tone may be caused by agents that interfere with the formation or function of contractile proteins (e.g., actin, myosin, tropomyosin, caldesmon, calponin or the like). This interference can occur directly or indirectly through, for example, inhibition of calcium modulation, phosphorylation or other metabolic pathways implicated in contraction of vascular smooth muscle cells.

Inhibition of cellular contraction (i.e., loss of vascular tone) may operate through two mechanisms to reduce the degree of vascular stenosis. First, inhibition of cellular contraction for a prolonged period of time limits the number of smooth muscle cells that migrate from the tunica media into the intima, the thickening of which results in vascular luminal stenosis. Second, inhibition of cellular contraction causes the smooth muscle wall to relax and dilate under normal vascular hydrostatic pressure (ie., blood pressure). Therapeutic agents, e.g., the cytochalasins, inhibit smooth muscle cell contraction without abolishing the protein synthesis necessary for traumatized, post-angioplasty or other surgically- or disease-damaged, smooth muscle cells to repair themselves. Protein synthesis is also necessary for the smooth muscle cells to secrete matrix, which fixes or retains the lumen in a state near its maximum systolic diameter as the vascular lesion stabilizes (i.e., a biologically-induced stenting effect).

This biological stenting effect not only results in an expanded vessel luminal cross-sectional area or diameter and increased blood flow rate through the vessel, but also significantly reduces elastic recoil following angioplasty. Elastic recoil is an acute closure of the vessel associated with vasospasm or early relaxation of the muscular wall, due to trauma shock resulting from vessel over-stretching by a balloon catheter during angioplasty. This spasm of the tunica media which leads to decreases in the luminal cross-sectional area may occur within hours, days or weeks after the balloon dilation, as restoration of vascular muscle wall tone occurs.

Recent observations during microscopic examination of atheroectomy specimens suggest that elastic recoil may occur in up to 25% of angioplasty procedures classified as successful, based on the initial post-procedure angiogram. Because the biological stenting procedure relaxes the artery wall following balloon angioplasty, the clinician can eliminate over-inflation and its resultant trauma shock as a means to diminish or delay the vessel spasm or elastic recoil. Reduction or elimination of over-inflation decreases trauma to the muscular wall of the vessel, thereby reducing the determinants of smooth muscle cell proliferation in the intima and, therefore, reducing the incidence or severity of restenosis.

Biological stenting also decreases the incidence of thrombus formation. In pig femoral arteries treated with cytochalasin B, for example, the incidence of mural microthrombi was decreased as compared to the balloon traumatized arteries that were not treated with the therapeutic agent. This phenomenon appears to be a secondary benefit that may result from the increased blood flow through the traumatized vessel, said benefit being obtained through the practice of the present invention. In arteries treated with sustained release dosage forms of cytochalasin B, cytochalasin B may also prevent the contraction and organization of platelets which is required for thrombus formation.

Cytochalasins are exemplary therapeutic agents capable of generating a biological stenting effect on vascular smooth muscle cells. Cytochalasins are thought to inhibit both migration and contraction of vascular smooth muscle cells by interacting with actin. The cytochalasins interact with the ends of filamentous actin to inhibit the elongation of the actin filaments. Low doses of cytochalasins (e.g., cytochalasin B) also disrupt microfilament networks of actin. In vitro data indicate that after vascular smooth muscle cells clear cytochalasin B, the cells regenerate enough polymerized actin to resume migration within about 24 hours. In vivo assessments reveal that vascular smooth muscle cells regain vascular tone within 2 to 4 days. It is during this recuperative period that the lumen diameter fixation and biological stenting effect occurs.

The therapeutic agent may be targeted, but is preferably administered directly to the traumatized vessel prior to, during or following the angioplasty or other traumatic event. The biological stenting effect of cytochalasin B, for example, is achievable using a single infusion of about 1 to about 24 ml, preferably about 5 to about 15 ml, of a vehicle plus the therapeutic agent into the traumatized region of the vessel wall at a dose concentration ranging from about 0.1 microgram of therapeutic agent/ml of vehicle to about 1.0, preferably about about 0.1 microgram of therapeutic agent/ml of vehicle to about 10.0 micrograms, and more preferably about about 0.01 microgram of therapeutic agent/ml of vehicle to about 10.0 micrograms, of therapeutic agent/ml of vehicle.

Inhibition of vascular smooth muscle cell migration (from the tunica media to the intima) has been demonstrated in the same dose range (Example 11); however, a sustained exposure of the vessel to the therapeutic agent is preferable in order to maximize these anti-migratory effects. If the vascular smooth muscle cells cannot migrate into the intima, they cannot proliferate there. Should vascular smooth muscle cells migrate to the intima, a subsequently administered anti-proliferative sustained release dosage form can inhibit intimal proliferation. As a result, the sustained release dosage form of the present invention, incorporating a cytochalasin or other anti-proliferative therapeutic agent, can be administered in combination with a free therapeutic agent which is preferably a cytoskeletal inhibitor. In this manner, a biological stenting effect, as well as an anti-proliferative or anti-migratory effect, can be achieved in a single dosing protocol.

The present invention also provides methods for the treatment of cancer and immune system-mediated diseases through local administration of a targeted particulate dosage form. The particulate dosage form is, for example, administered locally into primary and/or metastatic foci of cancerous target cells. Local administration is preferably conducted using an infusion needle or intraluminal administration route, infusing the particulate dosage form in the intercellular region of the tumor tissue or in luminal fluid surrounding the tumor cells.

Primary foci introduction is preferably conducted with respect to target cells that are generally situated in confined areas within a mammal, e.g., ovarian carcinomas located in the abdominal cavity. The dosage form of the present invention binds to the target cell population and, optionally, is internalized therein for release of the therapeutic agent over time. Local administration of dosage forms of the present invention to such primary foci results in a localized effect on such target cells, with limited exposure of other sensitive organs, e.g., the bone marrow and kidneys, to the therapeutic agent.

When metastatic foci constitute the target cell population, the administered microparticles and larger nanoparticles are primarily bound to the target cells situated near the infusion site and are, optionally, internalized for release of the therapeutic agent, thereby generating a marked and localized effect on the target cells immediately surrounding the infusion site. In addition, smaller nanoparticles follow interstitial fluid flow or lymphatic drainage channels and bind to target cells that are distal to the infusion site and undergoing lymphatic metastasis.

The targeted dosage forms of this embodiment of the present invention can be used in combination with more commonly employed immunoconjugate therapy. In this manner, the immunoconjugate achieves a systemic effect within the limits of systemic toxicity, while the dosage form of the present invention delivers a concentrated and sustained dose of therapeutic agent to the primary and metastatic foci, which often receive an inadequate therapeutic dose from such "systemic" immunoconjugate administration alone, and avoids or minimizes systemic toxic effects.

Where the target cell population can be accessed by local administration, the dosage forms of the present invention are utilized to control immune system-mediated diseases. Exemplary of such diseases are arthritis, sprue, uveitis, endophthalnitis, keratitis and the like. The target cell populations implicated in these embodiments of the present invention are confined to a body cavity or space, such as joint capsules, pleural and abdominal cavity, eye and subconjunctival space, respectively. Local administration is preferably conducted using an infusion needle for a intrapleural, intraperitoneal, intraocular or sub-conjunctival administration route.

This embodiment of the present invention provides a more intense, localized modulation of immune system cells with minimal effect on the systemic immune system cells. Optionally, the systemic cells of the immune system are simultaneously treatable with a chemotherapeutic agent conjugated to a binding protein or peptide. Such a conjugate preferably penetrates from the vascular lumen into target immune system cells.

The local particulate dosage form administration may also localize to normal tissues that have been stimulated to proliferate, thereby reducing or eliminating such pathological (i.e., hyperactive) conditions. An example of this embodiment of the present invention involves intraocular administration of a particulate dosage form coated with a binding protein or peptide that localizes to pericytes and smooth muscle cells of neovascularizing tissue. Proliferation of these pericytes causes degenerative eye disease. Preferred dosage forms of the present invention release compounds capable of suppressing the pathological proliferation of the target cell population. The preferred dosage forms can also release compounds that increase vessel lumen area and blood flow, reducing the pathological alterations produced by this reduced blood supply.

Method of the Invention

The invention provides a method of treating a mammal having, or at risk of, diminution in vessel lumen volume, area or diameter, e.g., stenosis or restenosis of a blood vessel. The method comprises the administration of at least one therapeutic agent in an amount effective to biologically stent a vessel, inhibit or reduce vascular remodeling of a vessel, inhibit or reduce vascular smooth muscle cell proliferation, or any combination thereof.

For the prevention of vessel lumen diminution associated with procedural vascular trauma, the therapeutic agent can be administered before, during and/or after the procedure, or any combination thereof. For example, for the prevention of restenosis, a series of spaced doses of the therapeutic agent, optionally, in sustained release dosage form, is preferably administered before, during and/or after the traumatic procedure (e.g., angioplasty). The dose may also be delivered locally, via an implantable device, e.g., a catheter, introduced into the afflicted vessel during the procedure. Preferably, a sustained release dosage form is administered via the implantable device during the traumatic procedure. After the traumatic procedure is conducted, a series of follow-up doses can be administered over time, preferably in a sustained release dosage form, for a time sufficient to substantially reduce the risk of, or to prevent, restenosis. A preferred therapeutic protocol duration for this purpose involves administration from about 3 to about 26 weeks after angioplasty.

It will be recognized by those skilled in the art that therapeutically/prophylactically effective dosages of the therapeutic agents and dosage forms will be dependent on several factors, including, e.g.: a) the binding affinity of the vascular smooth muscle binding protein, if any, in the dosage form; b) the atmospheric pressure and duration of the pressure applied during infusion; c) the time over which the therapeutic agent or dosage form administered resides at the vascular site; d) the nature of the therapeutic agent employed; e) the nature of the vascular trauma and therapy desired; f) for sustained release dosage forms, the rate of release of the therapeutic agent from the dosage form, and/or g) for sustained release dosage forms, the intercellular and/or intracellular localization of the dosage form. Those skilled practitioners trained to deliver drugs at therapeutically effective dosages (e.g., by monitoring drug levels and observing clinical effects in patients) will determine the optimal dosage for an individual patient based on experience and professional judgment. Those skilled in the art will recognize that infiltration of the therapeutic agent into the intimal layers of a traumatized vessel wall in free or sustained release dosage form is subject to variation and will need to be determined on an individual basis.

A therapeutically effective dosage of the therapeutic agent will be typically reached when the concentration of therapeutic agent in the fluid space between the balloons of the catheter is in the range of about $10^{-3}$ to $10^{-12}$ M. It will be recognized from the Examples provided herewith that therapeutic agents and dosage forms of the invention may only need to be delivered in an anti-proliferative therapeutic dosage sufficient to expose the proximal 6 to 9 cell layers of the intimal or tunica media cells lining the lumen to the therapeutic agent, whereas the anti-contractile dosage may need to expose the entire tunica media. Alternatively, the anti-proliferative therapeutic dosage sufficient to expose the inner 10%, preferably the inner 20%, and more preferably the inner 99%, of the tunica media cells lining the lumen to the therapeutic agent. This dosage can be determined empirically, e.g., by a) infusing vessels from suitable animal model systems and using immunohistochemical, fluorescent or electron microscopy methods to detect the agent and its effects (e.g., such as exemplified in the EXAMPLES below); and b) conducting suitable in vitro studies (see, for example, EXAMPLES 3, 4, and 5, below).

For example, with respect to catheter delivery, it will be recognized by those skilled in the art that therapeutically/prophylactically effective dosages of the therapeutic agents and dosage forms will be dependent on factors including: a) the atmospheric pressure applied during infusion; b) the time over which the agent administered resides at the vascular site; c) the form of the therapeutic or prophylactic agent employed; and/or d) the nature of the vascular trauma and therapy desired. Catheters which may be useful in the practice of the invention include catheters such as those disclosed in Just et al. (U.S. Pat. No. 5,232,444), Abusio et al. (U.S. Pat. No. 5,213,576), Shapland et al. (U.S. Pat. No.

5,282,785), Racchini et al. (U.S. Pat. No. 5,458,568), Wolinsky (U.S. Pat. No. 4,824,436), Spears (U.S. Pat. No. 4,512, 762) and Shaffer et al. (U.S. Pat. No. 5,049,132), the disclosures of which are incorporated by reference herein.

It will be recognized that where the therapeutic conjugate or dosage form is to be delivered with an infusion catheter, the therapeutic dosage required to achieve the desired inhibitory activity for a therapeutic conjugate or dosage form can also be determined through the use of in vitro studies. In a preferred aspect, the infusion catheter may be conveniently a double balloon or quadruple balloon catheter with a permeable membrane. In one representative embodiment, a therapeutically effective dosage of a therapeutic conjugate or dosage form is useful in treating vascular trauma resulting from disease (e.g., atherosclerosis, aneurysm, or the like) or vascular surgical procedures such as angioplasty, atheroectomy, placement of a stent (e.g., in a vessel), thrombectomy, and grafting. Atheroectomy may be performed, for example, by surgical excision, ultrasound or laser treatment, or by high pressure fluid flow. Grafting may be, for example, vascular grafting using natural or synthetic materials or surgical anastomosis of vessels such as, e.g., during organ grafting. Those skilled in the art will recognize that the appropriate therapeutic dosage for a given vascular surgical procedure (above) is determined in in vitro and in vivo animal model studies, and in human preclinical trials. In the EXAMPLES provided below, a therapeutic conjugate containing Roridin A and NR-AN-01 achieved a therapeutically effective dosage in vivo at a concentration which inhibited cellular protein synthesis in test cells in vitro by at least 5 to 50%, as judged by incorporation of radiolabeled amino acids.

In a preferred embodiment, about 0.3 atm (i.e., 300 mm of Hg) to about 3 atm of pressure applied for 15 seconds to 3 minutes to the arterial wall is adequate to achieve infiltration of a sustained release dosage form bound to the NR-AN-01 binding protein into the smooth muscle layers of a mammalian artery wall. Wolinsky et al., "Direct Intraarterial Wall Injection of Microparticles Via a Catheter: A Potential Drug Delivery Strategy Following Angioplasty," Am. Heart Jour., 122(4):1136–1140, 1991. Those skilled in the art will recognize that infiltration of a sustained release dosage form into a target cell population will probably be variable and will need to be determined on an individual basis.

A therapeutically effective dosage is generally the pericellular agent dosage in smooth muscle cell tissue culture, i.e., a dosage at which at a continuous exposure results in a therapeutic effect between the toxic and minimal effective doses. This therapeutic level is obtained in vivo by determining the size, number and therapeutic agent concentration and release rate required for particles infused between the smooth muscle cells of the artery wall to maintain this pericellular therapeutic dosage. The dosage form should release the therapeutic agent at a rate that approximates the pericellular dose of the following exemplary therapeutic agents: from about 0.01 to about 100 micrograms/ml nitroglycerin, from about 1.0 to about 1000 micrograms/ml of suramin, from about 0.001 to about 100 micrograms/ml for cytochalasin, and from about 0.01 to about 105 nanograms/ml of staurosporin as well as from about 0.001 to about 100 micrograms/ml taxol. Thus, for cytochalasin B, the sytemic dose results in about 5 to about 40, preferably about 8 to about 30, lambda of the solution entering the interstitial space surrounding the cells of the tunica media, and about 0.01 to about 4, preferably about 0.05 to about 3, ml of the solution delivered to the wall of the vessel via the adventitia.

The administration of a cellular therapeutic dose of, for example, cytochalasin B to vascular smooth muscle cells following balloon dilation trauma can be achieved by replacing the entire volume of the tunica media with the therapeutic agent so as to produce a biostenting effect, i.e., all cells are exposed to a concentration of the therapeutic agent effective to biologically stent the vessel. For example, a dose response study which employed swine femoral arteries showed that if the entire tunica media was infused using an infusion catheter with cytochalasin B in a range of about 0.1 µg/ml of vehicle to 10.0 µg/ml of vehicle, a biostenting effect resulted. That is, a more extensive retention of the artery lumen size (diameter or cross-sectional area) was observed relative to the artery lumen size produced by the dilating balloon. The therapeutic effect had a threshold level of 0.1 µg/ml cytochalasin B with no effect below this dose and no increase in therapeutic efficacy up to 10 µg/ml cytochalasin B. Thus, cytochalasin B has a wide therapeutic index which ranges from about 0.1 to about 10 µg/ml, with no evidence of toxicity at 10 µg/ml. Ten µg/ml is the maximum saturation concentration of cytochalasin B in saline. The therapeutic effect produced by cytochalasin B administration became more apparent over the 3 to 8 weeks following the balloon trauma.

To achieve a cellular therapeutic dose to produce a biostenting effect, i.e., one where each cell of the tunica media is exposed to a therapeutic concentration range, e.g., about 0.1 µg/ml to about 8.0 µg/ml of cytochalasin B, a catheter, e.g., a MIC2 or MIC3 catheter, is filled with a volume of the therapeutic agent in solution and delivered at a hub pressure which does not damage the vessel. For example, 9 to 24 ml (MIC2) or 5 to 10 ml (MIC3) of an 8.0 µg/ml cytochalasin B solution is delivered at a hub pressure of 4 to 5 atmospheres for a total of 90 seconds infusion time. Delivery of the NR-ML-05 monoclonal antibody to the tunica media under these conditions was achieved in both the swine femoral and coronary models. With the hub pressure and exposure times held constant, the amount of solution infused may vary because flow rate is determined by the tightness of fit. If the flow rate is below the recommended range, the fit is too tight to establish a uniform hydrostatic head, and therefore a uniform dose around the vessel wall does not exist. If the flow rate is above the recommended range, then the fit is too loose to establish the hydrostatic head required to force the solution into the interstitial region of the tunica media, and the dose to the individual cells is below the required therapeutic level.

It is also preferred that catheter administration of the therapeutic agent to the tunica media and adventitia produces minimal or no damage to the vessel wall by jetting or accentuating dissections produced by the PTCA procedure. Moreover, it is preferred that the hydrostatic head pressure at the interface of the infusion balloon and the vessel wall is between about 0.3 to about 1.5, preferably about 0.4 to about 0.8, and more preferably about 0.5 to about 0.75, atmospheres, so as to rapidly force the solution containing the therapeutic agent into the tunica media interstitial space without rupturing the small vessels in the adventitia, the origin of which is exposed to the hydrostatic head. Preferably, the infusion is accomplished by a hub pressure of about 4 to about 5 atm for a period of time from about 1 to about 4 minutes, preferably about 1 to 2 minutes. Also preferably, the infusion is accomplished at a pressure of about 0.3 to about 5 atm for about 15 seconds to about 3 minutes. Preferably, about 1 to about 1.5 mls are infused into 1 to about 3 traumatized lesions sites. This infusion regime will result in the penetration of an efficacious dose of the therapeutic agent to the smooth muscle cells of the vessel wall. Preferably, the therapeutic agent will be at a concentration of from about 0.01 μg/ml to about 8.0 μg/ml of infusate. Preferably, the therapeutic agent is a cytochalasin, and more preferably, cytochalasin B, or a functionally equivalent analog thereof.

Preferably, the administration of the therapeutic agent results in uniform delivery of the therapeutic agent to the tunica media. Moreover, the catheter administration of the therapeutic agent results in the delivery of an effective amount of the agent to the adventitia via the vasa vasorum, as well as the tunica media. Preferably, the therapeutic agent is also uniformly distributed to the adventitia. Catheter administration of a therapeutic agent, e.g., about 4 to about 24 ml of cytochalasin B at about 8.0 μg/ml, preferably results in a uniform pattern of therapeutic agent delivery, at a depth of penetration to at least about the inner 10%, more preferably to at least about the inner 20%, even more preferably to the inner 100%, of the tunica media. By the time a therapeutic agent diffused from the inner 10% of the tunica media to its outer limits in a swine coronary study, it was found that the cells at the outer limits were exposed to a therapeutic dose.

A preferred form of the therapeutic agent includes cytochalasin B in sterile saline at a concentration of about 8.0 μg/ml, in 30 ml vials, which should deliver the preferred cellular therapeutic dose described hereinabove needed to treat a single lesion. Preferably, the amount is uniformly distributed to the inner 20% of the tunica media and uniformly distributed to the adventitia.

In another embodiment of the present invention, a solution of a therapeutic agent is infused, in vivo or ex vivo, into the walls of isolated vessels (arteries or veins) to be used for vascular grafts. In this embodiment of the invention, the vessel that is to serve as the graft is excised or isolated and subsequently distended by an infusion of a solution of a therapeutic agent. Preferably the infusion is accomplished by a hub pressure of about 4 to about 5 atm for a period of time from about 1 to about 4 minutes, preferably about 1 to 2 minutes. This infusion regime will result in the penetration of an efficacious dose of the therapeutic agent to the smooth muscle cells of the vessel. Wall. Preferably, the therapeutic agent will be at a concentration of from about 0.01 μg/ml to about 0.8 μg/ml, more preferably from about 0.01 μg/ml to about 8.0 μg/ml of infusate. Preferably, the therapeutic agent is a cytochalasin, and more preferably, cytochalasin B, or a functionally equivalent analog thereof.

It is known to those of ordinary skill in the art that peripheral vessels that are used for vascular grafts in other peripheral sites or in coronary artery bypass grafts, frequently fail due to post surgical stenosis. Since cytochalasin B infusion maintains the vascular luminal area in surgically traumatized vessels by virtue of its biological stenting activity, its administration in this process can retard the ability of the vessel to contract, resulting in a larger luminal diameter or cross-sectional area. Furthermore, it is an advantage of this embodiment of the present invention that the administration of cytochalasin B in this manner can prevent the constriction or spasm that frequently occurs after vascular grafts are anastomosed to both their proximal and distal locations, that can lead to impaired function, if not total failure, of vascular grafts. Thus, the vessel stenting produced by cytochalasins should decrease the incidence of spasms, which can occur from a few days to several months following the graft procedure.

For example, in another embodiment of the invention, the therapeutic agents and dosage forms may be used in situations in which angioplasty is not sufficient to open a blocked artery, such as those situations which require the insertion of an intravascular stent or shunt or other implantable devices. Thus, the invention also provides stents, stets, adventitial wraps, indwelling catheters, synthetic grafts or shunts comprising the therapeutic agent. Useful therapeutic agents in this embodiment of the invention include anti-proliferative agents, e.g., cytoskeletal inhibitors. A preferred cytoskeletal inhibitor is a cytochalasin, for example, cytochalasin B or an analog thereof which is a functional equivalent of cytochalasin B. Another preferred cytoskeletal inhibitor of the invention is taxol or an analog of taxol which is a functional equivalent of taxol. Preferably, the anti-proliferative agent is in sustained release dosage form.

Thus, an implantable device, e.g., an intravascular stent or shunt, provides a mechanical means of providing an increase in luminal diameter of a vessel, in addition to that provided via the biological stenting action and/or anti-proliferative activity of the cytoskeletal inhibitor, such as cytochalasin B or taxol, releasably embedded therein or administered in solution or suspension during the interventional procedure. Furthermore, the placement of an implantable device comprising a therapeutic agent which is an inhibitor of smooth muscle cell proliferation provides an increased efficacy by reducing or preventing intimal proliferation. This inhibition of intimal smooth muscle cells and stroma produced by the smooth muscle allows for more rapid and complete re-endothelization following the intraventional placement of the device.

For the therapeutic conjugates of the invention, non-coupled vascular smooth muscle cell binding protein (e.g., free NR-AN-01 antibody) is preferably administered prior to administration of the therapeutic agent conjugate or dosage form to provide a blocker of non-specific binding to cross-reactive sites. Blocking of such sites is important because vascular smooth muscle cell binding proteins will generally have some low level of cross-reactivity with cells in tissues other than the desired smooth muscle cells. Such blocking can improve localization of the therapeutic conjugate or dosage form at the specific vascular site, e.g., by making more of the therapeutic conjugate available to the cells. As an example, non-coupled vascular smooth muscle binding protein is administered from about 5 minutes to about 48 hours, most preferably from about 5 minutes to about 30 minutes, prior to administration of the therapeutic conjugate or dosage form. In one preferred embodiment of the invention, the unlabeled specific "blocker" is a monovalent or bivalent form of an antibody (e.g., a whole antibody or an F(ab)'₂, Fab, Fab', or Fv fragment of an antibody). The monovalent form of the antibody has the advantage of minimizing displacement of the therapeutic conjugate or dosage form while maximizing blocking of the non-specific cross-reactive sites. The non-coupled vascular smooth muscle cell binding protein is administered in an amount effective to blocking binding of a least a portion of the non-specific cross-reactive sites in a patient. The amount may vary according to such factors as the weight of the patient and the nature of the binding protein. In general, about 0.06 mg to 0.20 mg per kg body weight or more of the unlabeled specific blocker is administered to a human.

In addition, a second irrelevant vascular smooth muscle cell binding protein may optionally be administered to a patient prior to administration of the therapeutic conjugate or dosage form to reduce non-specific binding of the therapeutic conjugate or dosage form to tissues. In a preferred embodiment, the irrelevant binding protein may be an antibody which does not bind to sites in the patient through antigen-specific binding, but instead binds in a non-specific manner, e.g., through Fc receptor binding reticuloendothelial cells, asialo-receptor binding, and by binding to ubiquitin-expressing cells. The irrelevant "blocker" decreases non-specific binding of the therapeutic conjugate or dosage form and thus reduces side-effects, e.g., tissue toxicity, associated with the use of the therapeutic conjugate or dosage form. The irrelevant "blocker" is advantageously administered from 5 minutes to 48 hours, most preferably from 15 minutes to one hour, prior to administration of the therapeutic conjugate or dosage form, although the length of time may vary depending upon the therapeutic conjugate and route or method of injection. Representative examples of irrelevant "blockers" include antibodies that are nonreactive with human tissues and receptors or cellular and serum proteins prepared from animal sources that when tested are found not to bind in a specific manner (e.g., with a $Ka<10^3 \text{ M}^{-1}$) to human cell membrane targets.

Kits Comprising an Implantable Delivery Device and at Least One Therapeutic Agent of the Invention The invention provides a kit comprising packing material enclosing, separately packaged, at least one implantable device adapted for the delivery of a therapeutic agent, e.g., a catheter, an adventitial wrap, a valve, a stent, a stet, a shunt or a synthetic graft, and at least one unit dosage form comprising the therapeutic agent, as well as instruction means for their use, in accord with the present methods. The unit dosage form may comprise an amount of at least one of the present therapeutic agents effective to accomplish the therapeutic results described herein when delivered locally and/or systemically. A preferred embodiment of the invention is a kit comprising a catheter adapted for the local delivery of at least one therapeutic agent to a site in the lumen of a mammalian vessel, along with instruction means directing its use in accord with the present invention. In a preferred aspect, the infusion catheter may be conveniently a double balloon or quadruple balloon catheter with a permeable membrane. Preferably, the therapeutic agent comprises a cytoskeletal inhibitor.

It is also envisioned that the kit of the invention comprises a non-catheter delivery device, e.g., an adventitial wrap, a valve, stet, stent or shunt, for systemic or local delivery. A valve, stent, wrap or shunt useful in the methods of the invention can comprise a biodegradable coating or porous non-biodegradable coating, e.g., a PTFE membrane, having dispersed therein one or more therapeutic agents of the invention, preferably a sustained release dosage form of the therapeutic agent.

Another embodiment of the invention is a kit comprising a device adapted for the local delivery of at least two therapeutic agents, a unit dosage of a first therapeutic agent, and a unit dosage of a second therapeutic agent, along with instruction means directing their use in accord with the present invention. The unit dosage forms of the first and second agents may be introduced via discrete lumens of a catheter, or mixed together prior to introduction into a single lumen of a catheter. If the unit dosage forms are introduced into discrete lumens of a catheter, the delivery of the agents to the vessel can occur simultaneously or sequentially. Moreover, a single lumen catheter may be employed to deliver a unit dosage form of one agent, followed by the reloading of the lumen with another agent and delivery of the other agent to the lumen of the vessel. Either or both unit dosages can act to reduce the diminution in vessel lumen diameter at the target site.

Alternatively, a unit dosage of one of the therapeutic agents may be administered locally, e.g., via catheter, while a unit dosage of another therapeutic agent is administered systemically, e.g., via oral administration.

The invention will be better understood by making reference to the following specific examples.

EXAMPLE 1

Binding to Vascular Smooth Muscle Cells in the Blood Vessel Wall in Vivo

Figure 1B:
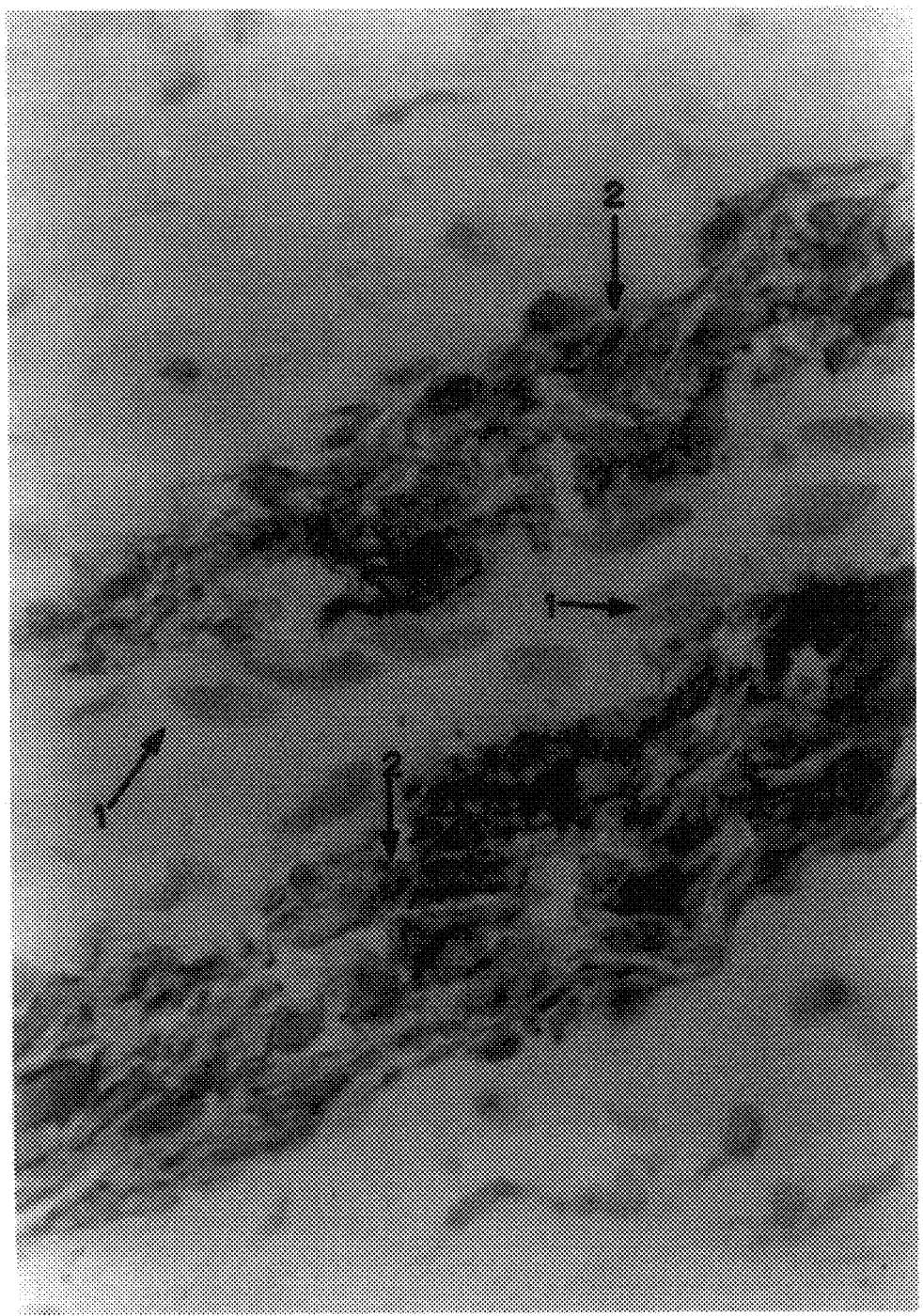
FIG. 1B is a photomicrograph of vascular smooth muscle cells in an artery of a 24-year-old male patient with vascular smooth muscle binding protein bound to the cell surface and membrane. The patient received the vascular smooth muscle binding protein by i.v. administration 4 days before the arterial tissue was prepared for histology.
Figure 2:
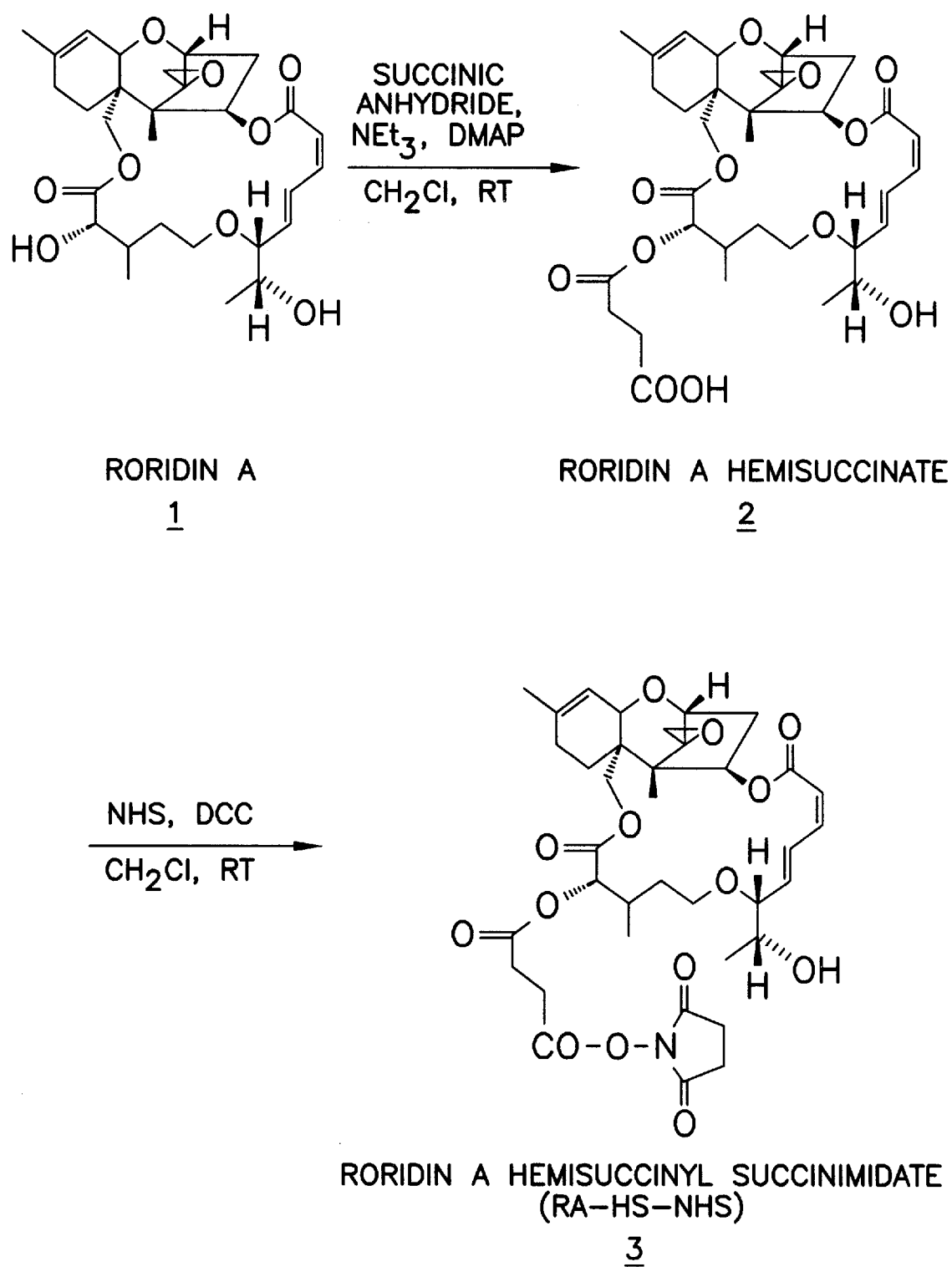
FIG. 2 depicts a first scheme for chemical coupling of a therapeutic agent to a vascular smooth muscle binding protein.
Figure 3:
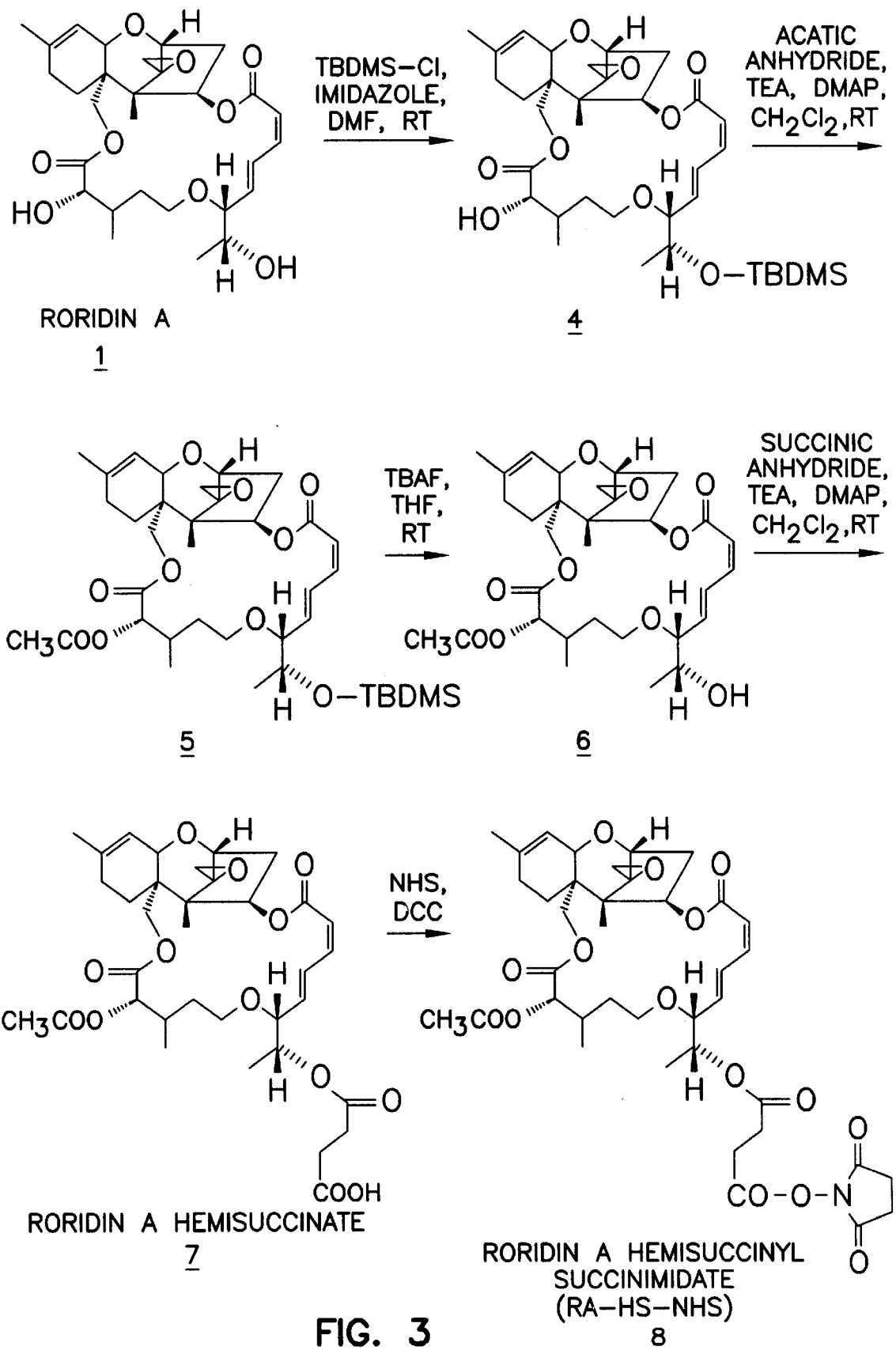
FIG. 3 depicts a second scheme for chemical coupling of a therapeutic agent to a vascular smooth muscle binding protein.

FIG. 1B illustrates the binding of NR-AN-01 (a murine IgG2b MAb) to the smooth muscle cells in the vascular wall of an artery in a 24-year old male patient, 4 days after the i.v. administration of NR-AN-01. FIG. 1B is a photomicrograph of a histological section taken through the medial region of an arterial wall of the patient after NR-AN-01 administration, where the section was reacted ex vivo with HRP-conjugated goat anti-mouse IgG. The reaction of the HRP-conjugate with NR-AN-01 MAb was visualized by adding 4-chloro-1-naphthol or 3,3'-diaminobenzidine tetrahydrochloride as a peroxidase substrate (chromogen). The reaction product of the substrate forms an insoluble purple or dark brown precipitate at the reaction site (shown at #2, FIG. 1B). A counter stain was used to visualize collagenous extracellular matrix material (shown at #2, FIG. 1B) or cell nuclei (#1, FIG. 1B). Smooth muscle cells are visualized under microscopic examination as purple stained cells (FIG. 1A and FIG. 1B). This photomicrograph (FIG. 1B) demonstrates the ability of the MAb to specifically bind to human vascular smooth muscle in vivo, and to be internalized by the cells and remain in the cells for extended periods.

EXAMPLE 2

Therapeutic Conjugates Containing Trichothecene Therapeutic Agents

Conjugates of NR-AN-01 and Roridin A were constructed by chemically coupling a hemisuccinate derivative of the trichothecene cytotoxin (as described below) to a monoclonal antibody designated NR-AN-01. Two conjugates were prepared, one coupled at the Roridin A 2' position and one at the 13' position. Two schemes were used in this synthesis, as depicted in FIG. 2 and FIG. 3. The conjugate was then purified from unreacted Roridin A by PD-10 SEPHAROSE® column chromatography (Pharmacia; Piscataway, N.J.), analyzed by size exclusion high pressure liquid chromatography, and the column fractions were characterized by SDS-PAGE and isoelectric focusing (IEF), as described below.

FIG. 2 shows diagrammatically the first reaction scheme for synthesis of Roridin A hemisuccinyl succinimidate (RA-HS-NHS) through a two step process with reagents: succinic anhydride, triethylamine ($NEt_3$) and dimethyl amino pyridine (DMAP) present in dichloromethane ($CH_2Cl_2$) at room temperature (RT); and, N-hydroxysuccinimide (NHS) and dicyclohexyl carbodiimide (DCC) reagents also in $CH_2Cl_2$ at RT.

FIG. 3 shows diagrammatically the second reaction scheme for synthesis of Roridin A hemisuccinyl succinimidate (RA-HS-NHS) through a five step process with reagents: t-butyl dimethyl silyl chloride (TBMS-Cl) and imidazole in dimethylformamide (DMF) at room temperature (RT); acetic anhydride, triethylamine (TEA), and diethylaminopyridine in dichloromethane ($CH_2Cl_2$) at RT; succinic anhydride, triethylamine (TEA) and dimethylaminopyridine (DMAP) in ($CH_2Cl_2$) at RT; and, N-hydroxysuccinimide (NHS) and dicyclohexyl carbodiimide (DCC) reagents.

Synthesis of 2' Roridin-A Hemisuccinic Acid (2):

To 0.5 g (0.94 mmol) of Roridin A, 15 ml of dichloromethane was added. To this solution with stirring was added 0.104 g (1.04 mmol) of succinic anhydride. To the reaction mixture, 0.2 ml of triethylamine in 5 ml dichloromethane was added. To the homogeneous reaction mixture, a catalytic amount of dimethylaminopyridine was added and stirred at room temperature for 15 hours. Completion of the reaction was followed by thin layer chromatography ($CH_2Cl_2$:$CH_3OH$=9.7:0.3 with few drops of acetic acid). At the end of the reaction, 0.3 ml of glacial acetic acid was added and the solvent removed under reduced pressure. The dried crude residue was partitioned between water and methylene chloride. The combined methylene chloride extracts (3×50 ml) were dried over anhydrous sodium sulfate, solvent was removed under vacuum and dried to yield 0.575 g (96%) of a crude mixture of three compounds. Preparative C18 HPLC separation of the crude mixture in 50% acetonitrile-water with 2% acetic acid yielded 0.36 g (60%) of 2 as a white solid.

Synthesis of Succinimidyl 2'-Roridin A Hemisuccinate (3):

To 0.3 g (0.476 mmol) of 2' Roridin A hemisuccinic acid in 30 ml dichloromethane, 0.055 g (0.478 mmol) N-hydroxysuccinimide was added. To the clear reaction mixture, 0.108 g (0.524 mmol) dicyclohexylcarbodiimide was added. The reaction mixture was stirred at room temperature for 6 hours. Completion of the reaction was followed by TLC ($CH_2Cl_2$:$CH_3OH$=9.7:0.3 with a few drops of acetic acid) as a developing solvent. A few drops of glacial acetic acid was added to the reaction mixture and the solvent was removed under reduced pressure. To the dried residue dichloromethane was added and the precipitated DCU was filtered. Solvent from the filtrate was removed under reduced pressure to yield a white solid. From the crude product, 0.208 g (60%) of 3 was purified by preparative HPLC in 50% acetonitrile with 2% acetic acid as a mobile phase.

Synthesis of 13'-t-Butyldimethylsilyl Roridin A (4):

To 72.3 mg (0.136 mmol) of Roridin A in 0.5 ml dimethylfornamide solution, 0.055 g (0.367 mmol) t-butyldimethylsilyl chloride and 0.025 g (0.368 mmol) of imidazole were added. The reaction mixture was stirred at room temperature for 15 hours. Completion of the reaction was followed by silica gel thin layer chromatography using 1% MeOH—$CHCl_3$ as a developing solvent. Solvent from the reaction mixture was removed in vacuo and dried. The crude product was partitioned between water and methylene chloride. Solvent from the combined methylene chloride extracts was removed under reduced pressure and dried. The crude product was purified by flash chromatography using EtOAc:Hexane (1:3) as an eluting solvent. Solvent from the eluants was removed under reduced pressure to yield 0.66 g (75%) of 4 as a solid.

Synthesis of 13'-t-Butyldimethylsilyl 2' Acetyl Roridin A (5):

To 0.1 g (0.155 mmol) of 13'-t-butyldimethylsilyl Roridin A in 10 ml dichloromethane, 0.3 ml acetic anhydride, 0.2 ml triethylamine and a few crystals of dimethylaminopyridine were added and stored at room temperature for 2 hours. Completion of the reaction was followed by TLC in 1% methanol-methylene chloride as a developing solvent. Solvent was removed under reduced pressure and purified by a silica gel column using 1% methanol-chloroform as an elution solvent. Solvent from the eluants was removed under vacuum to yield 0.085 g (80%) of 5 as a solid.

Synthesis of 2' Acetyl Roridin A (6):

To 0.05 g (0.073 mmol) of 2' acetyl 13'-t-butyldimethylsilyl Roridin A in 5 ml tetrahydrofuran, 0.3 ml of 1 M tetrabutyl-ammonium fluoride solution in THF was added. The reaction mixture was stirred at room temperature for 2 hours. Completion of the reaction was followed by silica gel thin layer chromatography using 1% MeOH—CHCl, as the developing solvent. Solvent from the reaction mixture was removed under reduced pressure and dried. The crude product was purified on a silica gel column using 1% $CH_3OH$—$CHCl_3$ as an eluting solvent. Solvent from the combined eluants were removed under vacuum to yield 0.020 g (48%) of 6 as a solid.

Synthesis of 2'-Acetyl 13'-hemisuccinyl Roridin A (7):

To 0.05 g (0.087 mmol) of 2'-acetyl Roridin A in 1 ml of dichloromethane, 0.025 g (0.25 mmol) succinic anhydride and 35 ml of triethylamine was added. A few crystals of dimethylaminopyridine was added as a catalyst. The reaction mixture was stirred at room temperature for 24 hours. Completion of the reaction was followed by thin layer chromatography using 5% MeOH—$CH_2Cl_2$ as developing solvent. At the end of the reaction 30 ml of glacial acetic acid was added. Solvent from the reaction mixture was removed under reduced pressure and dried. The crude product was partitioned between water and ethyl acetate. Solvent from the combined ethyl acetate fractions was removed under reduced pressure. Crude product was purified by passing through a silica gel column to yield 0.039 g (66%) of 7 as a white solid.

Synthesis of Succinimidyl 2'-Acetyl 13' -Roridin A Hemisuccinate (8):

To 0.036 g (0.0050 mmol) of 2'-acetyl 13'-Roridin A hemisuccinic acid in 2 ml dichloromethane, 0.009 g (0.09 mmol) N-hydroxysuccinimide was added. To a stirred solution, 0.012 g (0.059 mmol) dicyclohexylcarbodiimide was added. The reaction mixture was stirred at room temperature for 8 hours. Completion of the reaction was followed by silica gel thin layer chromatography using 5% MeOH—$CH_2Cl_2$ as a developing solvent. A few drops of glacial acetic acid was added to the reaction mixture. Solvent from the reaction mixture was removed under reduced pressure and dried. The crude product was purified on a silica gel column using 5% MeOH—$CH_2Cl_2$ as an eluting solvent. Solvent from the combined eluants was removed under vacuum to yield 0.025 g (61%) of 8 as a white solid.

Conjugation of Succinimidyl 2'-Roridin A Hemisuccinate (3) and Succinimidyl 2'-Acetyl 13'-Roridin A Hemisuccinate (8) to NR-AN-01 Whole Antibody (MAb):

Conjugation reactions were performed at pH 8.0 in borate buffer in the presence of 25% dimethylsulfoxide (DMSO) solvent at room temperature with gentle mixing for 45 minutes prior to purification by gel permeation chromatography. The molar trichothecene drug precursor to antibody offerings were 25:1 and 40:1 for the 2' and 13' Roridin A analogues (3 and 8), respectively. Antibody concentration was 0.9 to 1.0 mg/ml during the conjugation reaction.

A Typical 2' Analogue (3) Reaction with 25 mg of Antibody was as follows:

To 4.7 ml of 5.3 mg Ab/ml in phosphate buffered saline (i.e., PBS; 150 mM NaCl, 6.7 mM Phosphate, pH 7.3) was added 10 ml PBS and 5 ml of borate buffer (0.5 M, pH 8.0). With stirring gently to the reaction mixture, 6.3 ml of DMSO containing 1.37 mg of succinimidyl 2' Roridin A hemisuccinate (3) was then added dropwise over a 15 second period.

Purification:

To purify, one ml reaction aliquots were applied to Pharmacia PD-10 Sepharose® columns equilibrated in PBS. The eluted conjugate was collected in 2.4 to 4.8 ml fractions. The PD-10 purified conjugate aliquots were then pooled and concentrated on an Amicon PM-10 DiAflo® concentrator to 1.5 to 2.0 mg of Ab/ml; sterile filtered through a 0.2μ Gelman Acrodisc® and filled into sterile glass vials in 5 ml volume.

The 2' conjugate was quick frozen in liquid nitrogen and then stored at −70° C. until use. The 13' Roridin A NR-AN-01 conjugate was stored frozen or refrigerated (i.e., 5–10° C.).

Characterization of Conjugates:

Protein concentration was determined by BCA assay using the copper reagent method (Pierce Chemical Corp.).

Assessment of degree of antibody derivatization was performed by first hydrolyzing an aliquot of conjugate in 0.2 M carbonate, pH 10.3 for 4 hours (at room temperature for 2' conjugate or at 37° C. for the 13' conjugate) followed by filtration through a PM-30 membrane. The filtrate was then assayed for Roridin A on C-18 reverse phase HPLC using a mobile phase of 50:48:2 ratio $CH_3CN:H_2O:HOAC$, respectively. A 1.32 correction factor was used to correct for parallel macrocyclic ring decomposition that gives polar products during the hydrolysis of the 13' conjugate.

Size exclusion chromatography on DuPont Zorbax® HPLC and isoelectric focusing using Serva® gel plates (pH 3 to 10) were also performed. No indication of aggregation was observed by HPLC.

Immunoassay of the Roridin A-antibody conjugates was performed by either competitive ELISA using biotinylated-Ab with Streptavidin/Peroxidase detection or by a competitive cell binding assay using $^{125}$I-labeled antibody. Alternatively, immunoreactivity was measured under conditions of antigen saturation in a cell binding assay wherein antibody was first trace labeled with I-125 by the chloramine T method and then subsequently derivatized with 2' and 13' Roridin A precursors.

EXAMPLE 3

Kinetics of Binding to Smooth Muscle Cells

For administration by i.v. catheter, it is desirable that the therapeutic conjugates of the invention be administered in less than 3 to 5 minutes, so that blood flow can be reestablished in the patient. Therefore, studies were conducted to determine the binding kinetics of a smooth muscle binding protein with a Ka of >$10^9$ liter/mole. Because human vascular smooth muscle cells grow slowly in culture, and baboon smooth muscle cells were found to express the human CSPG cell surface marker, BO54 baboon artery smooth muscle cells and human A375 M/M (melanoma; ATCC #CRL1619) cells bearing CSPG surface marker were used in many of the studies described in the Examples, below.

For the kinetic binding studies, A375 M/M and BO54 cells were seeded in sterile 96 well microtiter plates at 2500 cells/well. Plates were wrapped in aluminum foil, and incubated at 37° C. overnight in a humidified atmosphere of 5% $CO_2$/95% air. After approximately 18 hr, incubation plates were removed and cells were fixed with 0.05% glutaraldehyde for 5 minutes to prevent membrane turnover. Following fixation, the plates were exhaustively washed with PBS containing 0.5% Tween-20®. Serial two-fold dilutions of an NR-AN-01 therapeutic conjugate containing Roridin A were prepared at protein concentrations of 10 mg/ml to 20 ng/ml, and each dilution was aliquoted into two wells. The plates were incubated at 4° C. with the NR-AN-01 for 5, 15, 30, and 60 minutes, after which the unbound protein was removed by aspiration and 100 ml of CS buffer was added (5% chicken serumi 0.5% Tween-20® in PBS) to each well. CS buffer was removed and the NR-AN-01 therapeutic conjugate bound to the cells was visualized by adding 100 ml of HRP-conjugated goat anti-mouse IgG (Sigma Chemical Co., St. Louis, Mo.) to each well; incubating at 4° C. for 1 hr.; washing with PBS/0.05% Tween® to remove unbound goat IgG; and, adding 2,2'-azino-bis(3-ethylbenzthiazoline-6-sulfonic acid (ABTS) chromogenic substrate (i.e., for HRP). After incubating for 30 minutes, the amount of NR-AN-01 bound to the cells was quantified by measuring the absorbance at 415 nm and 490 nm using an ELISA plate reader equipped for data acquisition by a Compaq computer.

Figure 4A:
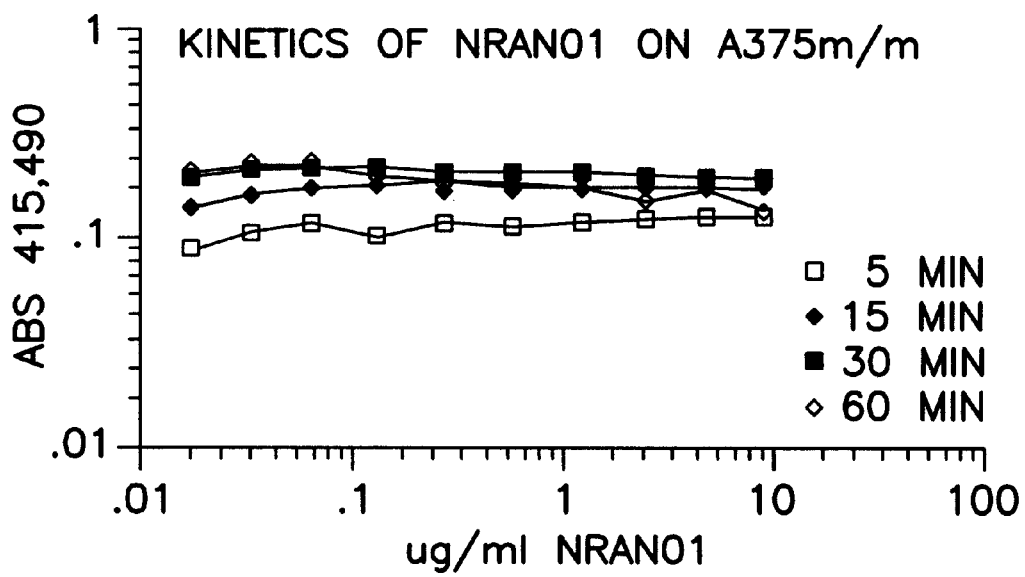
FIG. 4A graphically depicts experimental data showing rapid binding of vascular smooth muscle binding protein to marker-positive test cells in vitro.

FIG. 4A graphically depicts the results of in vitro studies in which A375m/m marker-positive cells were held at 4° C. (i.e., to prevent membrane turnover) for 5 minutes (open squares, FIG. 4A), 15 minutes (closed diamonds, FIG. 4A), 30 minutes (closed squares, FIG. 4A) or 60 minutes (open diamonds, FIG. 4A) with different concentrations of NR-AN-01 (NRAN01 μg/ml). The binding of the NR-AN-01 MAb to the A375 cells was quantified by washing to remove unbound antibody, adding HRP-conjugated goat anti-mouse IgG to react with the cell-bound MAb, washing to remove unbound goat second antibody, and adding 2,2'-azino-bis(3-ethylbenzthiazoline-6-sulfonic acid) (ABTS) substrate for peroxidase. Color development was monitored after 30 minutes at both 415 nm and 490 nm (ABS415,490).

Figure 4B:
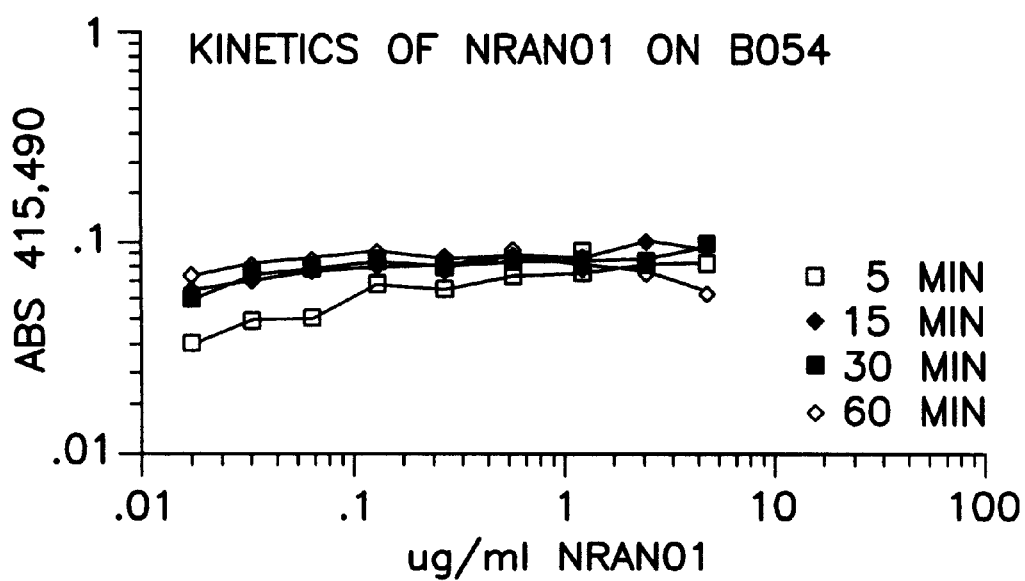
FIG. 4B graphically depicts experimental data showing rapid binding for control HT29 marker-negative cells, even in a 5' "pulse" treatment followed by a 24 hour recovery period prior to [3H]leucine exposure, but, in contrast, the RA-NR-AN-01 therapeutic conjugate is not cytotoxic to cells.

FIG. 4B graphically depicts the results of in vitro studies conducted in a manner similar to those described above in regard to FIG. 4A, but using BO54 marker-positive smooth muscle cells, i.e., instead of the A375 m/m cells.

The results presented in FIG. 4A and FIG. 4B show significant binding of NR-AN-01 to A375 and BO54 cells within 5 minutes at 4° C., even at the lowest dose of 20 ng/ml.

EXAMPLE 4

Effects of Roridin A and RA-NR-AN-01 Conjugates

The effects of Roridin A (RA) and RA-NR-AN-01 conjugates on cellular protein synthesis (i.e., by $^3$H-leucine incorporation) and metabolic activity (i.e., by mitochondrial MTT assay) were tested in the experiments detailed in EXAMPLE 5 and EXAMPLE 6, below. The studies in EXAMPLE 4 include experiments to determine the effects of long-term (i.e., 24 hour) treatment with the agents. The studies in EXAMPLE 5 include experiments to determine the effects of "pulse" (i.e., 5 minute) treatment on cells. In both studies, the cellular specificity of the effects were evaluated by including "target" cells (i.e., cells bearing the CSPG "marker") and non-target cells. For comparative purposes, free-RA (i.e., uncoupled) was also included in the studies. The effects on cellular protein synthesis or metabolic activity were evaluated either immediately following the treatment, or a "recovery period" was allowed (i.e., involving incubation of the cells overnight at 37° C.) to determine the long-term effects of the agents on the cell populations.

Metabolic Effects After 24 Hours Exposure:

While it is known that monoclonal antibody-drug conjugates may have a degree of specificity for cells bearing marker antigens when employed in vivo, it has proven more difficult in many systems to demonstrate in vitro specificity of action, especially with compounds that are lipophilic. Therefore, the present experiments were conducted in which the inhibitory effects of the NR-AN-01-Roridin A conjugate was tested on target and non-target cells over 24 hours. The results with RA-NR-AN-01 were compared to the effect of free Roridin A over the same 24-hour period. A modified methyl-tetrazolium blue (MTT) assay was utilized with 3-(4,5-dimethylthiazol-2-yl)-2,5-diphenyl tetrazolium bromide (Sigma) to determine cellular metabolic activity. This assay is thought to measure cellular mitochondrial dehydrogenase activity. For some of these studies, M14 (melanoma) and BO54 (smooth muscle) cell lines were used as marker-positive target cells and HT29 cells (colon carcinoma; ATCC #HTB38) were used as the non-target specificity control. In other studies, A375 was used as a marker-positive cell. The HT29 and M14 cells were seeded in 96-well microtiter plates at a concentration of $5.0 \times 10^3$ cells/well, and the BO54 cells were seeded at $2.5 \times 10^3$ cells/well. Serial two-fold dilutions of free Roridin A and 2'RA-HS-NR-AN-01 (i.e., Roridin A coupled through a hemisuccinate (HS) coupling agent at the 2' position to NR-AN-01) were prepared in DMEM over a range of protein concentrations from 20 mg/ml to 40 µg/ml. Test agents were added (in duplicate) to microtiter wells (100 ml/well), and the plates were wrapped in aluminum foil and incubated at 37° C. in a humidified atmosphere consisting of 5% $CO_2$/95% air for 24 hours. After 24 hours, medium was removed (by aspiration), fresh DMEM was added (100 ml/well), and the cells were returned to incubate for an additional overnight (i.e., 16–18 hours) "recovery period". At the end of the "recovery period" cellular metabolic activity was determined by adding 20 ml to each well of a 5 mg/ml MTT solution. The plates were covered and incubated at 37° C. for 4 hours and then the reaction was developed by adding 100 ml/well of 10% SDS/0.1 N HCl. The dark blue solubilized formazan reaction product was developed at room temperature after 16–18 hours and quantified using an ELISA microtiter plate reader at an absorbance of 570 nm.

Figure 5A:
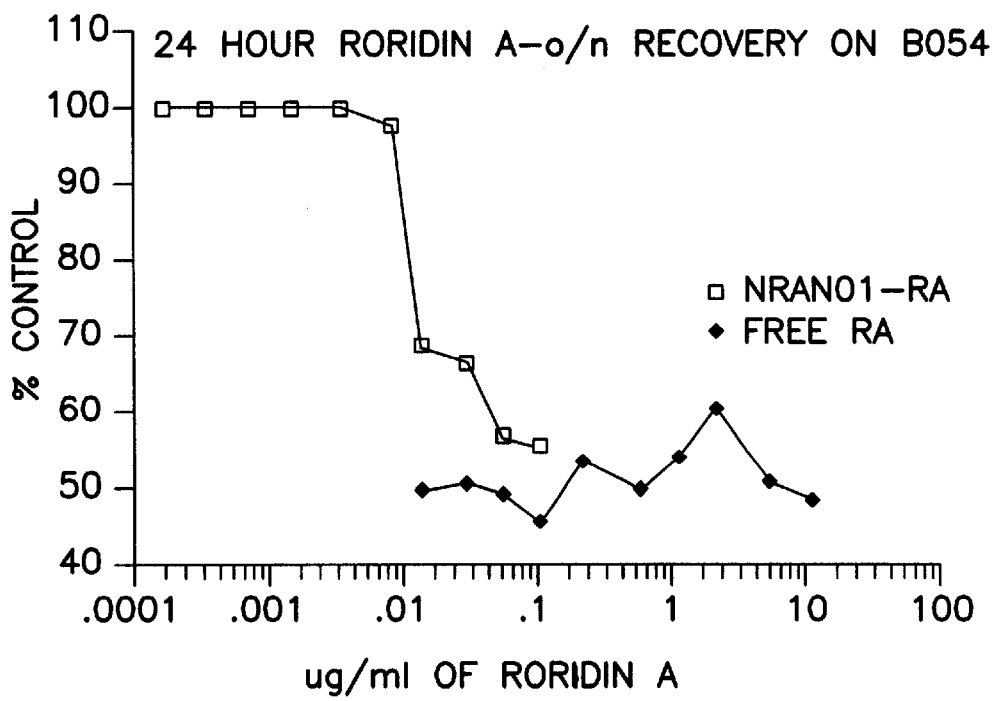

FIG. 5A graphically depicts the results of in vitro studies in which BO54 marker-positive smooth muscle cells were incubated with different concentrations of RA-NR-AN-01 (NRAN01-RA; open squares, FIG. 5A) or free Roridin A (Free RA; closed diamonds, FIG. 5A) for a period of 24 hours, washed, and then returned to culture for an additional 16–18 hour overnight (o/n) recovery period prior to testing metabolic activity in an MTT assay. The concentrations of Free RA and RA-NR-AN-01 are expressed as the calculated concentration of Roridin A (in mg/ml plotted on a log scale) in the assay (i.e., rather than the total mg/ml of NR-AN-01 protein in the assay), so that direct comparisons could be made. The metabolic activity of the cells in the MTT assay is presented as the percentage of the metabolic activity measured in a control untreated culture of cells (i.e., % control).

Figure 5B:
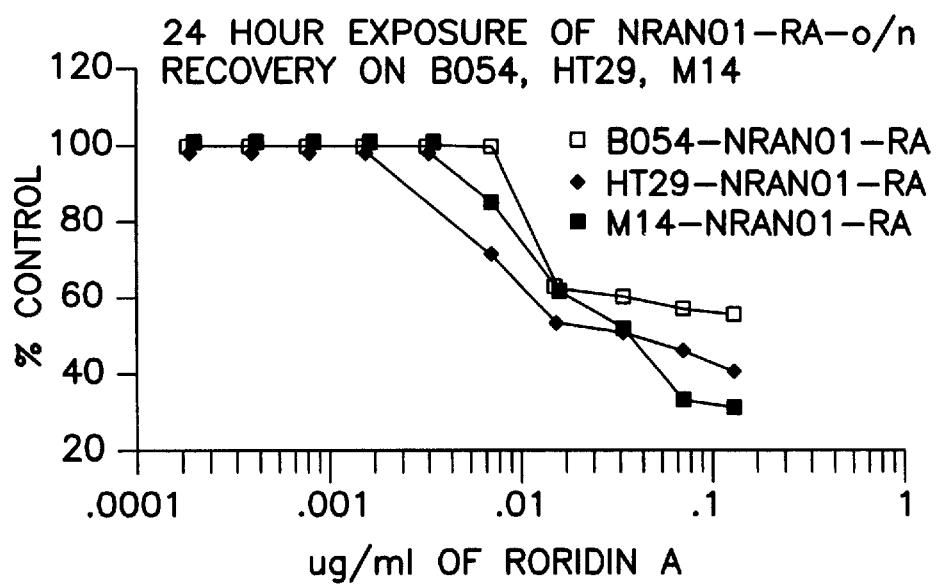

FIG. 5B graphically depicts the results of in vitro studies conducted in a manner similar to those described above in regard to FIG. 5A, but comparing the effects of only RA-NR-AN-01 (NRAN01-RA) on three different cell types: namely, BO54 marker-positive smooth muscle cells (BO54-NRAN01-RA; open squares, FIG. 5B); HT29 marker-negative control cells (HT29-NRAN01-RA; closed diamonds, FIG. 5B); and, M14 marker-positive cells (M14-NRAN01-RA; closed squares, FIG. 5B). As described above in regard to FIG. 5A, the concentrations in the present experiment are expressed in terms of ug/ml of Roridin A. Metabolic activity of the cells is expressed in a manner similar to that in FIG. 5A, i.e., as the percentage of activity measured in an untreated control culture of cells (% control).

The results presented in FIGS. 5A and FIG. 5B show that metabolic activity measured in the MTT assay was significantly decreased in all populations of test cells, even 16–18 hours after a 24-hour incubation in either free Roridin A or the 2' or 13' RA-NR-AN-01 conjugates. The effects of the RA-NR-AN-01-conjugates appeared to be non-specifically inhibitory for both target (BO54 and M14) and non-target (HT29) cells (FIGS. 5A and 5B). The inhibitory effects were observed at a free Roridin A or RA-conjugate concentration of >10 ng/ml.

For comparative purposes, a second study was conducted in which the effects of Pseudomonas exotoxin (PE) conjugates on cells were evaluated in a similar protocol. For these studies, target and non-target cells were treated with PE or PE-NR-AN-01 for 24 hours, and then allowed a "recovery period" (as above) before metabolic activity was tested in an MTT assay.

Figure 6A:
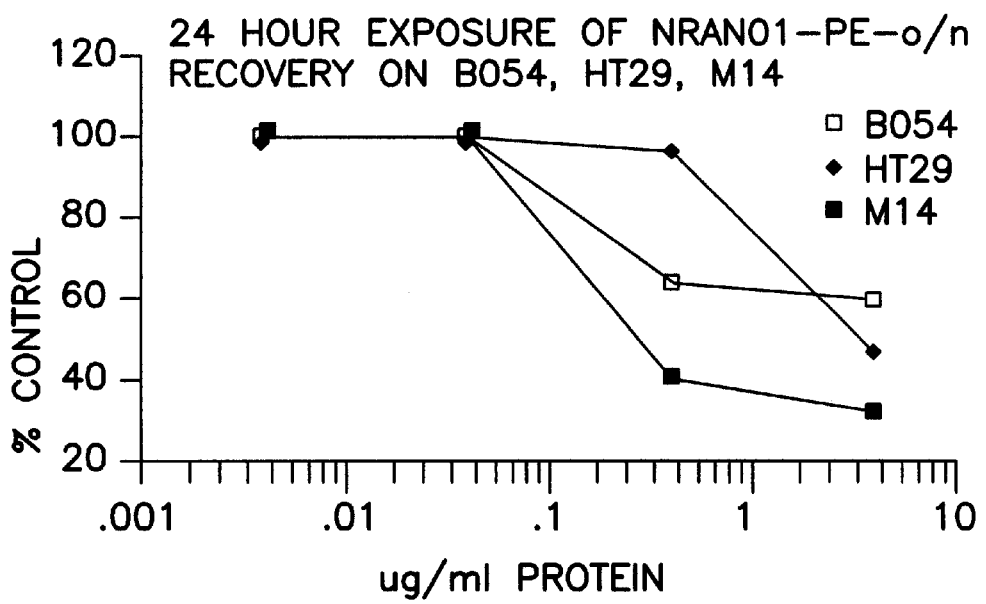

FIG. 6A graphically depicts the results of in vitro studies conducted in a manner similar to those described above in regard to FIG. 5A, but designed to study the metabolic effects of PE-NR-AN-01 (NRAN01-PE) on cells, i.e., rather than RA-NR-AN-01. Three different cell types were utilized: namely, BO54 marker-positive smooth muscle cells (BO54; open squares, FIG. 6A); HT29 marker-negative control cells (HT29; closed diamonds, FIG. 6A); and, M14 maker-positive cells (MT14; closed squares, FIG. 6A). In this study, the concentration of conjugate is expressed in 1 µg/ml NR-AN-01 protein (plotted on a log scale), and the metabolic activity is expressed as the percentage of the MTT activity measured in an untreated control culture (% control).

Figure 6B:
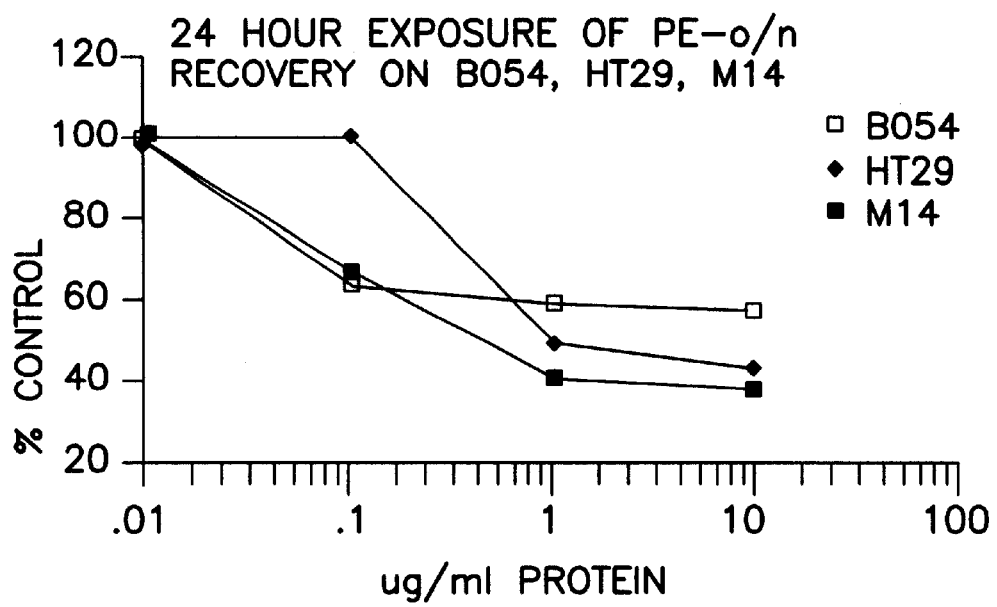

FIG. 6B graphically depicts the results of in vitro studies conducted in manner similar to those discussed above in regard to FIG. 6A, but designed to compare the effects obtained with free PE (PE) to those obtained above, i.e., in FIG. 6A, with PE-NR-AN-01. The cells, culture conditions, calculations, and presentation of the results are the same as in FIG. 6A, above.

The results presented in FIG. 6A and FIG. 6B show that 24 hours exposure to PE-NR-AN-01 or free PE was non-specifically inhibitory to cells at concentrations of >100 ng/ml.

While this type of non-specific inhibition was judged to be of potential value for biological atheroectomy, it was not considered desirable for treatment of restenosis following angioplasty where dead and dying cells may release factors that stimulate smooth muscle proliferation.

EXAMPLE 5

Effects of Pulse-Treatment on Cellular Activity

Additional studies were conducted to evaluate the effects of a short-term, i.e., 5 minute, exposure to a Roridin A-containing therapeutic conjugate on cells. In these studies, both metabolic activity (measured in MTT assays) and cellular protein synthesis (measured by $^3$H-leucine incorporation) were evaluated.

Effects After 5 Minutes of Exposure: Protein Synthesis

The effects of a 5-minute exposure to free Roridin A (RA) or a therapeutic conjugate were evaluated. Roridin A-NR-AN-01 coupled through a hemisuccinyl (HS) at either the 2' position (2'RA-HS-NR-AN-01) or the 13' position (13'RA-HS-NR-AN-01) were employed. (In the case of 13'RA-HS-NR-AN-01, the 2' position of Roridin A was also acetylated.) The RA, 2' or 13'RA-NR-AN-01 conjugates were diluted two fold in sterile DMEM over a range of concentrations from 400 ng/ml to 780 pg/ml of Roridin A. (The test samples were all normalized to Roridin A, so that direct comparisons could be made of the effects at comparable doses.) Samples were aliquoted (in duplicate) into duplicate microtiter plates at 100 ml/well and incubated at room temperature for five minutes.

Both short-term and long-term effects of the test samples on marker-positive A375 and marker-negative HT29 cells were determined. For studying the short-term effects, 100 ml/well of [$^3$H]-leucine (0.5 mCi/ml) was added immediately after the 5-minute treatment with conjugate (or RA) and protein synthesis was evaluated over a four-hour period. For determining the long-term effects, the cells were treated for 5 minutes, washed, and then returned to culture for a 24-hour "recovery" period in DMEM medium containing either 5% NBS/5% Serum Plus® (i.e., for A375 or HT29 cells) or 10% FBS (i.e., for BO54 cells). At the end of the "recovery" period, the incubation medium was removed (i.e., by aspiration) and $^3$H-leucine was added (as above). In both cases (i.e., whether short-term or long-term), protein synthesis of the cells was evaluated by incubating the cells with the $^3$H-leucine for 4 hours at 37° C. in a humidified chamber (as above), and all results are calculated by comparison with non-treated cells (i.e., 100% control). After 4 hours the $^3$H-leucine was removed, the cells were removed from the substrata by trypsin-treatment, aspirated (using a PHD™ cell harvester (Cambridge Technology, Inc., Cambridge, Mass.)) and collected by filtration on glass fiber filters. The glass fiber filters were dried and radioactivity quantified by liquid scintillation spectroscopy in a Beckman liquid scintillation counter.

Figure 7A:
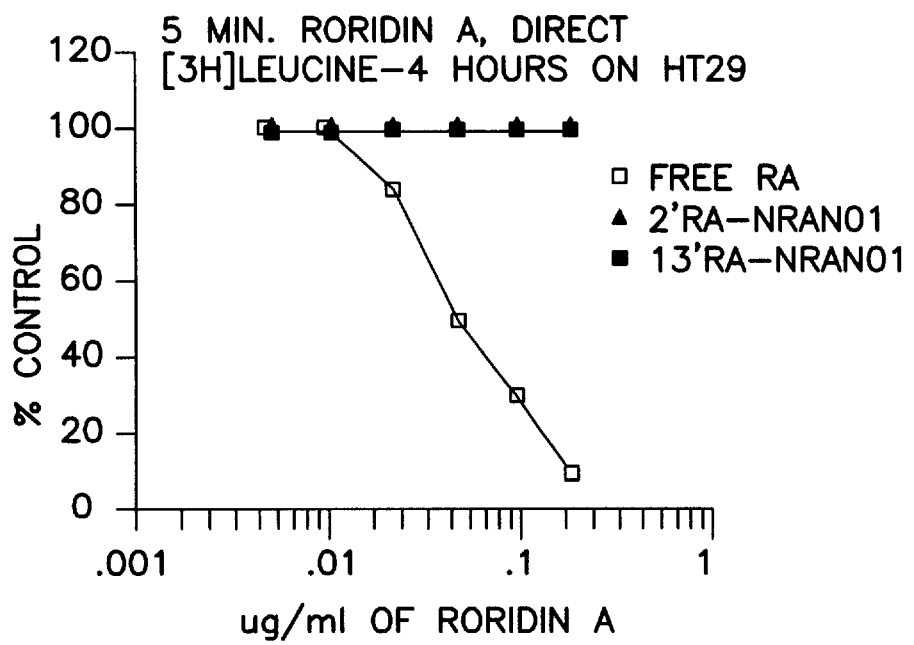
FIG. 7C presents graphically results of experiments showing that "pulse" treatment of cells in vitro with the RA-NR-AN-01 therapeutic conjugate inhibits cellular activity in marker-positive A375 cells, as measured by protein synthesis.
FIG. 7D presents graphically experimental data showing that "pulse" treatment of cells in vitro with the RA-NR-AN-01 therapeutic conjugate did not exert long-lasting inhibitory effects on cellular activity in marker-positive cells, since protein synthesis in A375 cells was not inhibited when the cells were allowed an overnight recovery period prior to testing in vitro.

FIG. 7A graphically depicts the results of in vitro studies conducted to investigate the effects on control HT29 marker-negative cells of a 5 minute exposure to different concentrations of Roridin A (Free RA; open squares, FIG. 7A), or 2'RA-NR-AN-01 (2'RA-NRAN01; closed squares, FIG. 7A), or 13'RA-NR-AN-01(13'RA-NRAN01; closed triangles, FIG. 7A) conjugates. The concentrations of Free RA, 2'RA-NR-AN-01 or 13'NR-AN-01 are expressed as the calculated concentration of Roridin A in the assay (in µg/ml plotted on a log scale), i.e., rather than the total µg/ml of NR-AN-01 protein, so that direct comparisons of the results can be made. For these studies, the cells were treated for 5 minutes, washed, and then returned to culture for 4 hours, during which time cellular protein synthesis was evaluated by adding 0.5 mCi/ml of $^3$H-leucine to the culture medium. At the end of the 4 hour period, cellular proteins were collected and radioactivity was determined. The results are expressed as the percentage of the radioactivity recorded in a control (non-treated) HT29 cell culture (i.e., %control).

Figure 7B:
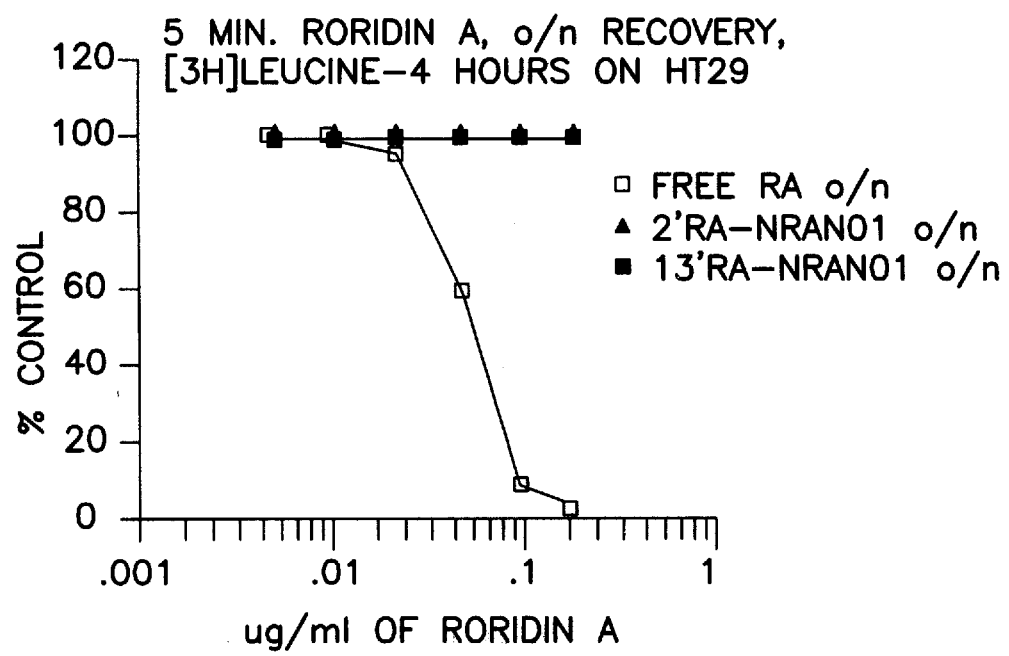

FIG. 7B graphically depicts the results of in vitro studies investigating the effects on control HT29 marker-negative cells of a 5 minute expose to different concentrations of Free RA (open squares, FIG. 7B), 2'RA-NRAN01 (closed squares, FIG. 7B), or 13'RA-NRAN01 (closed triangles, FIG. 7B), as described above in regard to FIG. 7A, but in the present experiments the cells were incubated for a 16–18 hour recovery period (i.e., overnight; o/n) prior to testing protein synthesis in a four hour $^3$H-leucine protein synthesis assay. The results are presented in a manner similar to those above in FIG. 7A.

The results presented in FIG. 7A and FIG. 7B show the short-term and long-term effects, respectively, of RA, 2'RA-HS-NR-AN-01, and 13'RA-HS-NR-AN-01 on protein synthesis by HT29 control cells. The results show a dose-response inhibition of cellular protein synthesis by the free Roridin A, but not by RA-NR-AN-01, in HT29 cells. The inhibition triggered by RA during the 5 minutes of incubation was still manifest after the 16–18 hours recovery period (FIG. 7B). In contrast, treatment of non-target HT29 cells with 2'RA-HS-NR-AN-01 or 13'RA-HS-NR-AN-01 did not result in detectable inhibition of protein synthesis. Thus, these results (in contrast to those obtained above over 24 hours) seem to suggest a surprising degree of specificity to the in vitro action of the NR-AN-01-conjugates when treatment was delivered in a 5-minute "pulse". However, it was also possible that the NR-AN-01-conjugate was inactive, and so additional experiments were conducted to evaluate the effect of the conjugates on target cells.

FIG. 7C graphically depicts the results of in vitro studies investigating the effects on A375m/m marker-positive cells of a 5 minute exposure to different concentrations of Free RA (open squares, FIG. 7C), 2'RA-NR-AN-01 (closed squares, FIG. 7C) or 13'RA-NR-AN-01 (closed triangles, FIG. 7C), as described above in regard to FIG. 7A. In the present studies, the A375 cells were incubated for 5 minutes in the test agent, washed, and tested for protein synthesis over the next 4 hours by adding 0.5 mCi/ml $^3$H-leucine to the culture medium. The results of the experiments are plotted in a manner similar to those described, above, in regard to FIG. 7A.

FIG. 7D graphically depicts the results of in vitro studies investigating the effects on A375 m/ml marker-positive cells of a 5 minute exposure to different concentrations of Free RA (open squares, FIG. 7D), 2'RA-NRAN01 (closed squares, FIG. 7D), 13'RA-NRAN01 (closed triangles, FIG. 7D), as described above in regard to FIG. 7B. In the present studies, the A375 cells were incubated for 5 minutes in the test agent, washed, and then returned to culture for a 16–18 hour recovery period (i.e., overnight; o/n Recovery), after which time protein synthesis was evaluated during a 4 hour $^3$H-leucine protein synthesis assay. The results of the experiments are plotted in a manner similar to those described above in regard to FIG. 7A.

The results presented in FIGS. 7C and FIG. 7D show the short-term and long-term effects, respectively, of RA, 2'RA-HS-NR-AN-01 and 13'-RA-HS-NR-AN-01 on protein synthesis by A375 target cells. Treatment of target cells with either the 2' or 13'RA-NR-AN-01 therapeutic conjugate resulted in a short-term inhibition of protein synthesis, i.e., observed immediately after the 5-minute pulse treatment (FIG. 7C). These findings, when combined with the findings in FIG. 7A and FIG. 7B, above, suggest that the RA-NR-AN-01 conjugates were active and that they were specifically inhibitory for target cells but not non-target cells. Interestingly, when "pulse" treated target cells were returned to culture no long-term inhibitory effects were observed (FIG. 7D). The results presented in FIGS. 7C and FIG. 7D again show that Roridin A is non-specifically inhibitory to test cells (i.e., in a manner similar to FIG. 7A and FIG. 7B, above) and that its effect on the cells is manifest even after a 16–18 hour recovery period. Thus, the specific effects of the RA-NR-AN-01 conjugates on target cells during a "pulse" treatment appear to be a property of the NR-AN-01 binding protein.

The results obtained with BO54 arterial smooth muscle cells were similar to those obtained with the A375 cells, above, i.e., free Roridin A showed a dose-response inhibition of protein synthesis in the short-term equated to be 60%, 66%, and 90% of control at 200 ng/ml, 100 ng/ml, and 50 ng/ml; and in long-term the effects on protein synthesis were equated to be 27%, 46%, and 98% of control at the same dosages. In contrast, the 2' or 13'RA-NR-AN-01 showed only 10–20% inhibition for short- or long-term effects on protein synthesis (i.e., >80% of control).

Thus, the results show a short-term specific reversible effect of Roridin A-conjugated NR-AN-01 on target cells when delivered as a "pulse" treatment. However, since only protein synthesis was evaluated in these experiments, it was possible that cellular metabolic activity might be affected in the cells as a result of the "pulse" treatment. Therefore, additional studies were conducted in which cellular metabolic activity was evaluated following "pulse" treatment.

Effects After 5 Minutes of Exposure: Metabolic Activity

MTT assays were conducted at 48 hours following a 5-minute exposure of target and non-target cells to RA or RA-NR-AN-01 conjugates. Target cells in these studies included BO54 and A375, and non-target cells included HT29 cells. Sterile 96 well microtiter plates were seeded with 2500 cells/well, wrapped in aluminum foil and incubated in a humidified chamber containing 5% $CO_2$/95% air for 16–18 hours. Serial two-fold dilutions of Roridin A (RA), 2'RA-HS-NR-AN-01 and 13'RA-HS-NR-AN-01 were prepared from 400 ng/ml to 780 pg/ml, and 100 ml aliquots of the dilutions were dispensed into duplicate wells. After 5 minutes exposure to the test samples, the cells were washed to remove the test samples, and fresh medium was added. The cells were allowed 48 hours of recovery prior to testing: i.e., plates were incubated for 48 hours, and then cellular metabolic activity was determined by adding 20 ml/well of a 5 mg/ml MTT solution. The plates were covered and incubated at 37° C. for 4 hours and then the reaction was developed as described above (see EXAMPLE 4, above). The dark blue solubilized formazan reaction product was developed at room temperature after a 16–18 hour incubation. The samples were quantified using an ELISA microtiter plate reader at an absorbance of 570 nm.

Figure 8A:
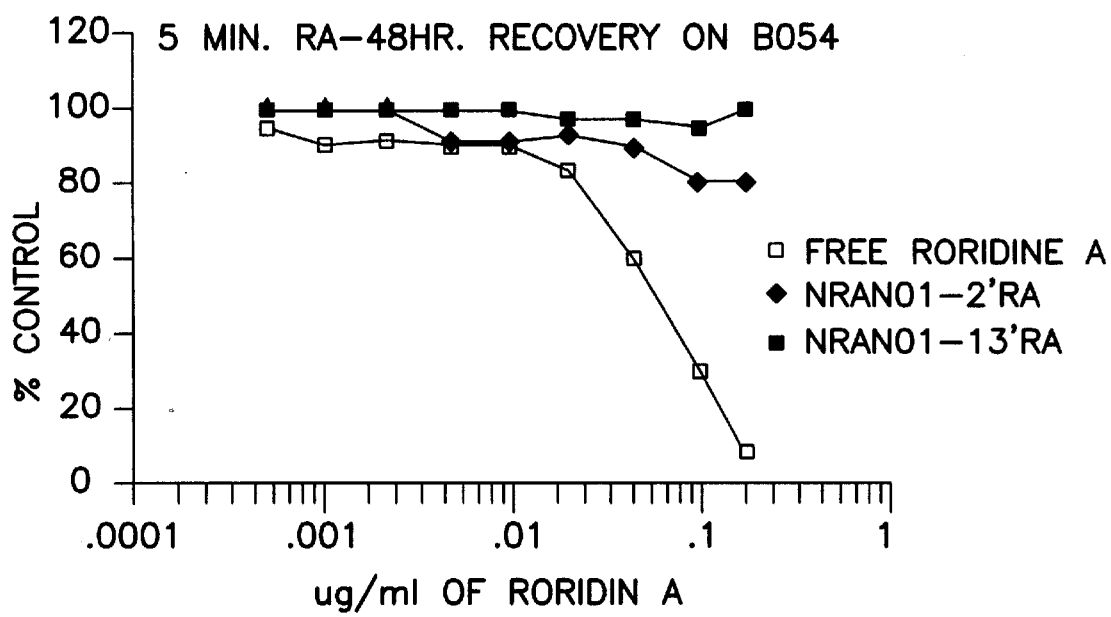
FIG. 8A presents graphically experimental data showing that while a "pulse" treatment of cells in vitro with free RA therapeutic agent was non-specifically cytotoxic, the RA-NR-AN-01 therapeutic conjugate did not exert long-lasting inhibitory effects on cellular activity in vascular smooth muscle cells, as evidenced by metabolic activity in BO54 cells that were allowed a 48 hour recovery period prior to testing.

FIG. 8A graphically depicts the results of in vitro studies investigating the effects on BO54 marker-positive smooth muscle cells of a 5 minute exposure to different concentrations of Roridin A (open squares, FIG. 8A), 2'RA-NR-AN-01 (NRAN01-2'RA; closed diamonds, FIG. 8A), or 13' RA-NR-AN-01 (NRAN01-13'RA; closed squares, FIG. 8A). The experiments were conducted in a manner similar to those described above in regard to FIG. 7B, but metabolic activity was assayed by MTT assay, i.e., rather than protein synthesis as in FIG. 7B, and cells were also given 48 hours to recover (rather than 24 hours, as in FIG. 7B). The results of the experiments are plotted in a manner similar to those described (above) in regard to FIG. 7A.

Figure 8B:
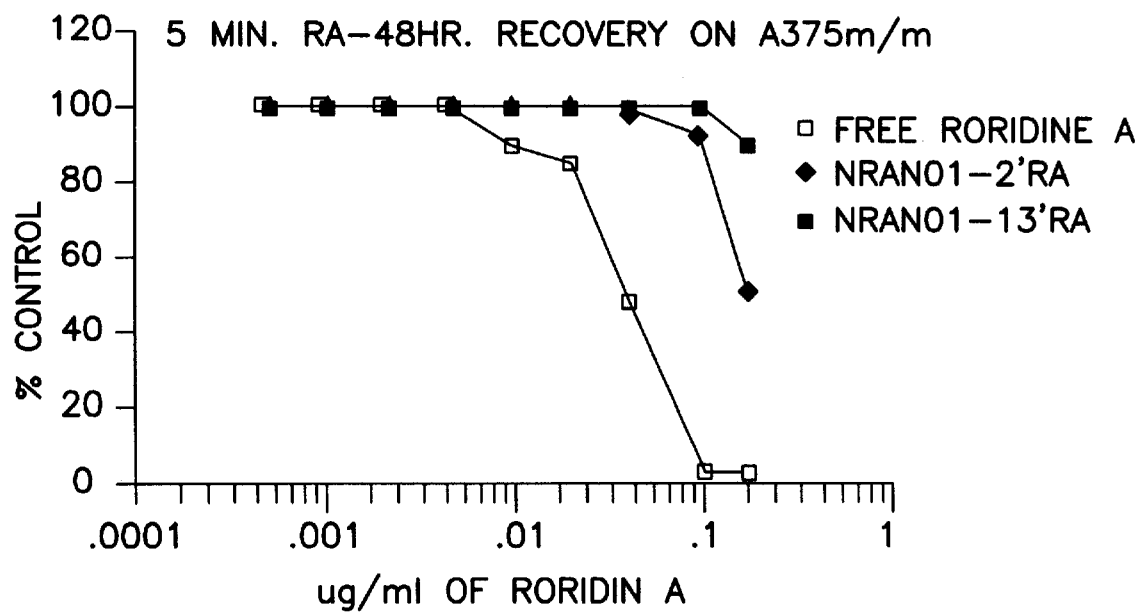
FIG. 8B graphically depicts experimental data similar to those presented in FIG. 8A, above, but using a second marker-positive cell type, namely A375, the data show that "pulse" treatment with the RA-NR-AN-01 therapeutic conjugate did not exert long-lasting inhibitory effects on cellular activity, as measured by metabolic activity in A375 cells that were allowed a 48 hour recovery period prior to testing.

FIG. 8B graphically depicts the results of in vitro studies investigating the effects on A375 m/m marker-positive cells of a 5 minute exposure to different concentrations of Roridin A (open squares, FIG. 8B), 2'RA-NR-AN-01 (NRAN01-2'RA; closed diamonds, FIG. 8B), 13'RA-NR-AN-01 (NRAN01-13'RA; closed squares, FIG. 8B). The experiments were conducted (and the results plotted) in a manner similar to those described above in regard to FIG. 8A.

FIG. 8C graphically depicts the results of in vitro studies investigating the effects on HT29 marker-negative cells of a 5 minute exposure to different concentrations of Roridin A (open squares, FIG. 8C), 2'RA-NR-AN-01 (NRAN01-2'RA; closed diamonds, FIG. 8C), 13'RA-NR-AN-01 (NRAN01-13'RA; closed squares, FIG. 8C). The experiments were conducted (and the results plotted) in a manner similar to those described above in regard to FIG. 8A.

The results presented in FIGS. 8A–8C show slight differences between the different RA-NR-AN-01 conjugates at the highest doses, but at the lower doses the 2' and 13'RA-NR-AN-01 did not significantly inhibit target cell (i.e., BO54 and A375) or non-target cell (i.e., HT29) metabolic activity over the long-term (i.e., 48 hours). Thus, the results suggest that the short-term inhibition of target cell protein synthesis (FIGS. 7C–7D, above) does not result in long-term metabolic effects on the cells, as measurable in MTT assays. That these assays were able to detect metabolic alterations in cells resulting from a 5 minute exposure is evidenced by the results obtained with free Roridin A. In this case, free Roridin A was non-specifically inhibitory to target and non-target cell types, even when the cells were exposed to the agent for only 5 minutes and then returned to culture for the 48-hour recovery period (FIGS. 8A–8C).

Thus, the findings with free Roridin A suggest that the MTT assay was capable of detecting metabolic alterations induced during a 5-minute exposure. Taken together these finding suggest that RA-NR-AN-01 conjugates can specifically inhibit target cell activity (i.e., protein synthesis) when administered in a "pulse" treatment, and that these effects were reversible without significant long-term effects on either protein synthesis or cellular metabolic activity (as measured in an MTT assay). These in vitro properties of the RA-NR-AN-01 conjugates were judged to be highly useful for inhibition of smooth muscle cell activity in vivo. Therefore, animal model studies were next conducted to evaluate the effects of these therapeutic conjugates in vivo.

EXAMPLE 6

Determination of Infusion Conditions in an Animal Model

The therapeutic conjugates of the invention are useful for inhibiting stenosis following vascular trauma or disease. In an illustrative example, vascular trauma that is induced during angioplasty is treated during the surgical procedure by removing the catheter used to perform the angioplasty, and inserting a balloon infusion catheter into the vessel. The infusion catheter is positioned with the instillation port (or, alternatively, a permeable membrane region) in the traumatized area of the vessel, and then pressure is applied to introduce the therapeutic conjugate. For example, an infusion catheter with two balloons may be used, and when one balloon is inflated on either side of the trauma site a fluid space is created that can be filled with a suitable infusion fluid containing the therapeutic conjugate. It has been reported previously that infusion of a horseradish peroxidase (HRP) marker enzyme at a pressure of 300 mm Hg over 45 seconds in dog or human coronary arteries resulted in penetration of the HRP into the vessel wall (Goldman et al., supra). However, HRP is a smaller molecule than NR-AN-01 and human and dog coronary arteries are also considerably smaller than the carotid or femoral arteries in the present domestic pig model system. Experiments were therefore conducted to determine, in a domestic pig model system, the infusion conditions suitable for delivery of a therapeutic conjugate to the vascular smooth muscle cells in carotid and femoral arteries. Delivery conditions were monitored by evaluating the penetration of the therapeutic conjugate into the vascular wall, and specific binding of the therapeutic conjugate to the vascular smooth muscle cells in the vessel wall.

Using an infusion catheter, the coronary and femoral arteries of domestic pigs or non-human primates were infused with NR-AN-01 for 45 seconds to 3 minutes at multiple pressures in the range of about 0.4 atmospheres (300 mm Hg) to 3 atmospheres. After infusion, the vessels were flushed with sterile saline and prepared for immunohistochemistry using HRP-conjugated goat anti-mouse IgG to detect the NR-AN-01 mouse IgG in the vessel wall. It was determined that full penetration was achieved of NR-AN-01 into these vessel walls at a pressure of atmospheres after 3 minutes.

Immunohistology was also used to determine which animal model systems expressed the target antigen for NR-AN-01. Vascular tissue sections from readily available experimental animal species were exposed to NR-AN-01, washed, and reacted with HRP-conjugated goat anti-mouse IgG. Only non-human primates and swine were found to share the 250 kD NR-AN-01 target antigen with man.

To determine whether NR-AN-01 could bind in a specific manner to its target antigen in vivo, the coronary and femoral arteries of domestic pigs were infused with therapeutic conjugates using an infusion catheter, the infusion sites were flushed with sterile saline, the surgical sites were then closed, and the animals were maintained for an additional 3–5 days. At the end of this time, the vascular infusion sites were excised and prepared for immunohistology, once again using goat anti-mouse IgG to identify NR-AN-01. NR-AN-01 was identified in the vessel wall of swine coronary and femoral arteries 3–5 days after surgery, and the NR-AN-01 appeared to be associated only with vascular smooth muscle cells. These findings suggest that NR-AN-01 is capable of specifically binding to its target antigen in vivo.

EXAMPLE 7

Inhibition of Vascular Smooth Muscle Cells in Vivo

Intimal smooth muscle proliferation that follows balloon catheter-induced trauma is a good model to evaluate the therapeutic efficacy of conjugates for inhibiting smooth muscle cell activity in vivo in response to vascular trauma, including restenosis following angioplasty. Domestic pigs were used to study the effects of NR-AN-01 (i.e., termed vascular smooth muscle binding protein or simply VSMBP in these studies; and therapeutic conjugates with Roridin A are termed VSMBP—RA). The events which normally follow balloon angioplasty in the porcine artery have been described previously (Steele et al., Circ. Res., 57: 105–112 (1985)). In these studies, dilation of the carotid artery using an oversized balloon (balloon: artery ratio approximately 1.5:1) resulted in complete endothelial denudation over an area of 1.5–2 cm in length. Although this length of traumatic injury was selected in an attempt to minimize thrombosis, there was still marked platelet deposition and thrombus formation. The procedure also resulted in dissection through the internal elastic lamina into the arterial media and necrosis of medial smooth muscle cells. Intimal thickening due to smooth muscle proliferation was apparent 7 days after injury and reached a mean maximum thickness of 85 mm at 14 days. The histological appearance of this neointima is very similar to the proliferative neointimal tissue of human restenosis (Schwartz et al., Circ, 82: 2190–2200 (1990)).

A single dose test protocol was conducted in domestic pigs with NR-AN-01-Roridin A conjugates. Localized administration of the test conjugates, i.e., through a catheter into a region of traumatized vessel confined by temporary slip ligatures, was designed to reduce systemic toxicity while providing a high level of exposure for the target smooth muscle cells. This intra-artery route of administration in animal model studies simulates the proposed route in human coronary arteries. The test protocol was designed as an initial in vivo screening of intra-arteriolar, site specific, catheter administered, vascular smooth muscle binding protein (VSMBP) conjugates.

Toxicity of free drug was also evaluated, i.e., for patho-biological effects on arteriolar smooth muscle cells. The therapeutically effective dosage of the Roridin A-NR-AN-01 conjugate was determined by in vitro studies, and the proper intra-arteriolar administration pressure was determined by administering free MAb and MAb conjugates to animals, as described above in Example 7.

Six domestic crossbred swine (Duroc X), weanling feeder pigs of approximately 30 pounds body weight, were used in the experiment. The animals were randomly assigned to the following treatment regimen where each pig has four different treatments divided between the right and left carotid and femoral arteries, one of which is a PBS control (Tables 1–3, below).

TABLE 1

| GROUP NO. | TREATMENT GROUP | MATERIAL DESCRIPTION |
|---|---|---|
| 1 | CONTROL, VSMBP | VSMBP, 200 µg/ml in PBS, pH 6.5 |
| 2 | CONTROL, PBS | PBS, pH 6.5, in injection sterile water |
| 3 | CONTROL, DRUG | Roridin A, 2.5 µg/ml in PBS, pH 6.5 |
| 4 | TEST, CONJUGATE | VSMBP-RA2' (200 µg/ml VSMBP & 2.5 µg/ml RA) |
| 5 | TEST, CONJUGATE | VSMBP-RA13' (200 µg/ml VSMBP & 3.1 µg/ml RA) |
| 6 | TEST, CONJ + RA | VSMBP-RA2' (200 µg/ml VSMBP & 2.5 µg/ml RA) PLUS free Roridin A (2.5 µg/ml) |
| 7 | TEST, CONJ + RA | VSMBP-RA13' (200 µg/ml VSMBP & 3.1 µg/ml RA) PLUS free Roridin A (2.5 µg/ml) |

Surgical Procedure:

Test conjugates and control compounds were administered as a single intra-artery infusion at the site of endothelial denuding and trauma induced by a balloon catheter. Both the carotid and femoral arteries were abraded over 1 cm to 2 cm of endothelium by intraluminal passage of a 23 cm, size 3 (femoral) and size 4 (carotid) Uresil Vascu-Flo® silicone occlusion balloon catheter (Uresil Technology Center, Skokie, Ill.), sufficiently distended with saline to generate slight resistance. This technique produced slight distension of the artery. Following this treatment, proximal and distal slip ligatures, 3-0 silk, were placed near the ends of the abraded region, and a size 8 French, Infant Feeding Catheter (Cutter-Resiflex, Berkeley, Calif.) attached to an Inflation Pro® (USCI, C.R. Bard, Inc., Billerica, Mass.) pressure syringe was used to administer the test conjugates and control compounds directly to the denuded segment at a pressure of three atmospheres for three minutes. The slip ligatures were removed after the three minute exposure period and arterial blood flow was reestablished. In these studies, branches of the femoral or carotid arteries were ligated with 00 silk suture as required to attain pressurized infusion in the treated region. The largest distal branch of the femoral artery (the saphenous artery) was incised and used as an entry site for the catheters which were then passed into the main femoral artery. Following this catheterization procedure in the main femoral artery, the secondary branch was ligated. In these cases, ligation or incision was used to allow entry of the catheters and the opening was then closed with 3 to 4 sutures of 5-0 monosilamen polybutester (Novafil, D & G Monofil Inc., Monati, PR).

Follow-up Procedures:

Following surgery, the pigs were kept in 3×5 foot indoor runs with cement floors during the quarantine and surgical recovery periods. They were then transferred to indoor/outdoor pens for the remainder of the five week healing period prior to collection of tissues for histology.

The animals recovered normally from surgery with no evidence of hemorrhage or inflammation at the surgical sites. All six animals were examined 5 to 6 days after treatment with a doppler stethoscope, and all arteries in each of the animals were patent. Post treatment all animals had normal appetite, activity and weight gain.

Gross Pathology and Histological Evaluation:

Five weeks following the traumatization and treatment of the arteries, the animals were sedated with 0.6 ml Telazol®/ (tiletamine hydrochloride; A.H. Robins Co., Richmond, Va.) and 0.5 ml xylazine (Lloyd Laboratories, Shenandoah, Iowa) per 30 lb body weight by intramuscular injection, heparinized (i.v. 2 ml sodium heparin, 1000 units/ml), and euthanized by i.v. pentobarbital. Both the right and left carotid and femoral arteries were removed with normal vessel included both proximal and distal to the treated segment. The arteries were measured and the location of ligatures and gross abnormalities noted. The arteries were transected at 2 mm intervals and arranged in order in cryomolds with O.C.T. (optimum cutting temperature) compound (Tissue Tek®, Miles Laboratories Inc., Elkhart, Ind.) and frozen in liquid nitrogen. The blocks were sectioned at 5 microns and stained with H&E, Massons Trichrome and Movats Pentachrome for morphological studies. Sections were also used for immunohistological staining of vascular smooth muscle.

Histological examination of the step sections of the arteries revealed marked inhibition of intimal smooth muscle proliferation in the regions traumatized and treated with RA-NR-AN-01 conjugates (Table 2). This inhibition was evident even at sub-gross evaluation of the vessels. The inhibition of intimal smooth muscle cell proliferation was produced with minimal or no histological evidence of smooth muscle cell death in the artery wall. A cross-sections of one such traumatized artery is provided in FIGS. 9A and 9B.

TABLE 2

INTIMAL SMOOTH MUSCLE PROLIFERATION IN TRAUMATIZED AND TREATED PORCINE ARTERIES

| TREATMENT | NO. ARTERIES EVALUATED | INTIMAL SMC HYPERTROPHY* ave. (range) |
|---|---|---|
| Control, MAB | 4 | 3.75 (3–4) |
| Control, PBS | 4 | 4 (4) |
| Control, RA | 2 | 4 (4) |
| Test, 2' RA | | |
| (High pressure) | 1 | 1 (1) |
| (Low pressure) | 1 | 3 (3) |
| Test, 13' RA | | |
| (High pressure) | 1 | 1 (1) |
| (Low pressure) | 1 | 1 (1) |

*Intimal SMC Hypertrophy: intimal smooth muscle cell hypertrophy scored on a scale from 1 + (minimal) to 4 + (maximal).

Figure 9A:
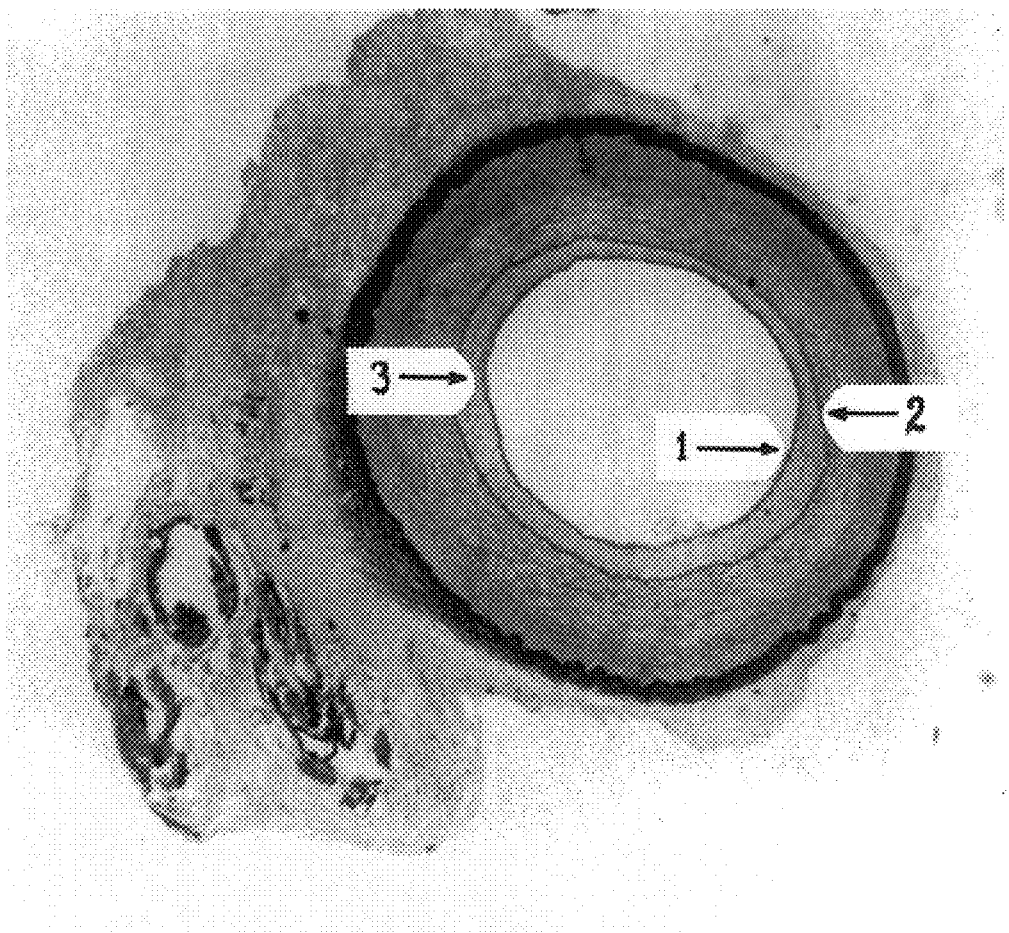
FIG. 9A shows stenosis due to intimal smooth muscle cell proliferation in a histological section of an untreated artery 5 weeks after angioplasty in an animal model.

The results presented in FIG. 9A show (at 160× magnification) a cross-sectional of an untreated artery 5 weeks after angioplasty. Dominant histological features of the artery include displacement of the endothelium (see #1 in FIG. 9A) away from the internal elastic lamina (see #2, FIG. 9A), apparently due to intimal smooth muscle proliferation (see #3, FIG. 9A).

Figure 9B:
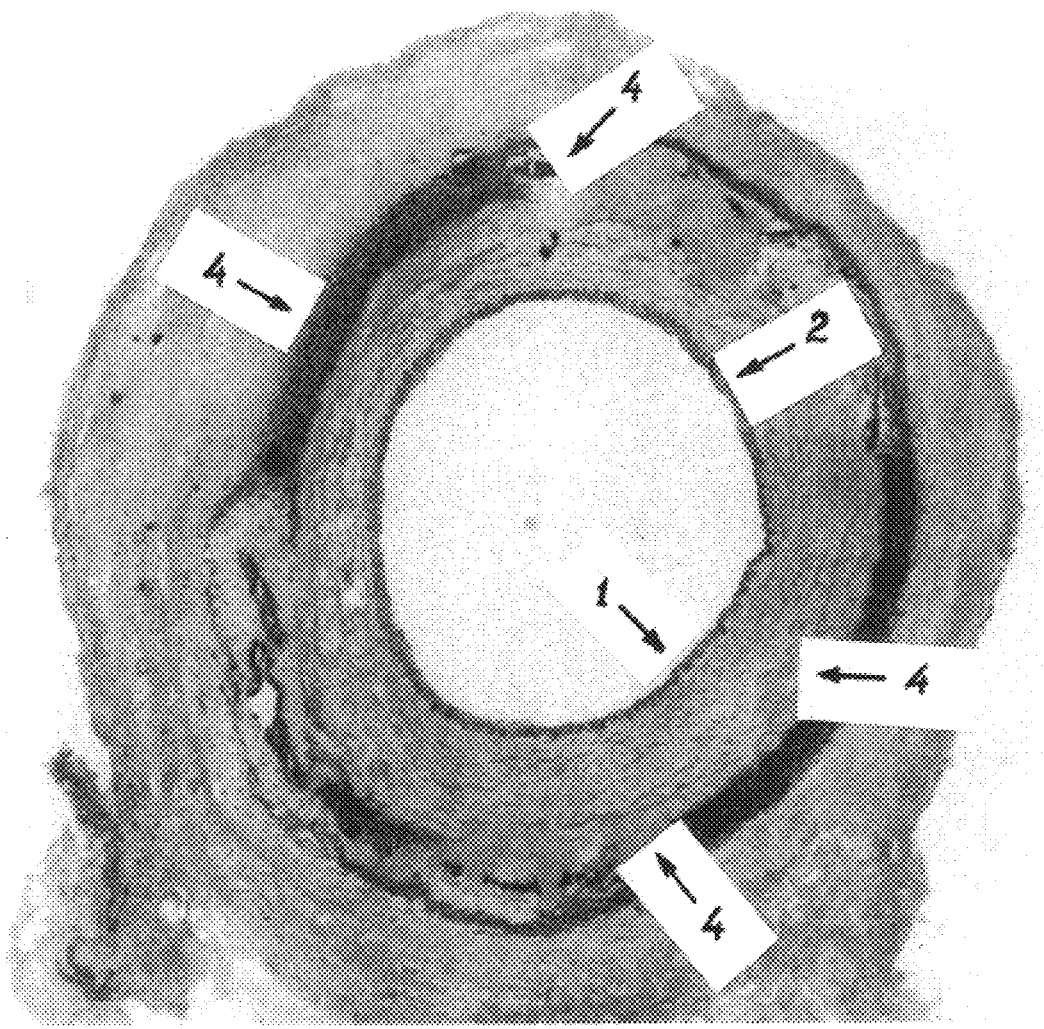
FIG. 9B shows inhibition of stenosis in a histological section of an artery treated with therapeutic conjugate at 5 weeks after angioplasty in an animal model.
Figure 10A:
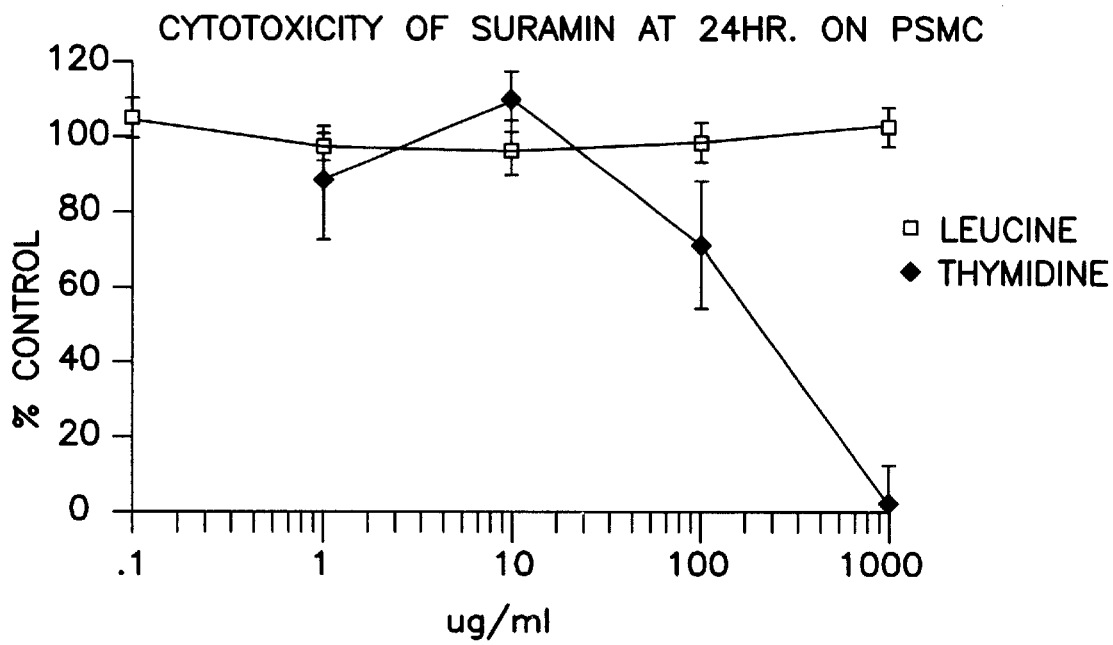
FIG. 10A graphically depicts experimental data comparing protein synthesis and DNA synthesis inhibition capability of suramin with respect to vascular smooth muscle cells.
Figure 10B:
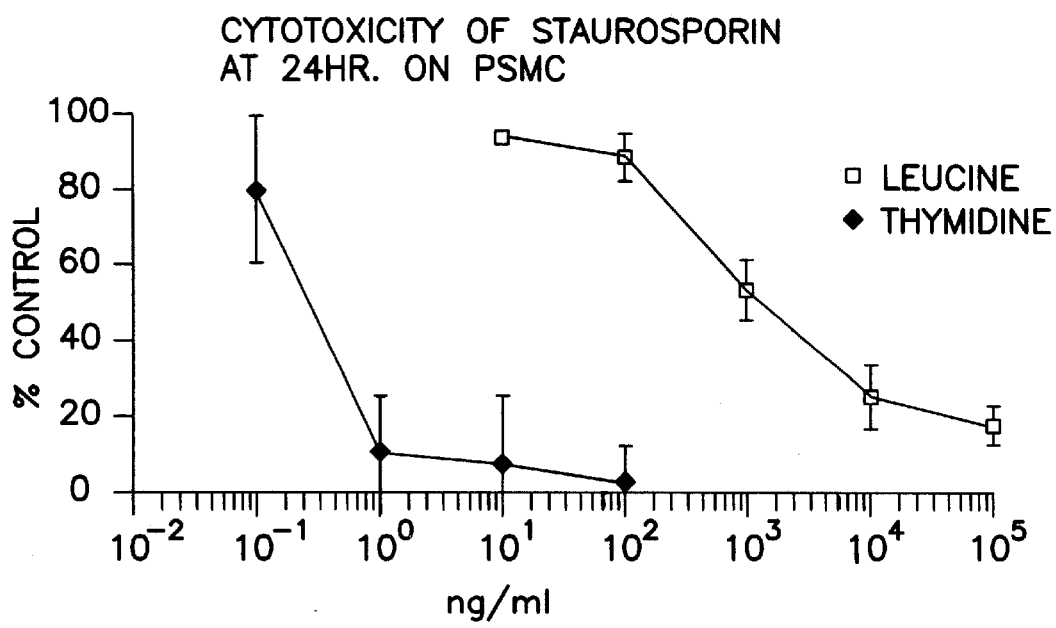
FIG. 10B graphically depicts experimental data comparing protein synthesis and DNA synthesis inhibition capability of staurosporin with respect to vascular smooth muscle cells.
Figure 10C:
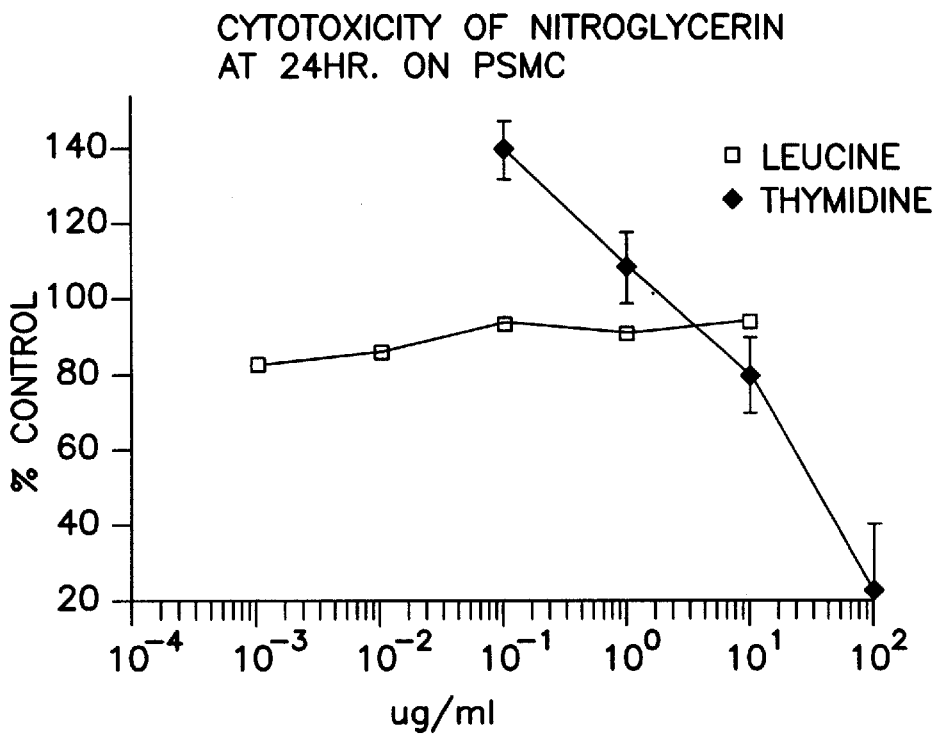
FIG. 10C graphically depicts experimental data comparing protein synthesis and DNA synthesis inhibition capability of nitroglycerin with respect to vascular smooth muscle cells.
Figure 10D:
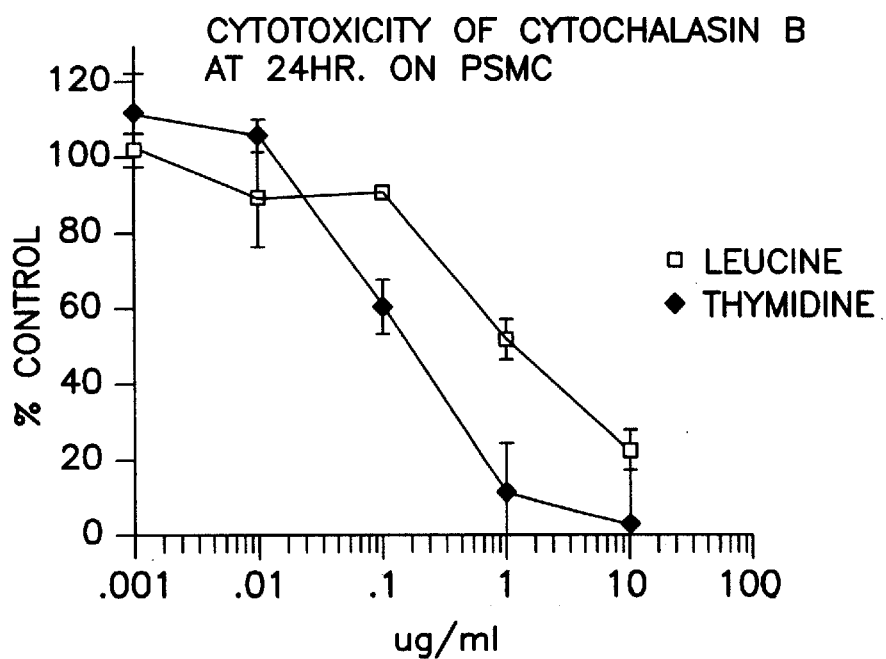
FIG. 10D graphically depicts experimental data comparing protein synthesis and DNA synthesis inhibition capability of cytochalasin B with respect to vascular smooth muscle cells.

The results presented in FIG. 9B show (at 160× magnification) a cross-section of a treated artery 5 weeks after angioplasty and infusion of the RA-NR-AN-01 therapeutic conjugate. The vessel in this section was subjected to greater mechanical stresses than the vessel shown in FIG. 9A, with multiple sites where the external elastic membrane was ruptured and associated proliferation of smooth muscle cells in the outer layers of the media was observed (i.e., see #4 in FIG. 9B). Treatment with therapeutic conjugate inhibited intimal hypertrophy, as evidenced by the lack of displacement of the endothelium (see #1, FIG. 9B) from the internal elastic lamina (see #2, FIG. 9B). Surprisingly, this inhibitory effect on intimal smooth muscle cells was accomplished without inhibiting hypertrophy of medial smooth muscle cells in the areas where the external elastic membrane was ruptured (see #4, FIG. 9B).

This is a highly fortunate result because wound healing proceeds in the treated vessel without the adverse consequences of intimal hyperplasia and stenosis, or necrosis of smooth muscle cells in the media.

In these histological studies, comparisons were also made of the effectiveness of both the 2' and the 13' -Roridin A conjugate with the finding that the 13' conjugate (i.e., 13'RA-HS-NR-AN-01) appeared to be more active in inhibiting intimal hyperplasia of smooth muscle cells than the 2' conjugate (i.e., 2'RA-HS-NR-AN-01). In this study, low pressure infusion of the 13' conjugate appeared to inhibit smooth muscle proliferation more effectively than high pressure and the 13' conjugate also appeared to be more effective than the 2' conjugate.

In FIG. 9B, therapeutic conjugate administered at the site following angioplasty resulted in approximately 95% inhibition of the smooth muscle hypertrophy that restricted the lumen of the untreated vessel (FIG. 9A). Significantly, the therapeutic conjugate exerted its effects on the smooth muscle cells migrating from the medial smooth muscle layers into the intima, without affecting either endothelium, or producing any signs of necrosis (i.e., cell death) in the smooth muscle cells in the medial layers of the arterial wall. Studies also failed to show any histological signs of mononuclear infiltration or fibrosis such as might result from toxic effects on the vessel wall. Also, visible signs of healing were observed in the intimal layers of treated vessels and with re-growth of endothelium observed, i.e., endothelial cells growing over the thin layer of smooth muscle cells in the intima that lie between the endothelium and internal elastic lamina (i.e., #1 and #2, FIG. 9B). These combined histological observations suggest the highly desirable features of wound healing, re-growth of endothelium and improved vascular strength following treatment with a therapeutic conjugate that inhibits smooth muscle hyperplasia in the intimal layers of the vessel.

EXAMPLE 8

Vascular Smooth Muscle Cell in Vitro DNA and Protein Synthesis Inhibition

The ability of various therapeutic agents to inhibit DNA synthesis and protein synthesis in vascular smooth muscle cells was tested. $^3$H-leucine and $^3$H-thymidine uptake and cytotoxicity assays were conducted in accordance with the following protocols.

5 Minute Exposure; $^3$H-leucine uptake: Vascular smooth muscle cells at 40,000 cells/ml were seeded in sterile 24 well plates at 1 ml/well. The plates were incubated overnight at 37° C., 5% $CO_2$, 95% air in a humidified atmosphere (saturation). Log dilutions of the therapeutic agent of interest were incubated with the vascular smooth muscle cells for 5 minutes or 24 hours. Samples of the therapeutic agents were diluted in DMEM:F-12 medium (Whittaker Bioproducts, Walkersville, Md.) with 5% fetal bovine serum (FBS, Gibco BRL, Gaithersburg, Md.) and 5% Serum Plus® (JRH Biosciences, Lenexa, Kans.). Following therapeutic agent incubation, the solution was aspirated, and 1 ml/well of 0.5 microcurie/ml $^3$H-leucine in leucine-free DMEM (Dulbecco's Modified Eagle's Medium) with 5% Serum Plus® was added. The plates were re-incubated overnight at 37° C., 5% $CO_2$ in a humidified atmosphere. The cells were visually graded using an inverted microscope using a scoring scale to determine viability and cell number. The 1 to 3 grade is based upon percent of cell viability and number compared to control wells, with 3=100%, 2=70%–100% and 1=0%–70%. A record of this scoring assisted in determining the immediate cytotoxic effect of the therapeutic agents. The medium was then aspirated, and the cells were washed twice with cold 5% TCA. 400 microliters of 0.2 M NaOH was added per well, and the plates were incubated for two hours at room temperature on a rotating platform. 200 microliters per well of the cell solution was transferred into plastic scintillation vials (Bio-Rad Laboratories), and 4 milliliters of Bio-Safe® II liquid scintillation fluid (Research Products InterCorp., Mount Prospect, Ill.) was added prior to vortexing. Vials were counted on a Beckman LS2800 liquid scintillation counter interfaced with Beckman "Data Capture" software for conversion to a Lotus 1-2-3® file and analysis using Lotus 1-2-3®.

5 Minute Exposure; $^3$H-thymidine uptake:

Vascular smooth muscle cells were incubated in complete medium with 5% FBS (Gibco) overnight at 37° C. in a humidified, 5% $CO_2$ environment in sterile 24 well plates. The medium was aspirated from the wells and serum free medium supplemented with growth factors (DMEM: F-12 basal medium supplemented with growth factor cocktail, catalog number I1884, which contains insulin (5 micrograms/ml), transferring (5 micrograms/ml) and sodium selenite (5 nanograms/ml), available from Sigma Chemical, St. Louis, Mo.) was added. Cells were incubated in this medium for 24 hours. For a 5 minute therapeutic agent exposure, log dilutions of the therapeutic agent were incubated with the cells in complete medium. After 5 minutes and medium aspiration, 1 ml/well of 1.0 microcurie/ml $^3$H-thymidine dispersed in complete medium was added. The 24 hour exposure involved incubation of the cells with 1 ml/well of 1.0 microcurie/ml of $^3$H-thymidine dispersed in complete medium and log dilutions of the therapeutic agent being tested. In both exposure trials, the cells were then incubated overnight at 37° C. in a humidified, 5% $CO_2$ environment. The cells were visually scored for viability and cell number. Cells were washed and prepared for transfer into plastic scintillation vials as described for the $^3$H-leucine protocol. Vials were counted on a Beckman LS2800 liquid scintillation counter interfaced with Beckman "Data Capture" software for conversion to a Lotus 1-2-3® file and analysis using Lotus 1-2-3®.

These protocols are amenable to use with other target cell populations, especially adherent monolayer cell types.

Morphological Cytotoxicity Evaluation-Pulsed Exposure:

Vascular smooth muscle cells were seeded at $4.0\times10^4$ cells/ml medium/well on a commercially prepared four well slide (Nunc, Inc., Naperville, Ill.). Enough slides were seeded to accommodate two pulsed exposure lengths (5 minutes and 24 hours) and prescribed increment evaluation points (24 hours to 128 hours). All slides were run in duplicate to reveal any assay anomalies. The therapeutic agent was diluted in the same medium used in the $^3$H-leucine and $^3$H-thymidine assays. Each four well slide was concentration bracketed to one log greater concentration (well "B"), one log lower concentration (well "D") of the minimal effective concentration (well "C"), as determined by the 3H-leucine and 3H-thymidine assays described above. As a control for normal morphology, one well (well "A") was left untreated (medium only). Incubation took place in a 37° C., 5% $CO_2$ humidified incubator. After each of the two (5 minutes and 24 hours) exposure points, the therapeutic agent medium was aspirated from each well, including the untreated well. One milliliter of fresh medium was then added to replace the aspirated medium. Re-incubation followed until each of the incremented evaluation points were achieved. At those points, the medium was aspirated and subsequently replaced with 1 ml of 10% neutral buffered formalin for one hour to allow for proper fixation. These fixed slides were stained by hematoxylin (nuclear) and eosin (cytoplasmic) for morphologic evaluation and grading.

Results:

The results of the 24 hour $^3$H-leucine protein inhibition assay and the 24 hour $^3$H-thymidine DNA synthesis inhibition assay are shown in FIGS. 10A–10D for suramin, staurosporin, nitroglycerin and cytochalasin B, respectively. All of the tested compounds showed an available therapeutic range (area under the curve of $^3$H-leucine assay is greater than that resulting from the $^3$H-thymidine assay), indicating usefulness in the practice of sustained release dosage form embodiments of the present invention. More specifically, the compounds inhibited the ability of vascular smooth muscle cells to undergo DNA synthesis in the presence of 5% FBS to a greater extent than they inhibited protein synthesis of vascular smooth muscle cells. The protein and DNA synthesis inhibitory effects of suramin, staurosporin, nitroglycerin and cytochalasin B during a 5 minute and 24 hour pulsed exposure are shown in FIGS. 10 A–D, respectively.

EXAMPLE 9

Specific Binding and Internalization of Targeted Particles by Vascular Smooth Muscle Cells The ability of vascular smooth muscle cells to bind and internalize particles coated with binding protein or peptide was demonstrated with monoclonal antibody (NR-AN-01) coated gold beads both in vitro and in vivo. The vascular smooth muscle cell tissue cultures (BO54), an antigen positive control cell line (A375) and an antigen negative control cell line (HT29) were incubated with 10 nm gold beads, with one group coated with NR-AN-01 and a second, uncoated control group. The cells were exposed to the beads as monolayer and cell suspension cultures, and were examined at six time points (i.e., 1 minute, 5 minutes, 15 minutes, 30 minutes, 60 minutes and 24 hours) for binding and internalization by electron microscopy.

Table 3 shows the results of the experimentation, indicating that the binding to the cell surface is specific. The relative grading system used throughout Table 3 represents a subjective assessment of particle binding, wherein 0=none; 1=minimal; 2=mild; 3=moderate; and 4=marked. If aggregates of particles settled on the monolayer surface of both the smooth muscle cells and the control cells, the particles were nonspecifically internalized by macro and micro phagocytosis. When the cells were maintained in a cell suspension, non-specific internalization was minimal or absent. Non-specific adherence of gold beads devoid of NR-AN-01 to surface mucin produced by HT29 cells was observed, resulting in modest non-specific internalization thereof. Vascular smooth muscle cell uptake of NR-AN-01 targeted gold beads was highly specific in cell suspension cultures.

TABLE 3

| Time | Grid | Product | Cell Line | Cell Surface | Primary vesicle micro/macro phagostasis pinocytosis | coated pit | secondary vesicle | lysosome | golgi | endoplasmic reticulum |
|---|---|---|---|---|---|---|---|---|---|---|
| | | | | | Cell Monolayer | | | | | |
| 1 min | Aa | 05 (G) | A375 | 2 | 0 | 0 | 0 | 0 | 0 | 0 |
| | Ba | 05 (G) | HT29 | 0 | 0 | 0 | 0 | 0 | 0 | 0 |
| | C | 05 (G) | B054 | 2 | 1 | 0 | 0 | 0 | 0 | 0 |
| | Eb | (G) | HT29 | 0 | 0 | 0 | 0 | 0 | 0 | 0 |
| | F | (G) | B054 | 0 | 0 | 0 | 0 | 0 | 0 | 0 |
| 5 min | Ac | 05 (G) | A375 | 4 | 1 | 0 | 0 | 0 | 0 | 0 |
| | Bb | 05 (G) | HT29 | 0 | 0 | 0 | 0 | 0 | 0 | 0 |
| | Ca | 05 (G) | B054 | 3 | 0 | 0 | 0 | 0 | 0 | 0 |
| | Dc | (G) | A375 | 0 | 0 | 0 | 0 | 0 | 0 | 0 |
| | Ea | (G) | HT29 | 0 | 0 | 0 | 0 | 0 | 0 | 0 |
| | Fa | (G) | B054 | 0 | 0 | 0 | 0 | 0 | 0 | 0 |
| 15 min | Aa | 05 (G) | A375 | 3 | 1 | 0 | 0 | 0 | 0 | 0 |
| | Bb | 05 (G) | HT29 | 0 | 0 | 0 | 0 | 0 | 0 | 0 |
| | Ca | 05 (G) | B054 | 2 | 1 | 0 | 0 | 0 | 0 | 0 |
| | Da | (G) | A375 | 0 | 0 | 0 | 0 | 0 | 0 | 0 |
| | Ea | (G) | HT29 | 0 | 0 | 0 | 0 | 0 | 0 | 0 |
| | Fa | (G) | B054 | 0 | 0 | 0 | 0 | 0 | 0 | 0 |
| 30 min | A | 05 (G) | A375 | 4 | 3 | 0 | 2 | 0 | 0 | 0 |
| | B | 05 (G) | HT29 | 0 | 0 | 0 | 0 | 0 | 0 | 0 |
| | C | 05 (G) | B054 | 3 | 2 | 0 | 1 | 0 | 0 | 0 |
| | D | (G) | A375 | 0 | 0 | 0 | 0 | 0 | 0 | 0 |
| | E | (G) | HT29 | 0 | 1 | 0 | 0 | 0 | 0 | 0 |
| | F | (G) | B054 | 1 | 1 | 0 | 0 | 0 | 0 | 0 |
| 60 min | Aa | 05 (G) | A375 | 4 | 3 | 2 | 3 | 2 | 0 | 1 |
| | Ba | 05 (G) | HT29 | 0 | 0 | 0 | 0 | 0 | 0 | 0 |
| | Cc | 05 (G) | B054 | 3 | 2 | 0 | 2 | 0 | 0 | 1 |
| | Da | (G) | A375 | 0 | 1 | 0 | 0 | 0 | 0 | 1 |
| | Ec | (G) | HT29 | 1 | 1 | 0 | 1 | 0 | 0 | 0 |
| | Fa | (G) | B054 | 1 | 2 | 0 | 1 | 0 | 0 | 0 |
| 24 hrs | Ab | 05 (G) | A375 | 2 | 1 | 1 | 2 | 4 | 0 | 2 |
| | Ba | 05 (G) | HT29 | 0 | 1 | 1 | 2 | 3 | 0 | 0 |
| | Cc | 05 (G) | B054 | 3 | 3 | 1 | 3 | 4 | 1 | 1 |
| | Da | (G) | A375 | 0 | 3 | 0 | 2 | 3 | 0 | 0 |
| | Eb | (G) | HT29 | 0 | 3 | 0 | 3 | 1 | 0 | 0 |
| | Fb | (G) | B054 | 0 | 2 | 0 | 2 | 3 | 0 | 0 |
| | | | | | Cell Pellets | | | | | |
| 1 min | 1A | 05 (G) | A375 | 2 | 0 | 0 | 0 | 0 | 0 | 0 |
| | 7A | 05 (G) | HT29 | 0 | 0 | 0 | 0 | 0 | 0 | 0 |
| | 13A | 05 (G) | B054 | 3 | 0 | 1 | 0 | 0 | 0 | 0 |
| | 1B | (G) | A375 | 0 | 0 | 0 | 0 | 0 | 0 | 0 |
| | 7B | (G) | HT29 | 0 | 0 | 0 | 0 | 0 | 0 | 0 |
| | 13B | (G) | B054 | 0 | 0 | 0 | 0 | 0 | 0 | 0 |
| 5 min | 2A | 05 (G) | A375 | 3 | 1 | 0 | 0 | 0 | 0 | 0 |
| | 8A | 05 (G) | HT29 | 0 | 0 | 0 | 0 | 0 | 0 | 0 |
| | 14A | 05 (G) | B054 | 2 | 1 | 0 | 0 | 0 | 0 | 0 |
| | 2B | (G) | A375 | 0 | 0 | 0 | 0 | 0 | 0 | 0 |
| | 8B | (G) | HT29 | 0 | 0 | 0 | 0 | 0 | 0 | 0 |
| | 15B | (G) | B054 | 0 | 0 | 0 | 0 | 0 | 0 | 0 |
| 15 min | 3A | 05 (G) | A375 | 4 | 1 | 0 | 1 | 0 | 0 | 0 |
| | 9A | 05 (G) | HT29 | 0 | 0 | 0 | 0 | 0 | 0 | 0 |
| | 15A | 05 (G) | B054 | 1 | 1 | 0 | 0 | 0 | 0 | 0 |
| | 3B | (G) | A375 | 0 | 0 | 0 | 0 | 0 | 0 | 0 |
| | 9B | (G) | HT29 | 0 | 0 | 0 | 0 | 0 | 0 | 0 |
| | 15B | (G) | B054 | 0 | 0 | 0 | 0 | 0 | 0 | 0 |
| 30 min | 4A | 05 (G) | A375 | 4 | 2 | 0 | 0 | 0 | 0 | 0 |
| | 10A | 05 (G) | HT29 | 0 | 0 | 0 | 0 | 0 | 0 | 0 |
| | 16A | 05 (G) | B054 | 2 | 1 | 0 | 0 | 0 | 0 | 0 |
| | 4B | (G) | A375 | 0 | 0 | 0 | 0 | 0 | 0 | 0 |
| | 10B | (G) | HT29 | 0 | 0 | 0 | 0 | 0 | 0 | 0 |
| | 16G | (G) | B054 | 0 | 0 | 0 | 0 | 0 | 0 | 0 |
| 60 min | 5A | 05 (G) | A375 | 3 | 3 | 0 | 2 | 1 | 0 | 0 |
| | 11A | 05 (G) | HT29 | 0 | 0 | 0 | 0 | 0 | 0 | 0 |
| | 17A | 05 (G) | B054 | 2 | 2 | 0 | 2 | 0 | 0 | 0 |
| | 5B | (G) | A375 | 0 | 0 | 0 | 0 | 0 | 0 | 0 |
| | 11B | (G) | HT29 | 0 | 0 | 0 | 0 | 0 | 0 | 0 |
| | 17B | (G) | B054 | 0 | 0 | 0 | 0 | 0 | 0 | 0 |
| 24 hrs | 6A | 05 (G) | A375 | 3 | 1 | 0 | 3 | 3 | 0 | 0 |
| | 12A | 05 (G) | HT29 | 0 | 0 | 0 | 0 | 0 | 0 | 0 |
| | 18A | 05 (G) | B054 | 2 | 1 | 0 | 1 | 3 | 0 | 0 |
| | 6B | (G) | A375 | 0 | 0 | 0 | 0 | 0 | 0 | 0 |

TABLE 3-continued

| Time Grid | Product | Cell Line | Cell Surface | Primary vesicle micro/macro phagostasis pinocytosis | coated pit | secondary vesicle | lysosome | golgi | endoplasmic reticulum |
|---|---|---|---|---|---|---|---|---|---|
| 12B | (G) | HT29 | 1 | 2 | 0 | 2 | 2 | 0 | 0 |
| 18B | (G) | BO54 | 0 | 0 | 0 | 0 | 0 | 0 | 0 |

Figure 11:
FIG. 11 shows a tangential section parallel to the inner surface of a smooth muscle cell which is magnified 62,500 times and is characterized by numerous endocytic vesicles, several of which contain antibody coated gold beads in the process of being internalized by the cell in vitro.
Figure 12:
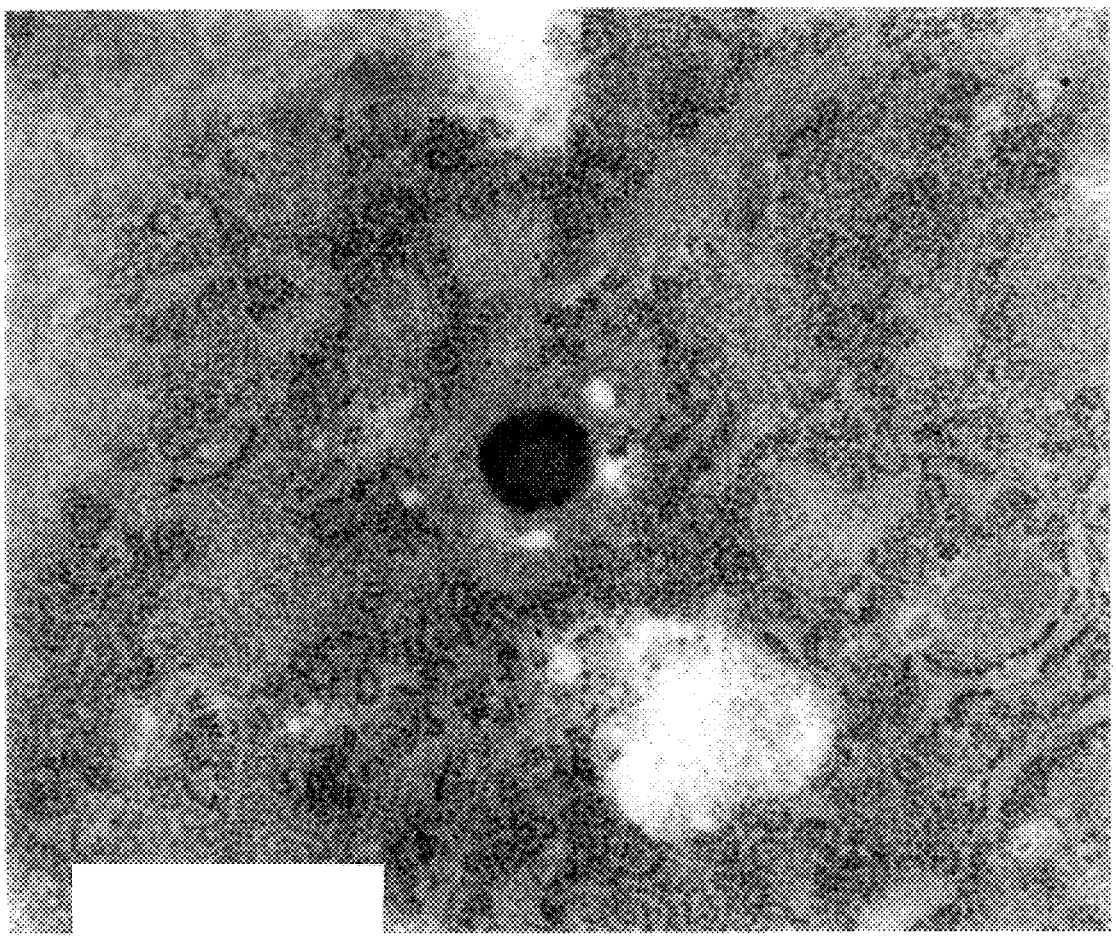
FIG. 12 shows a smooth muscle cell which is magnified 62,500 times and is characterized by a marked accumulation of gold beads in lysosomes at 24 hours following exposure of the cell to the beads in vitro.

FIG. 11 shows a tangential section parallel to the inner surface of a smooth muscle cell characterized by numerous endocytic vesicles, several of which contain antibody coated gold beads in the process of being internalized by the cell. These endocytic vesicles with particles attached to cell surface antigens were stimulated to fuse with lysosomes at a higher than expected rate for normal cell surface membrane recycling. The resultant marked accumulation of internalized particles was observed at the 24 hour time point and is shown in FIG. 12.

Figure 13:
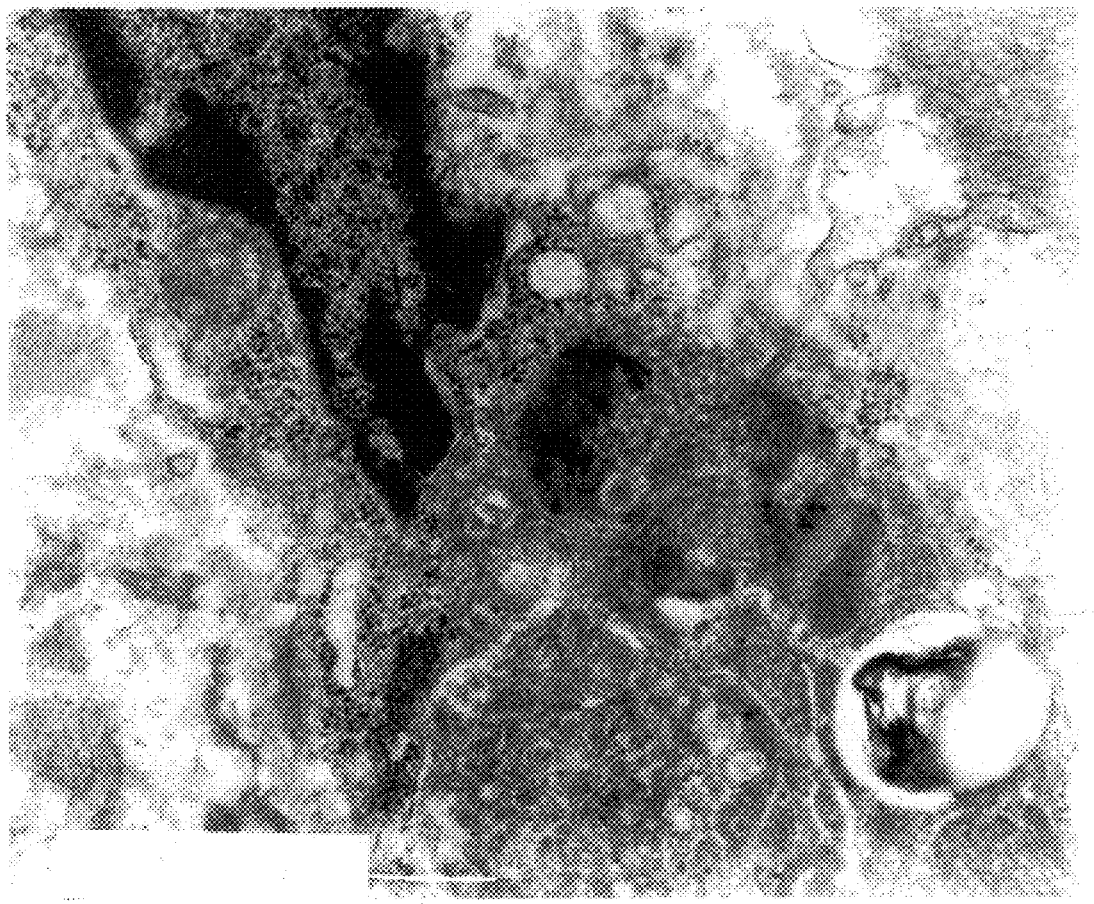
FIG. 13 shows a smooth muscle cell which is magnified 62,500 times and is characterized by accumulation of gold beads in lysosomes in vivo.

The targeted gold bead vascular smooth muscle cell surface binding, internalization and lysosome concentration was observed in vivo as well. NR-AN-01 coated gold beads were infused via intravascular catheter, open ended with treated area occluded proximally and distally with slip ligatures, at 3 atm pressure applied for 3 minutes into the wall of a pig femoral artery immediately following balloon trauma. The bead internalization rate varied with the degree of damage sustained by the vascular smooth muscle cell during the balloon trauma. Cells with minimal or no damage rapidly internalized the particles by endocytosis and phagocytosis, concentrating the internalized particles in lysosomes. Cells that were killed by the trauma exhibited surface bead binding. Cells that were damaged by the trauma but survived were characterized by bead surface binding with delayed internalization and lysosome concentration. FIG. 13 shows particulate concentration in the lysosomes in vivo at one week following bead administration.

EXAMPLE 10

Vascular Smooth Muscle in Vitro DNA and Protein Synthesis Inhibition by Staurosporin and Cytochalasin The ability of staurosporin and cytochalasin to inhibit in vitro DNA and protein synthesis in vascular smooth muscle cells was tested. $^3$H-leucine and $^3$H-thymidine uptake and cytotoxicity assays were conducted in accordance with the following protocols.

Cultured Cells:

BO54 cells (baboon smooth muscle cells) were derived from explants of aortic baboon smooth muscle cells. Cells were expanded in DMEM (Dulbecco's Modified Eagle's Medium): F-12 medium (Whittaker Bioproducts, Walkersville, Md.) with 5% fetal bovine serum (FBS, Gibco) and 5% Serum Plus® (JRH Biologicals) ("complete medium"), and a seed lot of cells was frozen in liquid nitrogen for future use at passage seven.

5 Minute Exposure; Protein Synthesis Assay:

Vascular smooth muscle cells at 40,000–50,000 cells/ml were seeded and processed as described in Example 8, "5 minute exposure; $^3$H-leucine uptake." Log dilutions of staurosporin (200 ng/ml, 20 ng/ml, 2 ng/ml, 0.2 ng/ml and 0.02 ng/ml) were dispersed in complete medium. For cytochalasin B, log dilutions at 20 μg/ml, 2.0 μg/ml, 0.2 μg/ml, 0.02 μg/ml and 0.002 μg/ml were dispersed in complete medium. Complete medium was then added to the control wells. One ml/well of each therapeutic agent dilution was added in quadruplicate wells, and the agent of interest was incubated with the vascular smooth muscle cells for 5 min at room temperature in a sterile ventilated hood. Following therapeutic agent incubation, the wells were subsequently treated as described in Example 8, "5 minute exposure; $^3$H-leucine uptake."

5 Minute Exposure; DNA Synthesis Assay:

Vascular smooth muscle BO54) cells were seeded and processed in 24 well plates, as described above under "5 Minute Exposure: Protein Synthesis Assay." After 5 min incubation with the test therapeutic agent, the medium was aspirated and 1 ml/well of 1.0 μCi/ml $^3$H-thymidine (rather than $^3$H-leucine) dispersed in complete medium was added. The cells were then incubated overnight at 37° C. in a humidified, 5% $CO_2$ environment. The toxic effect of the therapeutic agent was then determined, as described in the Protein Synthesis Assay, above.

24 and 120 Hour Exposure; Protein Synthesis Assay:

Vascular smooth muscle (BO54) cells at 20,000 cells/ml were seeded in sterile 24 well plates and incubated in complete medium (1 ml/well) overnight at 37° C., 5% $CO_2$, 95% air in a humidified atmosphere (saturation). Log dilutions of staurosporin (100 ng/ml, 10 ng/ml, 1 ng/ml, 0.1 ng/ml and 0.01 ng/ml) were dispersed sequentially in the two media, as described below. For cytochalasin B, log dilutions at 10 μg/ml, 1.0 μg/ml, 0.1 μg/ml, 0.01 μg/ml and 0.001 μg/ml were dispersed sequentially in the two media, as described below:

Medium (1)=Complete medium; and

Medium (2)=DMEM (leucine-free) with 0.5 μCi/ml $^3$H-leucine. Medium (2) is used for the final 24 hour incubation period of the experiment.

More specifically, in the 24 hour assay, each therapeutic agent was diluted in Medium (2), as noted above. Medium (1) was aspirated from the wells, and aliquots of therapeutic agent dilutions in Medium (2) were added in quadruplicate to the appropriate wells. Medium (2) was then added to the control wells.

In the 120 hour assay, each therapeutic agent was diluted in Medium (1), as noted above. Medium (1) was aspirated from the wells, and aliquots of therapeutic agent dilutions in Medium (1) were added in quadruplicate to the appropriate wells. Medium (1) was then added to the control wells. The medium was changed every 24 hours, and fresh therapeutic agent was added to the test wells. At 96 hr, (i.e., the fourth day), each therapeutic agent was diluted in Medium (2), as noted above. Medium (1) was aspirated from the wells, and aliquots of therapeutic agent dilutions in Medium (2) were added in quadruplicate to the appropriate wells. Medium (2) was then added to the control wells.

The test agents in $^3$H-leucine (and controls) were incubated overnight at 37° C., 5% $CO_2$ in a humidified atmosphere. The toxic effect of the therapeutic agents was then determined, as described in the 5 Minute Exposure: Protein Synthesis Assay, described above. In addition, the changes in cells at each dilution were photographed using a Zeiss microscope (Zeiss, West Germany) at 320×. The medium was then aspirated, and the cells were processed with TCA, as described above.

24 and 120 Hour Exposure; DNA Synthesis Assay:

This assay was performed according to the procedure described for "24 and 120 Hour Exposure; Protein Synthesis Assay", except Medium (2) in this 24 & 120 hr DNA Synthesis Assay is:

Medium (2)=Complete Medium with 1.0 $\mu$Ci/ml $^3$H-thymidine.

Medium (2) is used in the final 24 hour incubation of the experiment.

These protein and DNA synthesis assays are amenable for use with other target cell populations, especially adherent monolayer cell types.

Results:

The minimum effective dose (MED) of each agent was determined as a percentage of the control that was treated with medium only; 50% of control values was chosen as the cytotoxicity benchmark. At a 5 min exposure, staurosporin demonstrated an MED of 100 ng/ml in the protein synthesis assay and 1 ng/ml in the DNA assay. The 24 hour MED for staurosporin was 10 ng/ml in the protein synthesis assay and 1 ng/ml in the DNA synthesis assay. Both assays gave an MED of 1 ng/ml for a 120 hour exposure of staurosporin.

At a 5 minute exposure, cytochalasin B demonstrated an MED of 10 $\mu$g/ml in the protein synthesis assay as well as in the DNA assay. The 24 hour MED for cytochalasin B was 1.0 $\mu$g/ml in the protein synthesis assay and 0.1 $\mu$g/ml in the DNA synthesis assay. Both assays gave an MED of approximately 0.1 $\mu$g/ml for a 120 hour exposure of staurosporin.

Cytochalasin C and cytochalasin D therapeutic agents were tested at 24 and 48 hour exposures using the same dilutions as described for cytochalasin B, above. At 24 hours, cytochalasin C demonstrated an MED of 1.0 $\mu$g/ml in the protein synthesis assay and an MED of 0.01 $\mu$g/ml in the DNA synthesis assay. At 48 hours, cytochalasin C demonstrated an MED of 0.1 $\mu$g/ml in the protein synthesis assay and 0.01 $\mu$g/ml in the DNA synthesis assay. Cytochalasin D demonstrated an MED of 1.0 $\mu$g/ml in the 24 hour protein synthesis assay and an MED of 0.1 $\mu$g/ml in the 24 hr DNA synthesis assay. A 48 hour exposure to cytochalasin D gave an MED ranging between 0. 1 and 0.01 $\mu$g/ml in both the protein synthesis and DNA synthesis assays.

EXAMPLE 11

Vascular Smooth Muscle Cell Migration Inhibition

Scratch assays to determine the extent of smooth muscle cell migration inhibition by cytochalasin B were performed in accordance with the following protocol:

Vascular smooth muscle cells (BO54) were derived from explants of baboon aortic smooth muscle, as described in Example 10. The cells were grown in flat bottom, six well tissue culture plates, which hold about 5 ml of medium. The vascular smooth muscle cells were plated at 200,000 cells/well and placed at 37° C. in a humidified 5% $CO_2$ incubator for 18 hours. The wells were then scratched with a sterile portion of a single edge razor blade that was held by clamp or pliers and was brought aseptically into contact with the bottom of the well at a 90° angle. The cells from a small area along the scratch were removed by a sterile cotton tipped applicator while the blade was in contact with the bottom of the well. After incubation, the presence of cells in the "scratched" area is indicative of cell migration across the scratch line. A control incubation showed significant cellular migration, and serves as the standard against which the migration of cells exposed to the therapeutic agent is compared.

Briefly, a stock solution of cytochalasin B (Sigma Chemical Co.) in dimethyl sulfoxide (DMSO) at 1 mg/ml was prepared. Test dilutions of cytochalasin B or control medium were added. Each experiment included two sets of plates:

A set: Test agent exposure for 1, 3, 6, 8 and 10 days only; and

B set: Test agent exposure for 1, 3, 6, 8 and 10 days, followed by a seven day recovery time with control medium.

Both sets of plates were fixed (10% formalin in PBS) and stained (0.02% crystal violet) at the end of the timed exposures. Test concentrations for cytochalasin B were 1, 0.1 and 0.01 $\mu$g/ml, and a negative medium control was included. Fresh medium and drug were supplied 3 times per week.

Table 4 shows the results of these experiments. In this Table, "M" indicates Migration Grade, wherein −=no migration; +1=minimal; +2=mild; +3=moderate; and +4=marked (maximum density; limit of cell contact inhibition) migration of vascular smooth muscle cells into the cleared area adjacent to the scratch. In this Table, "T" denotes a morphological Toxicity Grade, wherein −=no toxicity; +1=minimal; +2=mild; +3=moderate; and +4=marked toxicity. The migration results are expressed as "Grade in the Cleared Area of the Well/Grade in an Undisturbed Region of the Well." The toxicity values represent a grade for all cells in each well.

The data indicate that cytochalasin B inhibits the migration (+1 to +2) of vascular smooth muscle cells into the cleared area adjacent to the scratch at a dose of 0.1 $\mu$g/ml with only minimal (− to +1) morphological toxicity. The data also show that the treated cells (0.1 $\mu$g/ml) regain the ability to migrate (+3 to +4) following removal of the therapeutic agent, even after 10 days of continuous exposure to the therapeutic agent.

TABLE 4

SCRATCH-MIGRATION ASSAY: INHIBITION OF VASCULAR SMOOTH MUSCLE CELL MIGRATION BY CYTOCHALASIN B

| Day | | Continuous Exposure Dosage $\mu$g/mL | | | | 7-day Recovery Post Exposure Dosage $\mu$g/mL | | | |
|---|---|---|---|---|---|---|---|---|---|
| | | Control 0.0 | 0.01 | 0.1 | 1.0 | Control 0.0 | 0.01 | 0.1 | 1.0 |
| 1 | M | +1/+3 | +1/+3 | +1/+3 | —/+2 | +3/+4 | +3/+4 | +3/+4 | +2/+3 |
| | T | — | — | — | +3 | — | — | — | +2 |

TABLE 4-continued

SCRATCH-MIGRATION ASSAY: INHIBITION OF VASCULAR
SMOOTH MUSCLE CELL MIGRATION BY CYTOCHALASIN B

| | | Continuous Exposure Dosage μg/mL | | | | 7-day Recovery Post Exposure Dosage μg/mL | | | |
|---|---|---|---|---|---|---|---|---|---|
| Day | | Control 0.0 | 0.01 | 0.1 | 1.0 | Control 0.0 | 0.01 | 0.1 | 1.0 |
| 3 | M | +3/+4 | +3/+4 | +1/+4 | —/+2 | +3/+4 | +3/+4 | +3/+4 | +2/+3 |
|   | T | — | — | +1 | +3 | — | — | — | +1 |
| 6 | M | +3/+4 | +3/+4 | +2/+4 | —/+2 | +4/+4 | +4/+4 | +3/+4 | +2/+3 |
|   | T | — | — | +1 | +4 | — | — | — | +3 |
| 8 | M | +3/+4 | +3/+4 | +2/+4 | —/+2 | +4/+4 | +4/+4 | +3/+4 | +2/+3 |
|   | T | — | — | +1 | +4 | — | — | — | +3 |
| 10 | M | +3/+4 | +3/+4 | +2/+4 | —/+2 | +4/+4 | +4/+4 | +4/+4 | +2/+3 |
|    | T | — | — | +1 | +4 | — | — | — | +3 |

EXAMPLE 12

Therapeutic Agent Cytotoxic Effects on Vascular Smooth Muscle Cells—Pulse and Continuous Exposure Vascular smooth muscle cells were exposed to a therapeutic agent in one of two exposure formats:
Pulse Exposure:
The pulse exposure protocol is described in Example 8 above (see "Morphological Cytotoxicity Evaluation—Pulsed Exposure").
Continuous Exposure:

The same methodology is used for continuous exposure morphological cytotoxicity evaluation as for the pulse exposure, except that the test wells were continuously exposed to therapeutic agent in medium during the exposure period. The medium and therapeutic agent were aspirated from each well daily, including from the untreated control well, and were replaced with 1 ml of fresh medium and therapeutic agent (or medium alone for control wells).

Re-incubation followed, until each of the incremental evaluation points of the long term continuous exposure protocol was achieved. These incremental evaluation time points were at 6, 24, 48, 72, 96, 120, 168, 216 and 264 hours. At the designated time period, the appropriate cells were fixed, stained and evaluated as in the pulse exposure protocol. The results of a continuous exposure experiment are shown in Table 5 for suramin, staurosporin and cytochalasin B. The 5 min and 24 hr data presented in Table 5 are correlates of the data contained in FIGS. 10A, 10B and 10C.

TABLE 5

MORPHOLOGICAL CYTOTOXICITY ASSAY
Drug & Dose

| | Cytochalasin B | | | | Suramin | | | | Staurosporine | | | |
|---|---|---|---|---|---|---|---|---|---|---|---|---|
| Exposure Protocol | 10 μg | 1 μg | 0.1 μg | 0.01 μg | 10 mg | 1 mg | 0.1 mg | 0.01 mg | 100 ng | 10 ng | 1 ng | 0.1 ng |
| 5 min + 2 hrs | 0.5 | 0 | 0 | — | 0 | 0 | 0 | — | 0 | 0 | 0 | — |
| 5 min + 6 hrs | 4 | 1 | 0 | — | 1 | 0 | 0 | — | 0 | 0 | 0 | — |
| 5 min + 24 hrs | 4 | 0.5 | 0 | — | 1 | 0 | 0 | — | 0 | 0 | 0 | — |
| 5 min + 48 hrs | 4 | 1 | 0 | — | 2 | 0 | 0 | — | 2 | 0 | 0 | — |
| 5 min + 72 hrs | 4.5 | 1 | 0 | — | 3 | 1 | 0 | — | 3 | 1.5 | 0 | — |
| 5 min + 96 hrs | 5 | 1 | 0 | — | 3 | 1 | 0 | — | 3.5 | 1.5 | 0 | — |
| 5 min + 120 hrs | 5 | 1 | 0 | — | 3 | 1 | 0 | — | 4 | 1.5 | 0 | — |
| Continuous 6 hrs | — | 3 | 0 | 0 | 3 | 1 | 0 | — | 0 | 0 | 0 | 0 |
| Continuous 24 hrs | — | 3 | 1 | 0 | 3 | 2 | 0 | — | — | 0 | 0 | 0 |
| 24 hrs + 24 hrs | — | 3 | 0.5 | 0 | 4 | 3 | 0 | — | — | 0.5 | 0 | 0 |
| 24 hrs + 48 hrs | — | 4 | 1 | 0 | 4 | 3 | 0 | — | — | 2 | 0 | 0 |
| 24 hrs + 72 hrs | — | 4 | 0.5 | 0 | 4 | 3 | 0.5 | — | — | 1 | 0 | 0 |
| 24 hrs + 96 hrs | — | 4 | 0 | 0 | 4 | 3.5 | 1 | — | — | 1.5 | 0 | 0 |
| 24 hrs + 120 hrs | — | 4 | 0 | 0 | — | — | — | — | — | 1.5 | 0 | 0 |
| Continuous 24 hrs | — | 3 | 0 | 0 | — | 1 | 1 | 0 | — | 3 | 1 | 0 |
| Continuous 48 hrs | — | 3 | 1 | 0 | — | 3 | 2 | 0 | — | 3 | 2 | 0 |
| Continuous 72 hrs | — | 3 | 1 | 0 | — | 4 | 3 | 0 | — | 3 | 2 | 0 |
| Continuous 96 hrs | — | 3 | 2 | 0 | — | 4 | 3 | 0 | — | 3 | 2 | 1 |
| Continuous 120 hrs | — | 3 | 1 | 0 | — | 5 | 4 | 0 | — | 3 | 2 | 1 |
| Continuous 168 hrs | — | 4 | 1 | 0 | — | 5 | 4 | 0 | — | 3 | 2 | 1 |
| Continuous 216 hrs | — | 4 | 1 | 0 | — | 5 | 4 | 0 | — | 3 | 2 | 1 |
| Continuous 264 hrs | — | 4 | 1 | 0 | — | 5 | 4 | 0 | — | 4 | 2 | 1 |

At an in vitro effective dosage, cytochalasin B (1 μg/ml; an anti-migration/contraction effective dose) and staurosporin (1 ng/ml; an anti-proliferative effective dose) exhibited a cytotoxicity grade of 1 (minimal) and 2 (mild), respectively. Independent studies have indicated that a grade of 3 (moderate) or less is preferred for a cytostatic, anti-proliferative agent of the present invention.

EXAMPLE 13

In Vivo BRDU Assay: Inhibition of Vascular Smooth Muscle Cell Proliferation

BRDU Assay:

In vivo vascular smooth muscle proliferation was quantitated by measuring incorporation of the base analog 5-bromo-2'-deoxyuridine (BRDU, available from Sigma Chemical Co.) into DNA during cellular DNA synthesis and proliferation. BRDU incorporation was demonstrated histochemically using commercially available anti-BRDU monoclonal antibodies. The 1 hour pulse labeling permits assessment of the number of cells undergoing division during the pulse period.

The BRDU pulse labeling protocol described above is used as a standard evaluation technique with in vivo pig vascular studies. Following surgical and treatment procedures (discussed, for example, in Examples 7 and 11 herein) and a post-surgical recovery period, pigs were sedated and pulsed with BRDU 1 hour prior to tissue collection.

Briefly, the pigs were sedated with tiletamine hydrochloride and xylazine (as in Example 7, "Gross Pathology and Histological Evaluation") by intramuscular injection. BRDU was then administered intravenously via the lateral ear vein. Two ml of BRDU at a concentration of 50 mg/ml was administered to each 30–40 lb pig. One hour later, the pigs were sacrificed by intravenously administered pentobarbital. Test artery segments were then removed (a segment included normal vessel located proximally and, if possible, distally with respect to the treated artery segment). The artery segments were transected at 2 mm intervals; arranged in order in cryomolds with O.C.T. (optimum cutting temperature) compound (Tissue Tek®, Miles Laboratories, Inc., Elkhart, Ind.); and frozen in liquid nitrogen. The blocks were sectioned at 5 microns and immunohistologically stained to detect BRDU using the following procedure.

BRDU-labeled Cell Detection:

After BRDU (1 g BRDU diluted in 17 ml sterile water and 3 ml 1 N NaOH) pulse labeling and test artery segment removal and sectioning (as above), immunohistochemical staining with anti-BRDU monoclonal antibody provides a visual means of determining a mitotic index over a specified time period. The immunohistochemical staining method was performed as follows:

1) 5 μm sections of test artery were dehydrated in cold acetone (−20° C.) for 10 minutes;
2) Sections were mounted on glass microscope slides, and the slides were dried in a 37° C. oven for 10 minutes;
3) Slides were rehydrated in PBS for 10 minutes;
4) Slides were subjected to Feulgen's acid hydrolysis using 1 N HCl, wherein two aliquots of 1 N HCl are preheated to 37° C. and 60° C. prior to proceeding;
5) Slides were rinsed with 1 ml of 1 N HCl at 37° C. for 1 min;
6) Slides were transferred to 60° C. 1 N HCL for 15 min;
7) Slides were rinsed with 1 ml of 1 N HCl at 37° C. for 1 min;
8) Slides were washed with room temperature PBS, using 3 changes of PBS at 5 min intervals;
9) Endogenous, cross-reactive sites on the sections were blocked with normal goat serum (1:25 in PBS) for 20 min;
10) Slides were washed with PBS, as in step 8;
11) Sections were incubated with mouse anti-BRDU antibody (DAKO Corporation, Carpinteria, Calif.) at 10 μg/ml for 30 min;
12) Slides were washed with PBS, as in step 8;
13) Sections were incubated with horseradish peroxidase-labeled (HRPO) goat anti-mouse IgG, (Jackson Immunoresearch Laboratories, Inc., West Grove, Pa.; diluted 1:20 in PBS) and 4% human AB serum for 30 min;
14) Slides were washed with PBS, as in step 8;
15) Sections were incubated with chromogen (3,3'-diaminobenzidine (DAB; Sigma) at 5 mg/ml in 200 ml PBS) and 200 μl of 30% $H_2O_2$ for 10 min;
16) Slides were washed with PBS, as in step 8;
17) Samples were counterstained with Gill I hematoxylin (Gill I Lerner Laboratories, Pittsburgh, Pa.; 30 dips);
18) Slides were washed with PBS, as in step 8; rinsed with a bluing solution (1 gm lithium carbonate in 500 ml $dH_2O$); washed with deionized water; and
19) Test samples were then dehydrated, cleared and coverslipped.

At the conclusion of this procedure, a positive immunohistological stain exhibits a brown color at the site(s) of reactivity.

Cytocidal agents inhibited BRDU uptake relative to a PBS control; however, cytochalasin B and staurosporin inhibited BRDU uptake (i.e., cell proliferation) without killing the vascular smooth muscle cells. The number of vascular smooth muscle cells labeled with BRDU was assigned a grade at 400× magnification as follows:

1 = ≦1/high power field (HPF);
2 = 2 to 5/HPF;
3 = >5 to ≦10/HPF; and
4 = >10/HPF.

Both cytochalasin B and staurosporin inhibited proliferation for 24 hours following balloon trauma (grade 1), yielding a BRDU labeling grade equivalent to that of a pre-trauma baseline (grade 1). PBS and monoclonal antibody controls exhibited grade 2.5 to 4 BRDU labeling during the same time period. At 4 days post-trauma, arteries treated with cytochalasin B or staurosporin, as well as PBS and monoclonal antibody controls, exhibited a BRDU labeling grade of 4. The anti-proliferative, non-cytocidal properties of cytochalasin B and staurosporin suggest that these agents are amenable to sustained release dosage formulations for reduction of vascular stenosis.

EXAMPLE 14

Direct Conjugation of NR-AN-01 Antibody to Carboxylic Functional Groups of a Latex Particle Antibody-coated latex particles (a model of an antibody-coated, sustained release dosage form) may be obtained using the following aseptic technique:

Conjugation:

To 4 ml 0.05 M sodium borate, pH 8.5, containing 0.01% Tween-20® (polyoxyethylene sorbitan monolaurate, Sigma) is added 0.5 ml PBS containing 5 mg NR-AN-01 monoclonal antibody. To this solution at room temperature is added, with vortexing, 2.5 ml of an aqueous suspension containing 50 mg of 1 μm diameter carboxylated latex particles. Immediately thereafter, 0.50 ml of water containing 100 mg of freshly dissolved 1(3-dimethyl-aminopropyl) 3-ethyl carbodiimide HCl is added with vortexing. The solution is then incubated with shaking for 1–2 hr at room temperature. The reaction mixture is then diluted with 50 ml of 50 mM phosphate buffer, pH 6.6, containing 0.2% gelatin stabilizer (phosphate/gelatin buffer). The mixture is centrifuged at 40,000×g for 2 hr at 4–10° C. The supernatant is decanted, and the pellet is resuspended in 50 ml phosphate/gelatin buffer using low level sonication for 10 sec. Centrifugation is repeated, and the pellet is resuspended two times, followed by resuspension in the phosphate/gelatin buffer. The conjugated particles are then lyophilized using standard protocols and sorbitol excipients.

Characterization:

(a) Sizing: Particle size homogeneity is assessed by laser anisotropy or, for particles larger than 1 $\mu$m, by microscopic examination.

(b) Specific Binding Assessment: Specific binding to smooth muscle cells is determined by histological examination of tissue or cell pellet microtome slices after incubation of protein/peptide conjugates with conjugated particles, with or without blocker protein/peptide included in the incubation mixture. Preferred detection techniques include second antibody assays (i.e., anti-mouse Ig) or competition assays (i.e., radioscintigraphic detection in conjunction with radioisotopically labeled protein/peptide conjugates).

(c) Assessment of the extent of protein/peptide derivitization: This determination is performed by coating the latex particles with radioisotopically labeled antibody, followed by detection of radioactivity associated with the coated particles.

The characterization of antibody-coated particles is described in Table 6.

TABLE 6

Characterization of NR-AN-01-Coated Latex Particles

| Particle Diameter | Offering of Ab/Particle | $\mu$g Ab Bound/ 5 mg Latex | Ab Molecules Per Particle |
|---|---|---|---|
| 1.2 $\mu$m | 40,000 | 42 | 3520 |
| 1.2 $\mu$m | 84,000 | 66 | 5470 |
| 0.4 $\mu$m | 32,000 | 99 | 3160 |
| 0.4 $\mu$m | 64,000 | 140 | 4550 |
| 0.1 $\mu$m | 932 | 140 | 65 |

The particle aggregation effect of pH during antibody conjugation is presented in Table 7.

TABLE 7

Effect of pH During Antibody Conjugation - Particle Aggregation

| Particle Diameter | pH* During Conjugation | Particle Aggregation** | |
|---|---|---|---|
| | | +Tween 20 ® | −Tween 20 ® |
| 1.2 $\mu$m | 8.5 | <5% | <2.5% |
| 1.2 $\mu$m | 7.0 | ≈20% | ≈10% |
| 1.2 $\mu$m | 5.5 | 10% | 100% |
| 0.4 $\mu$m | 8.5 | <10% | <5% |
| 0.4 $\mu$m | 7.0 | ≈30% | ≈20% |
| 0.4 $\mu$m | 5.5 | 100% | 100% |
| 0.1 $\mu$m | 8.5 | <20% | <10% |
| 0.1 $\mu$m | 7.0 | ≈50% | ≈40% |
| 0.1 $\mu$m | 5.5 | 100% | 100% |

*Using 50 mM MES (pH 5.5); phosphate (pH 7.0); or borate (pH 8.5) buffer, as described.
**As assessed by microscopic examination, on a scale of 0–100%.

These data suggest that proteins or peptides may be directly conjugated with sustained release dosage forms of the present invention. More specifically, poly-lactic/glycolic acid particulates having terminal carboxylic acid groups will be conjugated according to the procedure described herein or the alternative procedures described in the specification hereof.

EXAMPLE 15

In Vivo Studies of Cytochalasin B

Biodistribution of Cytochalasin B.

To determine the biodistribution of 30 cytochalasin B, mice were injected (i.p.) with 50 mg/kg cytochalasin B. Control mice were injected with DMSO/Tween 20/carboxymethyl cellulose ("vehicle"). The mice were sacrificed at 3, 12, 24 and 72 hours after cytochalasin B or vehicle administration. Organs were removed, homogenized, extracted and the amount of cytochalasin B in tissues quantitated by HPLC. About 75% of the cytochalasin B remained in the peritoneal cavity or at the injection site. Of the organs tested, the highest amount of cytochalasin B was found in the liver. Subsequent analyses showed that the maximum tolerated dose for cytochalsin B was 50 mg/kg, and that this dose may be administered every second day.

Cytochalasin B was also administered intravenously to mice at 3.5 mg/kg (in methanol or Tween 20/carboxymethyl cellulose). Mice were sacrificed at 2 minutes, 15 minutes, 30 minutes, 3 hours and 12 hours after cytochalasin B administration and tissue extracts analyzed for cytochalasin by TLC. The maximal recovery of cytochalasin B from tissue extracts was 32%. The data showed that cytochalasin B was localized to the lung and the injection site, and that 3.5 mg/kg of cytochalasin B resulted in no acute toxicity. By 12 hours after administration, there were very low levels of cytochalasin B in tissues.

$^3$H-cytochalasin B (2 $\mu$g; 30 $\mu$Ci/$\mu$g) was injected i.v. into BALB/c mice having urinary bladders that had been externally ligated. Animals were sacrificed at 15 minutes, 30 minutes, 2 hours or 16 hours post-injection. Organs were removed, blotted, weighed, air dried and assayed for radioactivity. Fifty—73% of the total injected dose was accounted for in the tissues sampled (blood, heart, brain, muscle, bone, lung, liver, spleen, stomach, kidney, intestines, and urinary bladder). Clearance of $^3$H-cytochalasin B from the blood was extremely rapid with less than 1% of the injected dose in circulation by 15 minutes. Only liver, skeletal muscle and intestines showed significant retention of $^3$H activity. All tissues had clearance of $^3$H activity to below 1.5% injected dose per gram of tissue by 16 hours.

Cytochalasin B Metabolism.

$^3$H-cytochalasin B at a dose of 1.5 or 8 $\mu$g/ml was mixed with viable or non-viable human liver slices and media, and the amount of $^3$H-cytochalasin B in media or tissue assessed by HPLC (Tables 8 and 9).

The cytotoxity of $^3$H-cytochalasin B and its subsequent metabolites was also assessed by evaluating dose dependent changes in mitochondrial function by monitoring 3-[4,5-dimethylthiazol-2yl]-2,5-diphenyltetrazolium bromide (MTT) activity following a 24 hour exposure of human liver slices to the test agent (Table 10).

TABLE 8

DISTRIBUTION OF $^3$H CYTOCHALASIN B MEDIA AND HUMAN LIVER TISSUE

| $^3$H Cytochalasin B ($\mu$g/ml) | Incubation System | Incubation Period at 37° C. (Hours) | % Activity in Media | % Activity in Tissue |
|---|---|---|---|---|
| 1.5 | Media/viable | 1 | 84 | 16 |
| 1.5 | tissue | 4 | 84 | 16 |
| 1.5 |  | 24 | 91 | 9 |
| 8 | Media/viable | 1 | 88 | 12 |
| 8 | tissue | 4 | 84 | 16 |
| 8 |  | 24 | 89 | 11 |
| 8 | Media/boiled | 1 | 83 | 17 |
| 8 | tissue | 4 | 87 | 13 |
| 8 |  | 24 | 87 | 13 |

TABLE 9

HUMAN LIVER SLICES METABOLISM STUDY NATURE OF TRITIUM ACTIVITY EXTENT OF METABOLIC CONVERSION

| $^3$H Cytochalasin B ($\mu$g/ml) | Incubation System | Incubation Period (Hours) | % Non extractable Activity | % Extractable Activity | % Metabolized of Extractable Activity |
|---|---|---|---|---|---|
| 8 | Media/viable | 1 | 0.5 | 99.5 | 24.2 |
| 8 | tissue | 4 | 1 | 99.0 | 59.4 |
| 8 |  | 24 | 1.3 | 98.7 | 98.0 |
| 1.5 | Media/viable | 1 | 0.5 | 99.5 | 43.0 |
| 1.5 | tissue | 4 | 0.6 | 99.4 | 77.0 |
| 1.5 |  | 24 | 0.4 | 99.6 | 98.7 |
| 8 | Media/boiled | 1 | 0.5 | 99.5 | 5 |
| 8 | tissue | 4 | 1 | 99.0 | 5 |
| 8 |  | 24 | 1.3 | 98.7 | 5 |
| 8 | Media Only | 1 | NA | NA | 5 |
| 8 |  | 4 | NA | NA | 4 |
| 8 |  | 24 | NA | NA | 5 |

TABLE 10

MTT Absorbance in Human Liver Slices Exposed to $^3$H-cytochalasin B for 24 hours.

| Dose Level ($\mu$g/ml) | MTT Absorbance |
|---|---|
| 0 (control) | 0.639 +/- 0.188 |
| 0.1 | 0.844 +/- 0.014 |
| 1.5 | 0.841 +/- 0.081 |
| 8.0 | 0.850 +/- 0.082 |

[a]MTT absorbance values reflect the mitochondrial viability in which high absorbance values represent viable mitochondria and while low absorbance values reflect nonfunctional mitochondria. Each value represents the mean +/- standard deviation optical density of triplicate liver samples.

The results in Tables 8–9 indicated that 98% of the $^3$H-cytochalasin B was metabolized within 24 hours of administration with greater than 80% of the total reactivity being present in the media and less than 20% in the tissue. The results in Table 10 indicated that $^3$H-cytochalasin B or its subsequent metabolites was not cytotoxic.

To determine the metabolism of $^3$H-cytochalasin B in human blood, $^3$H-cytochalasin B (8 $\mu$g/ml) was dissolved in saline; 1:1 dilution of saline and human plasma; or 1:1 dilution of saline and human whole blood. The mixtures were incubated for 20 hours at 37° C. and then analyzed by HPLC for stability and metabolism. $^3$H-cytochalasin B was not metabolized when mixed with either saline or plasma. However, $^3$H-cytochalasin B was metabolized by human whole blood with the metabolite having an HPLC retention time and profile consistent with that seen in the human liver slice assay (see above).

Toxicity Studies.

To determine the toxicity of cytochalasin B, rats (4 male and 4 female) were injected with 10 $\mu$g/ml cytochalasin B four times a day for 7 days (Table 11). Data regarding body weight changes, food consumption, food efficiency, hematology parameters, coagulation parameters, serum chemistry parameters, and gross necropsy findings were collected. The only parameter which suggested an adverse effect of cytochalasin B administration was an elevation of the mean relative heart weight in treated female animals. There were no gross or microscopic changes detected in the heart to account for the elevation. Thus, daily administration of cytochalasin B to rats at a dose of 800 $\mu$g/kg (for a total injected dose of 5600 $\mu$g/kg) may have an effect on heart weight of female (but not male) rats. However, clotted blood was not routinely removed from the heart lumens prior to weighing the heart.

TABLE 11

| Group Number | Number of Animals | | Treatment | Dose Level (µg/mL) | Route | Dosing Frequency | Dosing Duration |
|---|---|---|---|---|---|---|---|
| | Males | Females | | | | | |
| 1 | 4 | 4 | Biostent Control | 0 | IV | 4 times/day (2 hrs apart) | 7 days |
| 2 | 4 | 4 | Cytochalasin B | 10 | IV | 4 times/day (2 hrs apart) | 7 days |

To determine the toxicity of chronic cytochalasin B administration, cytochalasin B was administered intravenously to Sprauge-Dawley rats for seven days (Table 12). Data regarding food consumption, body weights, hematology parameters, clinical chemistry parameters, coagulation profiles, organ weights, clinical observations, gross necropsy findings and histopathology were collected. It was found that chronic intravenous administration of cytochalasin B at doses up to 600 µg/kg/day did not result in any indication of adverse effects or toxicity.

TABLE 12

| Group Number | Number of Animals | | Treatment | Dose Level (µg/mL) | Route | Dosing Frequency | Dosing Duration |
|---|---|---|---|---|---|---|---|
| | Males | Females | | | | | |
| 1* | 15 | 15 | Control | 0 | Intravenous injection | 4 times/day (≈2 hrs apart) | 7 days |
| 2 | 10 | 10 | Cytochalasin B | 1.3 | | | 7 days |
| 3 | 10 | 10 | | 3.9 | | | 7 days |
| 4* | 15 | 15 | | 7.5 | | | 7 days |
| 5* | 15 | 15 | | 7.5 | | | 7 days |

*Five animals/sex/group were used for a 14-day nontreatment recovery period and were euthanized on day 22
**Five animals/sex were euthanized on days 8, 15, and 22

A similar study in dogs (Table 13), which collected data on food consumption, body weights, hematology parameters, clinical chemistry parameters, coagulation profiles, organ weights, clinical observations, thoracic cavity ausculation, opthalmic examination, urinalysis, gross necropsy findings, and histopathology (high dose group), found that intravenous administration of cytochalasin B for seven consecutive days to beagle dogs at doses up to 648 µg/kg/day (a cumulative dose of 4,536 µg/kg) did not result in any indication of adverse effects or toxicity.

TABLE 13

| Group Number | Number of Animals | | Treatment | Dose Level (µg/mL) | Dose Volume (mL/kg); Flow Rate (mL/min) | Route | Dosing Frequency | Dosing Duration |
|---|---|---|---|---|---|---|---|---|
| | ♂ | ♀ | | | | | | |
| 1* | 6 | 6 | Control | 0 | 20; 10 | IV | 4 times/day (= 6 hrs apart) | 7 days |
| 2 | 4 | 4 | Cytochalasin B | 1.3 | 20; 10 | IV | 4 times/day (= 6 hrs apart) | 7 days |
| 3 | 4 | 4 | Cytochalasin B | 4.4 | 20; 10 | IV | 4 times/day (= 6 hrs apart) | 7 days |
| 4* | 6 | 6 | Cytochalasin B | 8.1 | 20; 10 | IV | 4 times/day (= 6 hrs apart) | 7 days |
| 5** | 6 | 6 | Cytochalasin B | 8.1 | 20; 10 | IV | 4 times/day (= 6 hrs apart) | 7 days |

♂ = males; ♀ = females; IV = intravenous infusion
*Two dogs/sex/group were held for a 14-day nontreatment recovery period and were euthanized on day 23
**Three dogs/sex were euthanized on days 9 and 23.

EXAMPLE 16

Biological Stenting of Balloon Traumatized Pig Arteries

Pig femoral arteries were traumatized as described in Example 7, and then treated with cytochalasin B. About 1.5 to about 2 ml of cytochalasin B at 0.1 µg/ml was infused into portions of the artery that had been separated from other portions by ligatures. The artery was then pressurized for 3 minutes and the fluid aspirated. Approximately 8 to about 30 lambda of the solution is retained in the interstitial space surrounding the cells in the tunica media. Ten femoral arteries (two arteries obtained from each of the 5 pigs that were treated according to the single dose protocol described in Example 7) were then evaluated histologically at 4 days or 3 weeks after cytochalasin B adminstration. The maximal luminal area of each artery was measured and calculated from digitized microscopic images by a BQ System IV computerized morphometric analysis system (R & M Biometrics, Inc., Nashville, Tenn.). This experiment was repeated with 5 additional pigs (two arteries per pig; cytochalasin B dose=0.1 µg/ml, applied for 3 minutes at 1 atm pressure; same time points). The data obtained from the two experiments were combined. Balloon traumatized pig arteries that had been treated with cytochalasin B displayed a larger luminal area at the 4 day and 3 week post-treatment time points, as compared to arteries treated with other test agents or controls.

The luminal area of the traumatized and cytochalasin B-treated segments of the arteries were also compared to the luminal area of the normal, untreated region of the femoral artery proximal to the test area. The results showed that the lumen area in the test region was approximately two times as large as the area of the normal control segment of the same artery. The negative control agents, PBS and monoclonal antibody NR-AN-01, showed no increase or a slight decrease in lumen area as compared to the normal control segment of the same artery.

Figure 14:
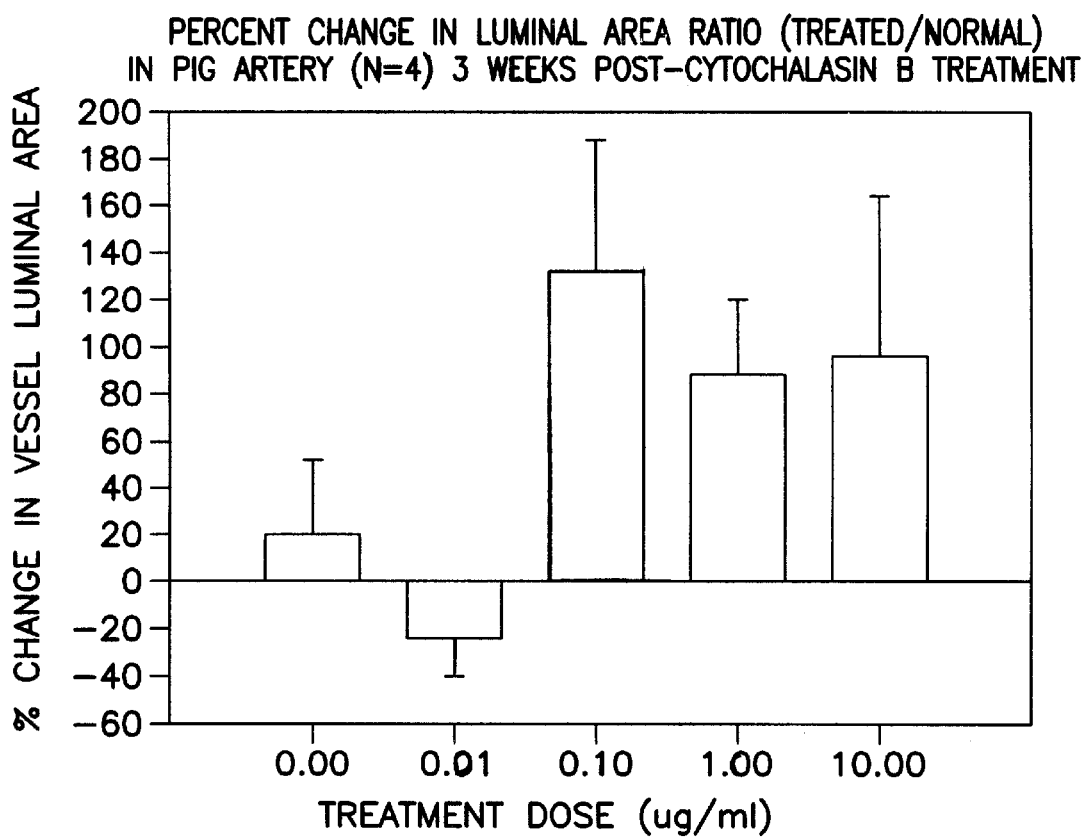
FIG. 14 depicts an in vivo dose response study of the effects of cytochalasin B on the luminal area of pig femoral arteries.
Figure 15:
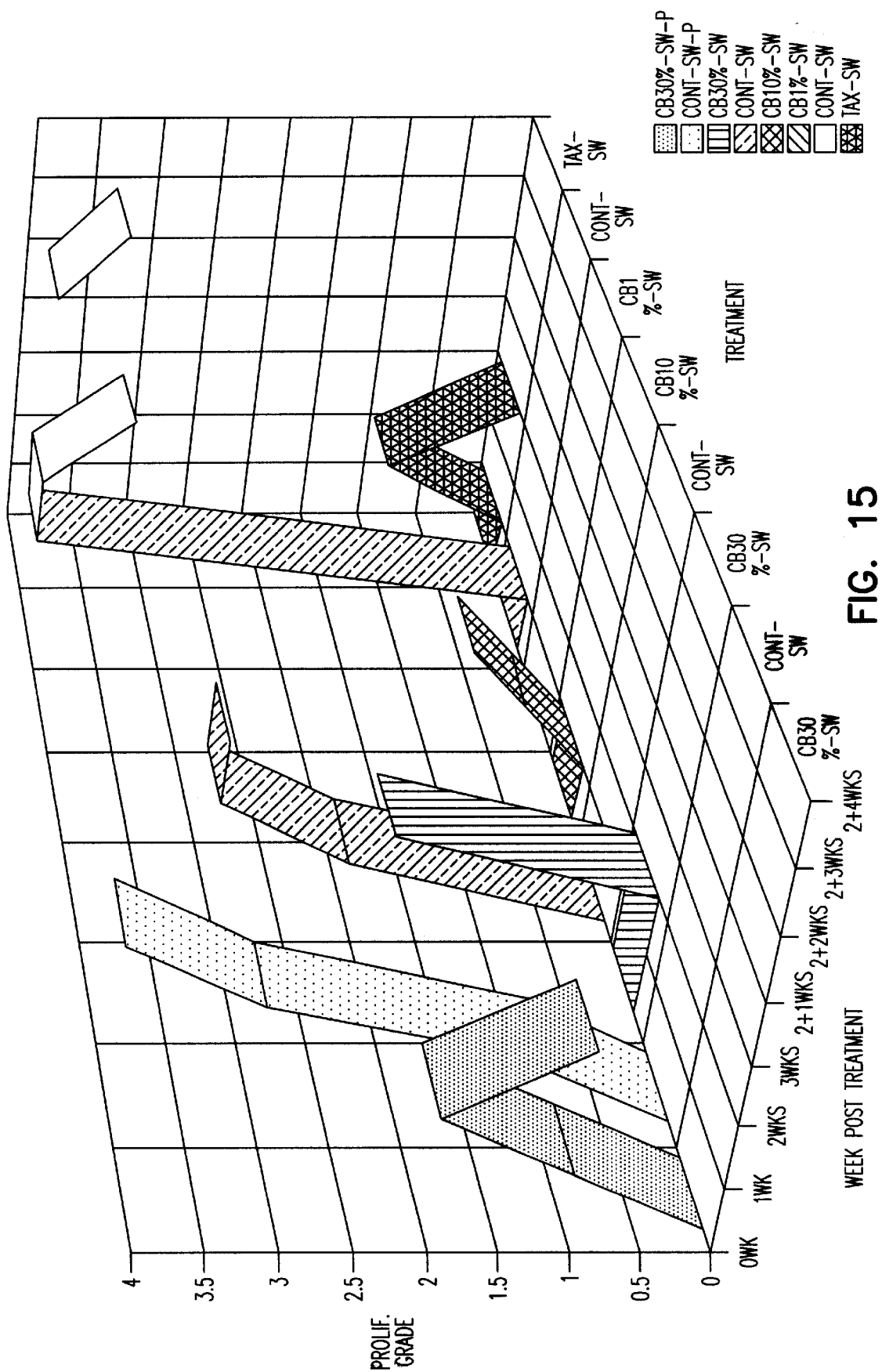
FIG. 15 is a graph depicting the inhibition of smooth muscle cell proliferation in traumatized vessels over time by cytochalasin B (CB) or taxol (TAX) administered in silicone wraps (SW).
Figure 16:
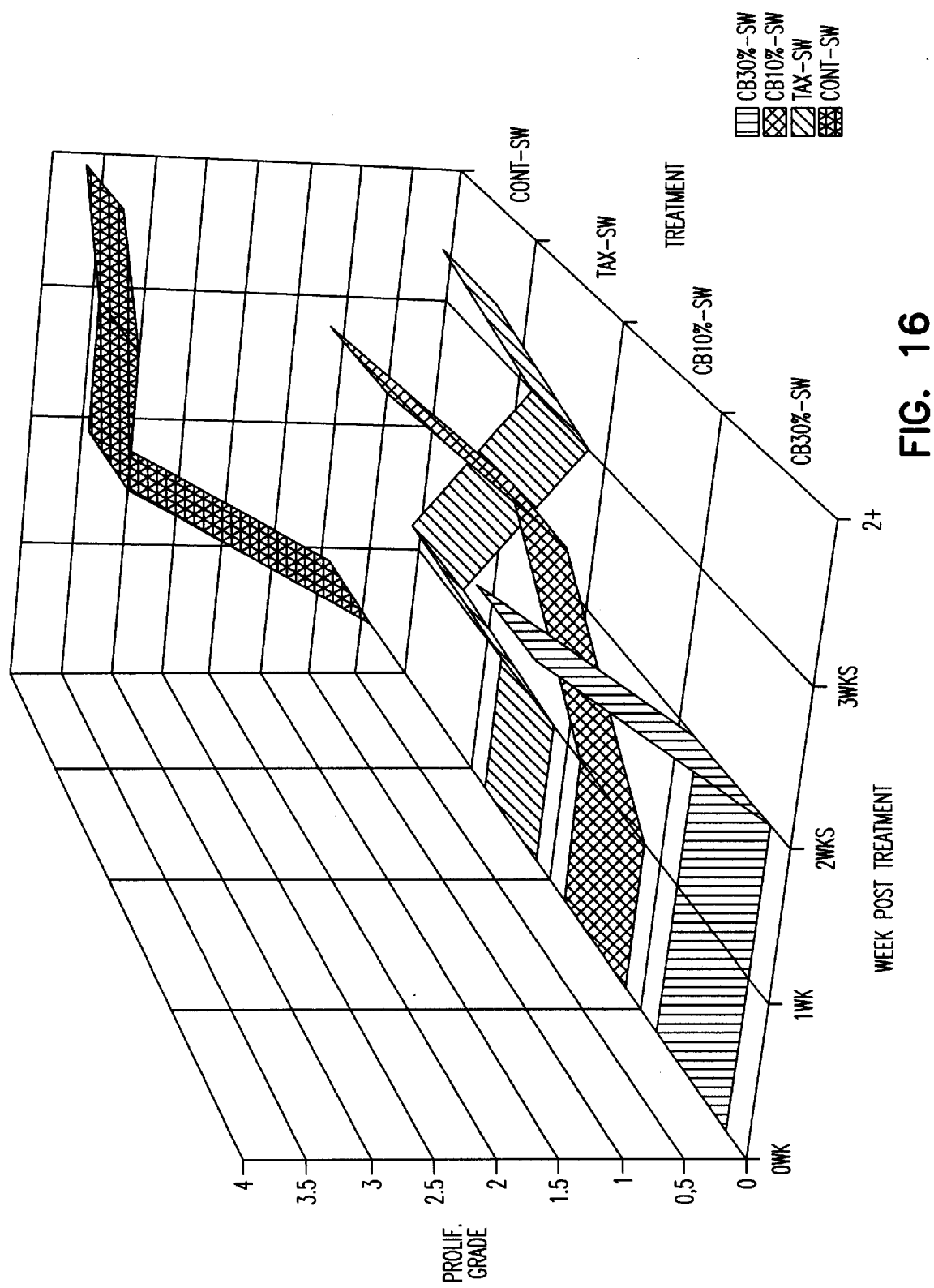
FIG. 16 is a graph depicting the inhibition of smooth muscle cell proliferation in traumatized vessels over time by 10% or 30% wt/wt CB in SW or 5% wt/wt TAX in SW.

A cytochalasin B dose response study was then conducted on 10 pigs, following the experimental protocol described in Example 7. Briefly, both femoral arteries in each of 2 pigs were treated with one of the following doses of cytochalasin B: 0.0 µg/ml (i.e., PBS negative control); 0.01 µg/ml; 0.10 µg/ml; 1.0 µg/ml; and 10.0 µg/ml as described above. The agent was delivered by intraluminal catheter at 1 atm pressure for 3 minutes, and the arteries were evaluated 3 weeks later by the morphometric analysis system described above. The ratio of treated artery luminal area to proximal normal artery luminal area was determined as a percent change in treated vs. normal area, or the artery lumen size (diameter or cross sectional area) of treated arteries relative to traumatized but untreated arteries. A significant threshold effect was observed at doses from 0.1 µg/ml (about a 140% increase) to 1.0 µg/ml (FIG. 14). The 10 µg/ml dose appeared to be toxic to the vascular smoothmucle cells. However, subsequent experiments (see below) demonstrated that both 0.01 µg/ml and 10 µg/ml doses were efficacious. The subthreshold dose (0.01 µg/ml) and negative control (PBS) exhibited about a ±20% change in luminal area.

Electron micrographs revealed that within one hour of balloon trauma, there was a depolymerization of the myofilaments in traumatized vessels, which are contractive organelles. The depolymerization of the myofilaments is a normal physiological response of vascular smooth muscle cells to trauma, and is the first step in their transformation from a contractile to a secretory and migratory cell. Treatment of traumatized swine arteries with about 0.1 to about 10.0 µg/ml of cytochalasin B did not result in an increased rate, or more extensive depolymerization, of the myofibrils. However, electron micrographs showed that the myofilament reformation was retarded. Based on the sustained increase in vessel diameter, the return to normal vascular contractility may be slowed more extensively than is suggested by the retarded return to normal morphology.

The traumatized and treated areas of the artery did not undergo the constriction or chronic geometrical (vascular) remodeling that normally occurred in sham controls in the pig, and which has been described in man, following PTCA. Cross sections of the artery showed a larger cross-sectional area of the total vessel, obtained by measuring the ratio of the vessel area inside the external elastic lamina (EEL) of the treated area to the mean of the total vessel area of the proximal and distal regions of the same artery, compared to arteries traumatized but not treated with cytochalasin B. In arteries that were traumatized with a torquable balloon that damages the vessel wall without tearing the tunica media, there was a more uniform intimal proliferation and the larger vessel size (area inside the EEL) resulted in a larger luminal cross-sectional area and a significant decrease in restenosis. When the vessels were extensively damaged and the tunica media was torn into, there was extensive proliferation and thrombus remodeling that resulted in highly variable intimal proliferation.

Thus, the administration of cytochalasin B to swine vascular smooth muscle cells by infusion catheter following balloon dilation trauma resulted in a more extensive retention of the artery lumen size (diameter or cross sectional area) than was produced by the dilating balloon. This effect was achieved by replacing the entire interstitial fluid volume between cells of the tunica media with the therapeutic agent.

Moreover, cytochalasin B has a wide therapeutic index which ranges from about 0.1 to 10 µg/ml, with no evidence of toxicity at 10 µg/ml. Ten µg/ml is the maximum saturation concentration of cytochalasin B in saline. Furthermore, the effect produced by cytochalasin B administration became more apparent over the 3 to 8 weeks following the balloon trauma. These data suggest that cytochalasin B acts as a "biological stent" when delivered to traumatized arteries.

Balloon traumatized swine femoral arteries from control and treated (0.1 µg/ml cytochalasin B) were evaluated at 1, 4, 7, 14, or 21 days after intervention. Morphometric analysis on frozen histologic sections of artery showed that cytochalasin B treated arteries reached a state of sustained dilation which changed very little between days 7 and 21. A two way analysis of variance indicated a statistically significant difference (p<0.05) in the artery lumen areas over three weeks between the cytochalasin B treated and diluent control groups.

A dose-response study of balloon traumatized swine coronary arteries showed that treatment with cytochalasin B at 0.1, 1.5 or 10.0 µg/ml (Table 14, "Biostent") resulted in sustained arterial dilation of the coronary luminal area at three weeks after intervention. Moreover, cytochalasin B administration did not result in myocardial or arterial lesions attributable to the cytochalasin B as evaluated histologically. No statistically and biologically significant changes attributable to cytochalasin B were seen in clinical chemistry parameters, hematology paremeters, body weights, blood pressure or electrocardiograms.

TABLE 14

SWINE CORONARY MORPHOMETRY DATA

| Group Dose (µg/ml)* | Days Post Surgery | Mean % Lumen Area | Std Dev | P-value Unpaired T-test |
|---|---|---|---|---|
| Saline | 4 | 96.5 | 15.2 | — |
| 0.1 µg/mL Biostent | 4 | 97.0 | 17.1 | 0.48 |
| 1.5 µg/mL Biostent | 4 | 101.7 | 6.8 | 0.28 |
| 10 µg/mL Biostent | 4 | 103.9 | 14.1 | 0.25 |
| Saline | 21 | 78.7 | 19.1 | — |
| 0.1 µg/mL Biostent | 21 | 98.0 | 15.5 | 0.004 |
| 1.5 µg/mL Biostent | 21 | 100.9 | 18.5 | 0.002 |
| 10 µg/mL Biostent | 21 | 110.9 | 19.2 | 0.004 |

*Dose is based on the concentration of cytochalasin B (µg/ml) in the about 8 to about 30 lambda volume of fluid delivered to about 10 to about 20% of the tunica media.

Swine coronary arteries were also traumatized by embolectomy or over-sized PTCA balloon, and then 8–16 ml of cytochalasin B at 8.0 µg/ml was infused into the arterial wall with a MIC catheter to achieve a therapeutic dose. Controls included a diluent control and a traumatized untreated control, and all animals were sacrificed 4 weeks after intervention and coronary arteries were fixed by perfusion. Morphometry was performed on selected sections from proximal, treated and distal segments of coronary arteries (Table 15).

TABLE 15

Swine Coronary Artery Study

| Group | Neointimal Area | | Luminal Area | | Arterial Area | |
|---|---|---|---|---|---|---|
| | Area | std | Area | std | Area | std |
| Untreated Control | 1.88 | 1.62 | 0.77 | 0.38 | 2.19 | 1.07 |
| Saline Treated Control | 1.39 | 1.13 | 0.73 | 0.37 | 1.88 | 0.96 |
| 8.0 μg/ml Cytochalasin B | 1.56 | 1.24 | 058 | 0.30 | 1.80 | 0.70 |

While the data shown in Table 15, in contrast to previous studies, showed that the local delivery of cytochalasin B did not result in a statistically significant increase in luminal area, the data does show that there was a trend toward beneficial arterial remodeling as evidenced by larger arterial area bounded by the external elastic lamina in the cytochalasin B treated arteries when compared to either of the controls. The diameter of, or the area within, the EEL of the artery can be compared to controls as an indicator of the degree of vascular remodeling. The lack of a statistically significant increase in luminal area may be due to increased sample variablility, increased neointimal formation, and/or increased degree of trauma.

In summary, these studies demonstrate that the administration of a cytoskeletal inhibitor, such as cytochalasin B, in an amount which can biologically stent a traumatized vessel may also be efficacious to inhibit or reduce the proliferation of vascular smooth muscle cells.

EXAMPLE 17

Sustained Release Formulations of Cytochalasin B and Taxol

To determine the efficacy of the local, sustained release dosage forms of cytochalasin B or taxol to inhibit restenosis, cytochalasin B or taxol in a supporting structure, e.g., a "wrap," was applied to the adventitial tissue surrounding a balloon traumatized rabbit carotid artery (Groups 1–11 ) or a balloon traumatized pig femoral artery (Group 12) (Table 16).

The arteries in the animals in Group 1a and 1b were treated with 20 mg of cytochalasin B in 1 g of a bovine collagen gel (BioCore, Inc., Topeka, Kans.) that was supported by, or enclosed in, a bovine collagen mesh wrap (Skin Temp-Biosynthetic Skin Dressing, BioCore, Inc., Topeka, Kans.). At 1 week post treatment, the cytochalasin B treated artery in animal 1233 showed no intimal or adventital proliferation. There was marked cell death in the outer zone of the tunica media with heterophils infiltrating the tunica media. Heterophils were present outside the wrap, but cytochalasin B inhibited heterophils and macrophages from infiltrating the wrap. The artery of the control (1249) animal had moderate intimal proliferation, and heterophils and histiocytes were infiltrating into the wrap. Cell death in the tunica media was minimal.

At 2 weeks post-treatment, there was minimal intimal and adventital proliferation in the cytochalasin B wrap-treated area of the artery (animal 1224). The intima was loosely arranged and there was minimal heterophil infiltration. Syncytial giant cells were present. In the artery of the control wrap animal (animal 1222), there was moderate intimal proliferation with heterophils and macrophage in the wrap area. These cells were visible in the tunica media.

At three weeks post-treatment, there was no intimal proliferation observed in the cytochalasin B wrap-treated area of the artery (1244). Heterophils and syncytial giant cells were present around the wrap. There was significant necrosis of the cells in the tunica media with infiltrating heterophils and macrophages. No endothelium was present. In the control (animal 1232) artery, there was marked intimal proliferation, with well organized adventitia and perivascular tissue. Heterophils and macrophages were infiltrating the wrap. The cells in the tunica media were viable and there was a mural thrombus in the vessel lumen. Thus, inhibition of intimal proliferation was seen in the arteries of Group 1a and 1b animals treated with cytochalasin B, however, there was significant reaction to the wrap material.

The arteries in the animals in Group 2a and 2b were treated with cytochalasin B (30% wt/wt; 300 mg cytochalasin B/g silicone) in a silicone wrap (Q-7 4840, Dow Corning, Midland, Mich.). One week post-trauma there was no significant intimal or adventitial proliferation of smooth muscle cells (SMCs) or mesenchymal tissue (animal 1229). There was significant necrosis of the SMCs in the outer zone of the tunica media. In areas that appeared to have been minimally traumatized by the torquable balloon there was minimal to no cellular necrosis. This indicated that traumatized cells were more prone to die when exposed to this dose of cytochalasin B but that this dose was not cytocidal to minimally traumatized or normal SMCs. There was minimal mononuclear and polymorphoneuclear cell infiltration into the tunica media. A few heterophils were seen infiltrating from the vessel lumen.

In the control animal (1228), there was less cellular necrosis in the tunica media, and the necrosis present was located in the inner zone rather than the outer zone of the artery wall. Thus, cytochalasin B inhibition of cellular repair appears to increase tunica media necrosis. The control also lacked tunica media or adventitial proliferation and organization of the perivascular clot. Cellular infiltration in any area was minimal.

Two weeks after initiating cytochalasin B treatment there was complete inhibition of intimal proliferation and only minimal perivascular clot organization which was primarily due to fibrin formation and not mesenchymal proliferation (animal 1227). There was mild infiltration of polymorphonuclear cells and minimal infiltration of mononuclear cells into the tunica media and adventitia. No endothelium was present in the wrap area, except for a few small isolated foci. The control artery (animal 1226) had moderate intimal proliferation and adventitial proliferation with mesenchymal organization of the perivascular clot area. Foci of endothelial proliferation were larger and more extensive in the control animal compared to the cytochalasin B treated vessel.

With 3 weeks exposure (animal 1212) to cytochalasin B in a silicone wrap, the vessel showed marked cell loss in the tunica media which was most severe in the outer zone. Cellular infiltration in the tunica media and adventitia was minimal and endothelilzation was only present in a few focal areas. There was moderate, irregular intimal proliferation; however, the intimal cells and what few endothelial cells that were present were unorganized and lack polarity. The inhibition of migration by cytochalasin B resulted in this loss of organization or polarity. The intimal proliferation was also mild in the control vessel (1230); however, the intima was well organized and was almost completely endothelized. There was minimal cell loss from the tunica media. Thus, significant intimal inhibition was seen in the first two weeks in Group 2 treated animals.

The vessels in the animals in Group 3a and 3b were treated with 8 mg cytochalasin B in 100 mg of a pluronic gel (F-127, BASF) that was supported by a 1 cm×1 cm bovine collagen mesh wrap. One week after treatment, the cytochalasin B treated artery of animal 1250 had mild intimal proliferation that was irregular in thickness. There was approximately 30% re-endothelization and the tunica media cells were viable with the most significant loss (mild) being in the inner zone of the tunica media. There was a marked pyogranulomatous reaction to the pluronic gel in the perivascular and adventitial region. Complete thrombosis of the control artery from animal 1261 prevented its evaluation.

At two weeks, the pluronic gel with cytochalasin B stimulated a marked pyogranulomatous reaction in the adventitial and perivascular tissue. There was mild, irregular intimal proliferation and complete endothelization. The tunica media cells were viable. There appeared to be a mild cell loss from the inner zone of the tunica media. The artery of the control animal (1247) had mild, irregular intimal proliferation, complete endothelization with plump endothelial cells and viable cells in the tunica media. There was marked pyogranulomatous inflammatory reaction to remnants of the pluronic gel.

At three weeks, the arteries of animals 1248 and 1246 showed remnants of the collagen wrap; however, the wrap was less resolved in the cytochalasin B treated animal (1248) than in the control (1246). This retardation of wrap resorbsion may result from cytochalasin B inhibition of macrophage migration and function. Both the treated and control had a moderate amount of intimal hyperplasia at 3 weeks, so there was no significant amount of intimal inhibition by cytochalasin B when administered in the pluronic gel. Foci of dystrophic mineralization were seen in the cytochalasin B treated artery. Thus, no inhibitory effect on the intima was observed in these animals (Group 3) at 1, 2 or 3 weeks after the initiation of treatment.

The arteries of the animals in Group 4a and b that were treated with 100 mg cytochalasin B (10% wt/wt) in a 1 g silicone wrap had significant inhibition of intimal proliferation at all time points. In the cytochalasin B wrap-treated artery of animal 1259, there was no intimal proliferation or adventitial fibrosis present at one week after treatment. Ectatic vessels were present in the adventitia and the perivascular clot was unorganized and composed of only fibrin. There was marked cell loss from the tunica media, especially in the outer zone. Heterophils were seen infiltrating the tunica media. In the control artery (1206), there was no intimal proliferation at 1 week; however, there was early fibrous organization of the perivascular clot. Cellular loss from the tunical media was more diffuse than in the cytochalasin B wrap which was most severe in the outer zone.

The cytochalasin B wrap-treated artery of animal 1253 had minimal intimal proliferation at two weeks, compared to the control (1258) wrap-treated artery which had maximal intimal proliferation. The intimal proliferation in the cytochalasin B wrap-treated artery was irregular and appeared to be the result of organizing mural thrombi by infiltrating SMC. There was only loose thin layers of platelets in the cytochalasin B wrap-treated artery, with margination of heterophils. There was no endothelization in the cytochalasin B wrap-treated artery and <20% endothelization in the control artery. The perivascular clot was unorganized and remained fibinous in the cytochalasin B wrap-treated artery and well organized in the control artery. The control artery had minimal cell loss from the tunica media while the cytochalasin B wrap-treated artery had marked cell loss.

At three weeks, the cytochalasin B wrap-treated artery (1251) showed minimal to no intimal proliferation. The intimal proliferation appeared to occur where there was less cell loss from the tunica media. There was early re-endothelization in the cytochalasin B wrap-treated artery, but the cells were often rounded, loosely attached and only a few scattered foci were present (<10%). The perivascular clot in the cytochalasin B wrap-treated artery was unorganized and still consisted of fibrin, whereas the control artery was well organized with fibroblasts and collagen matrix. The control artery was completely thrombosed, there was marked initmal production in distal areas of the thrombus which were less completely organized.

The arteries in the animals in Group 5a and b were treated with 50 mg taxol in 1 g of a silicone wrap (5% wt/wt). This treatment showed marked inhibition of intimal proliferation at all time points. The taxol wrap-treated artery (animal 1278 at 1 week) had no intimal or adventitial proliferation and the perivascular clot was fibrinous and unorganized. There was a marked loss of tunica media cells and no endothelial lining present. The control (1279) had mild intimal proliferation with very early fibrosis of the fibrinous perivascular clot. The lumen was approximately 85% re-endothelized. Both the treated and control arteries had mild heterophil infiltration into the tunica media and adventitia.

The artery from animal 1281, which had been treated for at two weeks with taxol, had no intimal proliferation, minimal adventitial fibrosis and marked cell necrosis in the tunica media with mild heterophil infiltration. Focal areas of necrosis and dystrophic mineralization were present in the adventitia and perivascular clot tissue. The artery from the control animal (1280) had moderate intimal proliferation, with marked organization of the adventitia and perivascular clot. The lumen was 100% re-endothelized and the tunica media SMCs were viable in the control artery.

At three weeks, the taxol wrap-treated artery (1242) had no intimal proliferation and was 50% re-endothelized with plump appearing endothelial cells. There was minimal organization of the perivascular clot and marked cell loss from the tunica media. There was mild infiltration of heterophils into the tunica media and marginating on the vessel lumenal surface. The control artery (1234) had marked intimal proliferation and fibrosis of the adventitia and perivascular clot. Cells in the tunica were viable.

In Group 6a and 6b, taxol-treated arteries also had a marked inhibition 2 weeks after the wrap was removed. Animal 1276 had a taxol wrap for 2 weeks, then the wrap was removed and the animal sacrificed 3 weeks later. Following the 3 week recovery period from the taxol wrap removal (1276) there was only minimal intimal proliferation, except in a few focal areas that appeared to be thickened due to SMC organization of mural thrombi, in this artery. The adventitia was well organized and there was a significant cell loss in the tunica media but the cells present were viable. The lumen was approximately 90% re-endothelized. The control (1277) artery had marked intimal proliferation, well organized perivascular and adventical tissue and was 100% re-endothelized.

The results observed for Group 7a animals demonstrated that cytochalasin B-treated arteries (10% wt/wt) showed no intimal proliferation for 2 weeks. The decrease in the release rate of the cytochalasin B, however, resulted in a mild intimal proliferation by week three after wrap placement. At one week (1257), the arteries showed no intimal proliferation, and a marked necrosis of tunical media SMCs with moderate heterophil infiltration. There was no endothelium and heterophils and macrophages were marginated along the lumen surface. Moreover, there was no evidence of platelet aggregates adhering to vessel wall. At two weeks (1265), the arteries were similar morphologically to the one week arteries. By three weeks (1266), the arteries showed mild irregular intimal proliferation. Furthermore, heterophils were rare in the tunica media, the lumen was 70% re-endothelized and there was early fibrosis in the adventitia with unorganized perivascular clot still present, in the treated arteries. This indicated that by 3 weeks the level of therapeutic agent had fallen below therapeutic level within the artery wall; however, there was still enough drug to have an inhibitory effect on clot organization immediately adjacent to the wrap.

The arteries of Group 8a animals, which were treated with 10% cytochalasin B for 2 weeks, then the wrap was removed and vessels evaluated 2 weeks later, had variable intimal proliferation within and between animals. The artery of animal 1254 had variable intimal proliferation which ranged from none to mild, well developed adventitial fibrosis, marked cell loss in the tunic media and focal areas of dystrophic mineralization in the outer tunica media and adventitia. The mild intimal proliferation areas were at the ends of the wrap area, suggesting an infiltration from the adjacent untreated artery regions. The lumen was approximately 60% re-endothelized. The artery of animal 1255 had mild to moderate intimal proliferation, viable cells in the tunica media and well organized tissue in the adventitia. The lumen was 100% re-endothelized. The artery in animal 1256 was completely thrombosed. Proximal to the chronic thrombus in the area of the wrap was an acute thrombus and there was moderate intimal proliferation.

While there was moderate intimal proliferation in the arteries of some animals, the proliferation in these arteries was still less than the controls in Group 9b. The mannitol control silicone wraps were on the artery for two weeks following balloon trauma and then removed and the animal necropsied and the artery histologically evaluated 1 week following wrap removal. Two of the arteries (1267 and 1268) had moderate intimal proliferation with 100% re-endothelization and one had maximum proliferation. The one with maximum intimal proliferation had an acute occluding thrombus present.

The arteries in the animals in Groups 10 and 11 were treated with 10 mg cytochalasin B loaded in 1 g of a silicone wrap (1% wt/wt) that was applied to the artery for 2 weeks, surgically removed, and histologically evaluated 2 or 4 weeks later, respectively. No significant difference was seen by qualitative evaluation between the test and control animals. Animals 1304 and 1305 had a cytochalasin B (1%) wrap for 2 weeks which was then removed. Two weeks after the removal the animal was sacrificed. The artery from animal 1304 showed moderate initmal proliferation in most areas of the wrap, in areas of marked tunica media cell necrosis and wall dystrophic mineralization the proliferation was mild. There was 100% re-endothelization and no heterophils were present in the intima or tunica media. The adventitia and perivascular clot area was well organized. The artery from animal 1305 was similar to the artery from animal 1304 morphologically. The artery from animal 1306 showed marked intimal proliferation, no infiltrating heterophils in the intima or tunica media and was 100% re-endothelized.

Animals 1307, 1308 and 1309 were exposed to a cytochalasin B (1%) wrap for 2 weeks which was then removed. Four weeks after removal the animals were sacrificed. The artery from animal 1307 had moderate intimal proliferation with focal areas of thickening due to mural thrombus organization by SMCs. There was significant loss of cells from the tunica media and the elastic elamina appear collapsed. A few heterophils were present in the adventitia. There were areas or sections in the wrap area with minimal intimal proliferation. The artery from animal 1308 showed moderate intimal proliferation with areas of marked cell loss in the tunica media and dystrophic mineralization in the outer zone of the tunica media. The vessel was 100% re-endothelized. The artery from animal 1309 had marked intimal proliferation with a well organized aventiticia and perivascular region. Animal 1311 was not evaluated due to thrombosis. The results of the artery from animal 1312 were quite variable, with sections showing a range of intimal proliferation, from mild to moderate. Endothelization appeared to be complete in these arteries.

The arteries from Group 12 animals (pig femoral arteries) that were treated with 30% wt/wt cytochalasin B loaded silicone wraps showed significantly inhibited intimal proliferation for the first two weeks. While there was intimal proliferation in the arteries 3 weeks later, the proliferation was still less than the proliferation observed for the controls.

TABLE 16

| ANIMAL # | GROUP # | TREATMENT | SURGERY DATE | NECROPSY DATE | TIME POST TREATMENT | GROUP |
|---|---|---|---|---|---|---|
| 1233 | 1a | CytoB + Bovine col gel + col mat | 2/28/96 | 3/7/96 | 1 wk | 1 |
| 1249 | 1b | Control + Bovine col gel + col mat | 2/28/96 | 3/7/96 | 1 wk | 3 |
| 1224 | 1a | CytoB + Bovine col gel + col mat | 2/28/96 | 3/15/96 | 2 wks | 2 |
| 1222 | 1b | Control + Bovine col gel + col mat | 2/28/96 | 3/15/96 | 2 wks | 3 |
| 1244 | 1a | CytoB + Bovine col gel + col mat | 2/28/96 | 3/20/96 | 3 wks | 1 |
| 1232 | 1b | Control + Bovine col gel + col mat | 2/28/96 | 3/20/96 | 3 wks | 3 |
| 1229 | 2a | CytoB 30% + silicone | 2/22/96 | 2/28/96 | 1 wk | 0 |
| 1228 | 2b | Control + silicone | 2/22/96 | 2/28/96 | 1 wk | 2 |
| 1227 | 2a | CytoB 30% + silicone | 2/22/96 | 3/7/96 | 2 wks | 0 |
| 1226 | 2b | Control + silicone | 2/22/96 | 3/7/96 | 2 wks | 3 |
| 1212 | 2a | CytoB 30% + silicone | 2/22/96 | 3/15/96 | 3 wks | 2 |
| 1230 | 2b | Control + silicone | 2/22/96 | 3/15/96 | 3 wks | 2 |
| 1250 | 3a | CytoB + pluronic gel + col. wrap | 3/7/96 | 3/15/96 | 1 wk | 2 |
| 1261 | 3b | Control + pluronic gel + col. wrap | 3/7/96 | 3/15/96 | 1 wk | NA |
| 1245 | 3a | CytoB + pluronic gel + col. wrap | 3/7/96 | 3/20/96 | 2 wks | 2 |
| 1247 | 3b | Control + pluronic gel + col. wrap | 3/7/96 | 3/20/96 | 2 wks | 2 |
| 1248 | 3a | CytoB + pluronic gel + col. wrap | 3/7/96 | 3/28/96 | 3 wks | 3 |
| 1246 | 3b | Control + pluronic gel + col. wrap | 3/7/96 | 3/28/96 | 3 wks | 3 |
| 1259 | 4a | CytoB 10%-mannitol + silicone | 4/8/96 | 4/15/96 | 1 wk | 0 |
| 1260 | 4b | Control-mannitol + silicone | 4/8/96 | 4/15/96 | 1 wk | 0 |

TABLE 16-continued

| ANIMAL # | GROUP # | TREATMENT | SURGERY DATE | NECROPSY DATE | TIME POST TREATMENT | GROUP |
|---|---|---|---|---|---|---|
| 1253 | 4a | CytoB 10%-mannito1 + silicone | 4/8/96 | 4/22/96 | 2 wks | 1 |
| 1258 | 4b | Control-mannitol + silicone | 4/8/96 | 4/22/96 | 2 wks | 4 |
| 1251 | 4a | CytoB 10%-mannitol + silicone | 4/8/96 | 4/29/96 | 3 wks | 0 |
| 1252 | 4b | Control-mannitol + silicone | 4/8/96 | 4/29/96 | 3 wks | 4 |
| 1278 | 5a | Taxol + silicone | 3/20/96 | 3/2//96 | 1 wk | 0 |
| 1279 | 5b | Control-silicone | 3/20/96 | 3/28/96 | 1 wk | 2 |
| 1281 | 5a | Taxol + silicone | 3/20/96 | 4/4/96 | 2 wks | 1 |
| 1280 | 5b | Control-silicone | 3/20/96 | 4/4/96 | 2 wks | 3 |
| 1242 | 5a | Taxol + silicone | 3/7/96 | 3/28/96 | 3 wks | 0 |
| 1243 | 5b | Control-silicone | 3/7/96 | 3/28/96 | 3 wks | 4 |
| 1276 | 6a | Taxol + silicone | 3/20/96 | 4/23/96 | 2 wks–3 wks | 1 |
| 1277 | 6b | Control-silicone | 3/20/96 | 4/23/96 | 2 wks–3 wks | 4 |
| 1257 | 7a | Cytob 10%-mannitol = silicone | 5/16/96 | 5/23/96 | 1 wk | 0 |
| 1265 | 7a | Cytob 10%-mannitol = silicone | 5/16/96 | 5/29/96 | 2 wks | 0 |
| 1266 | 7a | Cytob 10%-mannitol = silicone | 5/16/96 | 6/5/96 | 3 wks | 2 |
| | | Note: see control cases | 1260 = 1 wk | 1258 = 2 wks | 1252 = 3 wks | |
| 1254 | 8a | CytoB 10%-mannitol + silicone | 5/16/96 | 6/11/96 | 2 wks–2 wks | 0–2 |
| 1255 | 8a | CytoB 10%-mannitol + silicone | 5/16/96 | 6/11/96 | 2 wks–2 wks | 2–3 |
| 1256 | 8a | CytoB 10%-mannitol + silicone | 5/16/96 | 6/11/96 | 2 wks–2 wks | 3 |
| 1267 | 9b | Control-mannitol + silicone | 5/23/96 | 6/14/96 | 2 wks–1 wks | 3 |
| 1268 | 9b | Control-mannitol + silicone | 5/23/96 | 6/14/96 | 2 wks–1 wks | 3 |
| 1269 | 9b | Control-mannitol + silicone | 5/23/96 | 6/14/96 | 2 wks–1 wks | 4 |
| 1304 | 10a | CytoB 1%-mannitol + silicone | 6/10/96 | 7/9/96 | 2 wks–2 wks | 3 |
| 1305 | 10a | CytoB 1%-mannitol + silicone | 6/10/96 | 719/96 | 2 wks–2 wks | 3 |
| 1306 | 10a | CytoB 1%-mannitol + silicone | 6/10/96 | 719/96 | 2 wks–2 wks | 4 |
| 1307 | 11a | CytoB 1%-mannitol + silicone | 6/10/96 | 7/22/96 | 2 wks–4 wks | 3 |
| 1308 | 11a | CytoB 1%-mannitol + silicone | 6/10/96 | 7/22/96 | 2 wks–4 wks | 3 |
| 1309 | 11a | CytoB 1%-mannitol + silicone | 6/10/96 | 7/22/96 | 2 wks–4 wks | NA |
| 1310 | 11b | Control-mannitol + silicone | 6/10/96 | 7/22/96 | 2 wks–4 wks | 4 |
| 1311 | 11b | Control-mannitol + silicone | 6/10/96 | 7/22/96 | 2 wks–4 wks | NA |
| 1312 | 11b | Control-mannitol + silicone | 6/10/96 | 7/22/96 | 2 wks–4 wks | 3 |
| 1029LF | 12e | CytoB 30%-silicone wrap | 2/1/96 | 2/22/96 | 3 wks. | 2 |
| 1020RF | 12f | Control silicone wrap | 2/1/96 | 2/22/96 | 3 wks. | 3 |
| 1030LF | 12e | CytoB 30%-silicone wrap | 2/7/96 | 2/22/96 | 2 wks. | 1 |
| 1030RF | 12d | Control silicone wrap | 2/7/96 | 2/22/96 | 2 wks. | 4 |
| 1036LF | 12a | CytoB 30%-silicone wrap | 2/7/96 | 2/7/96 | 1 wl. | 1 |
| 1036RF | 12b | Control silicone wrap | 2/1/96 | 2/7/96 | 1 wk. | 1 |

In summary, intimal proliferation of traumatized pig arteries was significantly inhibited with both cytochalasin B and taxol in sustained release dosage form. The best controlled sustained release of therapeutic agent, without the stimulation of secondary inflammatory reaction, was obtained with an adventitial wrap material comprising silicone. The silicone wraps inhibited intimal proliferation with 30% and 10% loadings of cytochalasin B; however, as the level of release drops off between 2 and 3 weeks there was initiation of intimal proliferation. When wraps were left in place for 2 weeks then surgically removed and the arteries examined from 1 to 4 weeks later, there appeared to be an intimal proliferation rebound effect. The rebound effect occurred when the intimal proliferation of the artery treated with the therapeutic agent approaches, but is still less than, the intimal proliferation in the control artery. The animal treated with taxol appeared to have less of a rebound effect than the cytochalasin B treated arteries.

EXAMPLE 18

Delivery of Crystalline Cytochalasin B or Taxol

The in vivo tissue distribution of cytochalasin B administered in crystalline form was evaluated in balloon traumatized swine femoral arteries after local delivery. A femoral artery of a Yorkshire crossbred swine was balloon traumatized by overinflation and rotation of a Vascu-Flom Silicone embolectomy catheter. Balloon trauma was immediately followed by intravascular delivery of 10 µg/ml $^3$H-cytochalasin B crystals (Sigma Chemical Co., St. Louis, Mo.) in saline (saturated) for three minutes under 1 atm of pressure. Blood flow was resumed in the artery for five minutes prior to sacrifice of the animal. An analysis of the tissue distribution of $^3$H-cytochalasin B showed that this method was effective at delivering 31 ug of $^3$H-cytochalasin B which localized predominantly to the adventitia. $^3$H-cytochalasin B was visualized histologically by the presence of silver grains in an autoradiographic emulsion. Thus, these results showed that crystalline cytochalasin B can be delivered locally to a vessel wall in vivo.

Another study employed twenty, male, Sprague-Dawley rats. The rats underwent balloon trauma to their left carotid artery, followed by inter-arterial infusion of a solution containing 1 mg crystalline cytochalasin B in 300 ml vehicle (Hanks sterile salt solution with 0.5% Cremophor) or a diluent (saline) control. Animals were sacrificed immediately after infusion, and 2, 4, 7 and 14 days post-trauma and infusion. Post-sacrifice, the left and the right (control) carotid arteries were removed. Samples of arteries were obtained for quantitation of $^3$H-cytochalasin B by oxidation and scintillation counting, histopathology, autoradiography and vascular morphometry. Histopathology documented uniform, circumferential balloon trauma in the arterial wall of the left carotid arteries.

Autoradiographically, cytochalasin B crystals were present on day 0 in intraluminal fibrin clots, adherent to the intima but rarely present in the adventitia. By day 2, the number of crystals diminished compared to day 0, and by day 4 crystals were not detectable by autoradiography. The autoradiographic results correlated closely with quantitative assessment of ³H-cytochalasin B by oxidation and scintillation counts in which approximately 8 ug of cytochalasin B was present over the treated length of artery on day 0 and slightly less than 2 ng was present by day 2. However, one of the two animals sacrificed on day 4 still had cytochalasin B levels above background. Morphometric analysis of left carotid arteries of crystalline cytochalasin B treated rats compared to diluent treated rats showed no statistically significant reduction in neointima formation. However, the five treated rats had a higher mean luminal area and a smaller neointimal area than diluent treated control.

Cytochalasin B and taxol were administered periadventially. Three groups of seven adult male rats underwent balloon trauma of the left carotid artery immediately followed by periadventitial placement of either cytochalasin B crystals (7.8–11.8 mg/rat), taxol crystals (3.4–6.5 mg/rat), or no drug (control). The cytochalasin B and taxol crystals were placed in a uniform pattern which covered the surgically exposed surface of the carotid artery, followed by closure of surrounding subcutaneous skin and tissues by sutures. Fourteen days later rats were sacrificed and their carotid arteries processed for histologic and morphometric analysis.

Two cytochalasin B treated animals died due to acute hemorrhage at the surgical site and hypovolemic shock prior to the 14 day sacrifice point. Two additional cytochalasin B treated and one taxol treated animal were sacrificed with rapidly enlarging subcutaneous swelling and hemorrhage at the surgical site prior to the 14 day sacrifice point. All animals treated with either cytochalasin B or taxol crystals had significant toxicity at the surgical site which was characterized by varying degrees of hemorrhage, necrosis of the vessel wall, necrosis of adjacent skeletal muscle and inflammation. In addition, both the taxol and cytochalasin B treated animals had a delay in post-surgical weight gain.

The three cytochalasin B treated, 6 taxol treated and 7 control animals which survived to the 14 day sacrifice point were evaluated morphometrically. Taxol treated animals had statistically significantly larger luminal areas and no neointimal proliferation when compared to the balloon traumatized, untreated control animals in a two-tailed t-test with $p<0.05$. Cytochalasin B treated animals showed no statistical difference from the controls in luminal area, neointimal area, medial area, areas bounded by the internal and external elastic lamina or intimal to medial ratio.

To further evaluate the efficacy of crystalline taxol to inhibit neointimal formation in rats, four groups of 5–6 adult male rats underwent balloon trauma of the left carotid artery followed immediately by periadventitial delivery of 1, 0.1, 0.01 or 0 mg of taxol crystals in 500 mg of a pluronic polymer in gel matrix. Fourteen days later, the rats were sacrificed, serum was collected and their carotid arteries were processed for histologic and morphometric analysis.

Five animals (3—1 mg and 2—0.01 mg) died post-surgically due to technical difficulties. Grossly, myonecrosis of the adjacent skeletal muscle (pale white regions of the musculature) was present in 3/3, 1/5, 0/4 and 0/5 animals in the 1 mg, 0.1 mg, 0.01 mg and control groups, respectively. Histologically, myonecrosis was confirmed in the adjacent skeletal muscle and in some regions of the tunica media of the left carotid artery in the 1 mg treatment group but not in the other groups. Morphometrically, there was no statistical significance in luminal area, neointimal area, area bounded by the internal elastic lamina, area of the tunica media, area bounded by the external elastic lamina or neointimal/medial ratio when compared by analysis of variance using the excell data analysis software package.

Periadventitial treatment of rat carotid arteries with 1 mg taxol crystals in 500 mg of a pluronic gel resulted in gross myonecrosis of the adjacent musculature. While the number of animals surviving in this group was too low to assess for statistical significance in the reduction of neointimal formation, neointimal area was 38% less than that of control animals.

For animals treated with 0.1 and 0.01 mg taxol, a reduction in their neointimal area and neointimal/medial ratio was observed when compared to control animals, although this did not reach statistical significance given the small number of animals per group. Moreover, animals in the lower dose groups showed no (0.01 mg), minimal (0.1 mg) or limited (1.0 mg) toxicity, indicating that lower doses may be efficacious and exhibit fewer adverse side effects than doses greater than 1.0 mg.

All publications and patents are incorporated by reference herein, as though individually incorporated by reference, as long as they are not inconsistent with the disclosure. The invention is not limited to the exact details shown and described, for it should be understood that many variations and modifications may be made while remaining within the spirit and scope of the invention defined by the claims.

What is claimed is:

1. A kit comprising an implantable device adapted for the delivery of at least one therapeutic agent to a site in the lumen of a traumatized mammalian vessel and a unit dosage form comprising at least one cytoskeletal inhibitor in a liquid vehicle, wherein the administration of at least a portion of the unit dosage form to the vessel is effective to biologically stent the vessel.

2. The kit of claim 1 wherein the administration is sufficient for at least a portion of the unit dosage form to penetrate to at least about the inner 6 to 9 cell layers of the inner tunica media of the vessel.

3. The kit of claim 1 wherein the cytoskeletal inhibitor comprises taxol, a cytochalasin, or an analog thereof.

4. The kit of claim 3 wherein the cytoskeletal inhibitor comprises taxol.

5. The kit of claim 3 wherein the cytoskeletal inhibitor comprises an analog of taxol.

6. The kit of claim 3 wherein the cytochalasin comprises an analog of cytochalasin B.

7. The kit of claim 3 wherein the cytochalasin comprises cytochalasin A.

8. The kit of claim 3 wherein the cytochalasin comprises cytochalasin D.

9. The kit of claim 3 wherein the cytochalasin comprises cytochalasin B.

10. The kit of claim 9 wherein cytochalasin B is at about 0.01 to about 10 μg per ml of liquid vehicle.

11. The kit of claim 9 wherein cytochalasin B is at about 1.0 to about 10 μg per ml of liquid vehicle.

12. The kit of claim 1 wherein the vehicle is aqueous.

13. The kit of claim 1 wherein the implantable device is a catheter.

14. The kit of claim 13 wherein the implantable device is a catheter which delivers about 4 to about 25 ml of the unit dosage form.

15. The kit of claim 14 wherein the unit dosage form is administered for about 1 to about 5 minutes at about 0.3 atm to about 8 atm.

16. The kit of claim 13 wherein the catheter pore size is about 0.1 microns to about 8 microns in diameter.

17. The kit of claim 9 wherein the unit dosage form comprises a vial comprising about 10 to about 30 ml of about 0.01 μg to about 10 μg of cytochalasin B per ml of liquid vehicle.

18. The kit of claim 1 wherein the vial is labeled for use in treating or inhibiting stenosis or restenosis.

* * * * *